US011987818B2

(12) United States Patent
Borra-Garske et al.

(10) Patent No.: US 11,987,818 B2
(45) Date of Patent: May 21, 2024

(54) ENGINEERED IMINE REDUCTASES AND METHODS FOR THE REDUCTIVE AMINATION OF KETONE AND AMINE COMPOUNDS

(71) Applicant: Codexis, Inc., Redwood City, CA (US)

(72) Inventors: Margie Tabuga Borra-Garske, Palo Alto, CA (US); Oscar Alvizo, Fremont, CA (US); Melissa Ann Mayo, Foster City, CA (US); Stephan Jenne, Foster City, CA (US); Auric Anthony Sowell-Kantz, Fairfax, CA (US); Carmela Molinaro, Colonia, NJ (US)

(73) Assignee: Codexis, Inc., Redwood City, CA (US)

(*) Notice: Subject to any disclaimer, the term of this patent is extended or adjusted under 35 U.S.C. 154(b) by 162 days.

(21) Appl. No.: 17/330,686

(22) Filed: May 26, 2021

(65) Prior Publication Data
US 2021/0284973 A1 Sep. 16, 2021

Related U.S. Application Data

(62) Division of application No. 16/319,537, filed as application No. PCT/US2017/045838 on Aug. 8, 2017, now Pat. No. 11,046,936.

(60) Provisional application No. 62/380,165, filed on Aug. 26, 2016.

(51) Int. Cl.
C12N 9/06 (2006.01)
C12N 9/02 (2006.01)

(52) U.S. Cl.
CPC ......... *C12N 9/0028* (2013.01); *C12N 9/0036* (2013.01); *C12Y 105/01* (2013.01); *C12Y 106/00* (2013.01)

(58) Field of Classification Search
None
See application file for complete search history.

(56) References Cited

U.S. PATENT DOCUMENTS

| | | |
|---|---|---|
| 5,605,793 A | 2/1997 | Stemmer |
| 5,811,238 A | 9/1998 | Stemmer et al. |
| 5,830,721 A | 11/1998 | Stemmer et al. |
| 5,834,252 A | 11/1998 | Stemmer et al. |
| 5,837,458 A | 11/1998 | Minshull et al. |
| 5,928,905 A | 7/1999 | Stemmer et al. |
| 6,096,548 A | 8/2000 | Stemmer |
| 6,117,679 A | 9/2000 | Stemmer |
| 6,132,970 A | 10/2000 | Stemmer |
| 6,165,793 A | 12/2000 | Stemmer |
| 6,180,406 B1 | 1/2001 | Stemmer |
| 6,251,674 B1 | 6/2001 | Tobin et al. |
| 6,277,638 B1 | 8/2001 | Stemmer |
| 6,287,861 B1 | 9/2001 | Stemmer et al. |
| 6,287,862 B1 | 9/2001 | delCardayre et al. |
| 6,291,242 B1 | 9/2001 | Stemmer |
| 6,297,053 B1 | 10/2001 | Stemmer |
| 6,303,344 B1 | 10/2001 | Patten et al. |
| 6,309,883 B1 | 10/2001 | Minshull et al. |
| 6,319,713 B1 | 11/2001 | Patten et al. |
| 6,319,714 B1 | 11/2001 | Crameri et al. |
| 6,323,030 B1 | 11/2001 | Stemmer |
| 6,326,204 B1 | 12/2001 | delCardayre et al. |
| 6,335,160 B1 | 1/2002 | Patten et al. |
| 6,335,198 B1 | 1/2002 | delCardayre et al. |
| 6,344,356 B1 | 2/2002 | Stemmer |
| 6,352,859 B1 | 3/2002 | delCardayre et al. |
| 6,355,484 B1 | 3/2002 | Patten et al. |
| 6,358,740 B1 | 3/2002 | Patten et al. |
| 6,358,742 B1 | 3/2002 | Stemmer |
| 6,365,377 B1 | 4/2002 | Patten et al. |
| 6,365,408 B1 | 4/2002 | Stemmer |
| 6,368,861 B1 | 4/2002 | Crameri et al. |
| 6,372,497 B1 | 4/2002 | Stemmer |
| 6,376,246 B1 | 4/2002 | Crameri et al. |
| 6,379,964 B1 | 4/2002 | delCardayre et al. |
| 6,387,702 B1 | 5/2002 | Stemmer |
| 6,391,552 B2 | 5/2002 | Stemmer |
| 6,391,640 B1 | 5/2002 | Minshull et al. |
| 6,395,547 B1 | 5/2002 | Stemmer |
| 6,406,855 B1 | 6/2002 | Patten et al. |
| 6,406,910 B1 | 6/2002 | Patten et al. |
| 6,413,745 B1 | 7/2002 | Patten et al. |
| 6,413,774 B1 | 7/2002 | Stemmer |
| 6,420,175 B1 | 7/2002 | Stemmer |
| 6,423,542 B1 | 7/2002 | Crameri et al. |

(Continued)

FOREIGN PATENT DOCUMENTS

| | | |
|---|---|---|
| EP | 0641862 B2 | 12/2001 |
| WO | 95/22625 A1 | 8/1995 |

(Continued)

OTHER PUBLICATIONS

NCBI Reference Sequence WP_028934187.1 (downloaded and printed as PDF on Mar. 20, 2023).*
Tiwari, S., et al., "Prediction of probable genes by Fourier analysis of genomic sequences," Comput. Appl. Biosci. 13 (3):263-270 [1997].
Truppo, M.D., et al., "Development of an Improved Immobilized CAL-B for the Enzymatic Resolution of a Key Intermediate to Odanacatib," Organic Process Research & Development, 15:1033-1035 (2011).
Uberbacher, E.C., et al., "Discovering and Understanding Genes in Human DNA Sequence Using GRAIL," Methods Enzymol., 266:259-281 [1996].
Villa-Komaroff, L., et al., "A bacterial clone synthesizing proinsulin," Proc. Natl Acad. Sci. USA, 75:3727-3731 (1978).

(Continued)

*Primary Examiner* — Anand U Desai
(74) *Attorney, Agent, or Firm* — Codexis, Inc.

(57) ABSTRACT

The present application provides engineered polypeptides having imine or oxime reductase activity, polynucleotides encoding the engineered polypeptides, host cells capable of expressing the engineered polypeptides, and methods of using these engineered polypeptides with a range of ketone and amine substrate compounds to prepare secondary and tertiary amine product compounds.

16 Claims, No Drawings

Specification includes a Sequence Listing.

(56) References Cited

U.S. PATENT DOCUMENTS

| | | |
|---|---|---|
| 6,426,224 B1 | 7/2002 | Crameri et al. |
| 6,436,675 B1 | 8/2002 | Welch et al. |
| 6,444,468 B1 | 9/2002 | Stemmer et al. |
| 6,455,253 B1 | 9/2002 | Patten et al. |
| 6,479,652 B1 | 11/2002 | Crameri et al. |
| 6,482,647 B1 | 11/2002 | Stemmer |
| 6,489,146 B2 | 12/2002 | Stemmer et al. |
| 6,506,602 B1 | 1/2003 | Stemmer |
| 6,506,603 B1 | 1/2003 | Stemmer |
| 6,519,065 B1 | 2/2003 | Colbourne et al. |
| 6,521,453 B1 | 2/2003 | Crameri et al. |
| 6,528,311 B1 | 3/2003 | delCardayre et al. |
| 6,537,746 B2 | 3/2003 | Arnold et al. |
| 6,573,098 B1 | 6/2003 | Stemmer |
| 6,576,467 B1 | 6/2003 | Stemmer |
| 6,579,678 B1 | 6/2003 | Patten et al. |
| 6,586,182 B1 | 7/2003 | Patten et al. |
| 6,602,986 B1 | 8/2003 | Stemmer et al. |
| 6,613,514 B2 | 9/2003 | Patten et al. |
| 6,653,072 B1 | 11/2003 | Patten et al. |
| 6,716,631 B1 | 4/2004 | delCardayre et al. |
| 6,833,447 B1 | 12/2004 | Goldman et al. |
| 6,946,296 B2 | 9/2005 | Patten et al. |
| 6,946,458 B2 | 9/2005 | Turos |
| 6,961,664 B2 | 11/2005 | Selifonov et al. |
| 6,995,017 B1 | 2/2006 | Stemmer |
| 7,024,312 B1 | 4/2006 | Selifonov et al. |
| 7,058,515 B1 | 6/2006 | Selifonov et al. |
| 7,105,297 B2 | 9/2006 | Minshull et al. |
| 7,148,054 B2 | 12/2006 | delCardayre et al. |
| 7,288,375 B2 | 10/2007 | Stemmer et al. |
| 7,421,347 B2 | 9/2008 | Selifonov et al. |
| 7,430,477 B2 | 9/2008 | Selifonov et al. |
| 7,534,564 B2 | 5/2009 | Patten et al. |
| 7,620,500 B2 | 11/2009 | Mundorff et al. |
| 7,620,502 B2 | 11/2009 | Selifonov et al. |
| 7,629,170 B2 | 12/2009 | delCardayre et al. |
| 7,702,464 B1 | 4/2010 | Emig et al. |
| 7,747,391 B2 | 6/2010 | Gustafsson et al. |
| 7,747,393 B2 | 6/2010 | Fox |
| 7,751,986 B2 | 7/2010 | Gustafsson et al. |
| 7,776,598 B2 | 8/2010 | Patten et al. |
| 7,783,428 B2 | 8/2010 | Gustafsson et al. |
| 7,795,030 B2 | 9/2010 | Minshull et al. |
| 7,853,410 B2 | 12/2010 | Selifonov et al. |
| 7,868,138 B2 | 1/2011 | Stemmer et al. |
| 7,873,499 B2 | 1/2011 | Selifonov et al. |
| 7,904,249 B2 | 3/2011 | Selifonov et al. |
| 7,957,912 B2 | 6/2011 | Selifonov et al. |
| 8,383,346 B2 | 2/2013 | Colbeck et al. |
| 8,504,498 B2 | 8/2013 | Fox |
| 8,762,066 B2 | 6/2014 | Fox |
| 8,768,871 B2 | 7/2014 | Fox |
| 8,849,575 B2 | 9/2014 | Gustafsson et al. |
| 9,193,957 B2 | 11/2015 | Chen et al. |
| 11,046,936 B2 * | 6/2021 | Borra-Garske ...... C12N 9/0028 |
| 2006/0195947 A1 | 8/2006 | Davis et al. |
| 2008/0220990 A1 | 9/2008 | Fox |
| 2009/0312196 A1 | 12/2009 | Colbeck et al. |
| 2011/0262977 A1 | 10/2011 | Nagasawa et al. |
| 2015/0134315 A1 | 5/2015 | Sarmiento et al. |

FOREIGN PATENT DOCUMENTS

| | | |
|---|---|---|
| WO | 95/33836 A1 | 12/1995 |
| WO | 96/00787 A1 | 1/1996 |
| WO | 97/0078 A1 | 1/1997 |
| WO | 97/35966 A1 | 10/1997 |
| WO | 98/27230 A1 | 6/1998 |
| WO | 2000/42651 A1 | 7/2000 |
| WO | 2001/75767 A2 | 10/2001 |
| WO | 2009/008908 A2 | 1/2009 |
| WO | 2009/102899 A1 | 8/2009 |
| WO | 2009/102901 A1 | 8/2009 |
| WO | 2009/152336 A1 | 12/2009 |
| WO | 2011/035105 A1 | 3/2011 |
| WO | 2013/003290 A1 | 1/2013 |
| WO | 2013/110643 A1 | 8/2013 |
| WO | 2013/138339 A1 | 9/2013 |
| WO | 2014/120819 A1 | 8/2014 |
| WO | 2014/120821 A1 | 8/2014 |
| WO | 2015/048573 A1 | 4/2015 |
| WO | 2015/073555 A1 | 5/2015 |
| WO | 2016/085916 A1 | 6/2016 |

OTHER PUBLICATIONS

Wada, K., et al., "Codon usage tabulated from the GenBank genetic sequence data," Nucl. Acids Res., 20:2111-2118 [1992].

Wells, J.A., et al., "Cassette mutagenesis: an efficient method for generation of multiple mutations at defined sites," Gene, 34:315-323 (1985).

Wetmur, J. G., "DNA Probes: Applications of the Principles of Nucleic Acid Hybridization," Crit Rev Biochem Mol Biol, 26(3/4):227-259 (1991).

Wright, F., "The 'effective number of codons' used in a gene," Gene 87:23-29 [1990].

Yaegaki, K., et al., "Improved high-performance liquid chromatography method for quantitation of proline and hydroxyproline in biological materials," J Chromatogr., 356(1):163-70 [1986].

Yi, S., et al., "Covalent immobilization of omega-transaminase from Vibrio fluvialis JS17 on chitosan beads," Process Biochemistry 42(5): 895-898 (2007).

Zhang, J-H., et al., "Directed evolution of a fucosidase from a galactosidase by DNA shuffling and screening ,"Proc. Nat. Acad. Sci., U.S.A., 94:4504-4509 (1997).

Zhao, H., et al., "Molecular evolution by staggered extension process (StEP) in vitro recombination," Nat. Biotechnol., 16:258-261 (1998).

Gand, M., et al., "A NADH-accepting imine reductase variant: Immobilization and cofactor regeneration by oxidative deamination," Journal of Biotechnology, 230:11-18 [2016].

UniParc Database Accession No. UPI00056332DC dated Dec. 26, 2014.

Altschul, S., et al., "Basic local alignment search tool," J. Mol. Biol., 215: 403-410 (1990).

Altschul, S.F., et al., "Gapped BLAST and PSI-BLAST: a new generation of protein database search programs," Nucleic Acids Res., 25(17):3389-3402 (1997).

Baldino, Jr., F., et al., "High-Resolution in Situ Hybridization Histochemistry," Methods Enzymology, 168:761-777 (1989).

Batzer, M.A., "Erratum: Structure and variability of recently inserted Alu family members", Nucleic Acids Res 19:698-699 [1991].

Beaucage, S.L., et al., "Deoxynucleoside phosphoamidites—A new class of key intermediates for deoxypolynucleotide synthesis," Tetrahedron Letters, 22(20):1859-62 (1981).

Black, M.E., et al., "Creation of drug-specific herpes simplex virus type 1 thymidine kinase mutants for gene therapy," Proc Natl Acad Sci USA, 93:3525-3529 (1996).

Bolton, E.T., et al., "A General Method for the lisolation of RNA Complementary to DNA," Proc. Natl. Acad. Sci. USA 48:1390 (1962).

Botstein, D., et al., "Strategies and applications of in vitro mutagenesis," Science, 229(4719):1193-1201 [1985].

Breslauer, K.J., et al., "Predicting DNA duplex stability from the base sequence," Proc. Natl. Acad. Sci. USA, 83:3746-3750 (1986).

Caldwell, R.C., et al., "Mutagenic PCR," PCR Methods Appl., 3:S136-S140 (1994).

Carter, P., "Site-directed mutagenesis," Biochem. J., 237:1-7 (1986).

Christians, F.C., et al., "Directed evolution of thymidine kinase for AZT phosphorylation using DNA family shuffling," Nat. Biotechnol., 17:259-264 (1999).

Crameri, A., et al., "DNA shuffling of a family of genes from diverse species accelerates directed evolution", Nature, 391:288-291 (1998).

Crameri, A., et al., "Improved green fluorescent protein by molecular evolution using DNA shuffling," Nat. Biotechnol., 14(3):315-319 (1996).

(56) References Cited

OTHER PUBLICATIONS

Crameri, A., et al., "Molecular evolution of an arsenate detoxification pathway by DNA shuffling," Nat. Biotechnol., 15(5):436-438 (1997).
Dale, S.J., et al., "Oligonucleotide-directed random mutagenesis using the phosphorothioate method," Methods Mol. Biol., 57:369-74 (1996).
De Boer, H.A., et al., "The tac promoter: A functional hybrid derived from the trp and lac promoters," Proc. Natl Acad. Sci. USA, 80: 21-25 (1983).
Fasman, G.D.,CRC Practical Handbook of Biochemistry and Molecular Biology, CRC Press, Boca Raton, FL, pp. 3-70 [1989].
Freier, S.M., et al., "Improved free-energy parameters for predictions of RNA duplex stability," Proc. Natl. Acad. Sci USA, 83:9373-9377 (1986).
Gand, M., et al., "Characterization of three novel enzymes with imine reductase activity," J. Mol. Catal. B: Enzym., 110:126-132 [2014].
Greening, C., et al., "Mycobacterial F420H2-Dependent Reductases Promiscuously Reduce Diverse Compounds through a Common Mechanism," Frontiers in Microbiology, 8:1-10 [2017].
Guo, Z., et al., "3'-End-Forming Signals of Yeast mRNA," Mol. Cell. Biol., 15(11):5983-5990 [1995].
Henaut and Danchin in Neidhardt et al. [eds.], *Escherichia coli* and *Salmonella*, "Analysis and predictions from *Escherichia coli* Sequences, or *E. coli* in silico," ASM Press, Washington D.C., [1987], pp. 2047-2066.
Henikoff, S., et al., "Amino acid substitution matrices from protein blocks," Proc. Natl. Acad. Sci., 89:10915-10919 (1992).
Huber, T., et al., "Direct Reductive Amination of Ketones: Structure and Activity of S-Selective Imine Reductases from *Streptomyces*," Chem. Cat. Chem., 6(8):2248-2252 [2014].
Kierzek, R., et al., "Polymer-Supported RNA Synthesis and Its Application To Test the Nearest-Neighbor Model for Duplex Stability," Biochemistry, 25:7840-7846 (1986).
Koszelewski, D., et al., "Immobilization of omega-transaminases by encapsulation in a sol-gel/celite matrix," Journal of Molecular Catalysis B: Enzymatic, 63: 39-44 (2010).
Kramer, B., et al., "Different base/base mismatches are corrected with different efficiencies by the methyl-directed DNA mismatch-repair system of *E. coli*," Cell, 38(3):879-887 [1984].
Lee, S.D., et al., "*Pseudonocardia spinosispora* sp. nov., isolated from Korean soil," International J. Systematic Evol. Microbiol., 52: 1603-1608 [2002].
Ling, M., et al., "Approaches to DNA Mutagenesis:An Overview," Anal. Biochem., 254:157-78 (1997).
Martin, A.R., et al., "Characterization of free and immobilized (S)-aminotransferase for acetophenone production," Applied Microbiology and Biotechnology, 76(4): 843-851 (2007).
Mateo, C., et al., "Epoxy sepabeads: a novel epoxy support for stabilization of industrial enzymes via very intense multipoint covalent attachment," Biotechnology Progress 18(3):629-34 (2002).
Matthes, H.W.D., et al., "Simultaneous rapid chemical synthesis of over one hundred oligonucleotides on a microscale," EMBO J., 3(4):801-05 (1984).
Mcinerney, J.O., "GCUA: general codon usage analysis," Bioinformatics, 14(4):372-73 [1998].
Miller, S.P., et al., "Practical and Cost-Effective Manufacturing Route for the Synthesis of a B-Lactamase Inhibitor," Organic Letters, 16:174-177 [2014].
Minshull, J., et al., "Protein evolution by molecular breeding," Curr. Op. Chem. Biol., 3(3):284-290 (1999).
Mitsukura, K., et al., "Purification and Characterization of a Novel (R)-Imine Reductase from *Streptomyces* sp. GF3587," Biosci. Biotech. Biochem., 75(9):1778-1782 [2011].
Nakamura, Y., et al., "Codon usage tabulated from international DNA sequence databases: status for the year 2000," Nucl. Acids Res., 28:292 [2000].
Needleman, S., et al., "A general method applicable to the search for similarities in the amino acid sequence of two proteins," J. Mol. Biol. 48:443-453 (1970).
Pearson, W.R., "Improved tools for biological sequence comparison," Proc. Nat'l. Acad. Sci. USA, 85:2444-2448 (1988).
Romanos, M.A., et al., "Foreign gene expression in yeast: a review," Yeast 8:423-488 [1992].
Rychlik, W., et al., "Optimization of the annealing temperature for DNA amplification in vitro," Nucleic Acids Res, 18(21):6409-6412 (1990).
Simonen, M., et al., "Protein Secretion in *Bacillus* Species," Microbiological Reviews, 57:109-137 (1993).
Smith, M., "In vitro mutagenesis," Ann. Rev. Genet., 19:423-462 (1985).
Smith, T., et al., "Comparison of Biosequences," Adv. Appl. Math, 2:482-489 (1981).
Stellwagon, E., "Dye Affinity Chromatography," Current Protocols in Protein Science, Unit 9.2-9.2.16 [2001].
Stemmer, W., "DNA Shuffling by Random Fragmentation and Reassembly: In vitro Recombination for Molecular Evolution," Proc. Natl. Acad. Sci. USA, 91:10747-10751 (1994).
Stemmer, W.P.C., "Rapid evolution of a protein in vitro by DNA shuffling", Nature, 370:389-391 (1994).
Stenico, M., et al., "Codon usage in Caenorhabditis elegans: delineation of translational selection and mutational biases," Nucl. Acids Res. 22(13):2437-46 [1994].
Suggs, S.V., et al., "Use of synthetic oligodeoxyribonucleotides for the isolation of specific cloned DNA sequences," In Developmental Biology Using Purified Genes (Brown et al., eds.), pp. 683-693, Academic Press (1981).

\* cited by examiner

SEQUENCE LISTING

```
<160> NUMBER OF SEQ ID NOS: 270

<210> SEQ ID NO 1
<211> LENGTH: 879
<212> TYPE: DNA
<213> ORGANISM: Artificial Sequence
<220> FEATURE:
<223> OTHER INFORMATION: Imine reductase from Pseudonocardia
      spinosispora

<400> SEQUENCE: 1
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcaggag ccacctacct ggatggtgtg      360
attctgacca ttccaagcgg cattggcacc ccagaagcta ccattctgta ttcgggaccg     420
```

```
cgcagtacct tcgatgaaca tgaaagcgca ctgcgcgcat taggtccggg ggcgaccttt    480
gtaggggaag atcacggact ggctgcactg tatgatgcag caatgctgag cgtcatgtgg    540
ggcctgctga atggtttcct gcatggaacc gcactgctgg gaaccgcggg cgtttcggca    600
acctctgtgg ttccgatgct gggtcaaggt atcgaagcgg tgaccggttg gattgcgcgc    660
tacgcagatc agattgatgc cggtgtctat ccagcagacg acgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 2
<211> LENGTH: 292
<212> TYPE: PRT
<213> ORGANISM: Artificial Sequence
<220> FEATURE:
<223> OTHER INFORMATION: Imine reductase from Pseudonocardia
      spinosispora

<400> SEQUENCE: 2

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Thr Gly Trp Ile Ala Arg Tyr Ala Asp Gln
    210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270
```

Ala Glu Gly Arg Gly Gly Asp Ser Tyr Ala Ala Leu Ile Glu Gln Phe
            275                 280                 285

Arg Lys Ser Ala
    290

<210> SEQ ID NO 3
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 3

```
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgggta ttccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctgcactg tatgatgcag caatgctgag cgtcatgtgg     540
ggcctgctga atggtttcct gcatggaacc gcactgctgg aaccgcgggg cgtttcggca     600
acctctgtgg ttccgatgct gggtcaaggt atcgaagcgg tgaccggttg gattgcgcgc     660
tacgcagatc agattgatgc cggtgtctat ccagcagacg acgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                           879
```

<210> SEQ ID NO 4
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 4

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

```
Gly Ala Thr Tyr Leu Asp Gly Val Ile Leu Gly Ile Pro Ser Gly Ile
            115                 120                 125

Gly Thr Pro Glu Ala Thr Ile Leu Tyr Ser Gly Pro Arg Ser Thr Phe
        130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 5
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 5
atgagtgatt cccccgtacc tgtgactgtt ctgggtcttg gtctgatggg tcaggcctta     60
gcgggagcgt ttctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacca ttccaagcgg cattggcacc ccacatgcta ccattctgta ttcgggaccg    420
cgcagtacct tcgatgaaca tgaaagcgca ctgcgcgcat taggtccggg ggcgaccttt    480
gtaggggaag atcacggact ggctgcactg tatgatgcag caatgctgag cgtcatgtgg    540
ggcctgctga atggtttcct gcatggaacc gcactgctgg aaccgcgggg cgtttcggca    600
acctctgtgg ttccgatgct gggtcaaggt atcgaagcgg tgaccggttg gattgcgcgc    660
tacgcagatc agattgatgc cggtgtctat ccagcagacg acgccacgat tgataccag    720 cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879

<210> SEQ ID NO 6
```

<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 6

```
Met Ser Asp Ser Pro Val Pro Val Thr Val Leu Gly Leu Gly Leu Met
1               5                   10                  15
Gly Gln Ala Leu Ala Gly Ala Phe Leu Ala Ala Gly His Pro Thr Thr
            20                  25                  30
Val Trp Asn Arg Ser Ala Ala Lys Ala Asp Glu Leu Val Gly Arg Gly
        35                  40                  45
Ala Thr Leu Ala Ala Ser Pro Ala Ala Val Ala Ala Gly Ser Leu
    50                  55                  60
Ile Val Val Cys Val Thr Asp His Arg Ala Val Arg Glu Leu Leu Glu
65                  70                  75                  80
Pro Leu Gly Asp Ala Leu Pro Gly Arg Val Leu Val Asn Leu Thr Ser
                85                  90                  95
Gly Thr Ser Arg Glu Ala Arg Glu Asn Ala Glu His Thr Ala Ala Gln
            100                 105                 110
Gly Ala Thr Tyr Leu Asp Gly Val Ile Leu Thr Ile Pro Ser Gly Ile
        115                 120                 125
Gly Thr Pro His Ala Thr Ile Leu Tyr Ser Gly Pro Arg Ser Thr Phe
    130                 135                 140
Asp Glu His Glu Ser Ala Leu Arg Ala Leu Gly Pro Gly Ala Thr Phe
145                 150                 155                 160
Val Gly Glu Asp His Gly Leu Ala Ala Leu Tyr Asp Ala Ala Met Leu
                165                 170                 175
Ser Val Met Trp Gly Leu Leu Asn Gly Phe Leu His Gly Thr Ala Leu
            180                 185                 190
Leu Gly Thr Ala Gly Val Ser Ala Thr Ser Val Val Pro Met Leu Gly
        195                 200                 205
Gln Gly Ile Glu Ala Val Thr Gly Trp Ile Ala Arg Tyr Ala Asp Gln
    210                 215                 220
Ile Asp Ala Gly Val Tyr Pro Ala Asp Asp Ala Thr Ile Asp Thr Gln
225                 230                 235                 240
Arg Ala Ala Met Gln His Leu Val Glu Glu Ser Arg Ala Ala Gly Ile
                245                 250                 255
Asn Gly Glu Leu Pro Ala Phe Val Thr Lys Leu Ala Asp Arg Ala Val
            260                 265                 270
Ala Glu Gly Arg Gly Gly Asp Ser Tyr Ala Ala Leu Ile Glu Gln Phe
        275                 280                 285
Arg Lys Ser Ala
    290
```

<210> SEQ ID NO 7
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 7

```
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
```

```
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgaccg caccaagcgg cattggcacc ccagaagcta ccattctgta ttcgggaccg    420
cgcagtacct tcgatgaaca tgaaagcgca ctgcgcgcat taggtccggg ggcgaccttt    480 gtagggaag atcacggact ggctgcactg tatgatgcag caatgctgag catcatgtgg    540
ggcctgctga atggtttcct gcatggaacc gcactgctgg aaccgcgggg cgtttcggca    600
acctctgtgg ttccgatgct gggtcaaggt atcgaagcgg tgaccggttg gattgcgcgc    660
tacgcagatc agattgatgc cggtgtctat ccagcagacg acgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 8
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 8

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ala Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Ile Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Thr Gly Trp Ile Ala Arg Tyr Ala Asp Gln
    210                 215                 220
```

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
            245                 250                 255

Asn Gly Glu Leu Pro Ala Phe Val Thr Lys Leu Ala Asp Arg Ala Val
        260                 265                 270

Ala Glu Gly Arg Gly Gly Asp Ser Tyr Ala Ala Leu Ile Glu Gln Phe
    275                 280                 285

Arg Lys Ser Ala
    290

<210> SEQ ID NO 9
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 9
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgaccg gtccaagcgg cattggcacc ccagaagcta ccattctgta ttcgggaccg     420
cgcagtacct tcgatgaaca tgaaagcgca ctgcgcgcat taggtccggg ggcgaccttt     480
gtagggaag atcacggact ggctgcactg tatgatgcag caatgctgag cgtcatgtgg     540
ggcctgctga atggtttcct gcatggaacc gcactgctgg aaccgcgggg cgtttcggca     600
acctctgtgg ttccgatgct gggtcaaggt atcgaagcgg tgaccggttg gattgcgcgc     660
tacgcagatc agattgatgc cggtgtctat ccagcagacg acgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                            879

<210> SEQ ID NO 10
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 10

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

```
Ile Val Val Cys Val Thr Asp His Arg Ala Val Arg Glu Leu Leu Glu
 65                  70                  75                  80

Pro Leu Gly Asp Ala Leu Pro Gly Arg Val Leu Val Asn Leu Thr Ser
                 85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Gly Pro Ser Gly Ile
        115                 120                 125

Gly Thr Pro Glu Ala Thr Ile Leu Tyr Ser Gly Pro Arg Ser Thr Phe
130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Thr Gly Trp Ile Ala Arg Tyr Ala Asp Gln
210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 11
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 11
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctgcactg tatgatcatg caatgctgag cgtcatgtgg     540
ggcctgctga atggtttcct gcatggaacc gcactgctgg gaccgcgggg cgtttcggca     600
acctctgtgg ttccgatgct gggtcaaggt atcgaagcgg tgaccggttg gattgcgcgc     660
```

```
tacgcagatc agattgatgc cggtgtctat ccagcagacg acgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 12
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 12

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp His Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Thr Gly Trp Ile Ala Arg Tyr Ala Asp Gln
    210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

<210> SEQ ID NO 13
<211> LENGTH: 879

```
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 13
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat taggtccggg ggcgaccttt     480 gtagggaag atcacggact ggctaatctg tatgatgcag caatgctgag cgtcatgtgg      540
ggcctgctga atggtttcct gcatggaacc gcactgctgg aaccgcgggg cgtttcggca     600
acctctgtgg ttccgatgct gggtcaaggt atcgaagcgg tgaccggttg gattgcgcgc     660
tacgcagatc agattgatgc cggtgtctat ccagcagacg acgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                           879

<210> SEQ ID NO 14
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 14
```

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Leu
            165                 170                 175

Ser Val Met Trp Gly Leu Leu Asn Gly Phe Leu His Gly Thr Ala Leu
        180                 185                 190

Leu Gly Thr Ala Gly Val Ser Ala Thr Ser Val Val Pro Met Leu Gly
    195                 200                 205

Gln Gly Ile Glu Ala Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 15
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 15
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctgcactg tatgatgcag caatgctgag cgtcatgtgg     540
ggcctgctga atggtttcct gcatggaacc gcactgctgg aaccgcgggt gtttcggca     600
acctctgtgg ttccgatgct gggtcaaggt atcgaagcgg tgaccggttg gattgcgcgc     660
tacgcagatc agattgatgc cggtgtctat ccagcagact tggccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                            879

<210> SEQ ID NO 16
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 16

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
                35                  40                  45

Ala Thr Leu Ala Ala Ser Pro Ala Ala Val Ala Ala Gly Ser Leu
50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
                100                 105                 110

Gly Ala Thr Tyr Leu Asp Gly Val Ile Leu Thr Ile Pro Ser Gly Ile
            115                 120                 125

Gly Thr Pro Glu Ala Thr Ile Leu Tyr Ser Gly Pro Arg Ser Thr Phe
            130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
                180                 185                 190

Leu Gly Thr Ala Gly Val Ser Ala Thr Ser Val Val Pro Met Leu Gly
            195                 200                 205

Gln Gly Ile Glu Ala Val Thr Gly Trp Ile Ala Arg Tyr Ala Asp Gln
            210                 215                 220

Ile Asp Ala Gly Val Tyr Pro Ala Asp Leu Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
                260                 265                 270

Ala Glu Gly Arg Gly Gly Asp Ser Tyr Ala Ala Leu Ile Glu Gln Phe
            275                 280                 285

Arg Lys Ser Ala
        290
```

<210> SEQ ID NO 17
<211> LENGTH: 879
<212> TYPE: DNA
<213> ORGANISM: Artificial Sequence
<220> FEATURE:
<223> OTHER INFORMATION: Imine reductase variant from Pseudonocardia spinosispora

<400> SEQUENCE: 17

```
atgagtgatt cccccgtacc tgtgactgtt ctgggtcttg gtctgatggg tcaggcctta      60
gcgggagcgt tctggcagc cggtcaccct acgacggttt ggaatcgcag cgcagctaaa     120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
```

```
attctgacca ttccaagcgg cattggcacc ccagaagcta ccattctgta ttcgggaccg    420
cgcagtacct tcgatgaaca tgaaagcgca ctgcgcgcat taggtccggg ggcgaccttt    480 gtagggaag atcacggact ggctgcactg tgggatgcag caatgctgag cgtcatgtgg     540
ggcctgctga atggtttcct gcatggaacc gcactgctgg gaaccgcggg cgtttcggca    600
acctctgtgg ttcgatgct gggtcaaggt atcgaagcgg tgaccggttg gattgcgcgc     660
tacgcagatc agattgatgc cggtgtctat ccagcagacg acgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcaa aggtcgtgg tggtgactct     840 tacgctgcac tgattgaaca gtttcgcaag tcagcttaa                           879
```

<210> SEQ ID NO 18
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 18

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Trp Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Pro Met Leu Gly
        195                 200                 205

Gln Gly Ile Glu Ala Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
```

```
                    260                 265                 270
Ala Glu Gly Arg Gly Gly Asp Ser Tyr Ala Ala Leu Ile Glu Gln Phe
            275                 280                 285

Arg Lys Ser Ala
        290
```

<210> SEQ ID NO 19
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 19

```
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctgcactg tatgatgcag caatgctgag catcatgtgg     540
ggcctgctga atggtttcct gcatggaacc gcactgctgg gaaccgcggg cgtttcggca     600
acctctgtgg ttccgatgct gggtcaaggt atcgaagcgg tgaccggttg gattgcgcgc     660
tacgcagatc agattgatgc cggtgtctat ccagcagacg acgccacgat tgatacccag     720
cgttatgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                           879
```

<210> SEQ ID NO 20
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 20

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
```

```
            100                 105                 110
Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Ile Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Thr Gly Trp Ile Ala Arg Tyr Ala Asp Gln
    210                 215                 220

Ile Asp Ala Gly Val Tyr Pro Ala Asp Ala Thr Ile Asp Thr Gln
225                 230                 235                 240

Arg Tyr Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 21
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 21
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat taggtccggg gcgacctttt     480 gtagggaag atcacggact ggctgcactg tatgatgcag caatgctgag cgtcatgtgg     540
ggcctgctga atggtttcct gcatggaacc gcactgctgg aaccgcgggg cgtttcggca     600
acctctgtgg ttccgatgct gggtcaaggt atcgaaacag tgaccggttg gattgcgcgc     660
tacgcagatc agattgatgc cggtgtctat ccagcagacg acgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtgcag aaggtcgtgg tggtgactct     840
tacgctgcac tgattgaaca gtttcgcaag tcagcttaa                           879
```

<210> SEQ ID NO 22
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 22

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Thr Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 23
<211> LENGTH: 879
<212> TYPE: DNA
<213> ORGANISM: Artificial Sequence
<220> FEATURE:
<223> OTHER INFORMATION: Imine reductase variant from Pseudonocardia spinosispora

<400> SEQUENCE: 23

```
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat taggtccggg ggcgaccttt     480 gtagggggaag atcacggact ggctgcactg tatgatgcag caatgctgag cgtcatgtgg     540
ggcctgctga atggtttcct gcatggaacc gcactgctgg aaccgcgggg cgtttcggca     600
acctctgtgg ttccgatgct gggtcaaggt atcgaagcgg tgaccggtct tattgcgcgc     660
tacgcagatc agattgatgc cggtgtctat ccagcagacg acgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                            879
```

<210> SEQ ID NO 24
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 24

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205
```

Gln Gly Ile Glu Ala Val Thr Gly Leu Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
            245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 25
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 25
atgagtgatt cccccgtacc tgtgactgtt ctgggtcttg gtctgatggg tcaggcctta    60
gcggagcgt ttctggcagc cggtcaccct acgacggttt ggaatcgcag cgcagctaaa   120
gctgatgaac tggttggtcg cggtgcaacc ctggccgcgt ctcccgcggc tgccgtcgca   180
gcgggtagtc tgatcgttgt ttgcgtcaca gatcatcgtg cggtgcgcga actgctggaa   240
ccacttggcg atgcactgcc aggtcgcgtt ctggtcaacc tgacgagcgg tacgtcgcgt   300
gaagcccgtg agaacgcaga acatactgcg gctcagggag ccacctacct ggatggtgtg   360
attctgacca ttccaagcgg cattggcacc ccagaagcta ccattctgta ttcgggaccg   420
cgcagtacct tcgatgaaca tgaaagcgca ctgcgcgcat taggtccggg ggcgacccttt   480
gtaggggaag atcacggact ggctgcactg tatgatgcag caatgctgag cgtcatgtgg   540
ggcctgctga atggtttcct gcatggaacc gcactgctgg gaaccgcggg cgtttcggca   600
acctctgtgg ttccgatgct gggtcaaggt atcgaaaggg tgaccggttg gattgcgcgc   660
tacgcagatc agattgatgc cggtgtctat ccagcagacg acgccacgat tgatacccag   720
cgtgctgcaa tgcagcaccct ggtcgaggag agccgtgcgg cgggcatcaa tggcgaactt   780
ccggcgtttg tgaccaaact ggccgatcgc gcagtggcag aaggtcgtgg tggtgactct   840
tacgctgcac tgattgaaca gtttcgcaag tcagcttaa                          879

<210> SEQ ID NO 26
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 26

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
 50                  55                  60

Ile Val Val Cys Val Thr Asp His Arg Ala Val Arg Glu Leu Leu Glu
 65                  70                  75                  80

Pro Leu Gly Asp Ala Leu Pro Gly Arg Val Leu Val Asn Leu Thr Ser
                 85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Arg Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 27
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 27
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccaagggcta ccattctgta ttcgggaccg     420
cgcagtacct tcgatgaaca tgaaagcgca ctgcgcgcat aggtccgggg gcgaccttt      480 gtaggggaag atcacggact ggctgcactg tatgatgcag caatgctgag cgtcatgtgg     540
ggcctgctga atggtttcct gcatggaacc gcactgctgg aaccgcgggg cgtttcggca     600

```
acctctgtgg ttccgatgct gggtcaaggt atcgaagcgg tgaccggttg gattgcgcgc    660
tacgcagatc agattgatgc cggtgtctat ccagcagacg acgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

```
<210> SEQ ID NO 28
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 28
```

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65              70                  75                  80

Pro Leu Gly Asp Ala Leu Pro Gly Arg Val Leu Val Asn Leu Thr Ser
            85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Arg Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Thr Gly Trp Ile Ala Arg Tyr Ala Asp Gln
    210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

<210> SEQ ID NO 29
<211> LENGTH: 879
<212> TYPE: DNA
<213> ORGANISM: Artificial Sequence
<220> FEATURE:
<223> OTHER INFORMATION: Imine reductase variant from Pseudonocardia
spinosispora

<400> SEQUENCE: 29

```
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgtc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctgcactg tatgatgcag caggtctgag cgtcatgtgg     540
ggcctgctga atggtttcct gcatggaacc gcactgctgg aaccgcgggg cgtttcggca     600
acctctgtgg ttccgatgct gggtcaaggt atcgaagcgg tgaccggttg gattgcgcgc     660
tacgcagatc agattgatgc cggtgtctat ccagcagacg acgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                            879
```

<210> SEQ ID NO 30
<211> LENGTH: 292
<212> TYPE: PRT
<213> ORGANISM: Artificial Sequence
<220> FEATURE:
<223> OTHER INFORMATION: Imine reductase variant from Pseudonocardia
spinosispora

<400> SEQUENCE: 30

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Ser Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140
```

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Gly Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Thr Gly Trp Ile Ala Arg Tyr Ala Asp Gln
    210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 31
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 31
atgagtgatt cccccgtacc tgtgactgtt ctgggtcttg gtctgatggg tcaggcctta        60
gcgggagcgt ttctggcagc cggtcaccct acgacggttt ggaatcgcag cgcagctaaa       120
gctgatgaac tggttggtcg cggtgcaacc ctggccgcgt ctcccgcggc tgccgtcgca       180
gcgggtagtc tgatcgttgt ttgcgtcaca gatcatcgtg cggtgcgcga actgctggaa       240
ccacttggcg atgcactgcc aggtcgcgtt ctggtcaacc tgacgagcgg tacgtcgcgt       300
gaagcccgtg agaacgcaga acatactgcg gctcagggag ccacctacct ggatggtgtg       360
attctgacca ttccaagcgg cattggcacc ccagaagcta ccattctgta ttcgggaccg       420
cgcagtacct tcgatgaaca tgaaagcgca ctgcgcgcat aggtccgggg gcgacctttt       480
gtaggggaag atcacggact ggctgcactg tatgatgcag caatgagtag cgtcatgtgg       540
ggcctgctga atggtttcct gcatggaacc gcactgctgg aaccgcgggg cgtttcggca       600
acctctgtgg ttccgatgct gggtcaaggt atcgaagcgg tgaccggttg gattgcgcgc       660
tacgcagatc agattgatgc cggtgtctat ccagcagacg acgccacgat tgatacccag       720
cgtgctgcaa tgcagcacct ggtcgaggag agccgtgcgg cgggcatcaa tggcgaactt       780
ccggcgtttg tgaccaaact ggccgatcgc gcagtggcag aaggtcgtgg tggtgactct       840
tacgctgcac tgattgaaca gtttcgcaag tcagcttaa                             879

<210> SEQ ID NO 32
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 32

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65              70                  75                      80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
                100                 105                 110

Gly Ala Thr Tyr Leu Asp Gly Val Ile Leu Thr Ile Pro Ser Gly Ile
            115                 120                 125

Gly Thr Pro Glu Ala Thr Ile Leu Tyr Ser Gly Pro Arg Ser Thr Phe
130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Ser
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
            195                 200                 205

Gln Gly Ile Glu Ala Val Thr Gly Trp Ile Ala Arg Tyr Ala Asp Gln
        210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 33
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 33
atgagtgatt cccccgtacc tgtgactgtt ctgggtcttg gtctgatggg tcaggcctta     60
gcgggagcgt ttctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240

```
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacca ttccaagcgg cattggcacc ccagaagcta ccattctgta ttcgggaccg    420
cgcagtacct tcgatgaaca tgaaagcgca ctgcgcgcat taggtccggg ggcgaccttt    480 gtagggaag atcacggact ggctgcactg tatgatgcag caggtctgag cgtcatgtgg    540
ggcctgctga atggtttcct gcatggaacc gcactgctgg gaaccgcggg cgtttcggca    600
acctctgtgg ttccgatgct gggtcaaggt atcgaagcgg tgaccggttg gattgcgcgc    660
tacgcagatc agattgatgc cggtgtctat ccagcagacg acgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                          879
```

<210> SEQ ID NO 34
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 34

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Gly Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Thr Gly Trp Ile Ala Arg Tyr Ala Asp Gln
    210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
```

```
                245                 250                 255
Asn Gly Glu Leu Pro Ala Phe Val Thr Lys Leu Ala Asp Arg Ala Val
        260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 35
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 35
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt tgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctgcactg tatgatgcag caatgctgag cgtcatgtgg     540
ggcctgctga atggtttcct gcatggaacc gcactgctgg gaaccgcggg cgtttcggca     600
acctctgtgg ttccgatgct gggtcaaggt atcgaagttg tgaccggttg gattgcgcgc     660
tacgcagatc agattgatgc cggtgtctat ccagcagacg acgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                           879

<210> SEQ ID NO 36
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 36

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Gly Ser Leu
        50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
```

```
                    85                  90                  95
Gly Thr Ser Arg Glu Ala Arg Glu Asn Ala Glu His Thr Ala Ala Gln
                100                 105                 110

Gly Ala Thr Tyr Leu Asp Gly Val Ile Leu Thr Ile Pro Ser Gly Ile
            115                 120                 125

Gly Thr Pro Glu Ala Thr Ile Leu Tyr Ser Gly Pro Arg Ser Thr Phe
        130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
                180                 185                 190

Leu Gly Thr Ala Gly Val Ser Ala Thr Ser Val Val Pro Met Leu Gly
            195                 200                 205

Gln Gly Ile Glu Val Val Thr Gly Trp Ile Ala Arg Tyr Ala Asp Gln
        210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
                260                 265                 270

Ala Glu Gly Arg Gly Gly Asp Ser Tyr Ala Ala Leu Ile Glu Gln Phe
            275                 280                 285

Arg Lys Ser Ala
        290

<210> SEQ ID NO 37
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 37
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcaggag ccacctacct ggatggtgtg      360
attctgacca ttccaagcgg cattggcacc ccagaagcta ccattctgta ttcgggaccg     420
cgcagtacct tcgatgaaca tgaaagcgca ctgcgcgcat taggtccggg ggcgaccttt     480 gtagggaag atcacggact ggctgcactg tatgatattg caatgctgag cgtcatgtgg      540
ggcctgctga atggtttcct gcatggaacc gcactgctgg aaccgcgggg cgtttcggca     600
acctctgtgg ttccgatgct gggtcaaggt atcgaagcgg tgaccggttg gattgcgcgc     660
tacgcagatc agattgatgc cggtgtctat ccagcagacg acgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
```
tacgctgcac tgattgaaca gtttcgcaag tcagcttaa                                   879

<210> SEQ ID NO 38
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 38

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ile Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 39
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 39

```
atgagtgatt ccccgtacc tgtgactgtt ctgggtcttg gtctgatggg tcaggcctta        60
gcgggagcgt ttctggcagc cggtcaccct acgacggttt ggaatcgcag cgcagctaaa       120
gctgatgaac tggttggtcg cggtgcaacc ctggccgcgt ctcccgcggc tgccgtcgca       180
gcgggtagtc tgatcgttgt ttgcgtcaca gatcatcgtg cggtgcgcga actgctggaa       240
ccacttggcg atgcactgcc aggtcgcgtt ctggtcaacc tgacgagcgg tacgtcgcgt       300
gaagcccgtg agaacgcaga acatactgcg gctcagggag ccacctacct ggatggtgtg       360
attgaaacca ttccaagcgg cattggcacc ccagaagcta ccattctgta ttcgggaccg       420
cgcagtacct tcgatgaaca tgaaagcgca ctgcgcgcat taggtccggg ggcgaccttt       480
gtaggggaag atcacggact ggctgcactg tatgatgcag caatgctgag cgtcatgtgg       540
ggcctgctga atggtttcct gcatggaacc gcactgctgg aaccgcgggg cgtttcggca       600
acctctgtgg ttccgatgct gggtcaaggt atcgaagcgg tgaccggttg gattgcgcgc       660
tacgcagatc agattgatgc cggtgtctat ccagcagacg acgccacgat tgatacccag       720
cgtgctgcaa tgcagcacct ggtcgaggag agccgtgcgg cgggcatcaa tggcgaactt       780
ccggcgtttg tgaccaaact ggccgatcgc gcagtggcag aaggtcgtgg tggtgactct       840
tacgctgcac tgattgaaca gtttcgcaag tcagcttaa                              879
```

<210> SEQ ID NO 40
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 40

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Glu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190
```

Leu Gly Thr Ala Gly Val Ser Ala Thr Ser Val Val Pro Met Leu Gly
        195                 200                 205

Gln Gly Ile Glu Ala Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 41
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 41
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat taggtccggg ggcgacccttt     480 gtaggggaag atcacggact ggctgcactg tatgatgcag caatgctgag cgtcatgtgg     540
ggcctgctga tggtttcct gcatggaacc gcactgctgg gaaccgcggg cgtttcggca     600
acctctgtgg ttccgatgct gggtcaaggt atcgaaccag tgaccggttg gattgcgcgc     660
tacgcagatc agattgatgc cggtgtctat ccagcagacg acgccacgat tgatacccag     720
cgtgctgcaa tgcagcacct ggtcgaggag agccgtgcgg cgggcatcaa tggcgaactt     780
ccggcgtttg tgaccaaaact ggccgatcgc gcagtggcag aaggtcgtgg tggtgactct     840
tacgctgcac tgattgaaca gtttcgcaag tcagcttaa                            879

<210> SEQ ID NO 42
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 42

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
         35                  40                  45

Ala Thr Leu Ala Ala Ser Pro Ala Ala Val Ala Ala Gly Ser Leu
     50                  55                  60

Ile Val Val Cys Val Thr Asp His Arg Ala Val Arg Glu Leu Leu Glu
 65                  70                  75                  80

Pro Leu Gly Asp Ala Leu Pro Gly Arg Val Leu Val Asn Leu Thr Ser
                     85                  90                  95

Gly Thr Ser Arg Glu Ala Arg Glu Asn Ala Glu His Thr Ala Ala Gln
                100                 105                 110

Gly Ala Thr Tyr Leu Asp Gly Val Ile Leu Thr Ile Pro Ser Gly Ile
            115                 120                 125

Gly Thr Pro Glu Ala Thr Ile Leu Tyr Ser Gly Pro Arg Ser Thr Phe
        130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Pro Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 43
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 43
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacca ttccaagcgg cattggcacc ccagaagcta ccattctgta ttcgggaccg    420
cgcagtacct tcgatgaaca tgaaagcgca ctgcgcgcat taggtccggg ggcgacccttt   480

```
gtaggggaag atcacggact ggctgcactg tatgatgcag caatgctgag cgtcatgtgg    540
ggcctgctga atggtttcct gcatggaacc gcactgctgg gaaccgcggg cgtttcggca    600
acctctgtgg ttccgatgct gggtcaaggt atcgaagcgg tgaccggtat tattgcgcgc    660
tacgcagatc agattgatgc cggtgtctat ccagcagacg acgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 44
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 44

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Thr Gly Ile Ile Ala Arg Tyr Ala Asp Gln
    210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285
```

Arg Lys Ser Ala
    290

<210> SEQ ID NO 45
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 45

| | | | | | |
|---|---|---|---|---|---|
| atgagtgatt | cccccgtacc | tgtgactgtt | ctgggtcttg | gtctgatggg | tcaggcctta | 60 |
| gcgggagcgt | ttctggcagc | cggtcaccct | acgacggttt | ggaatcgcag | cgcagctaaa | 120 |
| gctgatgaac | tggttggtcg | cggtgcaacc | ctggccgcgt | ctcccgcggc | tgccgtcgca | 180 |
| gcgggtagtc | tgatcgttgt | tgcgtcaca | gatcatcgtg | cggtgcgcga | actgctggaa | 240 |
| ccacttggcg | atgcactgcc | aggtcgcgtt | ctggtcaacc | tgacgagcgg | tacgtcgcgt | 300 |
| gaagcccgtg | agaacgcaga | acatactgcg | gctcaggag | ccacctacct | ggatggtgtg | 360 |
| attctgacca | ttccaagcgg | cattggcacc | cagaagcta | ccattctgta | ttcgggaccg | 420 |
| cgcagtacct | tcgatgaaca | tgaaagcgca | ctgcgcgcat | taggtccggg | ggcgaccttt | 480 |
| gtaggggaag | atcacggact | ggctagtctg | tatgatgcag | caatgctgag | cgtcatgtgg | 540 |
| ggcctgctga | atggtttcct | gcatggaacc | gcactgctgg | aaccgcggg | cgtttcggca | 600 |
| acctctgtgg | ttccgatgct | gggtcaaggt | atcgaagcgg | tgaccggttg | gattgcgcgc | 660 |
| tacgcagatc | agattgatgc | cggtgtctat | ccagcagacg | acgccacgat | tgatacccag | 720 |
| cgtgctgcaa | tgcagcacct | ggtcgaggag | agccgtgcgg | cgggcatcaa | tggcgaactt | 780 |
| ccggcgtttg | tgaccaaact | ggccgatcgc | gcagtggcga | aggtcgtgg | tggtgactct | 840 |
| tacgctgcac | tgattgaaca | gtttcgcaag | tcagcttaa | | | 879 |

<210> SEQ ID NO 46
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 46

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
            130                 135                 140

Asp Glu His Glu Ser Ala Leu Arg Ala Leu Gly Pro Gly Ala Thr Phe
145                 150                 155                 160

Val Gly Glu Asp His Gly Leu Ala Ser Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 47
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 47

```
atgagtgatt cccccgtacc tgtgactgtt ctgggtcttg gtctgatggg tcaggcctta     60
gcgggagcgt ttctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacca ttccaagcgg cattggcacc ccagaagcta ccattctgta ttcgggaccg    420
cgcagtacct tcgatgaaca tgaaagcgca ctgcgcgcat aggtccgggg gcgacctttt    480
gtaggggaag atcacggact ggctgcactg tatgatgcag cacatctgag cgtcatgtgg    540
ggcctgctga atggtttcct gcatggaacc gcactgctgg aaccgcgggg cgtttcggca    600
acctctgtgg ttccgatgct gggtcaaggt atcgaagcgg tgaccggttg gattgcgcgc    660
tacgcagatc agattgatgc cggtgtctat ccagcagacg acgccacgat tgataccag     720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 48
<211> LENGTH: 292
<212> TYPE: PRT
<213> ORGANISM: Artificial Sequence

```
<220> FEATURE:
<223> OTHER INFORMATION: Imine reductase variant from Pseudonocardia
      spinosispora

<400> SEQUENCE: 48

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala His Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 49
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 49
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
```

```
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacca ttccaagcgg cattggcacc ccagaagcta ccattctgta ttcgggaccg    420
cgcagtacct tcgatgaaca tgaaagcgca ctgcgcgcat taggtccggg ggcgaccttt    480
gtaggggaag atcacggact ggctgcactg tatgatgcag caatgctgag cgtcatgtgg    540
ggcctgctga atggtttcct gcatggaacc gcactgctgg gaaccgcggg cgtttcggca    600
acctctgtgg ttccgatgct gggtcaaggt atcgaagcgg tgaccggttg gattgcgcgc    660
tacgcagatc agattgatgc cggtgtctat ccagcagacg acaaaacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 50
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 50

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Thr Gly Trp Ile Ala Arg Tyr Ala Asp Gln
    210                 215                 220

Ile Asp Ala Gly Val Tyr Pro Ala Asp Asp Lys Thr Ile Asp Thr Gln
```

```
                225                 230                 235                 240
Arg Ala Ala Met Gln His Leu Val Glu Glu Ser Arg Ala Ala Gly Ile
                    245                 250                 255

Asn Gly Glu Leu Pro Ala Phe Val Thr Lys Leu Ala Asp Arg Ala Val
                    260                 265                 270

Ala Glu Gly Arg Gly Gly Asp Ser Tyr Ala Ala Leu Ile Glu Gln Phe
                    275                 280                 285

Arg Lys Ser Ala
    290

<210> SEQ ID NO 51
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 51
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccatg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctgcactg tatgatgcag caatgctgag cgtcatgtgg     540
ggcctgctga atggtttcct gcatggaacc gcactgctgg aaccgcgggc gtttcggca     600 acctctgtgg ttccgatgct gggtcaaggt atctgtgcgg tgaccggttg gattgcgcgc     660
tacgcagatc agattgatgc cggtgtctat ccagcagacg acgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                           879

<210> SEQ ID NO 52
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 52

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
                20                  25                  30

Val Trp Asn Arg Ser Ala Ala Lys Ala Asp Glu Leu Val Gly Arg Gly
            35                  40                  45

Ala Thr Leu Ala Ala Ser Pro Ala Ala Ala Val Ala Ala Gly Ser Leu
        50                  55                  60

Ile Val Val Cys Val Thr Asp His Arg Ala Val Arg Glu Leu Leu Glu
```

```
              65                  70                  75                  80
Pro Leu Gly Asp Ala Leu Pro Gly Arg Val Leu Val Asn Leu Thr Ser
                    85                  90                  95
Gly Thr Ser Arg Glu Ala His Glu Asn Ala Glu His Thr Ala Ala Gln
                100                 105                 110
Gly Ala Thr Tyr Leu Asp Gly Val Ile Leu Thr Ile Pro Ser Gly Ile
            115                 120                 125
Gly Thr Pro Glu Ala Thr Ile Leu Tyr Ser Gly Pro Arg Ser Thr Phe
        130                 135                 140
Asp Glu His Glu Ser Ala Leu Arg Ala Leu Gly Pro Gly Ala Thr Phe
145                 150                 155                 160
Val Gly Glu Asp His Gly Leu Ala Ala Leu Tyr Asp Ala Ala Met Leu
                165                 170                 175
Ser Val Met Trp Gly Leu Leu Asn Gly Phe Leu His Gly Thr Ala Leu
            180                 185                 190
Leu Gly Thr Ala Gly Val Ser Ala Thr Ser Val Val Pro Met Leu Gly
        195                 200                 205
Gln Gly Ile Cys Ala Val Thr Gly Trp Ile Ala Arg Tyr Ala Asp Gln
    210                 215                 220
Ile Asp Ala Gly Val Tyr Pro Ala Asp Asp Ala Thr Ile Asp Thr Gln
225                 230                 235                 240
Arg Ala Ala Met Gln His Leu Val Glu Glu Ser Arg Ala Ala Gly Ile
                245                 250                 255
Asn Gly Glu Leu Pro Ala Phe Val Thr Lys Leu Ala Asp Arg Ala Val
            260                 265                 270
Ala Glu Gly Arg Gly Gly Asp Ser Tyr Ala Ala Leu Ile Glu Gln Phe
        275                 280                 285
Arg Lys Ser Ala
    290

<210> SEQ ID NO 53
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 53
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacca ttccaagcgg cattggcacc ccagaagcta ccattctgta ttcgggaccg    420
cgcagtacct tcgatgaaca tgaaagcgca ctgcgcgcat taggtccggg ggcgacctttt   480 gtagggggaag atcacggact ggctgcactg tatgatgcag caatgctgag cgtcatgtgg    540
ggcctgctga atggttttcct gcatggaacc gcactgctgg aaccgcgggg cgtttcggca    600
acctctgtgg ttccgatgct gggtcaaggt atcgaagcgg tgttgggttg gattgcgcgc    660
tacgcagatc agattgatgc cggtgtctat ccagcagacg acgccacgat tgatacccag    720
```

-continued

```
cgtgctgcaa tgcagcacct ggtcgaggag agccgtgcgg cgggcatcaa tggcgaactt      780
ccggcgtttg tgaccaaact ggccgatcgc gcagtggcag aaggtcgtgg tggtgactct      840
tacgctgcac tgattgaaca gtttcgcaag tcagcttaa                             879
```

<210> SEQ ID NO 54
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 54

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Leu Gly Trp Ile Ala Arg Tyr Ala Asp Gln
    210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

<210> SEQ ID NO 55
<211> LENGTH: 879
<212> TYPE: DNA
<213> ORGANISM: Artificial Sequence
<220> FEATURE:
<223> OTHER INFORMATION: Imine reductase variant from Pseudonocardia spinosispora

<400> SEQUENCE: 55

```
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctgcactg tatgatgcag caatgctgag catgatgtgg     540
ggcctgctga atggtttcct gcatggaacc gcactgctgg gaaccgcggg cgtttcggca     600
acctctgtgg ttccgatgct gggtcaaggt atcgaagcgg tgaccggttg gattgcgcgc     660
tacgcagatc agattgatgc cggtgtctat ccagcagacg acgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                            879
```

<210> SEQ ID NO 56
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 56

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175
```

```
Ser Met Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 57
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 57
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat aggtccgggg gcgacctttg     480 taggggaag atcacggact ggctgcactg tatgatgcag caatgctgag cgtcatgtgg     540
ggcctgctga atggtttcct gcatggaacc gcactgctgg aaccgcgggg cgtttcggca     600
acctctgtgg ttccgatgct gggtcaaggt atctgtgcgg tgaccggttg gattgcgcgc     660
tacgcagatc agattgatgc cggtgtctat ccagcagacg acgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                            879

<210> SEQ ID NO 58
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 58

Met Ser Asp Ser Pro Val Pro Val Thr Val Leu Gly Leu Gly Leu Met
1               5                   10                  15
```

-continued

Gly Gln Ala Leu Ala Gly Ala Phe Leu Ala Ala Gly His Pro Thr Thr
        20                  25                  30

Val Trp Asn Arg Ser Ala Ala Lys Ala Asp Glu Leu Val Gly Arg Gly
            35                  40                  45

Ala Thr Leu Ala Ala Ser Pro Ala Ala Val Ala Gly Ser Leu
 50                  55                  60

Ile Val Val Cys Val Thr Asp His Arg Ala Val Arg Glu Leu Leu Glu
 65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
130                 135                 140

Asp Glu His Glu Ser Ala Leu Arg Ala Leu Gly Pro Gly Ala Thr Phe
145                 150                 155                 160

Val Gly Glu Asp His Gly Leu Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Cys Ala Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 59
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 59
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt tgcgtcaca gatcatcgtg cggtgcgcga actgctggaa      240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ggattctgta ttcgggaccg     420

```
cgcagtacct tcgatgaaca tgaaagcgca ctgcgcgcat taggtccggg ggcgaccttt      480 gtagggaag atcacggact ggctgcactg tatgatgcag caatgctgag cgtcatgtgg       540
ggcctgctga atggtttcct gcatggaacc gcactgctgg gaaccgcggg cgtttcggca     600
acctctgtgg ttccgatgct gggtcaaggt atcgaagcgg tgaccggttg gattgcgcgc    660
tacgcagatc agattgatgc cggtgtctat ccagcagacg acgccacgat tgatacccag    720
cgtgctgcaa tgcagcacct ggtcgaggag agccgtgcgg cgggcatcaa tggcgaactt   780
ccggcgtttg tgaccaaact ggccgatcgc gcagtggcag aaggtcgtgg tggtgactct    840
tacgctgcac tgattgaaca gtttcgcaag tcagcttaa                            879
```

<210> SEQ ID NO 60
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 60

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
                20                  25                  30

Val Trp Asn Arg Ser Ala Ala Lys Ala Asp Glu Leu Val Gly Arg Gly
            35                  40                  45

Ala Thr Leu Ala Ala Ser Pro Ala Ala Val Ala Gly Ser Leu
        50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
                100                 105                 110

Gly Ala Thr Tyr Leu Asp Gly Val Ile Leu Thr Ile Pro Ser Gly Ile
            115                 120                 125

Gly Thr Pro Glu Ala Arg Ile Leu Tyr Ser Gly Pro Arg Ser Thr Phe
        130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
                180                 185                 190

Leu Gly Thr Ala Gly Val Ser Ala Thr Ser Val Val Pro Met Leu Gly
            195                 200                 205

Gln Gly Ile Glu Ala Val Thr Gly Trp Ile Ala Arg Tyr Ala Asp Gln
        210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
                260                 265                 270
```

Ala Glu Gly Arg Gly Gly Asp Ser Tyr Ala Ala Leu Ile Glu Gln Phe
            275                 280                 285

Arg Lys Ser Ala
    290

<210> SEQ ID NO 61
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 61

```
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctgcactg tatgatgcag caatgctgag cgtcatgtgg     540
ggcctgctga atggtttcct gcatggaacc gcactgctgg aaccgcgggg cgtttcggca     600
acctctgtgg ttccgatgct gggtcaaggt atcgttgcgg tgaccggttg gattgcgcgc     660
tacgcagatc agattgatgc cggtgtctat ccagcagacg acgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                           879
```

<210> SEQ ID NO 62
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 62

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

```
Gly Ala Thr Tyr Leu Asp Gly Val Ile Leu Thr Ile Pro Ser Gly Ile
            115                 120                 125

Gly Thr Pro Glu Ala Thr Ile Leu Tyr Ser Gly Pro Arg Ser Thr Phe
        130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Val Ala Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 63
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 63
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct cgatgaaca tgaaagcgca ctgcgcgcat taggtccggg ggcgaccttt     480
gtaggggaag atcacggact ggctgcactg tatgatgcag caatgctgag cgtcatgtgg     540
ggcctgctga atggtttcct gcatggaacc gcactgctgg aaccgcgggt cgtttcggca     600
acctctgtgg ttccgatgct gggtcaaggt atcgaagcgg tgatgggttg gattgcgcgc     660
tacgcagatc agattgatgc cggtgtctat ccagcagacg acgccacgat tgatacccag     720
cgtgctgcaa tgcagcacct ggtcgaggag agccgtgcgc gggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                          879

<210> SEQ ID NO 64
```

<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 64

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Met Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

<210> SEQ ID NO 65
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 65

```
atgagtgatt cccccgtacc tgtgactgtt ctgggtcttg gtctgatggg tcaggcctta    60
```

```
gcgggagcgt tctggcagc cggtcaccct acgacggttt ggaatcgcag cgcagctaaa      120
gctgatgaac tggttggtcg cggtgcaacc ctggccgcgt ctcccgcggc tgccgtcgca      180
gcgggtagtc tgatcgttgt ttgcgtcaca gatcatcgtg cggtgcgcga actgctggaa      240
ccacttggcg atgcactgcc aggtcgcgtt ctggtcaacc tgacgagcgg tacgtcgcgt      300
gaagcccgtg agaacgcaga acatactgcg gctcagggag ccacctacct ggatggtgtg      360
attctgacca ttccaagcgg cattggcacc ccagaagcta ccattctgta ttcgggaccg      420
cgcagtacct tcgatgaaca tgaaagcgca ctgcgcgcat taggtccggg ggcgaccttt      480
gtaggggaag atcacggact ggctgcactg tatgatgcag caatgctgag cgtcatgtgg      540
ggcctgctga atggtttcct gcatggaacc gcactgctgg gaaccgcggg cgtttcggca      600
acctctgtgg ttccgatgct gggtcaaggt tgggaagcgg tgaccggttg gattgcgcgc      660
tacgcagatc agattgatgc cggtgtctat ccagcagacg acgccacgat tgatacccag      720
cgtgctgcaa tgcagcacct ggtcgaggag agccgtgcgg cgggcatcaa tggcgaactt      780
ccggcgtttg tgaccaaact ggccgatcgc gcagtggcag aaggtcgtgg tggtgactct      840
tacgctgcac tgattgaaca gtttcgcaag tcagcttaa                            879
```

<210> SEQ ID NO 66  
<211> LENGTH: 292  
<212> TYPE: PRT  
<213> ORGANISM: Artificial Sequence  
<220> FEATURE:  
<223> OTHER INFORMATION: Imine reductase variant from Pseudonocardia spinosispora

<400> SEQUENCE: 66

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Val Thr Gly Trp Ile Ala Arg Tyr Ala Asp Gln
```

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
            245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 67
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 67
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcgac tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat aggtccgggg gcgacctttg     480 taggggaag atcacggact ggctgcactg tatgatgcag caatgctgag cgtcatgtgg      540
ggcctgctga atggtttcct gcatggaacc gcactgctgg aaccgcgggg cgtttcggca     600
acctctgtgg ttccgatgct gggtcaaggt cttgaagcgg tgaccggttg gattgcgcgc     660
tacgcagatc agattgatgc cggtgtctat ccagcagacg acgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                            879

<210> SEQ ID NO 68
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 68

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Thr Ala Val Ala Ala Gly Ser Leu

```
            50                  55                  60
Ile Val Val Cys Val Thr Asp His Arg Ala Val Arg Glu Leu Leu Glu
 65                  70                  75                  80

Pro Leu Gly Asp Ala Leu Pro Gly Arg Val Leu Val Asn Leu Thr Ser
                 85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Leu Glu Ala Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 69
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 69
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat aggtccgggg gcgacctttg     480
gtaggggaag atcacggact ggctgcactg tatgatgcag caatgctgag cgtcatgtgg     540
ggcctgctga atggtttcct gcatggaacc gcactgctgg gaaccgcggg cgtttcggca     600
acctctgtgg ttccgatgct gggtcaaggt cttgaagcgg tgaccggttg gattgcgcgc     660
```

```
tacgcagatc agattgatgc cggtgtctat ccagcagacg acgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 70
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 70

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Leu Glu Ala Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

<210> SEQ ID NO 71

<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 71

```
atgagtgatt ccccgtacc tgtgactgtt ctgggtcttg gtctgatggg tcaggcctta      60
gcggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca    180
gcgggtagtc tgatcgttgt tgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg   360
attctgacca ttccaagcgg cattggcacc ccagaagcta ccattctgta ttcgggaccg   420
cgcagtacct tcgatgaaca tgaaagcgca ctgcgcgcat taggtccggg ggcgaccttt   480
gtaggggaag atcacggact ggctgcactg tatgatgcag caatgctgag cgtcatgtgg   540
ggcctgctga atggtttcct gcatggaacc gcactgctgg aaccgcgggg cgtttcggca    600
acctctgtgg ttccgatgct gggtcaaggt atcggtgcgg tgaccggttg gattgcgcgc   660
tacgcagatc agattgatgc cggtgtctat ccagcagacg acgccacgat tgatacccag   720
cgtgctgcaa tgcagcaccect ggtcgaggag agccgtgcgg cgggcatcaa tggcgaactt   780
ccggcgtttg tgaccaaact ggccgatcgc gcagtggcag aaggtcgtgg tggtgactct   840
tacgctgcac tgattgaaca gtttcgcaag tcagcttaa                           879
```

<210> SEQ ID NO 72
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 72

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160
```

Val Gly Glu Asp His Gly Leu Ala Ala Leu Tyr Asp Ala Ala Met Leu
            165                 170                 175

Ser Val Met Trp Gly Leu Leu Asn Gly Phe Leu His Gly Thr Ala Leu
        180                 185                 190

Leu Gly Thr Ala Gly Val Ser Ala Thr Ser Val Pro Met Leu Gly
    195                 200                 205

Gln Gly Ile Gly Ala Val Thr Gly Trp Ile Arg Tyr Ala Asp Gln
    210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 73
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 73
atgagtgatt cccccgtacc tgtgactgtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcaggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat taggtccggg ggcgaccttt     480 gtagggaag atcacggact ggctgcactg tatgatgcag caatgctgag cgtcatgtgg     540
ggcctgctga atggtttcct gcatggaacc gcactgctgg gaaccgcggg cgtttcggca     600
acctctgtgg ttccgatgct gggtcaaggt atcgaagcga tgaccggttg gattgcgcgc     660
tacgcagatc agattgatgc cggtgtctat ccagcagacg acgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                           879

<210> SEQ ID NO 74
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 74

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
                35                  40                  45

Ala Thr Leu Ala Ala Ser Pro Ala Ala Val Ala Ala Gly Ser Leu
        50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
                100                 105                 110

Gly Ala Thr Tyr Leu Asp Gly Val Ile Leu Thr Ile Pro Ser Gly Ile
            115                 120                 125

Gly Thr Pro Glu Ala Thr Ile Leu Tyr Ser Gly Pro Arg Ser Thr Phe
        130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
                180                 185                 190

Leu Gly Thr Ala Gly Val Ser Ala Thr Ser Val Val Pro Met Leu Gly
            195                 200                 205

Gln Gly Ile Glu Ala Met Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
                260                 265                 270

Ala Glu Gly Arg Gly Gly Asp Ser Tyr Ala Ala Leu Ile Glu Gln Phe
            275                 280                 285

Arg Lys Ser Ala
    290

<210> SEQ ID NO 75
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 75
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
```

```
gaagcccgtg agaacgcaga acatactgcg gctcaggag  ccacctacct ggatggtgtg     360
attctgggtg gcccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctaatctg gttgatcatg caatgctgag cgtcatgtgg     540
ggcctgctga atggtttcct gcatggaacc gcactgctgg gaaccgcggg cgtttcggca     600
acctctgtgg ttccgatgct gggtcaaggt atcgaagtgg tgaccggttg gattgcgcgc     660
tacgcagatc agattgatgc cggtgtctat ccagcagacg acaagacgat tgataccag     720 cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                            879
```

<210> SEQ ID NO 76
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 76

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Gly Gly Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Val Asp His Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Val Val Thr Gly Trp Ile Ala Arg Tyr Ala Asp Gln
    210                 215                 220

Ile Asp Ala Gly Val Tyr Pro Ala Asp Asp Lys Thr Ile Asp Thr Gln
225                 230                 235                 240

Arg Ala Ala Met Gln His Leu Val Glu Glu Ser Arg Ala Ala Gly Ile
                245                 250                 255
```

Asn Gly Glu Leu Pro Ala Phe Val Thr Lys Leu Ala Asp Arg Ala Val
              260                 265                 270

Ala Glu Gly Arg Gly Gly Asp Ser Tyr Ala Ala Leu Ile Glu Gln Phe
          275                 280                 285

Arg Lys Ser Ala
        290

<210> SEQ ID NO 77
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 77

| | | |
|---|---|---|
| atgagtgatt cacctgtgcc cgtgacagtt ctgggtcttg gtctgatggg tcaggcctta | 60 |
| gcgggagcgt ttctggcagc cggtcaccct acgacggttt ggaatcgcag cgcagctaaa | 120 |
| gctgatgaac tggttggtcg cggtgcaacc ctggccgcgt ctcccgcggc tgccgtcgca | 180 |
| gcgggtagtc tgatcgttgt ttgcgtcaca gatcatcgtg cggtgcgcga actgctggaa | 240 |
| ccacttggcg atgcactgcc aggtcgcgtt ctggtcaacc tgacgagcgg tacgtcgcgt | 300 |
| gaagcccgtg agaacgcaga acatactgcg gctcagggag ccacctacct ggatggtgtg | 360 |
| attctgacgg gccaagcgg cattggcacc ccagaagcta ccattctgta ttcgggaccg | 420 |
| cgcagtacct tcgatgaaca tgaaagcgca ctgcgcgcat aggtccgggg gcgacctttt | 480 |
| gtaggggaag atcacggact ggctaatctg tacgatattg caatgctgag cgtcatgtgg | 540 |
| ggcctgctga atggtttcct gcatggaacc gcactgctgg gaaccgcggg cgtttcggca | 600 |
| acctctgtgg ttccgatgct gggtcaaggt atcggagtgg tgaccggttg gattgcgcgc | 660 |
| tacgcagatc agattgatgc cggtgtctat ccagcagacg acgcgacgat tgatacccag | 720 |
| cgtgctgcaa tgcagcacct ggtcgaggag agccgtgcgg cgggcatcaa tggcgaactt | 780 |
| ccggcgtttg tgaccaaaact ggccgatcgc gcagtggcag aaggtcgtgg tggtgactct | 840 |
| tacgctgcac tgattgaaca gtttcgcaag tcagcttaa | 879 |

<210> SEQ ID NO 78
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 78

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Gly Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ile Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Gly Val Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 79
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 79

```
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacgg gcccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctaatctg tacgatgccg caggcctgag cgtcatgtgg     540
ggcctgctga atggtttcct gcatggaacc gcactgctgg aaccgcgggc gtttcggca     600 acctctgtgg ttccgatgct gggtcaaggt atctgcgtgg tgaccggttg gattgcgcgc     660
tacgcagatc agattgatgc cggtgtctat ccagcagacg acaagacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tgtgactct     840 tacgctgcac tgattgaaca gtttcgcaag tcagcttaa                           879
```

<210> SEQ ID NO 80
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 80

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Gly Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Gly Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Cys Val Val Thr Gly Trp Ile Ala Arg Tyr Ala Asp Gln
    210                 215                 220

Ile Asp Ala Gly Val Tyr Pro Ala Asp Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 81
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 81

-continued

```
atgagtgatt cacctgtgcc cgtgacagtt ctgggtcttg gtctgatggg tcaggcctta    60
gcgggagcgt ttctggcagc cggtcaccct acgacggttt ggaatcgcag cgcagctaaa   120
gctgatgaac tggttggtcg cggtgcaacc ctggccgcgt ctcccgcggc tgccgtcgca   180
gcgggtagtc tgatcgttgt ttgcgtcaca gatcatcgtg cggtgcgcga actgctggaa   240
ccacttggcg atgcactgcc aggtcgcgtt ctggtcaacc tgacgagcgg tacgtcgcgt   300
gaagcccgtg agaacgcaga acatactgcg gctcagggag ccacctacct ggatggtgtg   360
attctgacga ttccaagcgg cattggcacc ccagaagcta ccattctgta ttcgggaccg   420
cgcagtacct tcgatgaaca tgaaagcgca ctgcgcgcat taggtccggg ggcgaccttt   480
gtagggaag atcacggact ggctgccctg gttgatattg caatgctgag cgtcatgtgg   540
ggcctgctga atggtttcct gcatggaacc gcactgctgg aaccgcggg cgtttcggca    600
acctctgtgg ttccgatgct gggtcaaggt atcggagtgg tgaccggttg gattgcgcgc   660
tacgcagatc agattgatgc cggtgtctat ccagcagacg acaagacgat tgatacccag   720
cgtgctgcaa tgcagcacct ggtcgaggag agccgtgcgg cgggcatcaa tggcgaactt   780
ccggcgtttg tgaccaaact ggccgatcgc gcagtggcag aaggtcgtgg tggtgactct   840
tacgctgcac tgattgaaca gtttcgcaag tcagcttaa                          879
```

<210> SEQ ID NO 82
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 82

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Val Asp Ile Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
```

```
                195                 200                 205
Gln Gly Ile Gly Val Val Thr Gly Trp Ile Ala Arg Tyr Ala Asp Gln
            210                 215                 220

Ile Asp Ala Gly Val Tyr Pro Ala Asp Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
            275                 280                 285

Arg Lys Ser Ala
            290

<210> SEQ ID NO 83
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 83
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacga ttccaagcgg cattggcacc ccagaagcta ccattctgta ttcgggaccg     420
cgcagtacct tcgatgaaca tgaaagcgca ctgcgcgcat aggtccgggg gcgaccttt      480
gtagggaag atcacggact ggctaatctg tacgatgcag caatgctgag cgtcatgtgg     540
ggcctgctga atggtttcct gcatggaacc gcactgctgg aaccgcggg cgtttcggca     600
acctctgtgg ttccgatgct gggtcaaggt atcgaagcgg tgaccggttg gattgcgcgc     660
tacgcagatc agattgatgc cggtgtctat ccagcagacg acaagacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                           879

<210> SEQ ID NO 84
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 84

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
```

```
         35                  40                  45
Ala Thr Leu Ala Ala Ser Pro Ala Ala Val Ala Ala Gly Ser Leu
 50                  55                  60

Ile Val Val Cys Val Thr Asp His Arg Ala Val Arg Glu Leu Leu Glu
 65                  70                  75                  80

Pro Leu Gly Asp Ala Leu Pro Gly Arg Val Leu Val Asn Leu Thr Ser
                 85                  90                  95

Gly Thr Ser Arg Glu Ala Arg Glu Asn Ala Glu His Thr Ala Ala Gln
                100                 105                 110

Gly Ala Thr Tyr Leu Asp Gly Val Ile Leu Thr Ile Pro Ser Gly Ile
            115                 120                 125

Gly Thr Pro Glu Ala Thr Ile Leu Tyr Ser Gly Pro Arg Ser Thr Phe
        130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Leu
                165                 170                 175

Ser Val Met Trp Gly Leu Leu Asn Gly Phe Leu His Gly Thr Ala Leu
                180                 185                 190

Leu Gly Thr Ala Gly Val Ser Ala Thr Ser Val Val Pro Met Leu Gly
            195                 200                 205

Gln Gly Ile Glu Ala Val Thr Gly Trp Ile Ala Arg Tyr Ala Asp Gln
        210                 215                 220

Ile Asp Ala Gly Val Tyr Pro Ala Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
                260                 265                 270

Ala Glu Gly Arg Gly Gly Asp Ser Tyr Ala Ala Leu Ile Glu Gln Phe
            275                 280                 285

Arg Lys Ser Ala
    290

<210> SEQ ID NO 85
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 85
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgggta ttccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctaatctg tacgatcatg cacacctgag cgtcatgtgg     540
```

```
ggcctgctga atggtttcct gcatggaacc gcactgctgg gaaccgcggg cgtttcggca      600
acctctgtgg ttccgatgct gggtcaaggt atcgaagtgg tgaccggttg gattgcgcgc      660
tacgcagatc agattgatgc cggtgtctat ccagcagacg acaagacgat tgatacccag      720
cgtgctgcaa tgcagcacct ggtcgaggag agccgtgcgg cgggcatcaa tggcgaactt      780
ccggcgtttg tgaccaaact ggccgatcgc gcagtggcag aaggtcgtgg tggtgactct      840
tacgctgcac tgattgaaca gtttcgcaag tcagcttaa                             879
```

<210> SEQ ID NO 86
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 86

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Gly Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp His Ala His Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Val Val Thr Gly Trp Ile Ala Arg Tyr Ala Asp Gln
    210                 215                 220

Ile Asp Ala Gly Val Tyr Pro Ala Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

<210> SEQ ID NO 87
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 87

```
atgagtgatt cacctgtgcc cgtgacagtt ctgggtcttg gtctgatggg tcaggcctta    60
gcgggagcgt ttctggcagc cggtcaccct acgacggttt ggaatcgcag cgcagctaaa   120
gctgatgaac tggttggtcg cggtgcaacc ctggccgcgt ctcccgcggc tgccgtcgca   180
gcgggtagtc tgatcgttgt ttgcgtcaca gatcatcgtg cggtgcgcga actgctggaa   240
ccacttggcg atgcactgcc aggtcgcgtt ctggtcaacc tgacgagcgg tacgtcgcgt   300
gaagcccgtg agaacgcaga acatactgcg gctcagggag ccacctacct ggatggtgtg   360
attctgggta ttccaagcgg cattggcacc ccagaagcta ccattctgta ttcgggaccg   420
cgcagtacct tcgatgaaca tgaaagcgca ctgcgcgcat aggtccgggg gcgacctttt   480
gtagggaag atcacggact ggctaatctg tacgatattg caatgctgag cgtcatgtgg   540
ggcctgctga atggtttcct gcatggaacc gcactgctgg aaccgcgggg cgtttcggca   600
acctctgtgg ttccgatgct gggtcaaggt atcggaactg tgaccggttg gattgcgcgc   660
tacgcagatc agattgatgc cggtgtctat ccagcagacg acgccacgat tgatacccag   720
cgtgctgcaa tgcagcacct ggtcgaggag agccgtgcgg cgggcatcaa tggcgaactt   780
ccggcgtttg tgaccaaact ggccgatcgc gcagtggcag aaggtcgtgg tggtgactct   840
tacgctgcac tgattgaaca gtttcgcaag tcagcttaa                          879
```

<210> SEQ ID NO 88
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 88

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Gly Ile Pro Ser Gly Ile
        115                 120                 125

Gly Thr Pro Glu Ala Thr Ile Leu Tyr Ser Gly Pro Arg Ser Thr Phe
    130                 135                 140
```

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ile Ala Met Leu
            165                 170                 175

Ser Val Met Trp Gly Leu Leu Asn Gly Phe Leu His Gly Thr Ala Leu
        180                 185                 190

Leu Gly Thr Ala Gly Val Ser Ala Thr Ser Val Val Pro Met Leu Gly
            195                 200                 205

Gln Gly Ile Gly Thr Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 89
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 89
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacgg gcccaagcgg cattggcacc ccagaagcta ccattctgta ttcgggaccg    420
cgcagtacct tcgatgaaca tgaaagcgca ctgcgcgcat taggtccggg ggcgaccttt    480
gtaggggaag atcacggact ggctgcactg tatgatgcag caatgctgag cgtcatgtgg    540
ggcctgctga atggtttcct gcatggaacc gcactgctgg aaccgcgggg cgtttcggca    600
acctctgtgg ttccgatgct gggtcaaggt atcggagtgg tgaccggttg gattgcgcgc    660
tacgcagatc agattgatgc cggtgtctat ccagcagacg acaagacgat tgataccccag   720 cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879

<210> SEQ ID NO 90
<211> LENGTH: 292
<212> TYPE: PRT
<213> ORGANISM: Artificial Sequence
<220> FEATURE:
<223> OTHER INFORMATION: Imine reductase variant from Pseudonocardia -continued spinosispora

<400> SEQUENCE: 90

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Gly Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Gly Val Val Thr Gly Trp Ile Ala Arg Tyr Ala Asp Gln
    210                 215                 220

Ile Asp Ala Gly Val Tyr Pro Ala Asp Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 91
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 91
atgagtgatt cacctgtgcc cgtgacagtt ctgggtcttg gtctgatggg tcaggcctta    60
gcgggagcgt tctggcagc cggtcaccct acgacggttt ggaatcgcag cgcagctaaa   120
gctgatgaac tggttggtcg cggtgcaacc ctggccgcgt ctcccgcggc tgccgtcgca   180
gcgggtagtc tgatcgttgt ttgcgtcaca gatcatcgtg cggtgcgcga actgctggaa   240

```
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgggta ttccaagcgg cattggcacc ccagaagcta ccattctgta ttcgggaccg    420
cgcagtacct tcgatgaaca tgaaagcgca ctgcgcgcat taggtccggg ggcgaccttt    480 gtagggaag atcacggact ggctgccctg tacgatcatg cacacctgag cgtcatgtgg    540
ggcctgctga atggtttcct gcatggaacc gcactgctgg gaaccgcggg cgtttcggca    600
acctctgtgg ttccgatgct gggtcaaggt atctgcgtgg tgaccggttg gattgcgcgc    660
tacgcagatc agattgatgc cggtgtctat ccagcagacg acaagacgat tgataccag    720 cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 92
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 92

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Gly Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp His Ala His Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Cys Val Val Thr Gly Trp Ile Ala Arg Tyr Ala Asp Gln
    210                 215                 220

Ile Asp Ala Gly Val Tyr Pro Ala Asp Asp Lys Thr Ile Asp Thr Gln
225                 230                 235                 240
```

```
Arg Ala Ala Met Gln His Leu Val Glu Glu Ser Arg Ala Ala Gly Ile
            245                 250                 255

Asn Gly Glu Leu Pro Ala Phe Val Thr Lys Leu Ala Asp Arg Ala Val
        260                 265                 270

Ala Glu Gly Arg Gly Gly Asp Ser Tyr Ala Ala Leu Ile Glu Gln Phe
    275                 280                 285

Arg Lys Ser Ala
    290

<210> SEQ ID NO 93
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 93
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt tgcgtcaca gatcatcgtg cggtgcgcga actgctggaa      240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacga ttccaagcgg cattggcacc ccagaagcta ccattctgta ttcgggaccg     420
cgcagtacct tcgatgaaca tgaaagcgca ctgcgcgcat taggtccggg ggcgacccttt     480 gtagggaag atcacggact ggctaatctg tacgatgccg caatgctgag cgtcatgtgg      540
ggcctgctga atggtttcct gcatggaacc gcactgctgg gaaccgcggg cgtttcggca     600
acctctgtgg ttccgatgct gggtcaaggt atcggagtgg tgaccggttg gattgcgcgc     660
tacgcagatc agattgatgc cggtgtctat ccagcagacg acgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                            879

<210> SEQ ID NO 94
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 94

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80
```

Pro Leu Gly Asp Ala Leu Pro Gly Arg Val Leu Asn Leu Thr Ser
            85                  90                  95

Gly Thr Ser Arg Glu Ala Arg Glu Asn Ala Glu His Thr Ala Ala Gln
        100                 105                 110

Gly Ala Thr Tyr Leu Asp Gly Val Ile Leu Thr Ile Pro Ser Gly Ile
    115                 120                 125

Gly Thr Pro Glu Ala Thr Ile Leu Tyr Ser Gly Pro Arg Ser Thr Phe
130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Gly Val Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 95
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 95
atgagtgatt cacctgtgcc cgtgacagtt ctgggtcttg gtctgatggg tcaggcctta     60
gcgggagcgt ttctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacga ttccaagcgg cattggcacc ccagaagcta ccattctgta ttcgggaccg    420
cgcagtacct tcgatgaaca tgaaagcgca ctgcgcgcat taggtccggg ggcgaccttt    480
gtaggggaag atcacggact ggctgccctg tacgatgccg cacacctgag cgtcatgtgg    540
ggcctgctga atggtttcct gcatggaacc gcactgctgg aaccgcgggc gtttcggca    600 acctctgtgg ttccgatgct gggtcaaggt atcgaagcgg tgaccggttg gattgcgcgc    660
tacgcagatc agattgatgc cggtgtctat ccagcagacg acaagacgat tgatacccag    720
cgtgctgcaa tgcagcacct ggtcgaggag agccgtgcgg cgggcatcaa tggcgaactt    780

```
ccggcgtttg tgaccaaact ggccgatcgc gcagtggcag aaggtcgtgg tggtgactct    840
tacgctgcac tgattgaaca gtttcgcaag tcagcttaa                          879
```

<210> SEQ ID NO 96
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 96

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala His Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Thr Gly Trp Ile Ala Arg Tyr Ala Asp Gln
    210                 215                 220

Ile Asp Ala Gly Val Tyr Pro Ala Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

<210> SEQ ID NO 97
<211> LENGTH: 879
<212> TYPE: DNA
<213> ORGANISM: Artificial Sequence
<220> FEATURE:
<223> OTHER INFORMATION: Imine reductase variant from Pseudonocardia spinosispora

<400> SEQUENCE: 97

```
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacgg gcccaagcgg cattggcacc ccagaagcta ccattctgta ttcgggaccg     420
cgcagtacct tcgatgaaca tgaaagcgca ctgcgcgcat taggtccggg ggcgaccttt     480
gtagggggaag atcacggact ggctaatctg tacgatgccg caatgctgag cgtcatgtgg     540
ggcctgctga atggtttcct gcatggaacc gcactgctgg aaccgcgggg cgtttcggca     600
acctctgtgg ttccgatgct gggtcaaggt atcgaagcgg tgaccggttg gattgcgcgc     660
tacgcagatc agattgatgc cggtgtctat ccagcagacg acgcgacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                            879
```

<210> SEQ ID NO 98
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 98

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Gly Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Leu
                165                 170                 175

Ser Val Met Trp Gly Leu Leu Asn Gly Phe Leu His Gly Thr Ala Leu
```

180                 185                 190
Leu Gly Thr Ala Gly Val Ser Ala Thr Ser Val Val Pro Met Leu Gly
            195                 200                 205

Gln Gly Ile Glu Ala Val Thr Gly Trp Ile Ala Arg Tyr Ala Asp Gln
        210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 99
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 99
atgagtgatt cacctgtgcc cgtgacagtt ctgggtcttg gtctgatggg tcaggcctta      60 gcggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacga ttccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctaatctg tacgatgccg caatgctgag cgtcatgtgg     540
ggcctgctga tggtttcct gcatggaacc gcactgctgg aaccgcgggg cgtttcggca     600
acctctgtgg ttccgatgct gggtcaaggt atctgcgctg tgaccggttg gattgcgcgc     660
tacgcagatc agattgatgc cggtgtctat ccagcagacg acaagacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                             879

<210> SEQ ID NO 100
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 100

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr

```
            20                  25                  30
Val Trp Asn Arg Ser Ala Ala Lys Ala Asp Glu Leu Val Gly Arg Gly
         35                  40                  45

Ala Thr Leu Ala Ala Ser Pro Ala Ala Val Ala Ala Gly Ser Leu
 50                  55                  60

Ile Val Val Cys Val Thr Asp His Arg Ala Val Arg Glu Leu Leu Glu
 65                  70                  75                  80

Pro Leu Gly Asp Ala Leu Pro Gly Arg Val Leu Val Asn Leu Thr Ser
                 85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Cys Ala Val Thr Gly Trp Ile Ala Arg Tyr Ala Asp Gln
    210                 215                 220

Ile Asp Ala Gly Val Tyr Pro Ala Asp Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 101
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 101
atgagtgatt cacctgtgcc cgtgacagtt ctgggtcttg gtctgatggg tcaggcctta     60
gcgggagcgt ttctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgggta ttccaagcgg cattggcacc ccagaagcta ccattctgta ttcgggaccg    420
cgcagtacct tcgatgaaca tgaaagcgca ctgcgcgcat taggtccggg ggcgaccttt    480
```

```
gtaggggaag atcacggact ggctgcactg tatgatgcag caatgctgag cgtcatgtgg    540
ggcctgctga atggtttcct gcatggaacc gcactgctgg gaaccgcggg cgtttcggca    600
acctctgtgg ttccgatgct gggtcaaggt atcggagctg tgaccggttg gattgcgcgc    660
tacgcagatc agattgatgc cggtgtctat ccagcagacg acaagacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcaa aggtcgtggt ggtgactct    840 tacgctgcac tgattgaaca gtttcgcaag tcagcttaa                          879
```

<210> SEQ ID NO 102
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 102

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65              70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Gly Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145             150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Gly Ala Val Thr Gly Trp Ile Ala Arg Tyr Ala Asp Gln
    210                 215                 220

Ile Asp Ala Gly Val Tyr Pro Ala Asp Lys Thr Ile Asp Thr Gln
225             230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285
```

Arg Lys Ser Ala
    290

<210> SEQ ID NO 103
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 103

```
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacga ttccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctgccctg tacgatattg cacacctgag cgtcatgtgg     540
ggcctgctga atggtttcct gcatggaacc gcactgctgg gaaccgcggg cgtttcggca     600
acctctgtgg ttccgatgct gggtcaaggt atcgaagtgg tgaccggttg gattgcgcgc     660
tacgcagatc agattgatgc cggtgtctat ccagcagacg acgcgacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                            879
```

<210> SEQ ID NO 104
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 104

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ile Ala His Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Val Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 105
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 105
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacga ttccaagcgg cattggcacc ccagaagcta ccattctgta ttcgggaccg     420
cgcagtacct tcgatgaaca tgaaagcgca ctgcgcgcat taggtccggg ggcgaccttt     480 gtagggaag atcacggact ggctgcactg tatgatgcag caatgctgag cgtcatgtgg     540
ggcctgctga atggtttcct gcatggaacc gcactgctgg aaccgcgggg cgtttcggca     600
acctctgtgg ttccgatgct gggtcaaggt atcgaaactg tgaccggttg gattgcgcgc     660
tacgcagatc agattgatgc cggtgtctat ccagcagacg acaagacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                           879

<210> SEQ ID NO 106
<211> LENGTH: 292
<212> TYPE: PRT

<213> ORGANISM: Artificial Sequence
<220> FEATURE:
<223> OTHER INFORMATION: Imine reductase variant from Pseudonocardia spinosispora

<400> SEQUENCE: 106

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Thr Val Thr Gly Trp Ile Ala Arg Tyr Ala Asp Gln
210                 215                 220

Ile Asp Ala Gly Val Tyr Pro Ala Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

<210> SEQ ID NO 107
<211> LENGTH: 879
<212> TYPE: DNA
<213> ORGANISM: Artificial Sequence
<220> FEATURE:
<223> OTHER INFORMATION: Imine reductase variant from Pseudonocardia spinosispora

<400> SEQUENCE: 107

```
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
```

```
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacca ttccaagcgg cattggcacc ccagaagcta ccattctgta ttcgggaccg    420
cgcagtacct tcgatgaaca tgaaagcgca ctgcgcgcat taggtccggg ggcgaccttt    480
gtaggggaag atcacggact ggctgccctg tacgatgccg cacacctgag cgtcatgtgg    540
ggcctgctga atggtttcct gcatggaacc gcactgctgg aaccgcgggc gtttcggca    600 acctctgtgg ttccgatgct gggtcaaggt atcgaacctg taccggttg gattgcgcgc    660 tacgcagatc agattgatgc cggtgtctat ccagcagacg acaagacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 108
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 108

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala His Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Pro Val Thr Gly Trp Ile Ala Arg Tyr Ala Asp Gln
    210                 215                 220
```

```
Ile Asp Ala Gly Val Tyr Pro Ala Asp Asp Lys Thr Ile Asp Thr Gln
225                 230                 235                 240

Arg Ala Ala Met Gln His Leu Val Glu Glu Ser Arg Ala Ala Gly Ile
            245                 250                 255

Asn Gly Glu Leu Pro Ala Phe Val Thr Lys Leu Ala Asp Arg Ala Val
        260                 265                 270

Ala Glu Gly Arg Gly Gly Asp Ser Tyr Ala Ala Leu Ile Glu Gln Phe
    275                 280                 285

Arg Lys Ser Ala
    290
```

<210> SEQ ID NO 109
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 109

```
atgagtgatt cacctgtgcc cgtgacagtt ctgggtcttg gtctgatggg tcaggcctta    60
gcgggagcgt ttctggcagc cggtcaccct acgacggttt ggaatcgcag cgcagctaaa   120
gctgatgaac tggttggtcg cggtgcaacc ctggccgcgt ctcccgcggc tgccgtcgca   180
gcgggtagtc tgatcgttgt ttgcgtcaca gatcatcgtg cggtgcgcga actgctggaa   240
ccacttggcg atgcactgcc aggtcgcgtt ctggtcaacc tgacgagcgg tacgtcgcgt   300
gaagcccgtg agaacgcaga acatactgcg gctcagggag ccacctacct ggatggtgtg   360
attctgacgg gcccaagcgg cattggcacc ccagaagcta ccattctgta ttcgggaccg   420
cgcagtacct tcgatgaaca tgaaagcgca ctgcgcgcat taggtccggg ggcgaccttt   480
gtagggaag atcacggact ggctaatctg tacgatgccg caatgctgag cgtcatgtgg   540
ggcctgctga atggtttcct gcatggaacc gcactgctgg aaccgcgggg cgtttcggca   600
acctctgtgg ttccgatgct gggtcaaggt atcggagtgg tgaccggttg gattgcgcgc   660
tacgcagatc agattgatgc cggtgtctat ccagcagacg acaagacgat tgatacccag   720
cgtgctgcaa tgcagcacct ggtcgaggag agccgtgcgg cgggcatcaa tggcgaactt   780
ccggcgtttg tgaccaaact ggccgatcgc gcagtggcag aaggtcgtgg tggtgactct   840
tacgctgcac tgattgaaca gtttcgcaag tcagcttaa                          879
```

<210> SEQ ID NO 110
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 110

```
Met Ser Asp Ser Pro Val Pro Val Thr Val Leu Gly Leu Gly Leu Met
1               5                   10                  15

Gly Gln Ala Leu Ala Gly Ala Phe Leu Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60
```

```
Ile Val Val Cys Val Thr Asp His Arg Ala Val Arg Glu Leu Leu Glu
 65                  70                  75                  80

Pro Leu Gly Asp Ala Leu Pro Gly Arg Val Leu Val Asn Leu Thr Ser
                 85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Gly Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Gly Val Val Thr Gly Trp Ile Ala Arg Tyr Ala Asp Gln
    210                 215                 220

Ile Asp Ala Gly Val Tyr Pro Ala Asp Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 111
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 111
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacgg gcccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctaatctg tacgatgccg caatgctgag cgtcatgtgg     540
ggcctgctga atggttttcc tgcatggaac gcactgctgg aaccgcgggc gtttcggca      600 acctctgtgg ttccgatgct gggtcaaggt atcgtagtgg tgaccggttg gattgcgcgc     660
tacgcagatc agattgatgc cggtgtctat ccagcagacg acaagacgat tgatacccag     720
```
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa    879

```
<210> SEQ ID NO 112
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 112
```

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Gly Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Val Val Thr Gly Trp Ile Ala Arg Tyr Ala Asp Gln
    210                 215                 220

Ile Asp Ala Gly Val Tyr Pro Ala Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

```
<210> SEQ ID NO 113
<211> LENGTH: 879
<212> TYPE: DNA
```

<213> ORGANISM: Artificial Sequence
<220> FEATURE:
<223> OTHER INFORMATION: Imine reductase variant from Pseudonocardia spinosispora

<400> SEQUENCE: 113

```
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcaggagg ccacctacct ggatggtgtg     360
attctgggta ttccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctaatctg tacgatgccg caatgctgag cgtcatgtgg     540
ggcctgctga atggtttcct gcatggaacc gcactgctgg aaccgcgggg cgtttcggca     600
acctctgtgg ttccgatgct gggtcaaggt atcggagtgg tgaccggttg gattgcgcgc     660
tacgcagatc agattgatgc cggtgtctat ccagcagacg acgcgacgat tgatacccag     720
cgtgctgcaa tgcagcacct ggtcgaggag agccgtgcgg cgggcatcaa tggcgaactt     780
ccggcgtttg tgaccaaaact ggccgatcgc gcagtggcag aaggtcgtgg tggtgactct     840
tacgctgcac tgattgaaca gtttcgcaag tcagcttaa                            879
```

<210> SEQ ID NO 114
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 114

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Gly Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Leu
```

```
                 165                 170                 175
Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Gly Val Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

<210> SEQ ID NO 115
<211> LENGTH: 879
<212> TYPE: DNA
<213> ORGANISM: Artificial Sequence
<220> FEATURE:
<223> OTHER INFORMATION: Imine reductase variant from Pseudonocardia spinosispora

<400> SEQUENCE: 115

```
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacga ttccaagcgg cattggcacc ccagaagcta ccattctgta ttcgggaccg     420
cgcagtacct tcgatgaaca tgaaagcgca ctgcgcgcat aggtccgggg gcgacctttt     480
gtaggggaag atcacggact ggctgcactg tatgatgcag caatgctgag cgtcatgtgg     540
ggcctgctga atggtttcct gcatggaacc gcactgctgg aaccgcgggc cgtttcggca     600
acctctgtgg ttccgatgct gggtcaaggt atcgtagtgg tgaccggttg gattgcgcgc     660
tacgcagatc agattgatgc cggtgtctat ccagcagacg acaagacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                             879
```

<210> SEQ ID NO 116
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 116

Met Ser Asp Ser Pro Val Pro Val Thr Val Leu Gly Leu Gly Leu Met

```
  1               5                  10                 15
Gly Gln Ala Leu Ala Gly Ala Phe Leu Ala Ala Gly His Pro Thr Thr
                20                  25                  30
Val Trp Asn Arg Ser Ala Ala Lys Ala Asp Glu Leu Val Gly Arg Gly
                35                  40                  45
Ala Thr Leu Ala Ala Ser Pro Ala Ala Val Ala Gly Ser Leu
 50                  55                  60
Ile Val Val Cys Val Thr Asp His Arg Ala Val Arg Glu Leu Leu Glu
 65                  70                  75                  80
Pro Leu Gly Asp Ala Leu Pro Gly Arg Val Leu Val Asn Leu Thr Ser
                85                  90                  95
Gly Thr Ser Arg Glu Ala Arg Glu Asn Ala Glu His Thr Ala Ala Gln
                100                 105                 110
Gly Ala Thr Tyr Leu Asp Gly Val Ile Leu Thr Ile Pro Ser Gly Ile
                115                 120                 125
Gly Thr Pro Glu Ala Thr Ile Leu Tyr Ser Gly Pro Arg Ser Thr Phe
                130                 135                 140
Asp Glu His Glu Ser Ala Leu Arg Ala Leu Gly Pro Gly Ala Thr Phe
145                 150                 155                 160
Val Gly Glu Asp His Gly Leu Ala Ala Leu Tyr Asp Ala Ala Met Leu
                165                 170                 175
Ser Val Met Trp Gly Leu Leu Asn Gly Phe Leu His Gly Thr Ala Leu
                180                 185                 190
Leu Gly Thr Ala Gly Val Ser Ala Thr Ser Val Val Pro Met Leu Gly
                195                 200                 205
Gln Gly Ile Val Val Thr Gly Trp Ile Ala Arg Tyr Ala Asp Gln
                210                 215                 220
Ile Asp Ala Gly Val Tyr Pro Ala Asp Lys Thr Ile Asp Thr Gln
225                 230                 235                 240
Arg Ala Ala Met Gln His Leu Val Glu Glu Ser Arg Ala Ala Gly Ile
                245                 250                 255
Asn Gly Glu Leu Pro Ala Phe Val Thr Lys Leu Ala Asp Arg Ala Val
                260                 265                 270
Ala Glu Gly Arg Gly Gly Asp Ser Tyr Ala Ala Leu Ile Glu Gln Phe
                275                 280                 285
Arg Lys Ser Ala
                290

<210> SEQ ID NO 117
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 117
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
```

-continued

```
attctgggta ttccaagcgg cattggcacc ccagaagcta ccattctgta ttcgggaccg    420
cgcagtacct tcgatgaaca tgaaagcgca ctgcgcgcat taggtccggg ggcgaccttt    480 gtagggaag atcacggact ggctgcactg tatgatgcag caatgctgag cgtcatgtgg    540
ggcctgctga atggtttcct gcatggaacc gcactgctgg aaccgcggg cgtttcggca    600 acctctgtgg ttccgatgct gggtcaaggt atctgcgtgg tgaccggttg gattgcgcgc    660
tacgcagatc agattgatgc cggtgtctat ccagcagacg acaagacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 118
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 118

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Gly Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Pro Met Leu Gly
        195                 200                 205

Gln Gly Ile Cys Val Val Thr Gly Trp Ile Ala Arg Tyr Ala Asp Gln
    210                 215                 220

Ile Asp Ala Gly Val Tyr Pro Ala Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270
```

Ala Glu Gly Arg Gly Gly Asp Ser Tyr Ala Ala Leu Ile Glu Gln Phe
            275                 280                 285

Arg Lys Ser Ala
        290

<210> SEQ ID NO 119
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 119

| | | | | | |
|---|---|---|---|---|---|
| atgagtgatt | cacctgtgcc | cgtgacagtt | ctgggtcttg | gtctgatggg | tcaggcctta | 60 |
| gcgggagcgt | ttctggcagc | cggtcaccct | acgacggttt | ggaatcgcag | cgcagctaaa | 120 |
| gctgatgaac | tggttggtcg | cggtgcaacc | ctggccgcgt | ctcccgcggc | tgccgtcgca | 180 |
| gcgggtagtc | tgatcgttgt | ttgcgtcaca | gatcatcgtg | cggtgcgcga | actgctggaa | 240 |
| ccacttggcg | atgcactgcc | aggtcgcgtt | ctggtcaacc | tgacgagcgg | tacgtcgcgt | 300 |
| gaagcccgtg | agaacgcaga | acatactgcg | gctcagggag | ccacctacct | ggatggtgtg | 360 |
| attctgggta | ttccaagcgg | cattggcacc | ccagaagcta | ccattctgta | ttcgggaccg | 420 |
| cgcagtacct | tcgatgaaca | tgaaagcgca | ctgcgcgcat | taggtccggg | ggcgaccttt | 480 |
| gtagggaag | atcacggact | ggctaatctg | gttgatcatg | caatgctgag | cgtcatgtgg | 540 |
| ggcctgctga | atggtttcct | gcatggaacc | gcactgctgg | gaaccgcggg | cgtttcggca | 600 |
| acctctgtgg | ttccgatgct | gggtcaaggt | atcgaagtgg | tgaccggttg | gattgcgcgc | 660 |
| tacgcagatc | agattgatgc | cggtgtctat | ccagcagacg | acaagacgat | tgatacccag | 720 |
| cgtgctgcaa | tgcagcacct | ggtcgaggag | agccgtgcgg | cgggcatcaa | tggcgaactt | 780 |
| ccggcgtttg | tgaccaaact | ggccgatcgc | gcagtggcag | aaggtcgtgg | tggtgactct | 840 |
| tacgctgcac | tgattgaaca | gtttcgcaag | tcagcttaa | | | 879 |

<210> SEQ ID NO 120
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 120

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Gly Ile Pro Ser Gly Ile
            115                 120                 125

Gly Thr Pro Glu Ala Thr Ile Leu Tyr Ser Gly Pro Arg Ser Thr Phe
        130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Val Asp His Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Val Val Thr Gly Trp Ile Ala Arg Tyr Ala Asp Gln
    210                 215                 220

Ile Asp Ala Gly Val Tyr Pro Ala Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 121
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 121

```
atgagtgatt cacctgtgcc cgtgacagtt ctgggtcttg gtctgatggg tcaggcctta    60
gcgggagcgt ttctggcagc cggtcaccct acgacggttt ggaatcgcag cgcagctaaa   120
gctgatgaac tggttggtcg cggtgcaacc ctggccgcgt ctcccgcggc tgccgtcgca   180
gcgggtagtc tgatcgttgt ttgcgtcaca gatcatcgtg cggtgcgcga actgctggaa   240
ccacttggcg atgcactgcc aggtcgcgtt ctggtcaacc tgacgagcgg tacgtcgcgt   300
gaagcccgtg agaacgcaga acatactgcg gctcagggag ccacctacct ggatggtgtg   360
attctgacgg cccaagcgg cattggcacc cagaagcta ccattctgta ttcgggaccg   420
cgcagtacct tcgatgaaca tgaaagcgca ctgcgcgcat taggtccggg ggcgaccttt   480 gtagggaag atcacggact ggctgcactg tatgatgcag caatgctgag cgtcatgtgg   540
ggcctgctga atggtttcct gcatggaacc gcactgctgg gaaccgcggg cgtttcggca   600
acctctgtgg ttccgatgct gggtcaaggt atctgcgtgg tgaccggttg gattgcgcgc   660
tacgcagatc agattgatgc cggtgtctat ccagcagacg acaagacgat tgatacccag   720
cgtgctgcaa tgcagcacct ggtcgaggag agccgtgcgg cgggcatcaa tggcgaactt   780
ccggcgtttg tgaccaaact ggccgatcgc gcagtggcag aaggtcgtgg tggtgactct   840
tacgctgcac tgattgaaca gtttcgcaag tcagcttaa                          879
```

<210> SEQ ID NO 122
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 122

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Gly Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Cys Val Val Thr Gly Trp Ile Ala Arg Tyr Ala Asp Gln
    210                 215                 220

Ile Asp Ala Gly Val Tyr Pro Ala Asp Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

<210> SEQ ID NO 123
<211> LENGTH: 879
<212> TYPE: DNA
<213> ORGANISM: Artificial Sequence
<220> FEATURE:
<223> OTHER INFORMATION: Imine reductase variant from Pseudonocardia spinosispora

<400> SEQUENCE: 123
atgagtgatt cacctgtgcc cgtgacagtt ctgggtcttg gtctgatggg tcaggcctta       60

```
gcgggagcgt tcctggcagc cggtcaccct acgacggttt ggaatcgcag cgcagctaaa      120
gctgatgaac tggttggtcg cggtgcaacc ctggccgcgt ctcccgcggc tgccgtcgca      180
gcgggtagtc tgatcgttgt ttgcgtcaca gatcatcgtg cggtgcgcga actgctggaa      240
ccacttggcg atgcactgcc aggtcgcgtt ctggtcaacc tgacgagcgg tacgtcgcgt      300
gaagcccgtg agaacgcaga acatactgcg gctcagggag ccacctacct ggatggtgtg      360
attctgacgg gcccaagcgg cattggcacc ccagaagcta ccattctgta ttcgggaccg      420
cgcagtacct tcgatgaaca tgaaagcgca ctgcgcgcat taggtccggg ggcgacctt      480 gtaggggaag atcacggact ggctaatctg tacgatattg caatgctgag cgtcatgtgg      540
ggcctgctga atggtttcct gcatggaacc gcactgctgg aaccgcgggg cgtttcggca      600
acctctgtgg ttccgatgct gggtcaaggt atcgtagtgg tgaccggttg gattgcgcgc      660
tacgcagatc agattgatgc cggtgtctat ccagcagacg acaagacgat tgatacccag      720
cgtgctgcaa tgcagcacct ggtcgaggag agccgtgcgg cgggcatcaa tggcgaactt      780
ccggcgtttg tgaccaaact ggccgatcgc gcagtggcag aaggtcgtgg tggtgactct      840
tacgctgcac tgattgaaca gtttcgcaag tcagcttaa                           879
```

<210> SEQ ID NO 124
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 124

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Gly Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ile Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205
```

Gln Gly Ile Val Val Thr Gly Trp Ile Ala Arg Tyr Ala Asp Gln
    210             215                 220

Ile Asp Ala Gly Val Tyr Pro Ala Asp Lys Thr Ile Asp Thr Gln
225             230                 235                 240

Arg Ala Ala Met Gln His Leu Val Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 125
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 125

```
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgggta ttccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctaatctg tacgatattg caatgctgag cgtcatgtgg     540
ggcctgctga atggtttcct gcatggaacc gcactgctgg aaccgcgggc gtttcggca      600
acctctgtgg ttccgatgct gggtcaaggt atcgaagcgg tgaccggttg gattgcgcgc     660
tacgcagatc agattgatgc cggtgtctat ccagcagacg acgcgacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                            879
```

<210> SEQ ID NO 126
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 126

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

```
Ala Thr Leu Ala Ala Ser Pro Ala Ala Ala Val Ala Ala Gly Ser Leu
 50                  55                  60

Ile Val Val Cys Val Thr Asp His Arg Ala Val Arg Glu Leu Leu Glu
 65                  70                  75                  80

Pro Leu Gly Asp Ala Leu Pro Gly Arg Val Leu Val Asn Leu Thr Ser
                 85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Gly Ile Pro Ser Gly Ile
        115                 120                 125

Gly Thr Pro Glu Ala Thr Ile Leu Tyr Ser Gly Pro Arg Ser Thr Phe
130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ile Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Thr Gly Trp Ile Ala Arg Tyr Ala Asp Gln
210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
        290

<210> SEQ ID NO 127
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 127
atgagtgatt cacctgtgcc cgtgacagtt ctgggtcttg gtctgatggg tcaggcctta    60
gcgggagcgt ttctggcagc cggtcaccct acgacggttt ggaatcgcag cgcagctaaa   120
gctgatgaac tggttggtcg cggtgcaacc ctggccgcgt ctcccgcggc tgccgtcgca   180
gcgggtagtc tgatcgttgt ttgcgtcaca gatcatcgtg cggtgcgcga actgctggaa   240
ccacttggcg atgcactgcc aggtcgcgtt ctggtcaacc tgacgagcgg tacgtcgcgt   300
gaagcccgtg agaacgcaga acatactgcg gctcagggag ccacctacct ggatggtgtg   360
attctgacga ttccaagcgg cattggcacc ccagaagcta ccattctgta ttcgggaccg   420
cgcagtacct tcgatgaaca tgaaagcgca ctgcgcgcat taggtccggg ggcgaccttt   480
gtaggggaag atcacggact ggctaatctg tacgatgccg caatgctgag cgtcatgtgg   540
ggcctgctga atggtttcct gcatggaacc gcactgctgg gaaccgcggg cgtttcggca   600
```

-continued

```
acctctgtgg ttccgatgct gggtcaaggt atctgcgtgg tgaccggttg gattgcgcgc    660
tacgcagatc agattgatgc cggtgtctat ccagcagacg acaagacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                            879
```

<210> SEQ ID NO 128
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 128

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Pro Met Leu Gly
        195                 200                 205

Gln Gly Ile Cys Val Val Thr Gly Trp Ile Ala Arg Tyr Ala Asp Gln
    210                 215                 220

Ile Asp Ala Gly Val Tyr Pro Ala Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

<210> SEQ ID NO 129
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora
<220> FEATURE:
<221> NAME/KEY: Misc_Feature
<222> LOCATION: (634)..(634)
<223> OTHER INFORMATION: n = a, c, g or t
<220> FEATURE:
<221> NAME/KEY: Misc_Feature
<222> LOCATION: (636)..(636)
<223> OTHER INFORMATION: n = a, c, g or t

<400> SEQUENCE: 129

```
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgggta ttccaagcgg cattggcacc ccagaagcta ccattctgta ttcgggaccg     420
cgcagtacct tcgatgaaca tgaaagcgca ctgcgcgcat taggtccggg ggcgacctt t    480
gtaggggaag atcacggact ggctaatctg gttgatcatg cacacctgag cgtcatgtgg     540
ggcctgctga atggtttcct gcatggaacc gcactgctgg aaccgcgggc gtttcggca     600
acctctgtgg ttccgatgct gggtcaaggt atcngngtgg tgaccggttg gattgcgcgc     660
tacgcagatc agattgatgc cggtgtctat ccagcagacg acgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                            879
```

<210> SEQ ID NO 130
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora
<220> FEATURE:
<221> NAME/KEY: Misc_Feature
<222> LOCATION: (212)..(212)
<223> OTHER INFORMATION: Xaa = Cys, Ter, Ser, Trp, Arg, Gly

<400> SEQUENCE: 130

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
```

```
                    85                  90                  95
Gly Thr Ser Arg Glu Ala Arg Glu Asn Ala Glu His Thr Ala Ala Gln
                100                 105                 110

Gly Ala Thr Tyr Leu Asp Gly Val Ile Leu Gly Ile Pro Ser Gly Ile
            115                 120                 125

Gly Thr Pro Glu Ala Thr Ile Leu Tyr Ser Gly Pro Arg Ser Thr Phe
        130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Val Asp His Ala His Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Xaa Val Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 131
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 131
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgggta ttccaagcgg cattggcacc ccagaagcta ccattctgta ttcgggaccg     420
cgcagtacct tcgatgaaca tgaaagcgca ctgcgcgcat aggtccgggg gcgacctttt     480 gtagggaag atcacggact ggctgcactg tatgatgcag caatgctgag cgtcatgtgg     540
ggcctgctga atggtttcct gcatggaacc gcactgctgg aaccgcgggg cgtttcggca     600
acctctgtgg ttccgatgct gggtcaaggt atcgaaactg tgaccggttg gattgcgcgc     660
tacgcagatc agattgatgc cggtgtctat ccagcagacg acgccacgat tgataccccag    720 cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
```
tacgctgcac tgattgaaca gtttcgcaag tcagcttaa                                879

<210> SEQ ID NO 132
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 132

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Gly Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Thr Val Thr Gly Trp Ile Ala Arg Tyr Ala Asp Gln
    210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

<210> SEQ ID NO 133
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 133

```
atgagtgatt cacctgtgcc cgtgacagtt ctgggtcttg gtctgatggg tcaggcctta     60
gcgggagcgt ttctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgggta ttccaagcgg cattggcacc ccagaagcta ccattctgta ttcgggaccg    420
cgcagtacct tcgatgaaca tgaaagcgca ctgcgcgcat taggtccggg ggcgaccttt    480
gtaggggaag atcacggact ggctaatctg tacgatgccg caatgctgag cgtcatgtgg    540
ggcctgctga atggtttcct gcatggaacc gcactgctgg aaccgcgggg cgtttcggca    600
acctctgtgg ttccgatgct gggtcaaggt atcggagtgg tgaccggttg gattgcgcgc    660
tacgcagatc agattgatgc cggtgtctat ccagcagacg acaagacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 134
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 134

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Gly Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Leu
                165                 170                 175

Ser Val Met Trp Gly Leu Leu Asn Gly Phe Leu His Gly Thr Ala Leu
            180                 185                 190
```

```
Leu Gly Thr Ala Gly Val Ser Ala Thr Ser Val Val Pro Met Leu Gly
        195                 200                 205

Gln Gly Ile Gly Val Val Thr Gly Trp Ile Ala Arg Tyr Ala Asp Gln
    210                 215                 220

Ile Asp Ala Gly Val Tyr Pro Ala Asp Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 135
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 135
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgggtg gcccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctaatctg tacgatgccg caatgctgag cgtcatgtgg     540
ggcctgctga atggtttcct gcatggaacc gcactgctgg gaaccgcggg cgtttcggca     600
acctctgtgg ttccgatgct gggtcaaggt atcgtagtgg tgaccggttg gattgcgcgc     660
tacgcagatc agattgatgc cggtgtctat ccagcagacg acaagacgat tgatacccag     720
cgtgctgcaa tgcagcacct ggtcgaggag agccgtgcgg cgggcatcaa tggcgaactt     780
ccggcgtttg tgaccaaaac tggccgatcgc gcagtggcag aaggtcgtgg tggtgactct     840
tacgctgcac tgattgaaca gtttcgcaag tcagcttaa                            879

<210> SEQ ID NO 136
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 136

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30
```

Val Trp Asn Arg Ser Ala Ala Lys Ala Asp Glu Leu Val Gly Arg Gly
         35                  40                  45

Ala Thr Leu Ala Ala Ser Pro Ala Ala Val Ala Ala Gly Ser Leu
 50                  55                  60

Ile Val Val Cys Val Thr Asp His Arg Ala Val Arg Glu Leu Leu Glu
 65                  70                  75                  80

Pro Leu Gly Asp Ala Leu Pro Gly Arg Val Leu Val Asn Leu Thr Ser
                 85                  90                  95

Gly Thr Ser Arg Glu Ala Arg Glu Asn Ala Glu His Thr Ala Ala Gln
                100                 105                 110

Gly Ala Thr Tyr Leu Asp Gly Val Ile Leu Gly Pro Ser Gly Ile
            115                 120                 125

Gly Thr Pro Glu Ala Thr Ile Leu Tyr Ser Gly Pro Arg Ser Thr Phe
            130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
            195                 200                 205

Gln Gly Ile Val Val Thr Gly Trp Ile Ala Arg Tyr Ala Asp Gln
        210                 215                 220

Ile Asp Ala Gly Val Tyr Pro Ala Asp Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 137
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 137
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacca ttccaagcgg cattggcacc ccagaagcta ccattctgta ttcgggaccg    420
cgcagtacct tcgatgaaca tgaaagcgca ctgcgcgcat taggtccggg ggcgaccttt    480

```
gtaggggaag atcacggact ggctgcactg tatgatgcag caatgctgag cgtcatgtgg      540
ggcctgctga atggtttcct gcatggaacc gcactgctgg gaaccgcggg cgtttcggca      600
acctctgtgg ttccgatgct gggtcaaggt atcgaagtgg tgaccggttg gattgcgcgc      660
tacgcagatc agattgatgc cggtgtctat ccagcagacg acaagacgat tgatacccag      720
cgtgctgcaa tgcagcacct ggtcgaggag agccgtgcgg cgggcatcaa tggcgaactt      780
ccggcgtttg tgaccaaact ggccgatcgc gcagtggcag aaggtcgtgg tggtgactct      840
tacgctgcac tgattgaaca gtttcgcaag tcagcttaa                             879
```

<210> SEQ ID NO 138
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 138

```
Met Ser Asp Ser Pro Val Pro Val Thr Val Leu Gly Leu Gly Leu Met
1               5                   10                  15
Gly Gln Ala Leu Ala Gly Ala Phe Leu Ala Ala Gly His Pro Thr Thr
            20                  25                  30
Val Trp Asn Arg Ser Ala Ala Lys Ala Asp Glu Leu Val Gly Arg Gly
        35                  40                  45
Ala Thr Leu Ala Ala Ser Pro Ala Ala Val Ala Ala Gly Ser Leu
    50                  55                  60
Ile Val Val Cys Val Thr Asp His Arg Ala Val Arg Glu Leu Leu Glu
65                  70                  75                  80
Pro Leu Gly Asp Ala Leu Pro Gly Arg Val Leu Val Asn Leu Thr Ser
                85                  90                  95
Gly Thr Ser Arg Glu Ala Arg Glu Asn Ala Glu His Thr Ala Ala Gln
            100                 105                 110
Gly Ala Thr Tyr Leu Asp Gly Val Ile Leu Thr Ile Pro Ser Gly Ile
        115                 120                 125
Gly Thr Pro Glu Ala Thr Ile Leu Tyr Ser Gly Pro Arg Ser Thr Phe
    130                 135                 140
Asp Glu His Glu Ser Ala Leu Arg Ala Leu Gly Pro Gly Ala Thr Phe
145                 150                 155                 160
Val Gly Glu Asp His Gly Leu Ala Ala Leu Tyr Asp Ala Ala Met Leu
                165                 170                 175
Ser Val Met Trp Gly Leu Leu Asn Gly Phe Leu His Gly Thr Ala Leu
            180                 185                 190
Leu Gly Thr Ala Gly Val Ser Ala Thr Ser Val Val Pro Met Leu Gly
        195                 200                 205
Gln Gly Ile Glu Val Val Thr Gly Trp Ile Ala Arg Tyr Ala Asp Gln
    210                 215                 220
Ile Asp Ala Gly Val Tyr Pro Ala Asp Lys Thr Ile Asp Thr Gln
225                 230                 235                 240
Arg Ala Ala Met Gln His Leu Val Glu Glu Ser Arg Ala Ala Gly Ile
                245                 250                 255
Asn Gly Glu Leu Pro Ala Phe Val Thr Lys Leu Ala Asp Arg Ala Val
            260                 265                 270
Ala Glu Gly Arg Gly Gly Asp Ser Tyr Ala Ala Leu Ile Glu Gln Phe
        275                 280                 285
```

Arg Lys Ser Ala
    290

<210> SEQ ID NO 139
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 139

```
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcaggagc cacctaccta ggatggtgtg     360
attctgacga ttccaagcgg cattggcacc cagaagcta ccattctgta ttcgggaccg      420
cgcagtacct tcgatgaaca tgaaagcgca ctgcgcgcat taggtccggg ggcgaccttt     480
gtagggaag atcacggact ggctgcactg tatgatgcag caatgctgag cgtcatgtgg      540
ggcctgctga tggtttcct gcatggaacc gcactgctgg aaccgcggg cgtttcggca       600
acctctgtgg ttccgatgct gggtcaaggt atcggagtgg tgaccggttg gattgcgcgc    660
tacgcagatc agattgatgc cggtgtctat ccagcagacg acaagacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                            879
```

<210> SEQ ID NO 140
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 140

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
            130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Gly Val Val Thr Gly Trp Ile Ala Arg Tyr Ala Asp Gln
210                 215                 220

Ile Asp Ala Gly Val Tyr Pro Ala Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
        290

<210> SEQ ID NO 141
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 141
atgagtgatt cacctgtgcc cgtgacagtt ctgggtcttg gtctgatggg tcaggcctta     60
gcgggagcgt ttctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacgg gcccaagcgg cattggcacc ccagaagcta ccattctgta ttcgggaccg    420
cgcagtacct tcgatgaaca tgaaagcgca ctgcgcgcat aggtccgggg gcgaccttt    480
gtaggggaag atcacggact ggctaatctg tacgatattg caatgctgag cgtcatgtgg    540
ggcctgctga atggtttcct gcatggaacc gcactgctgg aaccgcgggg cgtttcggca    600
acctctgtgg ttccgatgct gggtcaaggt atctgcgtgg tgaccggttg gattgcgcgc    660
tacgcagatc agattgatgc cggtgtctat ccagcagacg acgccacgat tgataccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879

<210> SEQ ID NO 142
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 142

```
Met Ser Asp Ser Pro Val Pro Val Thr Val Leu Gly Leu Gly Leu Met
1               5                   10                  15
Gly Gln Ala Leu Ala Gly Ala Phe Leu Ala Ala Gly His Pro Thr Thr
            20                  25                  30
Val Trp Asn Arg Ser Ala Ala Lys Ala Asp Glu Leu Val Gly Arg Gly
        35                  40                  45
Ala Thr Leu Ala Ala Ser Pro Ala Ala Val Ala Ala Gly Ser Leu
    50                  55                  60
Ile Val Val Cys Val Thr Asp His Arg Ala Val Arg Glu Leu Leu Glu
65                  70                  75                  80
Pro Leu Gly Asp Ala Leu Pro Gly Arg Val Leu Val Asn Leu Thr Ser
                85                  90                  95
Gly Thr Ser Arg Glu Ala Arg Glu Asn Ala Glu His Thr Ala Ala Gln
            100                 105                 110
Gly Ala Thr Tyr Leu Asp Gly Val Ile Leu Thr Gly Pro Ser Gly Ile
        115                 120                 125
Gly Thr Pro Glu Ala Thr Ile Leu Tyr Ser Gly Pro Arg Ser Thr Phe
    130                 135                 140
Asp Glu His Glu Ser Ala Leu Arg Ala Leu Gly Pro Gly Ala Thr Phe
145                 150                 155                 160
Val Gly Glu Asp His Gly Leu Ala Asn Leu Tyr Asp Ile Ala Met Leu
                165                 170                 175
Ser Val Met Trp Gly Leu Leu Asn Gly Phe Leu His Gly Thr Ala Leu
            180                 185                 190
Leu Gly Thr Ala Gly Val Ser Ala Thr Ser Val Val Pro Met Leu Gly
        195                 200                 205
Gln Gly Ile Cys Val Val Thr Gly Trp Ile Ala Arg Tyr Ala Asp Gln
    210                 215                 220
Ile Asp Ala Gly Val Tyr Pro Ala Asp Asp Ala Thr Ile Asp Thr Gln
225                 230                 235                 240
Arg Ala Ala Met Gln His Leu Val Glu Glu Ser Arg Ala Ala Gly Ile
                245                 250                 255
Asn Gly Glu Leu Pro Ala Phe Val Thr Lys Leu Ala Asp Arg Ala Val
            260                 265                 270
Ala Glu Gly Arg Gly Gly Asp Ser Tyr Ala Ala Leu Ile Glu Gln Phe
        275                 280                 285
Arg Lys Ser Ala
    290
```

<210> SEQ ID NO 143
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 143

```
atgagtgatt cacctgtgcc cgtgacagtt ctgggtcttg gtctgatggg tcaggcctta    60
gcgggagcgt ttctggcagc cggtcaccct acgacggttt ggaatcgcag cgcagctaaa   120
gctgatgaac tggttggtcg cggtgcaacc ctggccgcgt ctcccgcggc tgccgtcgca   180
```

```
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgggta ttccaagcgg cattggcacc ccagaagcta ccattctgta ttcgggaccg    420
cgcagtacct tcgatgaaca tgaaagcgca ctgcgcgcat taggtccggg ggcgaccttt    480
gtagggggag atcacggact ggctaatctg gttgatattg caatgctgag cgtcatgtgg    540
ggcctgctga atggtttcct gcatggaacc gcactgctgg aaccgcgggg cgtttcggca    600
acctctgtgg ttccgatgct gggtcaaggt atctgcgtgg tgaccggttg gattgcgcgc    660
tacgcagatc agattgatgc cggtgtctat ccagcagacg acaagacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 144
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 144

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Gly Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Val Asp Ile Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Cys Val Val Thr Gly Trp Ile Ala Arg Tyr Ala Asp Gln
    210                 215                 220

Ile Asp Ala Gly Val Tyr Pro Ala Asp Asp Lys Thr Ile Asp Thr Gln
```

```
                225                 230                 235                 240
Arg Ala Ala Met Gln His Leu Val Glu Glu Ser Arg Ala Ala Gly Ile
                    245                 250                 255

Asn Gly Glu Leu Pro Ala Phe Val Thr Lys Leu Ala Asp Arg Ala Val
                260                 265                 270

Ala Glu Gly Arg Gly Gly Asp Ser Tyr Ala Ala Leu Ile Glu Gln Phe
            275                 280                 285

Arg Lys Ser Ala
        290

<210> SEQ ID NO 145
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 145
atgagtgatt cacctgtgcc cgtgacagtt ctgggtcttg gtctgatggg tcaggcctta      60
gcgggagcgt tctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacgg ccccaagcgg cattggcacc ccagaagcta ccattctgta ttcgggaccg     420
cgcagtacct tcgatgaaca tgaaagcgca ctgcgcgcat taggtccggg gcgaccttt      480 gtaggggaag atcacggact ggctaatctg tacgatattg cacacctgag cgtcatgtgg     540
ggcctgctga atggtttcct gcatggaacc gcactgctgg aaccgcgggg cgtttcggca     600
acctctgtgg ttccgatgct gggtcaaggt atcggagtgg tgaccggttg gattgcgcgc     660
tacgcagatc agattgatgc cggtgtctat ccagcagacg acgcgacgat tgataccaag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                            879

<210> SEQ ID NO 146
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 146

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Ala Val Ala Ala Gly Ser Leu
    50                  55                  60

Ile Val Val Cys Val Thr Asp His Arg Ala Val Arg Glu Leu Leu Glu
```

```
                65                  70                  75                  80
Pro Leu Gly Asp Ala Leu Pro Gly Arg Val Leu Val Asn Leu Thr Ser
                        85                  90                  95
Gly Thr Ser Arg Glu Ala Arg Glu Asn Ala Glu His Thr Ala Ala Gln
                100                 105                 110
Gly Ala Thr Tyr Leu Asp Gly Val Ile Leu Thr Ala Pro Ser Gly Ile
                115                 120                 125
Gly Thr Pro Glu Ala Thr Ile Leu Tyr Ser Gly Pro Arg Ser Thr Phe
            130                 135                 140
Asp Glu His Glu Ser Ala Leu Arg Ala Leu Gly Pro Gly Ala Thr Phe
145                 150                 155                 160
Val Gly Glu Asp His Gly Leu Ala Asn Leu Tyr Asp Ile Ala His Leu
                165                 170                 175
Ser Val Met Trp Gly Leu Leu Asn Gly Phe Leu His Gly Thr Ala Leu
                180                 185                 190
Leu Gly Thr Ala Gly Val Ser Ala Thr Ser Val Val Pro Met Leu Gly
                195                 200                 205
Gln Gly Ile Gly Val Val Thr Gly Trp Ile Ala Arg Tyr Ala Asp Gln
            210                 215                 220
Ile Asp Ala Gly Val Tyr Pro Ala Asp Asp Ala Thr Ile Asp Thr Gln
225                 230                 235                 240
Arg Ala Ala Met Gln His Leu Val Glu Glu Ser Arg Ala Ala Gly Ile
                245                 250                 255
Asn Gly Glu Leu Pro Ala Phe Val Thr Lys Leu Ala Asp Arg Ala Val
                260                 265                 270
Ala Glu Gly Arg Gly Gly Asp Ser Tyr Ala Ala Leu Ile Glu Gln Phe
            275                 280                 285
Arg Lys Ser Ala
        290

<210> SEQ ID NO 147
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 147
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacga ttccaagcgg cattggcacc ccagaagcta ccattctgta ttcgggaccg     420
cgcagtacct tcgatgaaca tgaaagcgca ctgcgcgcat taggtccggg ggcgaccttt     480
gtagggggaag atcacggact ggctaatctg tacgatgccg cacacctgag cgtcatgtgg     540
ggcctgctga atggttttcct gcatggaacc gcactgctgg gaaccgcggg cgtttcggca     600
acctctgtgg ttccgatgct gggtcaaggt atcggagtgg tgaccggttg gattgcgcgc     660
tacgcagatc agattgatgc cggtgtctat ccagcagacg acaagacgat tgatacccag     720
```

```
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 148
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 148

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala His Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Gly Val Val Thr Gly Trp Ile Ala Arg Tyr Ala Asp Gln
    210                 215                 220

Ile Asp Ala Gly Val Tyr Pro Ala Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

<210> SEQ ID NO 149
<211> LENGTH: 879
<212> TYPE: DNA
<213> ORGANISM: Artificial Sequence

```
<220> FEATURE:
<223> OTHER INFORMATION: Imine reductase variant from Pseudonocardia
      spinosispora

<400> SEQUENCE: 149
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgggta ttccaagcgg cattggcacc ccagaagcta ccattctgta ttcgggaccg     420
cgcagtacct tcgatgaaca tgaaagcgca ctgcgcgcat aggtccgggg gcgaccttt      480
gtagggaag atcacggact ggctaatctg tacgatgccg caggcctgag cgtcatgtgg      540
ggcctgctga atggtttcct gcatggaacc gcactgctgg aaccgcggg cgtttcggca      600
acctctgtgg ttccgatgct gggtcaaggt atcgaagctg tgaccggttg gattgcgcgc     660
tacgcagatc agattgatgc cggtgtctat ccagcagacg acgccacgat tgataccccag    720
cgtgctgcaa tgcagcacct ggtcgaggag agccgtgcgg cgggcatcaa tggcgaactt     780
ccggcgtttg tgaccaaact ggccgatcgc gcagtggcaa aggtcgtggt ggtgactct      840
tacgctgcac tgattgaaca gtttcgcaag tcagcttaa                            879

<210> SEQ ID NO 150
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 150

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Gly Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Gly Leu
                165                 170                 175
```

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 151
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 151
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgggta ttccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctaatctg tacgatgccg caggcctgag cgtcatgtgg     540
ggcctgctga atggtttcct gcatggaacc gcactgctgg aaccgcgggg cgtttcggca     600
acctctgtgg ttccgatgct gggtcaaggt atctcgctg tgaccggttg gattgcgcgc      660
tacgcagatc agattgatgc cggtgtctat ccagcagacg acaagacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                           879

<210> SEQ ID NO 152
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 152

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Gly Ser Leu
50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Gly Ile Pro Ser Gly Ile
        115                 120                 125

Gly Thr Pro Glu Ala Thr Ile Leu Tyr Ser Gly Pro Arg Ser Thr Phe
130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Gly Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Cys Ala Val Thr Gly Trp Ile Ala Arg Tyr Ala Asp Gln
210                 215                 220

Ile Asp Ala Gly Val Tyr Pro Ala Asp Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 153
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 153
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacga ttccaagcgg cattggcacc ccagaagcta ccattctgta ttcgggaccg     420

```
cgcagtacct tcgatgaaca tgaaagcgca ctgcgcgcat taggtccggg ggcgaccttt    480
gtaggggaag atcacggact ggctaatctg tacgatgccg caatgctgag cgtcatgtgg    540
ggcctgctga atggtttcct gcatggaacc gcactgctgg gaaccgcggg cgtttcggca    600
acctctgtgg ttccgatgct gggtcaaggt atcgtagtgg tgaccggttg gattgcgcgc    660
tacgcagatc agattgatgc cggtgtctat ccagcagacg acaagacgat tgatacccag    720
cgtgctgcaa tgcagcaccc tggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 154
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 154

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Val Val Thr Gly Trp Ile Ala Arg Tyr Ala Asp Gln
    210                 215                 220

Ile Asp Ala Gly Val Tyr Pro Ala Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270
```

Ala Glu Gly Arg Gly Gly Asp Ser Tyr Ala Ala Leu Ile Glu Gln Phe
            275                 280                 285

Arg Lys Ser Ala
    290

<210> SEQ ID NO 155
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 155
atgagtgatt cacctgtgcc cgtgacagtt ctgggtcttg gtctgatggg tcaggcctta    60
gcgggagcgt ttctggcagc cggtcaccct acgacggttt ggaatcgcag cgcagctaaa   120
gctgatgaac tggttggtcg cggtgcaacc ctggccgcgt ctcccgcggc tgccgtcgca   180
gcgggtagtc tgatcgttgt ttgcgtcaca gatcatcgtg cggtgcgcga actgctggaa   240
ccacttggcg atgcactgcc aggtcgcgtt ctggtcaacc tgacgagcgg tacgtcgcgt   300
gaagcccgtg agaacgcaga acatactgcg gctcagggag ccacctacct ggatggtgtg   360
attctgacga ttccaagcgg cattggcacc ccagaagcta ccattctgta ttcgggaccg   420
cgcagtacct tcgatgaaca tgaaagcgca ctgcgcgcat taggtccggg ggcgaccttt   480
gtaggggaag atcacggact ggctaatctg tacgatgccg caggcctgag cgtcatgtgg   540
ggcctgctga atggtttcct gcatggaacc gcactgctgg aaccgcgggt cgtttcggca   600
acctctgtgg ttccgatgct gggtcaaggt atctgcgtgg tgaccggttg gattgcgcgc   660
tacgcagatc agattgatgc cggtgtctat ccagcagacg acaagacgat tgatacccag   720
cgtgctgcaa tgcagcacct ggtcgaggag agccgtgcgg cgggcatcaa tggcgaactt   780
ccggcgtttg tgaccaaact ggccgatcgc gcagtggcag aaggtcgtgg tggtgactct   840
tacgctgcac tgattgaaca gtttcgcaag tcagcttaa                          879

<210> SEQ ID NO 156
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 156

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
            115                 120                 125

Gly Thr Pro Glu Ala Thr Ile Leu Tyr Ser Gly Pro Arg Ser Thr Phe
        130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Gly Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Cys Val Val Thr Gly Trp Ile Ala Arg Tyr Ala Asp Gln
    210                 215                 220

Ile Asp Ala Gly Val Tyr Pro Ala Asp Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 157
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 157
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacga ttccaagcgg cattggcacc ccagaagcta ccattctgta ttcgggaccg     420
cgcagtacct cgatgaaca tgaaagcgca ctgcgcgcat aggtccgggg gcgaccttt     480
gtaggggaag atcacggact ggctaatctg ttgatattg aatgctgag cgtcatgtgg     540
ggcctgctga atggtttcct gcatggaacc gcactgctgg aaccgcggg cgtttcggca     600
acctctgtgg ttccgatgct gggtcaaggt atcgaagtgg tgaccggttg gattgcgcgc     660
tacgcagatc agattgatgc cggtgtctat ccagcagacg acaagacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                           879

<210> SEQ ID NO 158

<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 158

```
Met Ser Asp Ser Pro Val Pro Val Thr Val Leu Gly Leu Gly Leu Met
1               5                   10                  15
Gly Gln Ala Leu Ala Gly Ala Phe Leu Ala Ala Gly His Pro Thr Thr
            20                  25                  30
Val Trp Asn Arg Ser Ala Ala Lys Ala Asp Glu Leu Val Gly Arg Gly
        35                  40                  45
Ala Thr Leu Ala Ala Ser Pro Ala Ala Val Ala Ala Gly Ser Leu
    50                  55                  60
Ile Val Val Cys Val Thr Asp His Arg Ala Val Arg Glu Leu Leu Glu
65                  70                  75                  80
Pro Leu Gly Asp Ala Leu Pro Gly Arg Val Leu Val Asn Leu Thr Ser
                85                  90                  95
Gly Thr Ser Arg Glu Ala Arg Glu Asn Ala Glu His Thr Ala Ala Gln
            100                 105                 110
Gly Ala Thr Tyr Leu Asp Gly Val Ile Leu Thr Ile Pro Ser Gly Ile
        115                 120                 125
Gly Thr Pro Glu Ala Thr Ile Leu Tyr Ser Gly Pro Arg Ser Thr Phe
    130                 135                 140
Asp Glu His Glu Ser Ala Leu Arg Ala Leu Gly Pro Gly Ala Thr Phe
145                 150                 155                 160
Val Gly Glu Asp His Gly Leu Ala Asn Leu Val Asp Ile Ala Met Leu
                165                 170                 175
Ser Val Met Trp Gly Leu Leu Asn Gly Phe Leu His Gly Thr Ala Leu
            180                 185                 190
Leu Gly Thr Ala Gly Val Ser Ala Thr Ser Val Val Pro Met Leu Gly
        195                 200                 205
Gln Gly Ile Glu Val Val Thr Gly Trp Ile Ala Arg Tyr Ala Asp Gln
    210                 215                 220
Ile Asp Ala Gly Val Tyr Pro Ala Asp Lys Thr Ile Asp Thr Gln
225                 230                 235                 240
Arg Ala Ala Met Gln His Leu Val Glu Glu Ser Arg Ala Ala Gly Ile
                245                 250                 255
Asn Gly Glu Leu Pro Ala Phe Val Thr Lys Leu Ala Asp Arg Ala Val
            260                 265                 270
Ala Glu Gly Arg Gly Gly Asp Ser Tyr Ala Ala Leu Ile Glu Gln Phe
        275                 280                 285
Arg Lys Ser Ala
    290
```

<210> SEQ ID NO 159
<211> LENGTH: 879
<212> TYPE: DNA
<213> ORGANISM: Artificial Sequence
<220> FEATURE:
<223> OTHER INFORMATION: Imine reductase variant from Pseudonocardia spinosispora

<400> SEQUENCE: 159

```
atgagtgatt cacctgtgcc cgtgacagtt ctgggtcttg gtctgatggg tcaggcctta    60
```

```
gcgggagcgt tcctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt tgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacgg gcccaagcgg cattggcacc ccagaagcta ccattctgta ttcgggaccg    420
cgcagtacct tcgatgaaca tgaaagcgca ctgcgcgcat taggtccggg ggcgaccttt    480
gtaggggaag atcacggact ggctaatctg tacgatgccg caatgctgag cgtcatgtgg    540
ggcctgctga atggtttcct gcatggaacc gcactgctgg aaccgcgggc gtttcggca    600 acctctgtgg ttccgatgct gggtcaaggt atcgaagtgg tgaccggttg gattgcgcgc    660
tacgcagatc agattgatgc cggtgtctat ccagcagacg acaagacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 160
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 160

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Gly Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Val Val Thr Gly Trp Ile Ala Arg Tyr Ala Asp Gln
```

Ile Asp Ala Gly Val Tyr Pro Ala Asp Lys Thr Ile Asp Thr Gln
225                 230                 235                 240

Arg Ala Ala Met Gln His Leu Val Glu Glu Ser Arg Ala Ala Gly Ile
            245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 161
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 161

```
atgagtgatt cacctgtgcc cgtgacagtt ctgggtcttg gtctgatggg tcaggcctta    60
gcgggagcgt ttctggcagc cggtcaccct acgacggttt ggaatcgcag cgcagctaaa   120
gctgatgaac tggttggtcg cggtgcaacc ctggccgcgt ctcccgcggc tgccgtcgca   180
gcgggtagtc tgatcgttgt ttgcgtcaca gatcatcgtg cggtgcgcga actgctggaa   240
ccacttggcg atgcactgcc aggtcgcgtt ctggtcaacc tgacgagcgg tacgtcgcgt   300
gaagcccgtg agaacgcaga acatactgcg gctcagggag ccacctacct ggatggtgtg   360
attctgacgg gccaagcgg cattggcacc ccagaagcta ccattctgta ttcgggaccg   420
cgcagtacct tcgatgaaca tgaaagcgca ctgcgcgcat aggtccgggg gcgacctttt   480
gtaggggaag atcacggact ggctgccctg tacgatgccg caggcctgag cgtcatgtgg   540
ggcctgctga atggtttcct gcatggaacc gcactgctgg aaccgcgggg cgtttcggca   600
acctctgtgg ttccgatgct gggtcaaggt atcgtagtgg tgaccggttg gattgcgcgc   660
tacgcagatc agattgatgc cggtgtctat ccagcagacg acaagacgat tgatacccag   720
cgtgctgcaa tgcagcacct ggtcgaggag agccgtgcgg cgggcatcaa tggcgaactt   780
ccggcgtttg tgaccaaact ggccgatcgc gcagtggcag aaggtcgtgg tggtgactct   840
tacgctgcac tgattgaaca gtttcgcaag tcagcttaa                          879
```

<210> SEQ ID NO 162
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 162

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Ala Val Ala Ala Gly Ser Leu

```
                50                  55                  60
Ile Val Val Cys Val Thr Asp His Arg Ala Val Arg Glu Leu Leu Glu
 65                  70                  75                  80

Pro Leu Gly Asp Ala Leu Pro Gly Arg Val Leu Val Asn Leu Thr Ser
                 85                  90                  95

Gly Thr Ser Arg Glu Ala Arg Glu Asn Ala Glu His Thr Ala Ala Gln
                100                 105                 110

Gly Ala Thr Tyr Leu Asp Gly Val Ile Leu Thr Gly Pro Ser Gly Ile
            115                 120                 125

Gly Thr Pro Glu Ala Thr Ile Leu Tyr Ser Gly Pro Arg Ser Thr Phe
        130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Gly Leu
                165                 170                 175

Ser Val Met Trp Gly Leu Leu Asn Gly Phe Leu His Gly Thr Ala Leu
                180                 185                 190

Leu Gly Thr Ala Gly Val Ser Ala Thr Ser Val Val Pro Met Leu Gly
            195                 200                 205

Gln Gly Ile Val Val Thr Gly Trp Ile Ala Arg Tyr Ala Asp Gln
        210                 215                 220

Ile Asp Ala Gly Val Tyr Pro Ala Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
                260                 265                 270

Ala Glu Gly Arg Gly Gly Asp Ser Tyr Ala Ala Leu Ile Glu Gln Phe
            275                 280                 285

Arg Lys Ser Ala
    290

<210> SEQ ID NO 163
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 163
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacga ttccaagcgg cattggcacc ccagaagcta ccattctgta ttcgggaccg     420
cgcagtacct tcgatgaaca tgaaagcgca ctgcgcgcat aggtccgggg gcgacctttt     480
gtaggggaag atcacggact ggctaatctg tacgatattg cacacctgag cgtcatgtgg     540
ggcctgctga atggttttcc tgcatggaac gcactgctgg gaaccgcggg cgtttcggca     600
acctctgtgg ttccgatgct gggtcaaggt atcgaagtgg tgaccggttg gattgcgcgc     660
```

```
tacgcagatc agattgatgc cggtgtctat ccagcagacg acaagacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 164
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 164

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ile Ala His Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Val Val Thr Gly Trp Ile Ala Arg Tyr Ala Asp Gln
    210                 215                 220

Ile Asp Ala Gly Val Tyr Pro Ala Asp Lys Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

<210> SEQ ID NO 165

<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 165

```
atgagtgatt cacctgtgcc cgtgacagtt ctgggtcttg gtctgatggg tcaggcctta    60
gcggagcgt ttctggcagc cggtcaccct acgacggttt ggaatcgcag cgcagctaaa   120
gctgatgaac tggttggtcg cggtgcaacc ctggccgcgt ctcccgcggc tgccgtcgca   180
gcgggtagtc tgatcgttgt ttgcgtcaca gatcatcgtg cggtgcgcga actgctggaa   240
ccacttggcg atgcactgcc aggtcgcgtt ctggtcaacc tgacgagcgg tacgtcgcgt   300
gaagcccgtg agaacgcaga acatactgcg gctcagggag ccacctacct ggatggtgtg   360
attctgacca ttccaagcgg cattggcacc ccagaagcta cgattctgta ttcgggaccg   420
cgcagtacct tcgatgaaca tgaaagcgca ctgcgcgcat taggtccggg ggcgaccttt   480
gtaggggaag atcacggact ggctaacctg tatgatgcag caatgtcgag cgtgatgtgg   540
ggcctgctga atggtttcct gcatggaacc gcactgctgg aaccgcgggg cgtttcggca   600
acctctgtgg ttccgatgct gggtcaaggt tgggaagcgg tgactggtct aattgcgcgc   660
tacgcagatc agattgatgc cggtgtctat ccagcagacg atgccacgat tgatacccag   720
cgtgctgcaa tgcagcaccc tggtcgagga gccgtgcgg cgggcatcaa tggcgaactt   780
ccggcgtttg tgaccaaact ggccgatcgc gcagtggcag aaggtcgtgg tggtgactct   840
tacgctgcac tgattgaaca gtttcgcaag tcagcttaa                         879
```

<210> SEQ ID NO 166
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 166

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160
```

```
Val Gly Glu Asp His Gly Leu Ala Asn Leu Tyr Asp Ala Ala Met Ser
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Pro Met Leu Gly
        195                 200                 205

Gln Gly Trp Glu Ala Val Thr Gly Leu Ile Ala Arg Tyr Ala Asp Gln
        210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

```
<210> SEQ ID NO 167
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 167
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ggattctgta ttcgggaccg     420
cgcagtacct tcgatgaaca tgaaagcgca ctgcgcgcat aggtcccggg ggcgaccttt     480 gtagggaag atcacggact ggctaacctg tatgatgcag caatgttgag cgtgatgtgg     540
ggcctgctga atggtttcct gcatggaacc gcactgctgg aaccgcggg cgtttcggca     600 acctctgtgg ttccgatgct gggtcaaggt tgggaagcga tgactggtct aattgcgcgc     660
tacgcagatc agattgatgc cggtgtctat ccagcagacg atgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcaa aggtcgtgg tggtgactct     840 tacgctgcac tgattgaaca gtttcgcaag tcagcttaa                             879
```

```
<210> SEQ ID NO 168
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 168
```

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
                20                  25                  30

Val Trp Asn Arg Ser Ala Ala Lys Ala Asp Glu Leu Val Gly Arg Gly
            35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65              70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
                100                 105                 110

Gly Ala Thr Tyr Leu Asp Gly Val Ile Leu Thr Ile Pro Ser Gly Ile
            115                 120                 125

Gly Thr Pro Glu Ala Arg Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Leu
                165                 170                 175

Ser Val Met Trp Gly Leu Leu Asn Gly Phe Leu His Gly Thr Ala Leu
                180                 185                 190

Leu Gly Thr Ala Gly Val Ser Ala Thr Ser Val Val Pro Met Leu Gly
            195                 200                 205

Gln Gly Trp Glu Ala Met Thr Gly Leu Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
                260                 265                 270

Ala Glu Gly Arg Gly Gly Asp Ser Tyr Ala Ala Leu Ile Glu Gln Phe
            275                 280                 285

Arg Lys Ser Ala
    290

<210> SEQ ID NO 169
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 169
atgagtgatt cacctgtgcc cgtgacagtt ctgggtcttg gtctgatggg tcaggcctta    60
gcgggagcgt ttctggcagc cggtcaccct acgacggttt ggaatcgcag cgcagctaaa   120
gctgatgaac tggttggtcg cggtgcaacc ctggccgcgt ctcccgcggc tgccgtcgca   180
gcgggtagtc tgatcgttgt ttgcgtcaca gatcatcgtg cggtgcgcga actgctggaa   240
ccacttggcg atgcactgcc aggtcgcgtt ctggtcaacc tgacgagcgg tacgtcgcgt   300

-continued

```
gaagcccgtg agaacgcaga acatactgcg gctcaggag  ccacctacct ggatggtgtg    360
attctgacca ttccaagcgg cattggcacc ccagaagcta ggattctgta ttcgggaccg    420
cgcagtacct tcgatgaaca tgaaagcgca ctgcgcgcat aggtccgggg gcgacctttt   480 gtagggaag  atcacggact ggctaacctg tatgatgcag caatgttgag catgatgtgg    540
ggcctgctga atggtttcct gcatggaacc gcactgctgg gaaccgcggg cgtttcggca    600
acctctgtgg ttccgatgct gggtcaaggt tgggaagcga tgactggtat aattgcgcgc    660
tacgcagatc agattgatgc cggtgtctat ccagcagacg atgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                          879
```

<210> SEQ ID NO 170
<211> LENGTH: 292
<212> TYPE: PRT
<213> ORGANISM: Artificial Sequence
<220> FEATURE:
<223> OTHER INFORMATION: Imine reductase variant from Pseudonocardia
spinosispora

<400> SEQUENCE: 170

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Arg Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Leu
                165                 170                 175

Ser Met Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Met Thr Gly Ile Ile Ala Arg Tyr Ala Asp Gln
    210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255
```

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 171
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 171

```
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta cgattctgta ttcgggaccg     420
cgcagtacct tcgatgaaca tgaaagcgca ctgcgcgcat aggtccgggg gcgaccttt      480 gtaggggaag atcacggact ggctgccctg tatgatgcag caatgttgag catgatgtgg     540
ggcctgctga atggtttcct gcatggaacc gcactgctgg aaccgcgggg cgtttcggca     600
acctctgtgg ttccgatgct gggtcaaggt tgggaagcgg tgactggtct aattgcgcgc     660
tacgcagatc agattgatgc cggtgtctat ccagcagacg atgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                           879
```

<210> SEQ ID NO 172
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 172

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Met Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Val Thr Gly Leu Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 173
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 173
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacca ttccaagcgg cattggcacc ccagaagcta ggattctgta ttcgggaccg    420
cgcagtacct tcgatgaaca tgaaagcgca ctgcgcgcat taggtccggg gcgaccttt     480 gtagggaag atcacggact ggctgccctg tatgatgcag caatgtcgag cgtgatgtgg     540
ggcctgctga atggtttcct gcatggaacc gcactgctgg aaccgcgggg cgtttcggca    600
acctctgtgg ttccgatgct gggtcaaggt tgggaagcgg tgatggggttg gattgcgcgc   660 tacgcagatc agattgatgc cggtgtctat ccagcagacg atgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879

<210> SEQ ID NO 174
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 174

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Arg Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Ser
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Val Met Gly Trp Ile Ala Arg Tyr Ala Asp Gln
    210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 175
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 175

```
atgagtgatt cacctgtgcc cgtgacagtt ctgggtcttg gtctgatggg tcaggcctta    60
gcgggagcgt ttctggcagc cggtcaccct acgacggttt ggaatcgcag cgcagctaaa   120
gctgatgaac tggttggtcg cggtgcaacc ctggccgcgt ctcccgcggc tgccgtcgca   180
gcgggtagtc tgatcgttgt ttgcgtcaca gatcatcgtg cggtgcgcga actgctggaa   240
ccacttggcg atgcactgcc aggtcgcgtt ctggtcaacc tgacgagcgg tacgtcgcgt   300
gaagcccgtg agaacgcaga acatactgcg gctcagggag ccacctacct ggatggtgtg   360
attctgacca ttccaagcgg cattggcacc ccagaagcta cgattctgta ttcgggaccg   420
cgcagtacct tcgatgaaca tgaaagcgca ctgcgcgcat taggtccggg ggcgaccttt   480
gtagggaag atcacggact ggctaacctg tatgatgcag caatgtcgag cgtgatgtgg   540
ggcctgctga atggtttcct gcatggaacc gcactgctgg aaccgcgggt gtttcggca   600
acctctgtgg ttccgatgct gggtcaaggt tgggaagcga tgactggttg gattgcgcgc   660
tacgcagatc agattgatgc cggtgtctat ccagcagacg atgccacgat tgataccag   720
cgtgctgcaa tgcagcacct ggtcgaggag agccgtgcgg cgggcatcaa tggcgaactt   780
ccggcgtttg tgaccaaact ggccgatcgc gcagtggcag aaggtcgtgg tggtgactct   840
tacgctgcac tgattgaaca gtttcgcaag tcagcttaa                          879
```

<210> SEQ ID NO 176
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 176

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly 195                 200                 205
Gln Gly Trp Glu Ala Met Thr Gly Trp Ile Ala Arg Tyr Ala Asp Gln
        210                 215                 220
Ile Asp Ala Gly Val Tyr Pro Ala Asp Asp Ala Thr Ile Asp Thr Gln
225                 230                 235                 240
Arg Ala Ala Met Gln His Leu Val Glu Ser Arg Ala Ala Gly Ile
                245                 250                 255
Asn Gly Glu Leu Pro Ala Phe Val Thr Lys Leu Ala Asp Arg Ala Val
        260                 265                 270
Ala Glu Gly Arg Gly Gly Asp Ser Tyr Ala Ala Leu Ile Glu Gln Phe
        275                 280                 285
Arg Lys Ser Ala
        290

<210> SEQ ID NO 177
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 177
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcaggag ccacctacct ggatggtgtg      360
attctgacca ttccaagcgg cattggcacc ccagaagcta ggattctgta ttcgggaccg     420
cgcagtacct tcgatgaaca tgaaagcgca ctgcgcgcat taggtccggg ggcgaccttt     480
gtaggggaag atcacggact ggctaacctg tatgatgcag caatgtcgag cgttatgtgg     540
ggcctgctga atggtttcct gcatggaacc gcactgctgg gaaccgcggg cgtttcggca     600
acctctgtgg ttccgatgct gggtcaaggt tgggaagcgg tgactggttg gattgcgcgc     660
tacgcagatc agattgatgc cggtgtctat ccagcagacg atgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                            879

<210> SEQ ID NO 178
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 178

Met Ser Asp Ser Pro Val Pro Val Thr Val Leu Gly Leu Gly Leu Met
1               5                   10                  15
Gly Gln Ala Leu Ala Gly Ala Phe Leu Ala Ala Gly His Pro Thr Thr
        20                  25                  30
Val Trp Asn Arg Ser Ala Ala Lys Ala Asp Glu Leu Val Gly Arg Gly

```
                 35                  40                  45
Ala Thr Leu Ala Ala Ser Pro Ala Ala Val Ala Ala Gly Ser Leu
             50                  55                  60

Ile Val Val Cys Val Thr Asp His Arg Ala Val Arg Glu Leu Leu Glu
65                   70                  75                  80

Pro Leu Gly Asp Ala Leu Pro Gly Arg Val Leu Val Asn Leu Thr Ser
                 85                  90                  95

Gly Thr Ser Arg Glu Ala Arg Glu Asn Ala Glu His Thr Ala Ala Gln
             100                 105                 110

Gly Ala Thr Tyr Leu Asp Gly Val Ile Leu Thr Ile Pro Ser Gly Ile
         115                 120                 125

Gly Thr Pro Glu Ala Arg Ile Leu Tyr Ser Gly Pro Arg Ser Thr Phe
     130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                 165                 170                 175

Ser Val Met Trp Gly Leu Leu Asn Gly Phe Leu His Gly Thr Ala Leu
             180                 185                 190

Leu Gly Thr Ala Gly Val Ser Ala Thr Ser Val Val Pro Met Leu Gly
         195                 200                 205

Gln Gly Trp Glu Ala Val Thr Gly Trp Ile Ala Arg Tyr Ala Asp Gln
     210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                 245                 250                 255

Asn Gly Glu Leu Pro Ala Phe Val Thr Lys Leu Ala Asp Arg Ala Val
             260                 265                 270

Ala Glu Gly Arg Gly Gly Asp Ser Tyr Ala Ala Leu Ile Glu Gln Phe
         275                 280                 285

Arg Lys Ser Ala
    290

<210> SEQ ID NO 179
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 179
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta cgattctgta ttcgggaccg     420
cgcagtacct tcgatgaaca tgaaagcgca ctgcgcgcat aggtccgggg gcgacctttt     480
gtaggggaag atcacggact ggctaacctg tatgatgcag caatgtcgag cgttatgtgg     540
```

```
ggcctgctga atggtttcct gcatggaacc gcactgctgg gaaccgcggg cgtttcggca    600
acctctgtgg ttccgatgct gggtcaaggt atagaagcga tgatgggtat aattgcgcgc    660
tacgcagatc agattgatgc cggtgtctat ccagcagacg atgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 180
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 180

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Met Met Gly Ile Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

<210> SEQ ID NO 181
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 181

```
atgagtgatt cacctgtgcc cgtgacagtt ctgggtcttg gtctgatggg tcaggcctta    60
gcgggagcgt ttctggcagc cggtcaccct acgacggttt ggaatcgcag cgcagctaaa   120
gctgatgaac tggttggtcg cggtgcaacc ctggccgcgt ctcccgcggc tgccgtcgca   180
gcgggtagtc tgatcgttgt ttgcgtcaca gatcatcgtg cggtgcgcga actgctggaa   240
ccacttggcg atgcactgcc aggtcgcgtt ctggtcaacc tgacgagcgg tacgtcgcgt   300
gaagcccgtg agaacgcaga acatactgcg gctcagggag ccacctacct ggatggtgtg   360
attctgacca ttccaagcgg cattggcacc ccagaagcta cgattctgta ttcgggaccg   420
cgcagtacct tcgatgaaca tgaaagcgca ctgcgcgcat aggtccgggg gcgacctttt   480
gtaggggaag atcacggact ggctaacctg tatgatgcag caatgttgag cgtgatgtgg   540
ggcctgctga atggtttcct gcatggaacc gcactgctgg aaccgcgggg cgtttcggca   600
acctctgtgg ttccgatgct gggtcaaggt tgggaagcgg tgactggtat aattgcgcgc   660
tacgcagatc agattgatgc cggtgtctat ccagcagacg atgccacgat tgatacccag   720
cgtgctgcaa tgcagcacct ggtcgaggag agccgtgcgg cgggcatcaa tggcgaactt   780
ccggcgtttg tgaccaaact ggccgatcgc gcagtggcag aaggtcgtgg tggtgactct   840
tacgctgcac tgattgaaca gtttcgcaag tcagcttaa                         879
```

<210> SEQ ID NO 182
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 182

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140
```

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Leu
            165                 170                 175

Ser Val Met Trp Gly Leu Leu Asn Gly Phe Leu His Gly Thr Ala Leu
        180                 185                 190

Leu Gly Thr Ala Gly Val Ser Ala Thr Ser Val Val Pro Met Leu Gly
    195                 200                 205

Gln Gly Trp Glu Ala Val Thr Gly Ile Ile Ala Arg Tyr Ala Asp Gln
210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 183
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 183

```
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ggattctgta ttcgggaccg     420
cgcagtacct tcgatgaaca tgaaagcgca ctgcgcgcat taggtccggg ggcgacccttt   480
gtagggggaag atcacggact ggctgcactg tatgatgcag caatgttgag cgtgatgtgg     540
ggcctgctga atggtttcct gcatggaacc gcactgctgg aaccgcgggg cgtttcggca     600
acctctgtgg ttccgatgct gggtcaaggt tgggaagcga tgactggttg gattgcgcgc     660
tacgcagatc agattgatgc cggtgtctat ccagcagacg atgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                            879
```

<210> SEQ ID NO 184
<211> LENGTH: 292
<212> TYPE: PRT
<213> ORGANISM: Artificial Sequence
<220> FEATURE:
<223> OTHER INFORMATION: Imine reductase variant from Pseudonocardia -continued spinosispora

<400> SEQUENCE: 184

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Arg Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Met Thr Gly Trp Ile Ala Arg Tyr Ala Asp Gln
    210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 185
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 185
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240

```
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacca ttccaagcgg cattggcacc ccagaagcta ggattctgta ttcgggaccg    420
cgcagtacct tcgatgaaca tgaaagcgca ctgcgcgcat taggtccggg ggcgaccttt    480 gtagggaag atcacggact ggctgccctg tatgatgcag caatgtcgag cgtgatgtgg    540
ggcctgctga atggtttcct gcatggaacc gcactgctgg gaaccgcggg cgtttcggca    600
acctctgtgg ttccgatgct gggtcaaggt tgggaagcga tgactggttg gattgcgcgc    660
tacgcagatc agattgatgc cggtgtctat ccagcagacg atgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcaa aggtcgtgg tggtgactct    840 tacgctgcac tgattgaaca gtttcgcaag tcagcttaa                           879
```

<210> SEQ ID NO 186
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 186

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Arg Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Ser
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Met Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240
```

```
Arg Ala Ala Met Gln His Leu Val Glu Glu Ser Arg Ala Ala Gly Ile
            245                 250                 255

Asn Gly Glu Leu Pro Ala Phe Val Thr Lys Leu Ala Asp Arg Ala Val
        260                 265                 270

Ala Glu Gly Arg Gly Gly Asp Ser Tyr Ala Ala Leu Ile Glu Gln Phe
    275                 280                 285

Arg Lys Ser Ala
    290
```

<210> SEQ ID NO 187
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 187

```
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt tgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta cgattctgta ttcgggaccg     420
cgcagtacct tcgatgaaca tgaaagcgca ctgcgcgcat taggtccggg ggcgaccttt     480
gtaggggaag atcacggact ggctaacctg tatgatgcag caatgtcgag cgtgatgtgg     540
ggcctgctga atggtttcct gcatggaacc gcactgctgg gaaccgcggg cgtttcggca     600
acctctgtgg ttccgatgct gggtcaaggt ctagaagcga tgactggtat aattgcgcgc     660
tacgcagatc agattgatgc cggtgtctat ccagcagacg atgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                            879
```

<210> SEQ ID NO 188
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 188

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80
```

Pro Leu Gly Asp Ala Leu Pro Gly Arg Val Leu Asn Leu Thr Ser
            85                  90                  95

Gly Thr Ser Arg Glu Ala Arg Glu Asn Ala Glu His Thr Ala Ala Gln
        100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Leu Glu Ala Met Thr Gly Ile Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 189
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 189
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta cgattctgta ttcgggaccg     420
cgcagtacct tcgatgaaca tgaaagcgca ctgcgcgcat taggtccggg ggcgaccttt     480
gtaggggaag atcacggact ggctaacctg tatgatgcag caatgttgag catgatgtgg     540
ggcctgctga atggtttcct gcatggaacc gcactgctgg aaccgcgggc gtttcggca     600 acctctgtgg ttccgatgct gggtcaaggt atagaagcgg tgactggttg gattgcgcgc     660
tacgcagatc agattgatgc cggtgtctat ccagcagacc tcgccacgat tgatacccag     720
cgtgctgcaa tgcagcacct ggtcgaggag agccgtgcgg cgggcatcaa tggcgaactt     780

```
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 190
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 190

| | | | | | | | | | | | | | | |
|---|---|---|---|---|---|---|---|---|---|---|---|---|---|---|
| Met | Ser | Asp | Ser | Pro | Val | Pro | Val | Thr | Val | Leu | Gly | Leu | Gly | Met |
| 1 | | | | 5 | | | | | 10 | | | | | 15 |
| Gly | Gln | Ala | Leu | Ala | Gly | Ala | Phe | Leu | Ala | Ala | Gly | His | Pro | Thr | Thr |
| | | | 20 | | | | | 25 | | | | | 30 | | |
| Val | Trp | Asn | Arg | Ser | Ala | Ala | Lys | Ala | Asp | Glu | Leu | Val | Gly | Arg | Gly |
| | | | 35 | | | | | 40 | | | | | 45 | | |
| Ala | Thr | Leu | Ala | Ala | Ser | Pro | Ala | Ala | Val | Ala | Ala | Gly | Ser | Leu |
| 50 | | | | | 55 | | | | | 60 | | | | |
| Ile | Val | Val | Cys | Val | Thr | Asp | His | Arg | Ala | Val | Arg | Glu | Leu | Leu | Glu |
| 65 | | | | | 70 | | | | | 75 | | | | | 80 |
| Pro | Leu | Gly | Asp | Ala | Leu | Pro | Gly | Arg | Val | Leu | Val | Asn | Leu | Thr | Ser |
| | | | | 85 | | | | | 90 | | | | | 95 | |
| Gly | Thr | Ser | Arg | Glu | Ala | Arg | Glu | Asn | Ala | Glu | His | Thr | Ala | Ala | Gln |
| | | | | 100 | | | | | 105 | | | | | 110 | |
| Gly | Ala | Thr | Tyr | Leu | Asp | Gly | Val | Ile | Leu | Thr | Ile | Pro | Ser | Gly | Ile |
| | | | 115 | | | | | 120 | | | | | 125 | | |
| Gly | Thr | Pro | Glu | Ala | Thr | Ile | Leu | Tyr | Ser | Gly | Pro | Arg | Ser | Thr | Phe |
| | 130 | | | | | 135 | | | | | 140 | | | | |
| Asp | Glu | His | Glu | Ser | Ala | Leu | Arg | Ala | Leu | Gly | Pro | Gly | Ala | Thr | Phe |
| 145 | | | | | 150 | | | | | 155 | | | | | 160 |
| Val | Gly | Glu | Asp | His | Gly | Leu | Ala | Asn | Leu | Tyr | Asp | Ala | Ala | Met | Leu |
| | | | | 165 | | | | | 170 | | | | | 175 | |
| Ser | Met | Met | Trp | Gly | Leu | Leu | Asn | Gly | Phe | Leu | His | Gly | Thr | Ala | Leu |
| | | | 180 | | | | | 185 | | | | | 190 | | |
| Leu | Gly | Thr | Ala | Gly | Val | Ser | Ala | Thr | Ser | Val | Val | Pro | Met | Leu | Gly |
| | | | 195 | | | | | 200 | | | | | 205 | | |
| Gln | Gly | Ile | Glu | Ala | Val | Thr | Gly | Trp | Ile | Ala | Arg | Tyr | Ala | Asp | Gln |
| | 210 | | | | | 215 | | | | | 220 | | | | |
| Ile | Asp | Ala | Gly | Val | Tyr | Pro | Ala | Asp | Leu | Ala | Thr | Ile | Asp | Thr | Gln |
| 225 | | | | | 230 | | | | | 235 | | | | | 240 |
| Arg | Ala | Ala | Met | Gln | His | Leu | Val | Glu | Glu | Ser | Arg | Ala | Ala | Gly | Ile |
| | | | | 245 | | | | | 250 | | | | | 255 | |
| Asn | Gly | Glu | Leu | Pro | Ala | Phe | Val | Thr | Lys | Leu | Ala | Asp | Arg | Ala | Val |
| | | | 260 | | | | | 265 | | | | | 270 | | |
| Ala | Glu | Gly | Arg | Gly | Gly | Asp | Ser | Tyr | Ala | Ala | Leu | Ile | Glu | Gln | Phe |
| | | | 275 | | | | | 280 | | | | | 285 | | |
| Arg | Lys | Ser | Ala |
| | 290 | | |

<210> SEQ ID NO 191
<211> LENGTH: 879
<212> TYPE: DNA
<213> ORGANISM: Artificial Sequence
<220> FEATURE:
<223> OTHER INFORMATION: Imine reductase variant from Pseudonocardia spinosispora

<400> SEQUENCE: 191

```
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat taggtccggg gcgaccttt      480
gtagggaag atcacggact ggctaacctg tatgatgcag caatgtcgag cattatgtgg     540
ggcctgctga atggtttcct gcatggaacc gcactgctgg aaccgcggg cgtttcggca     600
acctctgtgg ttccgatgct gggtcaaggt tgggaagcgg tgactggtct aattgcgcgc     660
tacgcagatc agattgatgc cggtgtctat ccagcagacg atgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                            879
```

<210> SEQ ID NO 192
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 192

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Ile Met Trp Gly Leu Leu Asn Gly Phe Leu His Gly Thr Ala Leu
```

```
                 180                 185                 190
Leu Gly Thr Ala Gly Val Ser Ala Thr Ser Val Val Pro Met Leu Gly
            195                 200                 205

Gln Gly Trp Glu Ala Val Thr Gly Leu Ile Ala Arg Tyr Ala Asp Gln
        210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 193
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 193
atgagtgatt cacctgtgcc cgtgacagtt ctgggtcttg gtctgatggg tcaggcctta     60 gcggagcgt ttctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacca ttccaagcgg cattggcacc ccagaagcta cgattctgta ttcgggaccg    420
cgcagtacct tcgatgaaca tgaaagcgca ctgcgcgcat taggtccggg ggcgacctt     480 gtaggggaag atcacggact ggctaacctg tatgatgcag caatgtcgag cattatgtgg    540
ggcctgctga atggtttcct gcatggaacc gcactgctgg aaccgcgggg cgtttcggca    600
acctctgtgg ttccgatgct gggtcaaggt tgggaagcga tgactggtct aattgcgcgc    660
tacgcagatc agattgatgc cggtgtctat ccagcagacg atgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879

<210> SEQ ID NO 194
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 194

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
```

```
                     20                  25                  30
Val Trp Asn Arg Ser Ala Ala Lys Ala Asp Glu Leu Val Gly Arg Gly
                 35                  40                  45
Ala Thr Leu Ala Ala Ser Pro Ala Ala Val Ala Ala Gly Ser Leu
             50                  55                  60
Ile Val Val Cys Val Thr Asp His Arg Ala Val Arg Glu Leu Leu Glu
 65                  70                  75                  80
Pro Leu Gly Asp Ala Leu Pro Gly Arg Val Leu Val Asn Leu Thr Ser
                 85                  90                  95
Gly Thr Ser Arg Glu Ala Arg Glu Asn Ala Glu His Thr Ala Ala Gln
                100                 105                 110
Gly Ala Thr Tyr Leu Asp Gly Val Ile Leu Thr Ile Pro Ser Gly Ile
                115                 120                 125
Gly Thr Pro Glu Ala Thr Ile Leu Tyr Ser Gly Pro Arg Ser Thr Phe
                130                 135                 140
Asp Glu His Glu Ser Ala Leu Arg Ala Leu Gly Pro Gly Ala Thr Phe
145                 150                 155                 160
Val Gly Glu Asp His Gly Leu Ala Asn Leu Tyr Asp Ala Ala Met Ser
                165                 170                 175
Ser Ile Met Trp Gly Leu Leu Asn Gly Phe Leu His Gly Thr Ala Leu
                180                 185                 190
Leu Gly Thr Ala Gly Val Ser Ala Thr Ser Val Val Pro Met Leu Gly
                195                 200                 205
Gln Gly Trp Glu Ala Met Thr Gly Leu Ile Ala Arg Tyr Ala Asp Gln
                210                 215                 220
Ile Asp Ala Gly Val Tyr Pro Ala Asp Ala Thr Ile Asp Thr Gln
225                 230                 235                 240
Arg Ala Ala Met Gln His Leu Val Glu Glu Ser Arg Ala Ala Gly Ile
                245                 250                 255
Asn Gly Glu Leu Pro Ala Phe Val Thr Lys Leu Ala Asp Arg Ala Val
                260                 265                 270
Ala Glu Gly Arg Gly Gly Asp Ser Tyr Ala Ala Leu Ile Glu Gln Phe
                275                 280                 285
Arg Lys Ser Ala
    290

<210> SEQ ID NO 195
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 195
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat taggtccggg ggcgaccttt     480
```

```
gtaggggaag atcacggact ggctgcactg tatgatgcag caatgctgag cgtcatgtgg    540
ggcctgctga atggtttcct gcatggaacc gcactgctgg gaaccgcggg cgtttcggca    600
acctctgtgg ttccgatgct gggtcaaggt tgggaagcgg tgactggttg gattgcgcgc    660
tacgcagatc agattgatgc cggtgtctat ccagcagacc tcgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcaa aggtcgtgg tggtgactct    840 tacgctgcac tgattgaaca gtttcgcaag tcagcttaa                           879
```

<210> SEQ ID NO 196
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora
<400> SEQUENCE: 196

```
Met Ser Asp Ser Pro Val Pro Val Thr Val Leu Gly Leu Gly Leu Met
 1               5                  10                  15

Gly Gln Ala Leu Ala Gly Ala Phe Leu Ala Ala Gly His Pro Thr Thr
             20                  25                  30

Val Trp Asn Arg Ser Ala Ala Lys Ala Asp Glu Leu Val Gly Arg Gly
         35                  40                  45

Ala Thr Leu Ala Ala Ser Pro Ala Ala Val Ala Ala Gly Ser Leu
     50                  55                  60

Ile Val Val Cys Val Thr Asp His Arg Ala Val Arg Glu Leu Leu Glu
 65                  70                  75                  80

Pro Leu Gly Asp Ala Leu Pro Gly Arg Val Leu Val Asn Leu Thr Ser
                 85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Val Thr Gly Trp Ile Ala Arg Tyr Ala Asp Gln
    210                 215                 220

Ile Asp Ala Gly Val Tyr Pro Ala Asp Leu Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285
```

Arg Lys Ser Ala
        290

<210> SEQ ID NO 197
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 197

```
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctgccctg tatgatgcag caatgtcgag cgtgatgtgg     540
ggcctgctga atggtttcct gcatggaacc gcactgctgg gaaccgcggg cgtttcggca     600
acctctgtgg ttccgatgct gggtcaaggt atagaagcga tgactggtct aattgcgcgc     660
tacgcagatc agattgatgc cggtgtctat ccagcagacg atgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                           879
```

<210> SEQ ID NO 198
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 198

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Ser
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Met Thr Gly Leu Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 199
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 199
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacca ttccaagcgg cattggcacc ccagaagcta cgattctgta ttcgggaccg    420
cgcagtacct tcgatgaaca tgaaagcgca ctgcgcgcat taggtccggg ggcgaccttt    480
gtaggggaag atcacggact ggctgccctg tatgatgcag caatgtcgag cattatgtgg    540
ggcctgctga atggtttcct gcatggaacc gcactgctgg aaccgcgggg cgtttcggca    600
acctctgtgg ttccgatgct gggtcaaggt tgggaagcgg tgttgggtct aattgcgcgc    660
tacgcagatc agattgatgc cggtgtctat ccagcagacg atgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879

<210> SEQ ID NO 200
<211> LENGTH: 292
<212> TYPE: PRT

<213> ORGANISM: Artificial Sequence
<220> FEATURE:
<223> OTHER INFORMATION: Imine reductase variant from Pseudonocardia spinosispora

<400> SEQUENCE: 200

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Ser
                165                 170                 175

Ser Ile Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Val Leu Gly Leu Ile Ala Arg Tyr Ala Asp Gln
    210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

<210> SEQ ID NO 201
<211> LENGTH: 879
<212> TYPE: DNA
<213> ORGANISM: Artificial Sequence
<220> FEATURE:
<223> OTHER INFORMATION: Imine reductase variant from Pseudonocardia spinosispora

<400> SEQUENCE: 201

| | | |
|---|---|---|
| atgagtgatt cacctgtgcc cgtgacagtt ctgggtcttg gtctgatggg tcaggcctta | | 60 |
| gcgggagcgt ttctggcagc cggtcaccct acgacggttt ggaatcgcag cgcagctaaa | | 120 |

```
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacca ttccaagcgg cattggcacc ccagaagcta cgattctgta ttcgggaccg    420
cgcagtacct tcgatgaaca tgaaagcgca ctgcgcgcat taggtccggg ggcgaccttt    480
gtaggggaag atcacggact ggctgccctg tatgatgcag caatgtcgag cattatgtgg    540
ggcctgctga atggtttcct gcatggaacc gcactgctgg aaccgcgggt cgtttcggca    600
acctctgtgg ttccgatgct gggtcaaggt tgggaagcgg tgactggtat aattgcgcgc    660
tacgcagatc agattgatgc cggtgtctat ccagcagacg atgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 202
<211> LENGTH: 292
<212> TYPE: PRT
<213> ORGANISM: Artificial Sequence
<220> FEATURE:
<223> OTHER INFORMATION: Imine reductase variant from Pseudonocardia
    spinosispora

<400> SEQUENCE: 202

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Ser
                165                 170                 175

Ser Ile Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Val Thr Gly Ile Ile Ala Arg Tyr Ala Asp Gln
    210                 215                 220
```

```
Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
            245                 250                 255

Asn Gly Glu Leu Pro Ala Phe Val Thr Lys Leu Ala Asp Arg Ala Val
        260                 265                 270

Ala Glu Gly Arg Gly Gly Asp Ser Tyr Ala Ala Leu Ile Glu Gln Phe
    275                 280                 285

Arg Lys Ser Ala
    290

<210> SEQ ID NO 203
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 203
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta cgattctgta ttcgggaccg     420
cgcagtacct tcgatgaaca tgaaagcgca ctgcgcgcat taggtccggg ggcgaccttt     480 gtagggaag atcacggact ggctaacctg tatgatgcag caatgtcgag catgatgtgg     540
ggcctgctga atggtttcct gcatggaacc gcactgctgg aaccgcgggg cgtttcggca     600
acctctgtgg ttccgatgct gggtcaaggt atcgaagcgg tgaccggttg gattgcgcgc     660
tacgcagatc agattgatgc cggtgtctat ccagcagacg atgccacgat tgatacccag     720
cgtgctgcaa tgcagcacct ggtcgaggag agccgtgcgc gggcatcaa tggcgaactt     780 ccggcgtttg tgaccaaact ggccgatcgc gcagtggcag aaggtcgtgg tggtgactct     840
tacgctgcac tgattgaaca gtttcgcaag tcagcttaa                           879

<210> SEQ ID NO 204
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 204

Met Ser Asp Ser Pro Val Pro Val Thr Val Leu Gly Leu Gly Leu Met
1               5                   10                  15

Gly Gln Ala Leu Ala Gly Ala Phe Leu Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60
```

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
            85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
            115                 120                 125

Gly Thr Pro Glu Ala Thr Ile Leu Tyr Ser Gly Pro Arg Ser Thr Phe
        130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Met Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Thr Gly Trp Ile Ala Arg Tyr Ala Asp Gln
210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 205
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 205
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacca ttccaagcgg cattggcacc ccagaagcta cgattctgta ttcgggaccg    420
cgcagtacct cgatgaaca tgaaagcgca ctgcgcgcat aggtccgggg gcgaccttt    480 gtaggggaag atcacggact ggctaacctg tatgatgcag caatgttgag cattatgtgg    540
ggcctgctga atggtttcct gcatggaacc gcactgctgg gaaccgcggg cgtttcggca    600
acctctgtgg ttccgatgct gggtcaaggt atcgaagcgg tgactggtat aattgcgcgc    660
tacgcagatc agattgatgc cggtgtctat ccagcagacg acgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879

<210> SEQ ID NO 206
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 206

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Leu
                165                 170                 175

Ser Ile Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Thr Gly Ile Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 207
<211> LENGTH: 879
<212> TYPE: DNA

<213> ORGANISM: Artificial Sequence
<220> FEATURE:
<223> OTHER INFORMATION: Imine reductase variant from Pseudonocardia spinosispora

<400> SEQUENCE: 207

| | | | | | |
|---|---|---|---|---|---|
| atgagtgatt | cacctgtgcc | cgtgacagtt | ctgggtcttg | gtctgatggg | tcaggcctta | 60 |
| gcgggagcgt | ttctggcagc | cggtcaccct | acgacggttt | ggaatcgcag | cgcagctaaa | 120 |
| gctgatgaac | tggttggtcg | cggtgcaacc | ctggccgcgt | ctcccgcggc | tgccgtcgca | 180 |
| gcgggtagtc | tgatcgttgt | ttgcgtcaca | gatcatcgtg | cggtgcgcga | actgctggaa | 240 |
| ccacttggcg | atgcactgcc | aggtcgcgtt | ctggtcaacc | tgacgagcgg | tacgtcgcgt | 300 |
| gaagcccgtg | agaacgcaga | acatactgcg | gctcagggag | ccacctacct | ggatggtgtg | 360 |
| attctgacca | ttccaagcgg | cattggcacc | ccagaagcta | ggattctgta | ttcgggaccg | 420 |
| cgcagtacct | tcgatgaaca | tgaaagcgca | ctgcgcgcat | taggtccggg | ggcgaccttt | 480 |
| gtaggggaag | atcacggact | ggctaacctg | tatgatgcag | caatgtcgag | cattatgtgg | 540 |
| ggcctgctga | atggtttcct | gcatggaacc | gcactgctgg | aaccgcgggg | cgtttcggca | 600 |
| acctctgtgg | ttccgatgct | gggtcaaggt | tgggaagcgg | tgactggttg | gattgcgcgc | 660 |
| tacgcagatc | agattgatgc | cggtgtctat | ccagcagacg | atgccacgat | tgatacccag | 720 |
| cgtgctgcaa | tgcagcacct | ggtcgaggag | agccgtgcgg | cgggcatcaa | tggcgaactt | 780 |
| ccggcgtttg | tgaccaaact | ggccgatcgc | gcagtggcag | aaggtcgtgg | tggtgactct | 840 |
| tacgctgcac | tgattgaaca | gtttcgcaag | tcagcttaa | | | 879 |

<210> SEQ ID NO 208
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 208

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Arg Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser

```
            165                 170                 175
Ser Ile Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

<210> SEQ ID NO 209
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 209

```
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctaacctg tatgatgcag caatgttgag cgtgatgtgg     540
ggcctgctga atggtttcct gcatggaacc gcactgctgg aaccgcgggg cgtttcggca     600
acctctgtgg ttccgatgct gggtcaaggt tgggaagcga tgttgggttg gattgcgcgc     660
tacgcagatc agattgatgc cggtgtctat ccagcagacg acgccacgat tgatacccag     720
cgtgctgcaa tgcagcacct ggtcgaggag agccgtgccg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                            879
```

<210> SEQ ID NO 210
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 210

Met Ser Asp Ser Pro Val Pro Val Thr Val Leu Gly Leu Gly Leu Met

```
              1               5                  10                 15
            Gly Gln Ala Leu Ala Gly Ala Phe Leu Ala Ala Gly His Pro Thr Thr
                           20                  25                  30
            Val Trp Asn Arg Ser Ala Ala Lys Ala Asp Glu Leu Val Gly Arg Gly
                           35                  40                  45
            Ala Thr Leu Ala Ala Ser Pro Ala Ala Val Ala Gly Ser Leu
              50                  55                  60
            Ile Val Val Cys Val Thr Asp His Arg Ala Val Arg Glu Leu Leu Glu
             65                  70                  75                  80
            Pro Leu Gly Asp Ala Leu Pro Gly Arg Val Leu Val Asn Leu Thr Ser
                           85                  90                  95
            Gly Thr Ser Arg Glu Ala Arg Glu Asn Ala Glu His Thr Ala Ala Gln
                          100                 105                 110
            Gly Ala Thr Tyr Leu Asp Gly Val Ile Leu Thr Ile Pro Ser Gly Ile
                          115                 120                 125
            Gly Thr Pro Glu Ala Thr Ile Leu Tyr Ser Gly Pro Arg Ser Thr Phe
                          130                 135                 140
            Asp Glu His Glu Ser Ala Leu Arg Ala Leu Gly Pro Gly Ala Thr Phe
            145                 150                 155                 160
            Val Gly Glu Asp His Gly Leu Ala Asn Leu Tyr Asp Ala Ala Met Leu
                          165                 170                 175
            Ser Val Met Trp Gly Leu Leu Asn Gly Phe Leu His Gly Thr Ala Leu
                          180                 185                 190
            Leu Gly Thr Ala Gly Val Ser Ala Thr Ser Val Val Pro Met Leu Gly
                          195                 200                 205
            Gln Gly Trp Glu Ala Met Leu Gly Trp Ile Ala Arg Tyr Ala Asp Gln
                          210                 215                 220
            Ile Asp Ala Gly Val Tyr Pro Ala Asp Asp Ala Thr Ile Asp Thr Gln
            225                 230                 235                 240
            Arg Ala Ala Met Gln His Leu Val Glu Glu Ser Arg Ala Ala Gly Ile
                          245                 250                 255
            Asn Gly Glu Leu Pro Ala Phe Val Thr Lys Leu Ala Asp Arg Ala Val
                          260                 265                 270
            Ala Glu Gly Arg Gly Gly Asp Ser Tyr Ala Ala Leu Ile Glu Gln Phe
                          275                 280                 285
            Arg Lys Ser Ala
                          290

<210> SEQ ID NO 211
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 211
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
```

```
attctgacca ttccaagcgg cattggcacc ccagaagcta ccattctgta ttcgggaccg    420
cgcagtacct tcgatgaaca tgaaagcgca ctgcgcgcat taggtccggg ggcgaccttt    480 gtagggaag atcacggact ggctgccctg tatgatgcag caatgttgag cattatgtgg     540
ggcctgctga atggtttcct gcatggaacc gcactgctgg gaaccgcggg cgtttcggca    600
acctctgtgg ttccgatgct gggtcaaggt atcgaagcgg tgatgggttg gattgcgcgc    660
tacgcagatc agattgatgc cggtgtctat ccagcagacg atgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                          879
```

<210> SEQ ID NO 212
<211> LENGTH: 292
<212> TYPE: PRT
<213> ORGANISM: Artificial Sequence
<220> FEATURE:
<223> OTHER INFORMATION: Imine reductase variant from Pseudonocardia
    spinosispora

<400> SEQUENCE: 212

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Ile Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Ile Glu Ala Val Met Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270
```

Ala Glu Gly Arg Gly Gly Asp Ser Tyr Ala Ala Leu Ile Glu Gln Phe
            275                 280                 285

Arg Lys Ser Ala
    290

<210> SEQ ID NO 213
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 213
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ggattctgta ttcgggaccg     420
cgcagtacct tcgatgaaca tgaaagcgca ctgcgcgcat taggtccggg ggcgacctttt    480 gtaggggaag atcacggact ggctaacctg tatgatgcag caatgtcgag cgtgatgtgg     540
ggcctgctga atggtttcct gcatggaacc gcactgctgg gaaccgcggg cgtttcggca     600
acctctgtgg ttccgatgct gggtcaaggt ctagaagcgg tgatgggtat aattgcgcgc     660
tacgcagatc agattgatgc cggtgtctat ccagcagacc tcgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcaa aggtcgtgg tggtgactct     840 tacgctgcac tgattgaaca gtttcgcaag tcagcttaa                            879

<210> SEQ ID NO 214
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 214

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Arg Ile Leu Tyr Ser Gly Pro Arg Ser Thr Phe
        130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Leu Glu Ala Val Met Gly Ile Ile Ala Arg Tyr Ala Asp Gln
        210                 215                 220

Ile Asp Ala Gly Val Tyr Pro Ala Asp Leu Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
        290

<210> SEQ ID NO 215
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 215
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta cgattctgta ttcgggaccg     420
cgcagtacct tcgatgaaca tgaaagcgca ctgcgcgcat taggtccggg ggcgaccttt     480
gtaggggaag atcacggact ggctaacctg tatgatgcag caatgtcgag cgtgatgtgg     540
ggcctgctga atggtttcct gcatggaacc gcactgctgg gaaccgcggg cgtttcggca     600
acctctgtgg ttccgatgct gggtcaaggt tgggaagcga tgttgggttg gattgcgcgc     660
tacgcagatc agattgatgc cggtgtctat ccagcagacc tcgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                           879

```
<210> SEQ ID NO 216
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 216

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Met Leu Gly Trp Ile Ala Arg Tyr Ala Asp Gln
    210                 215                 220

Ile Asp Ala Gly Val Tyr Pro Ala Asp Leu Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 217
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 217
atgagtgatt cacctgtgcc cgtgacagtt ctgggtcttg gtctgatggg tcaggcctta     60
```

```
gcgggagcgt tctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacca ttccaagcgg cattggcacc ccagaagcta cgattctgta ttcgggaccg    420
cgcagtacct tcgatgaaca tgaaagcgca ctgcgcgcat taggtccggg ggcgaccttt    480
gtaggggaag atcacggact ggctgccctg tatgatgcag caatgttgag catgatgtgg    540
ggcctgctga atggtttcct gcatggaacc gcactgctgg aaccgcgggg cgtttcggca    600
acctctgtgg ttccgatgct gggtcaaggt ctagaagcga tgactggttg gattgcgcgc    660
tacgcagatc agattgatgc cggtgtctat ccagcagacg acgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                          879
```

<210> SEQ ID NO 218
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 218

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Met Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205
```

```
Gln Gly Leu Glu Ala Met Thr Gly Trp Ile Ala Arg Tyr Ala Asp Gln
    210                 215                 220
Ile Asp Ala Gly Val Tyr Pro Ala Asp Ala Thr Ile Asp Thr Gln
225                 230                 235                 240
Arg Ala Ala Met Gln His Leu Val Glu Ser Arg Ala Ala Gly Ile
                245                 250                 255
Asn Gly Glu Leu Pro Ala Phe Val Thr Lys Leu Ala Asp Arg Ala Val
                260                 265                 270
Ala Glu Gly Arg Gly Gly Asp Ser Tyr Ala Ala Leu Ile Glu Gln Phe
            275                 280                 285
Arg Lys Ser Ala
    290
```

```
<210> SEQ ID NO 219
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 219
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta cgattctgta ttcgggaccg     420
cgcagtacct tcgatgaaca tgaaagcgca ctgcgcgcat taggtccggg ggcgaccttt     480
gtaggggaag atcacggact ggctgcactg tatgatgcag caatgtcgag cgttatgtgg     540
ggcctgctga tggtttcct gcatggaacc gcactgctgg gaaccgcggg cgtttcggca     600
acctctgtgg ttccgatgct gggtcaaggt ctagaagcga tgactggttg gattgcgcgc     660
tacgcagatc agattgatgc cggtgtctat ccagcagacg atgccacgat tgatacccag     720
cgtgctgcaa tgcagcaccT ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                           879
```

```
<210> SEQ ID NO 220
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 220

Met Ser Asp Ser Pro Val Pro Val Thr Val Leu Gly Leu Gly Leu Met
1               5                   10                  15
Gly Gln Ala Leu Ala Gly Ala Phe Leu Ala Ala Gly His Pro Thr Thr
            20                  25                  30
Val Trp Asn Arg Ser Ala Ala Lys Ala Asp Glu Leu Val Gly Arg Gly
        35                  40                  45
```

```
Ala Thr Leu Ala Ala Ser Pro Ala Ala Ala Val Ala Ala Gly Ser Leu
     50                  55                  60

Ile Val Val Cys Val Thr Asp His Arg Ala Val Arg Glu Leu Leu Glu
 65                  70                  75                  80

Pro Leu Gly Asp Ala Leu Pro Gly Arg Val Leu Val Asn Leu Thr Ser
                 85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
            115                 120                 125

Gly Thr Pro Glu Ala Thr Ile Leu Tyr Ser Gly Pro Arg Ser Thr Phe
130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Ser
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
            195                 200                 205

Gln Gly Leu Glu Ala Met Thr Gly Trp Ile Ala Arg Tyr Ala Asp Gln
210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
            275                 280                 285

Arg Lys Ser Ala
290

<210> SEQ ID NO 221
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 221
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ggattctgta ttcgggaccg     420
cgcagtacct tcgatgaaca tgaaagcgca ctgcgcgcat aggtccgggg gcgaccttt     480 gtaggggaag atcacggact ggctaacctg tatgatgcag caatgtcgag catgatgtgg     540
ggcctgctga atggtttcct gcatggaacc gcactgctgg aaccgcgggg cgtttcggca     600
```

-continued

```
acctctgtgg ttccgatgct gggtcaaggt ctagaagcgg tgactggtct aattgcgcgc    660
tacgcagatc agattgatgc cggtgtctat ccagcagacg atgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 222
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 222

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Arg Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Met Met Trp Gly Leu Leu Asn Gly Phe Leu His Gly Thr Ala Leu
            180                 185                 190

Leu Gly Thr Ala Gly Val Ser Ala Thr Ser Val Pro Met Leu Gly
        195                 200                 205

Gln Gly Leu Glu Ala Val Thr Gly Leu Ile Ala Arg Tyr Ala Asp Gln
    210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

-continued

```
<210> SEQ ID NO 223
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 223
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc cagaagcta ggattctgta ttcgggaccg      420
cgcagtacct tcgatgaaca tgaaagcgca ctgcgcgcat taggtccggg ggcgaccttt     480
gtaggggaag atcacggact ggctaacctg tatgatgcag caatgttgag cgttatgtgg     540
ggcctgctga atggtttcct gcatggaacc gcactgctgg gaaccgcggg cgtttcggca     600
acctctgtgg ttccgatgct gggtcaaggt tgggaagcgg tgactggtct aattgcgcgc     660
tacgcagatc agattgatgc cggtgtctat ccagcagacg atgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                            879

<210> SEQ ID NO 224
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 224

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Arg Ile Leu Tyr Ser Gly Pro Arg Ser Thr Phe
    130                 135                 140

Asp Glu His Glu Ser Ala Leu Arg Ala Leu Gly Pro Gly Ala Thr Phe
```

```
                145                 150                 155                 160
Val Gly Glu Asp His Gly Leu Ala Asn Leu Tyr Asp Ala Ala Met Leu
                    165                 170                 175

Ser Val Met Trp Gly Leu Leu Asn Gly Phe Leu His Gly Thr Ala Leu
                    180                 185                 190

Leu Gly Thr Ala Gly Val Ser Ala Thr Ser Val Val Pro Met Leu Gly
                    195                 200                 205

Gln Gly Trp Glu Ala Val Thr Gly Leu Ile Ala Arg Tyr Ala Asp Gln
                    210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                    245                 250                 255

Asn Gly Glu Leu Pro Ala Phe Val Thr Lys Leu Ala Asp Arg Ala Val
                    260                 265                 270

Ala Glu Gly Arg Gly Gly Asp Ser Tyr Ala Ala Leu Ile Glu Gln Phe
                    275                 280                 285

Arg Lys Ser Ala
        290
```

<210> SEQ ID NO 225
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 225

| | | |
|---|---|---|
| atgagtgatt cacctgtgcc cgtgacagtt ctgggtcttg gtctgatggg tcaggcctta | 60 |
| gcgggagcgt ttctggcagc cggtcaccct acgacggttt ggaatcgcag cgcagctaaa | 120 |
| gctgatgaac tggttggtcg cggtgcaacc ctggccgcgt ctcccgcggc tgccgtcgca | 180 |
| gcgggtagtc tgatcgttgt ttgcgtcaca gatcatcgtg cggtgcgcga actgctggaa | 240 |
| ccacttggcg atgcactgcc aggtcgcgtt ctggtcaacc tgacgagcgg tacgtcgcgt | 300 |
| gaagcccgtg agaacgcaga acatactgcg gctcagggag ccacctacct ggatggtgtg | 360 |
| attctgacca ttccaagcgg cattggcacc ccagaagcta cgattctgta ttcgggaccg | 420 |
| cgcagtacct tcgatgaaca tgaaagcgca ctgcgcgcat aggtccgggg gcgaccttt | 480 |
| gtaggggaag atcacggact ggctaacctg tatgatgcag caatgtcgag cgttatgtgg | 540 |
| ggcctgctga atggtttcct gcatggaacc gcactgctgg aaccgcgggc gtttcggca | 600 |
| acctctgtgg ttccgatgct gggtcaaggt tgggaagcgg tgactggtat aattgcgcgc | 660 |
| tacgcagatc agattgatgc cggtgtctat ccagcagacg atgccacgat tgatacccag | 720 |
| cgtgctgcaa tgcagcacct ggtcgaggag agccgtgcgg cgggcatcaa tggcgaactt | 780 |
| ccggcgtttg tgaccaaact ggccgatcgc gcagtggcag aaggtcgtgg tggtgactct | 840 |
| tacgctgcac tgattgaaca gtttcgcaag tcagcttaa | 879 |

<210> SEQ ID NO 226
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 226

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Val Thr Gly Ile Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 227
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 227
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300

```
gaagcccgtg agaacgcaga acatactgcg gctcagggag ccacctacct ggatggtgtg    360
attctgacca ttccaagcgg cattggcacc ccagaagcta cgattctgta ttcgggaccg    420
cgcagtacct tcgatgaaca tgaaagcgca ctgcgcgcat taggtccggg ggcgaccttt    480
gtaggggaag atcacggact ggctaacctg tatgatgcag caatgtcgag cattatgtgg    540
ggcctgctga atggtttcct gcatggaacc gcactgctgg gaaccgcggg cgtttcggca    600
acctctgtgg ttccgatgct gggtcaaggt ctagaagcga tgactggttg gattgcgcgc    660
tacgcagatc agattgatgc cggtgtctat ccagcagacg atgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                          879
```

<210> SEQ ID NO 228
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 228

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Ile Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Leu Glu Ala Met Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255
```

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 229
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 229

```
atgagtgatt cacctgtgcc cgtgacagtt ctgggtcttg gtctgatggg tcaggcctta    60
gcgggagcgt ttctggcagc cggtcaccct acgacggttt ggaatcgcag cgcagctaaa   120
gctgatgaac tggttggtcg cggtgcaacc ctggccgcgt ctcccgcggc tgccgtcgca   180
gcgggtagtc tgatcgttgt ttgcgtcaca gatcatcgtg cggtgcgcga actgctggaa   240
ccacttggcg atgcactgcc aggtcgcgtt ctggtcaacc tgacgagcgg tacgtcgcgt   300
gaagcccgtg agaacgcaga acatactgcg gctcagggag ccacctacct ggatggtgtg   360
attctgacca ttccaagcgg cattggcacc ccagaagcta ccattctgta ttcgggaccg   420
cgcagtacct tcgatgaaca tgaaagcgca ctgcgcgcat taggtccggg ggcgaccttt   480
gtaggggaag atcacggact ggctaacctg tatgatgcag caatgtcgag catgatgtgg   540
ggcctgctga tggtttcct gcatggaacc gcactgctgg aaccgcgggg cgtttcggca   600
acctctgtgg ttccgatgct gggtcaaggt tgggaagcga tgactggtat aattgcgcgc   660
tacgcagatc agattgatgc cggtgtctat ccagcagacg atgccacgat tgatacccag   720
cgtgctgcaa tgcagcacct ggtcgaggag agccgtgcgg cgggcatcaa tggcgaactt   780
ccggcgtttg tgaccaaact ggccgatcgc gcagtggcag aaggtcgtgg tggtgactct   840
tacgctgcac tgattgaaca gtttcgcaag tcagcttaa                          879
```

<210> SEQ ID NO 230
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 230

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

```
Gly Thr Ser Arg Glu Ala Arg Glu Asn Ala Glu His Thr Ala Ala Gln
                100                 105                 110

Gly Ala Thr Tyr Leu Asp Gly Val Ile Leu Thr Ile Pro Ser Gly Ile
            115                 120                 125

Gly Thr Pro Glu Ala Thr Ile Leu Tyr Ser Gly Pro Arg Ser Thr Phe
        130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Met Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Met Thr Gly Ile Ile Ala Arg Tyr Ala Asp Gln
    210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 231
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 231
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacca ttccaagcgg cattggcacc ccagaagcta ggattctgta ttcgggaccg    420
cgcagtacct cgatgaaca tgaaagcgca ctgcgcgcat taggtccggg gcgacctttc    480
gtaggggaag atcacggact ggctaacctg tatgatgcag caatgtcgag cattatgtgg    540
ggcctgctga atggtttcct gcatggaacc gcactgctgg aaccgcgggg cgtttcggca    600
acctctgtgg ttccgatgct gggtcaaggt ctagaagcga tgactggttg gattgcgcgc    660
tacgcagatc agattgatgc cggtgtctat ccagcagacg atgccacgat tgataccccag   720 cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
```
tacgctgcac tgattgaaca gtttcgcaag tcagcttaa                              879

<210> SEQ ID NO 232
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 232

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Arg Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Ile Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Leu Glu Ala Met Thr Gly Trp Ile Ala Arg Tyr Ala Asp Gln
    210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 233
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 233

```
atgagtgatt cacctgtgcc cgtgacagtt ctgggtcttg gtctgatggg tcaggcctta    60
gcgggagcgt ttctggcagc cggtcaccct acgacggttt ggaatcgcag cgcagctaaa   120
gctgatgaac tggttggtcg cggtgcaacc ctggccgcgt ctcccgcggc tgccgtcgca   180
gcgggtagtc tgatcgttgt ttgcgtcaca gatcatcgtg cggtgcgcga actgctggaa   240
ccacttggcg atgcactgcc aggtcgcgtt ctggtcaacc tgacgagcgg tacgtcgcgt   300
gaagcccgtg agaacgcaga acatactgcg gctcagggag ccacctacct ggatggtgtg   360
attctgacca ttccaagcgg cattggcacc ccagaagcta ccattctgta ttcgggaccg   420
cgcagtacct tcgatgaaca tgaaagcgca ctgcgcgcat taggtccggg ggcgaccttt   480
gtagggaag atcacggact ggctaacctg tatgatgcag caatgtcgag catgatgtgg   540
ggcctgctga atggtttcct gcatggaacc gcactgctgg gaaccgcggg cgtttcggca   600
acctctgtgg ttccgatgct gggtcaaggt tgggaagcga tgactggtat aattgcgcgc   660
tacgcaaatc agattgatgc cggtgtctat ccagcagacg atgccacgat tgatacccag   720
cgtgctgcaa tgcagcacct ggtcgaggag agccgtgcgg cgggcatcaa tggcgaactt   780
ccggcgtttg tgaccaaact ggccgatcgc gcagtggcag aaggtcgtgg tggtgactct   840
tacgctgcac tgattgaaca gtttcgcaag tcagcttaa                         879
```

<210> SEQ ID NO 234
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 234

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Met Met Trp Gly Leu Leu Asn Gly Phe Leu His Gly Thr Ala Leu
            180                 185                 190
```

Leu Gly Thr Ala Gly Val Ser Ala Thr Ser Val Pro Met Leu Gly
        195                 200                 205

Gln Gly Trp Glu Ala Met Thr Gly Ile Ile Ala Arg Tyr Ala Asn Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
                260                 265                 270

Ala Glu Gly Arg Gly Gly Asp Ser Tyr Ala Ala Leu Ile Glu Gln Phe
            275                 280                 285

Arg Lys Ser Ala
        290

<210> SEQ ID NO 235
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 235
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacca ttccaagcgg cattggcacc ccagaagcta ccattctgta ttcgggaccg    420
cgcagtacct tcgatgaaca tgaaagcgca ctgcgcgcat taggtccggg ggcgaccttt    480
gtaggggaag atcacggact ggctaacctg tatgatgcag caatgtcgag catgatgtgg    540
ggcctgctga atggtttcct gcatggaacc gcactgctgg aaccgcgggg cgtttcggca    600
acctctgtgg ttccgatgct gggtcaaggt tgggaagcga tgactggtat aattgcgcgc    660
tacgcagatc agattgatgc cggtgtctat ccagcagacg atgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgttttct    840 tacgctgcac tgattgaaca gtttcgcaag tcagcttaa                           879

<210> SEQ ID NO 236
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 236

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
            35                  40                  45

Ala Thr Leu Ala Ala Ser Pro Ala Ala Val Ala Ala Gly Ser Leu
 50                  55                  60

Ile Val Val Cys Val Thr Asp His Arg Ala Val Arg Glu Leu Leu Glu
 65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
                100                 105                 110

Gly Ala Thr Tyr Leu Asp Gly Val Ile Leu Thr Ile Pro Ser Gly Ile
            115                 120                 125

Gly Thr Pro Glu Ala Thr Ile Leu Tyr Ser Gly Pro Arg Ser Thr Phe
130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Met Met Trp Gly Leu Leu Asn Gly Phe Leu His Gly Thr Ala Leu
                180                 185                 190

Leu Gly Thr Ala Gly Val Ser Ala Thr Ser Val Val Pro Met Leu Gly
            195                 200                 205

Gln Gly Trp Glu Ala Met Thr Gly Ile Ile Ala Arg Tyr Ala Asp Gln
210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
                260                 265                 270

Ala Glu Gly Arg Gly Gly Val Ser Tyr Ala Ala Leu Ile Glu Gln Phe
            275                 280                 285

Arg Lys Ser Ala
        290

<210> SEQ ID NO 237
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 237
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct cgatgaaca tgaaagcgca ctgcgcgcat aggtccgggg gcgacctttg     480
gtaggggaag atcacggact ggctaacctg tatgatgcag caatgtcgag catgatgtgg     540

```
ggcctgctga atggtttcct gcatggaacc gcactgctgg gaaccgcggg cgtttcggca    600
acctctgtgg ttccgatgct gggtcaaggt tgggaagcga tgactggtat aattgcgcgc    660
tacgcagatc agattgatgt tggtgtctat ccagcagacg atgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 238
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 238

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Met Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Met Thr Gly Ile Ile Ala Arg Tyr Ala Asp Gln
    210                 215                 220

Ile Asp Val Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
```

<210> SEQ ID NO 239
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 239

```
atgagtgatt cacctgtgcc cgtgacagtt ctgggtcttg gtctgatggg tcaggcctta    60
gcggagcgt ttctggcagc cggtcaccct acgacggttt ggaatcgcag cgcagctaaa   120
gctgatgaac tggttggtcg cggtgcaacc ctggccgcgt ctcccgcggc tgccgtcgca   180
gcgggtagtc tgatcgttgt ttgcgtcaca gatcatcgtg cggtgcgcga actgctggaa   240
ccacttggcg atgcactgcc aggtcgcgtt ctggtcaacc tgacgagcgg tacgtcgcgt   300
gaagcccgtg agaacgcaga acatactgcg gctcagggag ccacctacct ggatggtgtg   360
attctgacca ttccaagcag gattggcacc ccagaagcta ccattctgta ttcgggaccg   420
cgcagtacct tcgatgaaca tgaaagcgca ctgcgcgcat taggtccggg ggcgaccttt   480
gtagggaag atcacggact ggctaacctg tatgatgcag caatgtcgag catgatgtgg   540
ggcctgctga atggtttcct gcatggaacc gcactgctgg aaccgcggg cgtttcggca   600
acctctgtgg ttccgatgct gggtcaaggt tgggaagcga tgactggtat aattgcgcgc   660
tacgcagatc agattgatgc cggtgtctat ccagcagacg atgccacgat tgataccag   720
cgtgctgcaa tgcagcacct ggtcgaggag agccgtgcgg cgggcatcaa tggcgaactt   780
ccggcgtttg tgaccaaact ggccgatcgc gcagtggcag aaggtcgtgg tggtgactct   840
tacgctgcac tgattgaaca gtttcgcaag tcagcttaa                          879
```

<210> SEQ ID NO 240
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 240

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Arg Ile
        115                 120                 125

Gly Thr Pro Glu Ala Thr Ile Leu Tyr Ser Gly Pro Arg Ser Thr Phe
```

```
                     130                 135                 140
Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Met Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Met Thr Gly Ile Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 241
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 241
atgagtgatt cacctgtgcc cgtgacagtt ctgggtcttg gtctgatggg tcaggcctta    60
gcgggagcgt ttctggcagc cggtcaccct acgacggttt ggaatcgcag cgcagctaaa   120
gctgatgaac tggttggtcg cggtgcaacc ctggccgcgt ctcccgcggc tgccgtcgca   180
gcgggtagtc tgatcgttgt ttgcgtcaca gatcatcgtg cggtgcgcga actgctggaa   240
ccacttggcg atgcactgcc aggtcgcgtt ctggtcaacc tgacgagcgg tacgtcgcgt   300
gaagcccgtg agaacgcaga acatactgcg gctcagggag ccacctacct ggatggtgtg   360
attctgacca ttccaagcgg cattggcacc ccagaagcta ccattctgta ttcgggaccg   420
cgcagtacct tcgatgaaca tgaaagcgca ctgcgcgcat taggtccggg ggcgacccttt  480 gtaggggaag atcacggact ggctaacctg tatgatgcag caatgtcgag catgatgtgg   540
ggcctgctga atggtttcct gcatggaacc gcactgctgg aaccgcgggg cgtttcggca   600
acctctgtgg ttccgatgct gggtcaaggt tgggaagcga tgactagtat aattgcgcgc   660
tacgcagatc agattgatgc cggtgtctat ccagcagacg atgccacgat tgatacccag   720
cgtgctgcaa tgcagcacct ggtcgaggag agccgtgcgg cgggcatcaa tggcgaactt   780
ccggcgtttg tgaccaaact ggccgatcgc gcagtggcag aaggtcgtgg tggtgactct   840
tacgctgcac tgattgaaca gtttcgcaag tcagcttaa                         879

<210> SEQ ID NO 242
<211> LENGTH: 292
<212> TYPE: PRT
<213> ORGANISM: Artificial Sequence
<220> FEATURE:
```

<223> OTHER INFORMATION: Imine reductase variant from Pseudonocardia
      spinosispora

<400> SEQUENCE: 242

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65              70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Met Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Met Thr Ser Ile Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 243
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 243
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180

-continued

```
gcgggtagtc tgatcgttgt ttgcgtcaca gatcatcgtg cggtgcgcga actgctggaa      240
ccacttggcg atgcactgcc aggtcgcgtt ctggtcaacc tgacgagcgg tacgtcgcgt      300
gaagcccgtg agaacgcaga acatactgcg gctcagggag ccacctacct ggatggtgtg      360
attctgacca ttccaagcgg cattggcacc cagaagcta ccattctgta ttcgggaccg       420
cgcagtacct tcgatgaaca tgaaagcgca ctgcgcgcat taggtccggg ggcgaccttt      480
gtaggggaag atcacggact ggctaacctg tatgatgcaa tgatgtcgag catgatgtgg      540
ggcctgctga atggtttcct gcatggaacc gcactgctgg gaaccgcggg cgtttcggca      600
acctctgtgg ttccgatgct gggtcaaggt tgggaagcga tgactggtat aattgcgcgc      660
tacgcagatc agattgatgc cggtgtctat ccagcagacg atgccacgat tgatacccag      720
cgtgctgcaa tgcagcacct ggtcgaggag agccgtgcgg cgggcatcaa tggcgaactt      780
ccggcgtttg tgaccaaact ggccgatcgc gcagtggcag aaggtcgtgg tggtgactct      840
tacgctgcac tgattgaaca gtttcgcaag tcagcttaa                            879
```

<210> SEQ ID NO 244  
<211> LENGTH: 292  
<212> TYPE: PRT  
<213> ORGANISM: Artificial Sequence  
<220> FEATURE:  
<223> OTHER INFORMATION: Imine reductase variant from Pseudonocardia spinosispora

<400> SEQUENCE: 244

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Met Met Ser
                165                 170                 175

Ser Met Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Met Thr Gly Ile Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240
```

```
Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 245
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 245
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacca ttccaagcgg cattggcacc ccagaagcta ccattctgta ttcgggaccg    420
cgcagtacct tcgatgaaca tgaaagcgca ctgcgcgcat taggtccggg ggcgacctttt   480 gtaggggaag atcacggact ggctaacctg tatgatgcag caatgtcgag catgatgtgg    540
ggcctgctga atggtttcct gcatggaacc gcactgctgg aaccgcgggg cgtttcggca    600
acctctgtgg ttccgatgct gggtcaaggt tggcatgcga tgactggtat aattgcgcgc    660
tacgcagatc agattgatgc cggtgtctat ccagcagacg atgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879

<210> SEQ ID NO 246
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 246

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80
```

```
Pro Leu Gly Asp Ala Leu Pro Gly Arg Val Leu Val Asn Leu Thr Ser
            85                  90                  95

Gly Thr Ser Arg Glu Ala Arg Glu Asn Ala Glu His Thr Ala Ala Gln
        100                 105                 110

Gly Ala Thr Tyr Leu Asp Gly Val Ile Leu Thr Ile Pro Ser Gly Ile
    115                 120                 125

Gly Thr Pro Glu Ala Thr Ile Leu Tyr Ser Gly Pro Arg Ser Thr Phe
130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Met Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp His Ala Met Thr Gly Ile Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 247
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 247
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat aggtccgggg gcgacctttt     480 gtagggaag atcacggact ggctaacctg tatgatgcag caatgtcgag catgatgtgg     540
ggcctgctga atggtttcct gcatggaacc gcactgctgg aaccgcgggc gtttcggca     600 acctctgtgg ttcgatgct gggtcaaggt tggagggcga tgactggtat aattgcgcgc     660
tacgcagatc agattgatgc cggtgtctat ccagcagacg atgccacgat tgatacccag     720
cgtgctgcaa tgcagcacct ggtcgaggag agccgtgcgg cgggcatcaa tggcgaactt     780
```

```
ccggcgtttg tgaccaaact ggccgatcgc gcagtggcag aaggtcgtgg tggtgactct    840
tacgctgcac tgattgaaca gtttcgcaag tcagcttaa                          879
```

<210> SEQ ID NO 248
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 248

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Met Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Arg Ala Met Thr Gly Ile Ile Ala Arg Tyr Ala Asp Gln
    210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

<210> SEQ ID NO 249
<211> LENGTH: 879
<212> TYPE: DNA
<213> ORGANISM: Artificial Sequence
<220> FEATURE:

<223> OTHER INFORMATION: Imine reductase variant from Pseudonocardia
      spinosispora

<400> SEQUENCE: 249

```
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct cgatgaaca tgaaagcgca ctgcgcgcat taggtccggg ggcgacccttt    480
gtagggaag atcacggact ggctaacctg tatgatgcag caatgtcgag catgatgtgg     540
ggcctgctga atggtttcct gcatggaacc gcactgctgg aaccgcggg cgtttcggca     600
acctctgtgg ttccgatgct gggtcaaggt tggaaagcga tgactggtat aattgcgcgc     660
tacgcagatc agattgatgc cggtgtctat ccagcagacg atgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                           879
```

<210> SEQ ID NO 250
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 250

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175
```

Ser Met Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Lys Ala Met Thr Gly Ile Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 251
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 251

```
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc cagaagctac cattctgta ttcgggaccg     420
cgcagtacct tcgatgaaca tgaaagcgca ctgcgcgcat taggtccggg ggcgaccttt     480
gtaggggaag atcacggact ggctaacctg tatgatgcag caatgtcgag catgatgtgg     540
ggcctgctga atggtttcct gcatggaacc gcactgctgg aaccgcgggc gtttcggca     600
acctctgtgg ttccgatgct gggtagtggt tgggaagcga tgactggtat aattgcgcgc     660
tacgcagatc agattgatgc cggtgtctat ccagcagacg atgccacgat tgataccag     720
cgtgctgcaa tgcagcacct ggtcgaggag agccgtgcgg cgggcatcaa tggcgaactt     780
ccggcgtttg tgaccaaact ggccgatcgc gcagtgcga aaggtcgtgg tggtgactct     840
tacgctgcac tgattgaaca gtttcgcaag tcagcttaa                             879
```

<210> SEQ ID NO 252
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 252

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Met Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Ser Gly Trp Glu Ala Met Thr Gly Ile Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 253
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 253
atgagtgatt cacctgtgcc cgtgacagtt ctgggtcttg gtctgatggg tcaggcctta        60
gcgggagcgt ttctggcagc cggtcaccct acgacggttt ggaatcgcag cgcagctaaa       120
gctgatgaac tggttggtcg cggtgcaacc ctggccgcgt ctcccgcggc tgccgtcgca       180
gcgggtagtc tgatcgttgt ttgcgtcaca gatcatcgtg cggtgcgcga actgctggaa       240
ccacttggcg atgcactgcc aggtcgcgtt ctggtcaacc tgacgagcgg tacgtcgcgt       300
gaagcccgtg agaacgcaga acatactgcg gctcagggag ccacctacct ggatggtgtg       360
attctgacca ttccaagcgg cattggcacc ccagaagcta ccattctgta ttcgggaccg       420

```
cgcagtacct tcgatgaaca tgaaagcgca ctgcgcgcat taggtccggg ggcgaccttt    480
gtaggggaag atcacggact ggctaacctg tatgatcgag caatgtcgag catgatgtgg    540
ggcctgctga atggtttcct gcatggaacc gcactgctgg gaaccgcggg cgtttcggca    600
acctctgtgg ttccgatgct gggtcaaggt tgggaagcga tgactcgtat aattgcgcgc    660
tacgcagatc agattgatgc cggtgtctat ccagcagacg atgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 254
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 254

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Met Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Met Thr Arg Ile Ile Ala Arg Tyr Ala Asp Gln
    210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
```

```
              275                 280                 285

Arg Lys Ser Ala
    290

<210> SEQ ID NO 255
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 255
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat taggtccggg ggcgaccttt     480
gtaggggaag atcacggact ggctaacctg tatgatgcag caatgtcgag catgatgtgg     540
ggcctgctga atggtttcct gcatggaacc gcactgctgg aaccgcgggg cgtttcggca     600
acctctgtgg ttccgcttct gggtcaaggt tgggaagcga tgactggtat aattgcgcgc     660
tacgcagatc agattgatgc cggtgtctat ccagcagacg atgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                            879

<210> SEQ ID NO 256
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 256

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
```

```
            115                 120                 125
Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Met Met Trp Gly Leu Leu Asn Gly Phe Leu His Gly Thr Ala Leu
            180                 185                 190

Leu Gly Thr Ala Gly Val Ser Ala Thr Ser Val Val Pro Leu Leu Gly
        195                 200                 205

Gln Gly Trp Glu Ala Met Thr Gly Ile Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 257
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 257
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagctc ttattctgta ttcgggaccg     420
cgcagtacct cgatgaaca tgaaagcgca ctgcgcgcat taggtccggg ggcgaccttt     480
gtaggggaag atcacggact ggctaacctg tatgatgcag caatgtcgag catgatgtgg     540
ggcctgctga atggtttcct gcatggaacc gcactgctgg aaccgcgggg cgtttcggca     600
acctctgtgg ttccgatgct gggtcaaggt tgggaagcga tgactggtat aattgcgcgc     660
tacgcagatc agattgatgc cggtgtctat ccagcagacg atgccacgat tgatacccag     720
cgtgctgcaa tgcagcacct ggtcgaggag agccgtgcgg cgggcatcaa tggcgaactt     780
ccggcgtttg tgaccaaact ggccgatcgc gcagtggcag aaggtcgtgg tggtgactct     840
tacgctgcac tgattgaaca gtttcgcaag tcagcttaa                           879

<210> SEQ ID NO 258
<211> LENGTH: 292
```

<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 258

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Leu Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Met Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Met Thr Gly Ile Ile Ala Arg Tyr Ala Asp Gln
    210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 259
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 259
atgagtgatt cacctgtgcc cgtgacagtt ctgggtcttg gtctgatggg tcaggcctta    60
gcgggagcgt ttctggcagc cggtcaccct acgacggttt ggaatcgcag cgcagctaaa   120

```
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacca ttccaagcgg cattggccgt ccagaagcta ccattctgta ttcgggaccg    420
cgcagtacct tcgatgaaca tgaaagcgca ctgcgcgcat taggtccggg ggcgaccttt    480 gtagggaag atcacggact ggctaacctg tatgatgcag caatgtcgag catgatgtgg    540
ggcctgctga atggtttcct gcatggaacc gcactgctgg gaaccgcggg cgtttcggca    600
acctctgtgg ttccgatgct gggtcaaggt tgggaagcga tgactggtat aattgcgcgc    660
tacgcagatc agattgatgc cggtgtctat ccagcagacg atgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 260  
<211> LENGTH: 292  
<212> TYPE: PRT  
<213> ORGANISM: Artificial Sequence  
<220> FEATURE:  
<223> OTHER INFORMATION: Imine reductase variant from Pseudonocardia spinosispora

<400> SEQUENCE: 260

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Arg Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Met Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Met Thr Gly Ile Ile Ala Arg Tyr Ala Asp Gln
    210                 215                 220
```

| Ile | Asp | Ala | Gly | Val | Tyr | Pro | Ala | Asp | Asp | Ala | Thr | Ile | Asp | Thr | Gln |
| 225 | | | | | 230 | | | | | 235 | | | | | 240 |

| Arg | Ala | Ala | Met | Gln | His | Leu | Val | Glu | Glu | Ser | Arg | Ala | Ala | Gly | Ile |
| | | | | 245 | | | | | 250 | | | | | 255 | |

| Asn | Gly | Glu | Leu | Pro | Ala | Phe | Val | Thr | Lys | Leu | Ala | Asp | Arg | Ala | Val |
| | | | 260 | | | | | 265 | | | | | 270 | | |

| Ala | Glu | Gly | Arg | Gly | Gly | Asp | Ser | Tyr | Ala | Ala | Leu | Ile | Glu | Gln | Phe |
| | | 275 | | | | | 280 | | | | | 285 | | | |

Arg Lys Ser Ala
    290

<210> SEQ ID NO 261
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 261

| atgagtgatt | cacctgtgcc | cgtgacagtt | ctgggtcttg | gtctgatggg | tcaggcctta | 60 |
| gcgggagcgt | ttctggcagc | cggtcaccct | acgacggttt | ggaatcgcag | cgcagctaaa | 120 |
| gctgatgaac | tggttggtcg | cggtgcaacc | ctggccgcgt | ctcccgcggc | tgccgtcgca | 180 |
| gcgggtagtc | tgatcgttgt | tgcgtcaca | gatcatcgtg | cggtgcgcga | actgctggaa | 240 |
| ccacttggcg | atgcactgcc | aggtcgcgtt | ctggtcaacc | tgacgagcgg | tacgtcgcgt | 300 |
| gaagcccgtg | agaacgcaga | acatactgcg | gctcagggag | ccacctacct | ggatggtgtg | 360 |
| attctgacca | ttccaagcgg | cattggcacc | ccagaagcta | ccattctgta | ttcgggaccg | 420 |
| cgcagtacct | tcgatgaaca | tgaaagcgca | ctgcgcgcat | taggtccggg | ggcgaccttt | 480 |
| gtaggggaag | atcacggact | ggctaacctg | tatgatgcag | caatgtcgag | catgatgtgg | 540 |
| ggcctgctga | atggtttcct | gcatggaacc | gcactgctgg | gaaccgcggg | cgtttcggca | 600 |
| acctctgtgg | ttccgatgct | gggtcaaggt | tgggaagcga | tgactaatat | aattgcgcgc | 660 |
| tacgcagatc | agattgatgc | cggtgtctat | ccagcagacg | atgccacgat | tgatacccag | 720 |
| cgtgctgcaa | tgcagcacct | ggtcgaggag | agccgtgcgg | cgggcatcaa | tggcgaactt | 780 |
| ccggcgtttg | tgaccaaact | ggccgatcgc | gcagtggcag | aaggtcgtgg | tggtgactct | 840 |
| tacgctgcac | tgattgaaca | gtttcgcaag | tcagcttaa | | | 879 |

<210> SEQ ID NO 262
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 262

| Met | Ser | Asp | Ser | Pro | Val | Pro | Val | Thr | Val | Leu | Gly | Leu | Gly | Leu | Met |
| 1 | | | | 5 | | | | | 10 | | | | | 15 | |

| Gly | Gln | Ala | Leu | Ala | Gly | Ala | Phe | Leu | Ala | Ala | Gly | His | Pro | Thr | Thr |
| | | | 20 | | | | | 25 | | | | | 30 | | |

| Val | Trp | Asn | Arg | Ser | Ala | Ala | Lys | Ala | Asp | Glu | Leu | Val | Gly | Arg | Gly |
| | | | 35 | | | | | 40 | | | | | 45 | | |

| Ala | Thr | Leu | Ala | Ala | Ser | Pro | Ala | Ala | Val | Ala | Ala | Gly | Ser | Leu |
| | 50 | | | | | 55 | | | | | 60 | | | |

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Met Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Met Thr Asn Ile Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290

<210> SEQ ID NO 263
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 263
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa    120
gctgatgaac tgattggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacca ttccaagcgg cattggcacc ccagaagcta ccattctgta ttcgggaccg    420
cgcagtacct cgatgaaca tgaaagcgca ctgcgcgcat aggtccgggg gcgacctttg    480
gtaggggaag atcacggact ggctaacctg tatgatgcag caatgtcgag catgatgtgg    540
ggcctgctga atggtttcct gcatggaacc gcactgctgg aaccgcgggg cgtttcggca    600
acctctgtgg ttccgatgct gggtcaaggt tgggaagcga tgactggtat aattgcgcgc    660

-continued

```
tacgcagatc agattgatgc cggtgtctat ccagcagacg atgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

<210> SEQ ID NO 264
<211> LENGTH: 292
<212> TYPE: PRT
<213> ORGANISM: Artificial Sequence
<220> FEATURE:
<223> OTHER INFORMATION: Imine reductase variant from Pseudonocardia spinosispora

<400> SEQUENCE: 264

```
Met Ser Asp Ser Pro Val Pro Val Thr Val Leu Gly Leu Gly Leu Met
 1               5                  10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Ile Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Asn Leu Tyr Asp Ala Ala Met Ser
                165                 170                 175

Ser Met Met Trp Gly Leu Leu Asn Gly Phe Leu His Gly Thr Ala Leu
            180                 185                 190

Leu Gly Thr Ala Gly Val Ser Ala Thr Ser Val Val Pro Met Leu Gly
        195                 200                 205

Gln Gly Trp Glu Ala Met Thr Gly Ile Ile Ala Arg Tyr Ala Asp Gln
    210                 215                 220

Ile Asp Ala Gly Val Tyr Pro Ala Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

<210> SEQ ID NO 265
<211> LENGTH: 879

```
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 265
atgagtgatt cacctgtgcc cgtgacagtt ctgggtcttg gtctgatggg tcaggccta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
attctgacca ttccaagcgg cattggcacc ccagaagcta ccattctgta ttcgggaccg     420
cgcagtacct tcgatgaaca tgaaagcgca ctgcgcgcat taggtccggg ggcgaccttt     480
gtagggaag atcacggact ggctaacctg tatgatgcag caatgtcgag catgatgtgg      540
ggcctgctga atggtttcct gcatggaacc gcactgctgg aaccgcgggg cgtttcggca     600
acctctgtgg ttccgatgct gggtaaaggt tgggaagcga tgactggtat aattgcgcgc    660
tacgcagatc agattgatgc cggtgtctat ccagcagacg atgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879

<210> SEQ ID NO 266
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 266

Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160
```

```
Val Gly Glu Asp His Gly Leu Ala Asn Leu Tyr Asp Ala Ala Met Ser
            165                 170                 175

Ser Met Met Trp Gly Leu Leu Asn Gly Phe Leu His Gly Thr Ala Leu
        180                 185                 190

Leu Gly Thr Ala Gly Val Ser Ala Thr Ser Val Val Pro Met Leu Gly
            195                 200                 205

Lys Gly Trp Glu Ala Met Thr Gly Ile Ile Ala Arg Tyr Ala Asp Gln
        210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
            260                 265                 270

Ala Glu Gly Arg Gly Gly Asp Ser Tyr Ala Ala Leu Ile Glu Gln Phe
        275                 280                 285

Arg Lys Ser Ala
    290
```

```
<210> SEQ ID NO 267
<211> LENGTH: 879
<212> TYPE: DNA
<213> ORGANISM: Artificial Sequence
<220> FEATURE:
<223> OTHER INFORMATION: Imine reductase variant from Pseudonocardia
      spinosispora

<400> SEQUENCE: 267
atgagtgatt cacctgtgcc cgtgacagtt ctgggtcttg gtctgatggg tcaggcctta     60
gcgggagcgt ttctggcagc cggtcaccct acgacggttt ggaatcgcag cgcagctaaa    120
gctgatgaac tggttggtcg cggtgcaacc ctggccgcgt ctcccgcggc tgccgtcgca    180
gcgggtagtc tgatcgttgt ttgcgtcaca gatcatcgtg cggtgcgcga actgctggaa    240
ccacttggcg atgcactgcc aggtcgcgtt ctggtcaacc tgacgagcgg tacgtcgcgt    300
gaagcccgtg agaacgcaga acatactgcg gctcagggag ccacctacct ggatggtgtg    360
attctgacca ttccaagcgg cattggcacc ccagaagcta ggattctgta ttcgggaccg    420
cgcagtacct tcgatgaaca tgaaagcgca ctgcgcgcat taggtccggg ggcgaccttt    480 gtagggggaag atcacggact ggctaacctg tatgatgcag caatgtcgag catgatgtgg    540
ggcctgctga atggtttcct gcatggaacc gcactgctgg aaccgcgggg cgtttcggca    600
acctctgtgg ttccgatgct gggtcaaggt tgggaagcga tgactggtat aattgcgcgc    660
tacgcagatc agattgatgc cggtgtctat ccagcagacg atgccacgat tgataccccag    720 cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                           879
```

```
<210> SEQ ID NO 268
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 268
```

Met Ser Asp Ser Pro Val Pro Val Thr Val Leu Gly Leu Gly Leu Met
1               5                   10                  15
Gly Gln Ala Leu Ala Gly Ala Phe Leu Ala Ala Gly His Pro Thr Thr
            20                  25                  30
Val Trp Asn Arg Ser Ala Ala Lys Ala Asp Glu Leu Val Gly Arg Gly
                35                  40                  45
Ala Thr Leu Ala Ala Ser Pro Ala Ala Val Ala Ala Gly Ser Leu
50                  55                  60
Ile Val Val Cys Val Thr Asp His Arg Ala Val Arg Glu Leu Leu Glu
65                  70                  75                  80
Pro Leu Gly Asp Ala Leu Pro Gly Arg Val Leu Val Asn Leu Thr Ser
                85                  90                  95
Gly Thr Ser Arg Glu Ala Arg Glu Asn Ala Glu His Thr Ala Ala Gln
                100                 105                 110
Gly Ala Thr Tyr Leu Asp Gly Val Ile Leu Thr Ile Pro Ser Gly Ile
            115                 120                 125
Gly Thr Pro Glu Ala Arg Ile Leu Tyr Ser Gly Pro Arg Ser Thr Phe
130                 135                 140
Asp Glu His Glu Ser Ala Leu Arg Ala Leu Gly Pro Gly Ala Thr Phe
145                 150                 155                 160
Val Gly Glu Asp His Gly Leu Ala Asn Leu Tyr Asp Ala Ala Met Ser
                165                 170                 175
Ser Met Met Trp Gly Leu Leu Asn Gly Phe Leu His Gly Thr Ala Leu
                180                 185                 190
Leu Gly Thr Ala Gly Val Ser Ala Thr Ser Val Val Pro Met Leu Gly
            195                 200                 205
Gln Gly Trp Glu Ala Met Thr Gly Ile Ile Ala Arg Tyr Ala Asp Gln
210                 215                 220
Ile Asp Ala Gly Val Tyr Pro Ala Asp Asp Ala Thr Ile Asp Thr Gln
225                 230                 235                 240
Arg Ala Ala Met Gln His Leu Val Glu Glu Ser Arg Ala Ala Gly Ile
                245                 250                 255
Asn Gly Glu Leu Pro Ala Phe Val Thr Lys Leu Ala Asp Arg Ala Val
                260                 265                 270
Ala Glu Gly Arg Gly Gly Asp Ser Tyr Ala Ala Leu Ile Glu Gln Phe
            275                 280                 285
Arg Lys Ser Ala
            290

<210> SEQ ID NO 269
<211> LENGTH: 879
<212> TYPE: DNA
<213> ORGANISM: Artificial Sequence
<220> FEATURE:
<223> OTHER INFORMATION: Imine reductase variant from Pseudonocardia spinosispora

<400> SEQUENCE: 269

```
atgagtgatt cacctgtgcc cgtgacagtt ctgggtcttg gtctgatggg tcaggcctta      60
gcgggagcgt ttctggcagc cggtcaccct acgacggttt ggaatcgcag cgcagctaaa     120
gctgatgaac tggttggtcg cggtgcaacc ctggccgcgt ctcccgcggc tgccgtcgca     180
gcgggtagtc tgatcgttgt ttgcgtcaca gatcatcgtg cggtgcgcga actgctggaa     240
ccacttggcg atgcactgcc aggtcgcgtt ctggtcaacc tgacgagcgg tacgtcgcgt     300
gaagcccgtg agaacgcaga acatactgcg gctcagggag ccacctacct ggatggtgtg     360
```

```
attctgacca ttccaagcgg cattggcacc ccagaagcta ccattctgta ttcgggaccg    420
cgcagtacct tcgatgaaca tgaaagcgca ctgcgcgcat taggtccggg ggcgaccttt    480 gtagggaag atcacggact ggctgcactg tatgatgcag caatgctgag cgtcatgtgg     540
ggcctgctga atggtttcct gcatggaacc gcactgctgg gaaccgcggg cgtttcggca    600
acctctgtgg ttccgatgct gggtcaaggt atcgaagcgg tgaccggttg gattgcgcgc    660
tacgcagatc agattgatgc cggtgtctat ccagcagacg acgccacgat tgatacccag    720
cgtgctgcaa tgcagcacct ggtcgaggag agccgtgcgg cgggcatcaa tggcgaactt    780
ccggcgtttg tgaccaaact ggccgatcgc gcagtggcag aaggtcgtgg tggtgactct    840
tacgctgcac tgattgaaca gtttcgcaag tcagcttaa                          879
```

<210> SEQ ID NO 270
<211> LENGTH: 292
<212> TYPE: PRT
<213> ORGANISM: Artificial Sequence
<220> FEATURE:
<223> OTHER INFORMATION: Imine reductase variant from Pseudonocardia
      spinosispora

<400> SEQUENCE: 270

```
Met Ser Asp Ser Pro Val Pro Val Thr Val Leu Gly Leu Gly Leu Met
1               5                   10                  15

Gly Gln Ala Leu Ala Gly Ala Phe Leu Ala Ala Gly His Pro Thr Thr
            20                  25                  30

Val Trp Asn Arg Ser Ala Ala Lys Ala Asp Glu Leu Val Gly Arg Gly
        35                  40                  45

Ala Thr Leu Ala Ala Ser Pro Ala Ala Val Ala Ala Gly Ser Leu
    50                  55                  60

Ile Val Val Cys Val Thr Asp His Arg Ala Val Arg Glu Leu Leu Glu
65                  70                  75                  80

Pro Leu Gly Asp Ala Leu Pro Gly Arg Val Leu Val Asn Leu Thr Ser
                85                  90                  95

Gly Thr Ser Arg Glu Ala Arg Glu Asn Ala Glu His Thr Ala Ala Gln
            100                 105                 110

Gly Ala Thr Tyr Leu Asp Gly Val Ile Leu Thr Ile Pro Ser Gly Ile
        115                 120                 125

Gly Thr Pro Glu Ala Thr Ile Leu Tyr Ser Gly Pro Arg Ser Thr Phe
    130                 135                 140

Asp Glu His Glu Ser Ala Leu Arg Ala Leu Gly Pro Gly Ala Thr Phe
145                 150                 155                 160

Val Gly Glu Asp His Gly Leu Ala Ala Leu Tyr Asp Ala Ala Met Leu
                165                 170                 175

Ser Val Met Trp Gly Leu Leu Asn Gly Phe Leu His Gly Thr Ala Leu
            180                 185                 190

Leu Gly Thr Ala Gly Val Ser Ala Thr Ser Val Pro Met Leu Gly
        195                 200                 205

Gln Gly Ile Glu Ala Val Thr Gly Trp Ile Ala Arg Tyr Ala Asp Gln
    210                 215                 220

Ile Asp Ala Gly Val Tyr Pro Ala Asp Asp Ala Thr Ile Asp Thr Gln
225                 230                 235                 240

Arg Ala Ala Met Gln His Leu Val Glu Glu Ser Arg Ala Ala Gly Ile
                245                 250                 255

Asn Gly Glu Leu Pro Ala Phe Val Thr Lys Leu Ala Asp Arg Ala Val
```

-continued

```
              260                 265                 270
Ala Glu Gly Arg Gly Gly Asp Ser Tyr Ala Ala Leu Ile Glu Gln Phe
            275                 280                 285
Arg Lys Ser Ala
        290
```

ENGINEERED IMINE REDUCTASES AND METHODS FOR THE REDUCTIVE AMINATION OF KETONE AND AMINE COMPOUNDS

The present application is Divisional of co-pending of U.S. patent application Ser. No. 16/319,537, filed Jan. 22, 2019, a national stage application filed under 35 USC § 371 and claims priority to international application to PCT International Application No PCT/US17/45838, filed Aug. 8, 2017, which claims priority to U.S. Prov. Pat. Appln. Ser. No. 62/380,165, filed Aug. 26, 2016, hereby incorporated by reference in its entirety for all purposes.

TECHNICAL FIELD

The present invention provides engineered polypeptides having imine and/or or oxime reductase activity useful for the production of secondary amines, as well as compositions and methods utilizing these engineered polypeptides.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "CX2-151USP1_ST25.txt", a creation date of Aug. 26, 2016, and a size of 511 kilobytes. The Sequence Listing filed via EFS-Web is part of the specification and is incorporated in its entirety by reference herein.

BACKGROUND

Chiral secondary amines are important building blocks in pharmaceutical industry. However, there are only a handful of biocatalytic routes known to produce this class of chiral amine compounds. The existing chemical methods use chiral boron reagents, transition metal based reductive methods or protecting group strategies that require multi step synthesis for the overall reduction of an imine.

There are a few reports in the literature of the biocatalytic synthesis of stable cyclic amines Imine reductases or "IREDs" were purified and characterized from *Streptomyces* sp. GF3587 and GF3546 and shown to reduce 2-methyl-1-pyrroline stereoselectively (See, Mitsukura et al., Biosci. Biotech. Biochem., 75:1778-1782 [2011)]; Huber et al. Chem. Cat. Chem., 6:2248-2252 [2014]). Reduction to acyclic amines and amino acids with alkyl groups has also been shown using native imine reductases (Gand et. al., J. Mol. Catal. B: Enzym., 110:126-132 [2014]). The use of an IRED as the starting enzyme for the production of amines at industrial scale is dependent on identifying the right variant with the highest activity.

The prevalence of bacterial strains that are resistant to existing antibiotics underscores the need for development of new antibacterial agents. Antibiotic cocktails that are formulated to target multiple modes of action are becoming increasingly more popular. Bacteria have become very efficient at neutralizing β-lactam antibiotics by hydrolyzing the compounds with β-lactamase. Relebactam is a β-lactamase inhibitor that disables the enzyme allowing the antibiotic to act on its target. Chemical synthesis of relebactam is a multi-step process, one of which requires the stereoselective addition of benzyloxyamine. The low yield of this chemical step makes the use of an enzyme an attractive alternative.

SUMMARY

The present invention provides novel biocatalysts and associated methods to use for the synthesis of chiral secondary amines by direct reduction of imine substrates. The biocatalysts of the disclosure are engineered polypeptide variants of the wild-type gene from *Pseudonocardia spinosispora* which encodes an imine reductase" or "IRED" having the amino acid sequence of SEQ ID NO:2. These engineered polypeptides are capable of catalyzing the conversion of an imine to a secondary amine.

The present invention provides an engineered polypeptide comprising an amino acid sequence with at least 80% sequence identity to a reference sequence of SEQ ID NO:2, comprising at least one substitution at one or more positions selected from 57/211, 87/175, 103/212, 122, 123, 124/178, 124, 132, 134, 169, 171, 173, 175, 176, 178/242, 178, 211, 212, 213, 214, 215, 217, 234, and 235, wherein the positions are numbered with reference to SEQ ID NO:2. In some additional embodiments, the engineered polypeptide comprises at least one substitution selected from 57T/211L, 87S/175G, 103H/212C, 122E, 123G, 124A/178I, 124G, 132H/R, 134R, 169N/S, 171W, 173H/I, 175G/H, 176S, 178I//242Y, 178M, 211L/W, 212C/G/V, 213P/R/T/V, 214M, 215L/M, 217I/L, 234L, and 235K, wherein the positions are numbered with reference to SEQ ID NO:2. In some embodiments, the engineered polypeptide comprises at least one substitution selected from A57T/I211L, P87S/M175G, R103H/E212C, L122E, T123G, I124A/V178I, I124G, E132H/R, T134R, A169N/S, Y171W, A173H/I, M175G/H, L176S, V178I/A242Y, V178M, I211L/W, E212C/G/V, A213P/R/T/V, V214M, T215L/M, W217I/L, D234L, and A235K, wherein the positions are numbered with reference to SEQ ID NO:2. In some further embodiments, the engineered polypeptide comprises an amino acid sequence with at least 80% sequence identity to any even-numbered sequence set forth in SEQ ID NO:4 to SEQ ID NO:74.

The present invention also provides an engineered polypeptide comprising an amino acid sequence with at least 80% sequence identity to a reference sequence of SEQ ID NO:270, comprising at least two substitutions selected from the substitution sets: 123/124/169/171/173/213/235, 123/124/169/212/213/235, 123/169/171/173/212/213/235, 123/169/171/173/213/235, 123/169/173/175/213/235, 123/169/173/212/213, 123/169/175, 123/169/175/212/235, 123/169/212/213, 123/173/175/212/213/235, 123/212/213/235, 123/212/235, 123/169/171/173/175/212/213, 123/169/173, 123/169/212/213/235, 123/213, 124/169, 124/169/173/175/212/213, 124/169/173/212/213, 124/169/173/212/213/235, 124/169/175/212/213/235, 124/169/212/213/235, 124/169/213/235, 124/175/212/213/235, 124/212/213/235, 134/169/176/178/211/214, 134/169/176/178/211, 134/169/176/178/211/217, 134/169/176/211/215/217/234, 134/169/176/211, 134/169/178/211/214/217, 134/169/211/214/217, 134/169/211/217, 134/176/211/214, 134/176/211/215, 134/211/214, 169/171/173/213/235, 169/173/175/213/235, 169/175/212/213/235, 169/176/178/211/214, 169/176/178/211/214/217, 169/176/178/211/217, 169/176/178, 169/176/178/211/214/217, 169/176/211/214, 169/176/211/214/215/234, 169/176/211/214/217, 169/176/211/217, 169/176/214/215/217, 169/178/217, 169/178/234, 169/211/214/215, 169/211/217, 169/212/213, 169/212/235, 169/212/213/235, 169/235, 171/173/212/213/235, 173/175/213, 175/213/235, 175/235, 176/178/211/215/217, 176/178/211/217, 176/211/214, 176/214/217, 178/211/214, 178/211/217, 178/215, 211/234, 212/213/235, and 213/235, wherein the positions are numbered with reference to SEQ ID NO:270. In some embodiments, the engineered polypeptide comprises at least one substitution set selected from 123G/124G/169N/171V/173H/213V/235K, 123G/124G/169N/212V/213V/235K, 123G/169N/171V/173H/213V/235K, 123G/169N/171V/173I/212C/213V/235K, 123G/169N/173H/175H/213V/235K, 123G/169N/173I/212G/213T, 123G/169N/175G, 123G/169N/175G/212C/235K, 123G/169N/212G/213V, 123G/173H/175H/212C/213V/235K, 123G/212C/213V/235K, 123G/212G/235K, 123G/169N/171V/173H/175H/212X/213V, 123G/169N/173I, 123G/169N/212G/213V/235K, 123G/213T, 124G/169N, 124A/169N/173I/175H/212G/213V, 124G/169N/173I/212C/213V, 124G/169N/173I/212G/213V, 124G/169N/173I/212V/213V/235K, 124G/169N/175G/212C/213V/235K, 124G/169N/212G/213V/235K, 124G/169N/212V/213V/235K, 124G/175G/212V/213V/235K, 124G/169N/213V/235K, 124G/212C/213V/235K, 124G/212G/213V/235K, 134R/169N/176S/178I//211L/214M, 134R/169N/176S/178I//211W, 134R/169N/176S/178M/211L/217L, 134R/169N/176S/211L/215M/217I/234L, 134R/169N/176S/211W, 134R/169N/178M/211W/214M/217I, 134R/169N/211W/214M/217L, 134R/169N/211W/217L, 134R/176S/211W/214M, 134R/176S/211W/215M, 134R/211W/214M, 169N/171V/173I/213V/235K, 169N/173I/175H/213V/235K, 169N/175G/212C/213V/235K, 169N/M175H/E212G/A213V/A235K 169N/176S/178I//211L/214M, 169N/176S/178I//211W/214M/217L, 169N/176S/178I//211W/217L 169N/176S/178M, 169N/176S/178M/211W/214M/217I, 169N/176S/211W/214M, 169N/176S/211W/214M/215L/234L, 169N/176S/211W/217I, 169N/176S/211W/217L, 169N/176S/214M/215M/217I, 169N/176S/211L/214M/217I, 169N/178I//217I, 169N/178M/234L, 169N/211W/214M/215L, 169N/211W/217I, 169N/212C/235K, 169N/212C/213V/235K, 169N/212G/213V, 169N/212V/213V/235K, 169N/235K, 171V/173I/212G/213V/235K, 173I/175H/213V, 175H/213P/235K, 175H/235K, 176S/178I/211W/215L/217L, 176S/178I/211W/217I, 176S/211L/214M, 176S/214M/217L, 178M/211L/214M, 178M/211W/217L, 178I//215M, 211W/234L, 212G/213V/235K, 212V/213V/235K, 213T/235K, and 213V/235K, wherein the positions are numbered with reference to SEQ ID NO:270. In some further embodiments, the engineered polypeptide comprises at least one substitution set selected from T123G/I124G/A169N/Y171V/A173H/A213V/A235K, T123G/I124G/A169N/E212V/A213V/A235K, T123G/A169N/Y171V/A173H/A213V/A235K, T123G/A169N/Y171V/A173I/E212C/A213V/A235K, T123G/A169N/A173H/M175H/A213V/A235K, T123G/A169N/A173I/E212G/A213T, T123G/A169N/M175G, T123G/A169N/M175G/E212C/A235K, T123G/A169N/E212G/A213V, T123G/A173H/M175H/E212C/A213V/A235K, T123G/E212C/A213V/A235K, T123G/E212G/A235K, T123G/A169N/Y171V/A173H/M175H/E212X/A213V, T123G/A169N/A173I, T123G/A169N/E212G/A213V/A235K, T123G/A213T, I124G/A169N, I124A/A169N/A173I/M175H/E212G/A213V, I124G/A169N/A173I/E212C/A213V, I124G/A169N/A173I/E212G/A213V, I124G/A169N/A173I/E212V/A213V/A235K, I124G/A169N/M175G/E212C/A213V/A235K, I124G/A169N/E212G/A213V/A235K, I124G/A169N/E212V/A213V/A235K, I124G/M175G/E212V/A213V/A235K, I124G/A169N/A213V/A235K, I124G/E212C/A213V/A235K, I124G/E212G/A213V/A235K, T134R/A169N/L176S/V178I/211L/V214M, T134R/A169N/L176S/V178I/211W, T134R/A169N/L176S/V178M/I211L/W217L, T134R/A169N/L176S/I211L/T215M/W217I/D234L, T134R/A169N/L176S/I211W, T134R/A169N/V178M/I211W/V214M/W217I, T134R/A169N/I211W/V214M/W217L, T134R/A169N/I211W/W217L, T134R/L176S/I211W/V214M, 134R/L176S/I211W/T215M, T134R/I211W/V214M, A169N/Y171V/A173I/A213V/A235K, A169N/A173I/M175H/A213V/A235K, A169N/M175G/E212C/A213V/A235K, A169N/M175H/E212G/A213V/A235K, A169N/L176S/V178I/I211L/V214M, A169N/L176S/V178I/I211W/V214M/W217L, A169N/L176S/V178I/I211W/W217L, A169N/L176S/V178M, A169N/L176S/V178M/I211W/V214M/W217I, A169N/L176S/I211W/V214M, A169N/L176S/I211W/V214M/T215L/D234L, A169N/L176S/I211W/W217I, A169N/L176S/I211W/W217L, A169N/L176S/V214M/T215M/W217I, A169N/L176S/I211L/V214M/W217I, A169N/V178I/W217I, A169N/V178M/D234L, A169N/I211W/V214M/T215L, A169N/I211W/W217I, A169N/E212C/A235K, A169N/E212C/A213V/A235K, A169N/E212G/A213V, A169N/E212V/A213V/A235K, A169N/A235K, Y171V/A173I/E212G/A213V/A235K, A173I/M175H/A213V, M175H/A213P/A235K, M175H/A235K, L176S/V178I/I211W/T215L/W217L, L176S/V178I/I211W/W217I, L176S/I211L/V214M, L176S/V214M/W217L, V178M/I211L/V214M, V178M/I211W/W217L, V178I/T215M, I211W/D234L, E212G/A213V/A235K, E212V/A213V/A235K, A213T/A235K, and A213V/A235K, wherein the positions are numbered with reference to SEQ ID NO:270. In some further embodiments, the engineered polypeptide comprises an amino acid sequence with at least 80% sequence identity to any even-numbered sequence set forth in SEQ ID NO:76 to SEQ ID NO:232.

The present invention further provides an engineered polypeptide comprising an amino acid sequence with at least 80% sequence identity to a reference sequence of SEQ ID NO:229, comprising at least one substitution at one or more positions selected from 45, 127, 130, 134, 174, 206, 209, 212, 216, 223, 227, and 279, wherein the positions are numbered with reference to SEQ ID NO:229. In some additional embodiments, the engineered polypeptide comprises at least one substitution selected from 45I, 127R, 130R, 134L/R, 174M, 206L, 209K/S, 212H/K/R, 216N/R/S, 223N, 227V, and 279V, wherein the positions are numbered with reference to SEQ ID NO:229. In some further embodiments, the engineered polypeptide comprises at least one substitution selected from V45I, G127R, T130R, T134L/R, A174M, M206L, Q209K/S, E212H/K/R, G216N/R/S, D223N, A227V, and D279V, wherein the positions are numbered with reference to SEQ ID NO:229. In some additional embodiments, the engineered polypeptide comprises an amino acid sequence with at least 80% sequence identity to any even-numbered sequence set forth in SEQ ID NO:234 to SEQ ID NO:270.

The present invention also provides an engineered polynucleotide encoding at least one engineered polypeptide described in the above paragraphs. In some embodiments, the engineered polynucleotide comprises the odd-numbered sequences set forth in SEQ ID NO:3 to SEQ ID NO:267.

The present invention further provides an engineered polynucleotide encoding an engineered imine or oxime reductase polypeptide, wherein the engineered polynucleotides comprise substitution(s) at positions 12/15/18/21/27, 169/631/633, 259/523/524/525, 308/634/635/636, 364/365/366, 367/368/369, 370/371, 370/371/372/532, 394/396, 394/395/396, 401/402, 505/506/507, 512/513, 517/518/519, 523/524/525, 526/527/528, 532/534, 532/724/725, 631/633, 631/632/633, 634/635/636, 635/636, 637/638, 637/639, 637/639, 638/639, 640, 643/644/645, 644/645, 649/650/651, 700/701/702, and 703/704/705, wherein the positions are numbered with reference to SEQ ID NO:1. In some embodiments, the engineered polynucleotide encoding the engineered imine or oxime reductase polypeptide comprises at least one of the following substitution(s)/substitution sets selected from 12A/15T/18G/21C/27A, 169A/631C/633T, 259T/523G/524G/525T, 308A/634T/635G/636T, 364G/365A/366A, 367G/368G/369T, 370G/371G, 370G/371C/372A/532A, 394C/396T, 394A/395G/396G, 401G/402G, 505A/506A/507T, 505A/506G/507T, 512G/513G, 517A/518T/519T, 517C/518A/519T, 523C/524A/525T, 523G/524G/525T, 526A/527G/528T, 532A/534G, 532A/724T/725A, 631C/633T, 631T/632G/633G, 634T/635G/636T, 635G/636T, 635T/636T, 637A/638G, 637A/639A, 637C/639A, 638T/639T, 640A, 643T/644T/645G, 644T/645G, 649A/650T/651T, 649C/650T/651T, 700T/701T/702G, and 703A/704A/705A, and wherein the positions are numbered with reference to SEQ ID NO:1. In some additional embodiments, the engineered polynucleotide encoding the engineered imine or oxime reductase comprises at least one of the following substitution(s)/substitution sets selected from C12A/C15T/A18G/T21C/T27A, G169A/A631C/C633T, C259T/A523G/T524G/G525T, G308A/G634T/A635G/A636T, C364G/T365A/G366A, A367G/C368G/C369T, A370G/T371G, A370G/T371C/T372A/G532A, G394C/A396T, G394A/A395G/A396G, C401G/C402G, G505A/C506A/A507T, G505A/C506G/A507T, A512G/T513G, G517A/C518T/A519T, G517C/C518A/A519T, A523C/T524A/G525T, A523G/T524G/G525T, C526A/T527G/G528T, G532A/C534G, G532A/G724T/C725A, A631C/C633T, A631T/T632G/C633G, G634T/A635G/A636T, A635G/A636T, A635T/A636T, G637A/C638G, G637A/G639A, G637C/G639A, C638T/G639T, G640A, A643T/C644T/C645G, C644T/C645G, T649A/G650T/G651T, T649C/G650T/G651T, G700T/A701T/C702G, and G703A/C704A/C705A, and wherein the positions are numbered with reference to SEQ ID NO:1.

The present invention also provides an engineered polynucleotide encoding an engineered imine or oxime reductase polypeptide, wherein the engineered polynucleotides comprise substitution(s) at positions 367/368/369/505/506/507/513/519/523/524/525/634/635/636/639/703/704/705, 369/370/371/372/505/506/507/513/519/638/703/704/705, 369/370/371/372/507/513/519/523/524/525/635/638/703/704/705, 369/505/506/507/511/512/517/518/519/638/703/704/705, 369/505/506/507/513/517/518/519/523/524/525/638/703/704/705, 369/505/506/507/513/519/523/524/525/634/635/636/638/703/704/705, 369/505/506/507/513/519/635/638/703/704/705, 401/402/505/506/507/526/527/532/534/631/632/633/645/702, 401/402/505/506/507/526/527/532/534/631/633/640/645/702, 401/402/505/506/507/526/527/532/534/631/633/645/649/650/651/702, 401/402/505/506/507/526/527/534/631/632/633/645/702, 401/402/505/506/507/526/527/534/631/633/644/645/649/650/651/700/701, 401/402/505/506/507/526/532/534/631/632/633/640/645/649/650/651/702, 401/402/505/506/507/526/534/631/632/633/640/645/649/650/651/702, 401/402/505/506/507/526/534/631/632/633/645/649/650/651/702, 401/402/507/526/527/534/631/632/633/640/645/702, 401/402/507/526/527/534/631/632/633/644/645/702, 401/402/526/534/631/632/633/640/645/702, 402/505/506/507/526/527/532/534/631/632/633/640/645/649/650/651/702, 402/505/506/507/526/527/532/534/702, 402/505/506/507/526/527/532/534/631/633/640/645/702, 402/505/506/507/526/527/532/534/631/632/633/640/645/649/650/651/702, 402/505/506/507/526/527/534/631/632/633/640/643/644/645/700/701, 402/505/506/507/526/527/534/631/632/633/640/645/702, 402/505/506/507/526/527/534/631/632/633/645/649/650/651/702, 402/505/506/507/526/527/534/631/632/633/645/649/650/651/702, 402/505/506/507/526/527/534/631/633/640/644/645/649/650/651/702, 402/505/506/507/526/532/534/645/649/650/651, 402/505/506/507/526/534/631/632/633/645/649/650/651/702, 402/507/526/527/532/534/631/632/633/643/644/645/649/650/651/702, 402/507/526/527/532/534/631/632/633/645/649/650/651/702, 402/507/526/532/534/631/633/640/645, 402/507/526/532/534/631/632/633/645/649/650/651/702, 402/526/527/534/631/633/640/645/702, 505/506/507/526/527/532/534/631/632/633/640/645/649/650/651/702, 505/506/507/526/527/532/534/631/632/633/645/649/650/651/702, 505/506/507/526/534/631/632/633/640/643/644/645, 507/526/527/534/633/640/645/649/650/651/702, 507/526/532/534/644/645/702, and 631/632/633/645/700/701, wherein the positions are numbered with reference to SEQ ID NO:269. In some embodiments, the engineered polynucleotide encoding the engineered imine or oxime reductase polypeptide comprises at least one of the following substitution(s)/substitution sets selected from 367G/368G/369T/505A/506A/507T/513C/519C/523G/524G/525C/634T/635G/636C/639T/703A/704A/705G, 369G/370G/371G/372C/505A/506A/507T/513C/519C/638T/703A/704A/705G, 369G/370G/371G/372C/507C/513C/519C/523G/524G/525C/635T/638T/703A/704A/705G, 369G/505A/506A/507T/511G/512T/517A/518T/519T/638T/703A/704A/705G, 369G/505A/506A/507T/513C/517A/518T/519T/523C/524A/525C/638T/703A/704A/705G, 369G/505A/506A/507T/513C/519C/523G/524G/525C/634T/635G/636C/638T/703A/704A/705G, 369G/505A/506A/507T/513C/519C/635T/638T/703A/704A/705G, 401G/402G/505A/506A/507C/526T/527C/532A/534G/631C/633A/645T/649C/650T/651A/702T, 401G/402G/505A/506A/507C/526T/527C/532A/534T/631C/633A/640A/645T/702T, 401G/402G/505A/506A/507C/526T/527C/532A/534T/631T/632G/633G/645T/702T, 401G/402G/505A/506A/507C/526T/527C/534G/631C/633A/644T/645G/649A/650T/651A/700C/701T, 401G/402G/505A/506A/507C/526T/527C/534T/631T/632G/633G/645T/702T, 401G/402G/505A/506A/507C/526T/532A/534G/631T/632G/633G/640A/645T/649A/650T/651A/702T, 401G/402G/505A/506A/507C/526T/534G/631T/632G/633G/640A/645T/649C/650T/651A/702T, 401G/402G/505A/506A/507C/526T/534T/631T/632G/633G/645T/649C/650T/651A/702T, 401G/402G/507C/526T/527C/534G/631T/632G/633G/640A/645T/702T, 401G/402G/507C/526T/527C/534G/631T/632G/633G/644T/645G/702T, 401G/402G/526T/534G/631T/632G/633G/640A/645T/702T, 402G/505A/506A/507C/526T/527C/532A/534T/631T/632G/633G/640A/645T/649C/650T/651A/702T, 402G/505A/506A/507C/526T/527C/532A/534G/702T, 402G/505A/506A/507C/526T/527C/532A/534T/631C/633A/640A/645T/702T, 402G/505A/506A/507C/526T/527C/532A/534T/631T/632G/633G/640A/645T/649C/650T/651A/702T, 402G/505A/506A/507C/526T/527C/534G/631C/633A/640A/645T/649A/650T/651A/702T, 402G/505A/506A/507C/526T/527C/534G/631T/632G/633G/640A/643T/644T/645G/700C/701T, 402G/505A/506A/507C/526T/527C/534G/631T/632G/633G/640A/645T/702T, 402G/505A/506A/507C/526T/527C/534G/631T/632G/633G/645T/649C/650T/651A/702T, 402G/505A/506A/507C/526T/527C/534T/631T/632G/633G/645T/649A/650T/651A/702T, 402G/505A/506A/507C/526T/527C/534T/633A/640A/644T/645G/649A/650T/651A/702T, 402G/505A/506A/507C/526T/532A/534T/633A/645T/700C/701T, 402G/505A/506A/507C/526T/532A/534T/645T/649A/650T/651A, 402G/505A/506A/507C/526T/534G/631T/632G/633G/ 645T/649A/650T/651A/702T, 402G/507C/526T/527C/ 532A/534T/631T/632G/633G/643T/644T/645G/649C/ 650T/651A/702T, 402G/507C/526T/527C/532A/534T/ 631T/632G/633G/645T/649A/650T/651A/702T, 402G/ 507C/526T/532A/534G/631C/633A/640A/645T, 402G/ 507C/526T/532A/534G/631T/632G/633G/645T/649C/ 650T/651A/702T, 402G/526T/527C/534T/631C/633A/ 640A/645T/702T, 505A/506A/507C/526T/527C/532A/ 534G/631T/632G/633G/640A/645T/649A/650T/651A/ 702T, 505A/506A/507C/526T/527C/532A/534T/631T/ 632G/633G/645T/649C/650T/651A/702T, 505A/506A/ 507C/526T/534G/631T/632G/633G/640A/643T/644T/ 645G, 507C/526T/527C/534G/633A/640A/645T/649C/ 650T/651A/702T, 507C/526T/527C/534G/633A/640A/ 645T/649C/650T/651A/702T, 507C/526T/532A/534T/ 644T/645G/702T, and 631T/632G/633G/645T/700C/701T, wherein the positions are numbered with reference to SEQ ID NO:269. In some further embodiments, the engineered polynucleotide encoding the engineered imine or oxime reductase polypeptide comprises at least one of the following substitution(s)/substitution sets selected from A367G/ C368G/C369T/G505A/C506A/A507T/T513C/A519C/ A523G/T524G/G525C/G634T/A635G/A636C/G639T/ G703A/C704A/C705G, C369G/A370G/T371G/T372C/ G505A/C506A/A507T/T513C/A519C/C638T/G703A/ C704A/C705G, C369G/A370G/T371G/T372C/A507C/ T513C/519C/A523G/T524G/G525C/A635T/C638T/ G703A/C704A/C705G, C369G/G505A/C506A/A507T/ T511G/A512T/G517A/C518T/A519T/C638T/G703A/ C704A/C705G, C369G/G505A/C506A/A507T/T513C/ G517A/C518T/A519T/A523C/T524A/G525C/C638T/ G703A/C704A/C705G, C369G/G505A/C506A/A507T/ T513C/A519C/A523G/T524G/G525C/G634T/A635G/ A636C/C638T/G703A/C704A/C705G, C369G/G505A/ C506A/A507T/T513C/A519C/A635T/C638T/G703A/ C704A/C705G, C401G/C402G/G505A/C506A/A507C/ C526T/T527C/G532A/C534G/A631C/C633A/C645T/ T649C/G65 OT/G651A/C702T, C401G/C402G/G505A/ C506A/A507C/C526T/T527C/G532A/C534T/A631C/ C633A/G640A/C645T/C702T, C401G/C402G/G505A/ C506A/A507C/C526T/T527C/G532A/C534T/A631T/ T632G/C633G/C645T/C702T, C401G/C402G/G505A/ C506A/A507C/C526T/T527C/C534G/A631C/C633A/ C644T/C645G/T649A/G65 OT/G651A/G700C/A701T, C401G/C402G/G505A/C506A/A507C/C526T/T527C/ C534T/A631T/T632G/C633G/C645T/C702T, C401G/ C402G/G505A/C506A/A507C/C526T/G532A/C534G/ A631T/T632G/C633G/G640A/C645T/T649A/G650T/ G651A/C702T, C401G/C402G/G505A/C506A/A507C/ C526T/C534G/A631T/T632G/C633G/G640A/C645T/ T649C/G65 OT/G651A/C702T, C401G/C402G/G505A/ C506A/A507C/C526T/C534T/A631T/T632G/C633G/ C645T/T649C/G650T/G651A/C702T, C401G/C402G/ A507C/C526T/T527C/C534G/A631T/T632G/C633G/ G640A/C645T/C702T, C401G/C402G/A507C/C526T/ T527C/C534G/A631T/T632G/C633G/C644T/C645G/ C702T, C401G/C402G/C526T/C534G/A631T/T632G/ C633G/G640A/C645T/C702T, C402G/G505A/C506A/ A507C/C526T/T527C/G532A/C534T/A631T/T632G/ C633G/G640A/C645T/T649C/G650T/G651A/C702T, C402G/G505A/C506A/A507C/C526T/T527C/G532A/ C534G/C702T, C402G/G505A/C506A/A507C/C526T/ T527C/G532A/C534T/A631C/C633A/G640A/C645T/ C702T, C402G/G505A/C506A/A507C/C526T/T527C/ G532A/C534T/A631T/T632G/C633G/G640A/C645T/ T649C/G650T/G651A/C702T, C402G/G505A/C506A/ A507C/C526T/T527C/C534G/A631C/C633A/G640A/ C645T/T649A/G650T/G651A/C702T, C402G/G505A/ C506A/A507C/C526T/T527C/C534G/A631T/T632G/ C633G/G640A/A643T/C644T/C645G/G700C/A701T, C402G/G505A/C506A/A507C/C526T/T527C/C534G/ A631T/T632G/C633G/G640A/C645T/C702T, C402G/ G505A/C506A/A507C/C526T/T527C/C534G/A631T/ T632G/C633G/C645T/T649C/G650T/G651A/C702T, C402G/G505A/C506A/A507C/C526T/T527C/C534T/ A631T/T632G/C633G/C645T/T649A/G650T/G651A/ C702T, C402G/G505A/C506A/A507C/C526T/T527C/ C534T/C633A/G640A/C644T/C645G/T649A/G650T/ G651A/C702T, C402G/G505A/C506A/A507C/C526T/ G532A/C534G/C633A/C645T/G700C/A701T, C402G/ G505A/C506A/A507C/C526T/G532A/C534T/C645T/ T649A/G650T/G651A, C402G/G505A/C506A/A507C/ C526T/C534G/A631T/T632G/C633G/C645T/T649A/ G650T/G651A/C702T, C402G/A507C/C526T/T527C/ G532A/C534T/A631T/T632G/C633G/A643T/C644T/ C645G/T649C/G65 OT/G651A/C702T, C402G/A507C/ C526T/T527C/G532A/C534T/A631T/T632G/C633G/ C645T/T649A/G650T/G651A/C702T, C402G/A507C/ C526T/G532A/C534G/A631C/C633A/G640A/C645T, C402G/A507C/C526T/G532A/C534G/A631T/T632G/ C633G/C645T/T649C/G650T/G651A/C702T, C402G/ C526T/T527C/C534T/A631C/C633A/G640A/C645 T/C702T, G505A/C506A/A507C/C526T/T527C/G532A/ C534G/A631T/T632G/C633G/G640A/C645T/T649A/G65 OT/G651A/C702T, G505A/C506A/A507C/C526T/T527C/ G532A/C534T/A631T/T632G/C633G/C645T/T649C/ G650T/G651A/C702T, G505A/C506A/A507 C/C526T/ C534G/A631 T/T632G/C633G/G640A/A643 T/C644T/ C645G, A507C/C526T/T527 C/C534G/C633A/G640A/ C645 T/T649C/G650T/G651A/C702T, A507C/C526T/ G532A/C534T/C644T/C645G/C702T, and A631T/T632G/ C633G/C645T/G700C/A701T, wherein the positions are numbered with reference to SEQ ID NO:269.

The present invention also provides an engineered polynucleotide encoding an engineered imine or oxime reductase polypeptide, wherein the engineered polynucleotide comprises substitution(s) at positions 133, 379/381, 388/389/ 390, 400/401/402, 401/402, 520/521/522, 616/618, 625, 625/626/627, 634, 634/635/636, 634/636, 646, 646/647, 646, 667, 680/681, and 836/837, wherein the positions are numbered with reference to SEQ ID NO:229. In some embodiments, the engineered polynucleotide encoding the engineered imine or oxime reductase polypeptide comprises at least one of the following substitution(s)/substitution sets selected from 133A, 379A/381G, 388C/389G/390T, 400C/ 401T/402T, 401G/402G, 520A/521T/522G, 616C/618T, 625A, 625A/626G/627T, 634A, 634A/635G/636G, 634C/ 636T, 646A, 646A/647A, 646C, 667A, 680T/681T, and 836T/837T, wherein the positions are numbered with reference to SEQ ID NO:229. In some further embodiments, the engineered polynucleotide encoding the engineered imine or oxime reductase polypeptide comprises at least one of the following substitution(s)/substitution sets selected from G133A, G379A/C381G, A388C/C389G/C390T, A400C/ C401T/C402T, C401G/C402G, G520A/C521T/A522G, A616C/C618T, C625A, C625A/A626G/A627T, G634A, G634A/A635G/A636G, G634C/A636T, G646A, G646A/ G647A, G646C, G667A, C680T/C681T, and A836T/C837T, wherein the positions are numbered with reference to SEQ ID NO:229.

The present invention further provides vectors comprising at least one engineered polynucleotide described above. In some embodiments, the vectors further comprise at least one control sequence.

The present invention also provides host cells comprising the vectors provided herein. In some embodiments, the host cell produces at least one engineered polypeptide provided herein.

The present invention further provides methods of producing an engineered imine or oxime reductase polypeptide, comprising the steps of culturing the host cell provided herein under conditions such that the engineered polynucleotide is expressed and the engineered polypeptide is produced. In some embodiments, the methods further comprise the step of recovering the engineered polypeptide.

DESCRIPTION OF THE INVENTION

Unless defined otherwise, all technical and scientific terms used herein generally have the same meaning as commonly understood by one of ordinary skill in the art to which this invention pertains. Generally, the nomenclature used herein and the laboratory procedures of cell culture, molecular genetics, microbiology, organic chemistry, analytical chemistry and nucleic acid chemistry described below are those well-known and commonly employed in the art. Such techniques are well-known and described in numerous texts and reference works well known to those of skill in the art. Standard techniques, or modifications thereof, are used for chemical syntheses and chemical analyses. All patents, patent applications, articles and publications mentioned herein, both supra and infra, are hereby expressly incorporated herein by reference.

Although any suitable methods and materials similar or equivalent to those described herein find use in the practice of the present invention, some methods and materials are described herein. It is to be understood that this invention is not limited to the particular methodology, protocols, and reagents described, as these may vary, depending upon the context they are used by those of skill in the art. Accordingly, the terms defined immediately below are more fully described by reference to the invention as a whole.

It is to be understood that both the foregoing general description and the following detailed description are exemplary and explanatory only and are not restrictive of the present invention. The section headings used herein are for organizational purposes only and not to be construed as limiting the subject matter described. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

As used in this specification and the appended claims, the singular forms "a", "an" and "the" include plural referents unless the context clearly indicates otherwise. Thus, for example, reference to "a polypeptide" includes more than one polypeptide. Similarly, "comprise," "comprises," "comprising" "include," "includes," and "including" are interchangeable and not intended to be limiting.

It is to be understood that where descriptions of various embodiments use the term "comprising," those skilled in the art would understand that in some specific instances, an embodiment can be alternatively described using language "consisting essentially of" or "consisting of." It is to be further understood that where descriptions of various embodiments use the term "optional" or "optionally" the subsequently described event or circumstance may or may not occur, and that the description includes instances where the event or circumstance occurs and instances in which it does not. It is to be understood that both the foregoing general description, and the following detailed description are exemplary and explanatory only and are not restrictive of this disclosure. The section headings used herein are for organizational purposes only and not to be construed as limiting the subject matter described.

ABBREVIATIONS

The abbreviations used for the genetically encoded amino acids are conventional and are as follows:

| Amino Acid | Three-Letter | One-Letter Abbreviation |
|---|---|---|
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | HIS | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

When the three-letter abbreviations are used, unless specifically preceded by an "L" or a "D" or clear from the context in which the abbreviation is used, the amino acid may be in either the L- or D-configuration about α-carbon ($C_\alpha$). For example, whereas "Ala" designates alanine without specifying the configuration about the α-carbon, "D-Ala" and "L-Ala" designate D-alanine and L-alanine, respectively.

When the one-letter abbreviations are used, upper case letters designate amino acids in the L-configuration about the α-carbon and lower case letters designate amino acids in the D-configuration about the α-carbon. For example, "A" designates L-alanine and "a" designates D-alanine. When polypeptide sequences are presented as a string of one-letter or three-letter abbreviations (or mixtures thereof), the sequences are presented in the amino (N) to carboxy (C) direction in accordance with common convention.

The abbreviations used for the genetically encoding nucleosides are conventional and are as follows: adenosine (A); guanosine (G); cytidine (C); thymidine (T); and uridine (U). Unless specifically delineated, the abbreviated nucleotides may be either ribonucleosides or 2'-deoxyribonucleosides. The nucleosides may be specified as being either ribonucleosides or 2'-deoxyribonucleosides on an individual basis or on an aggregate basis. When nucleic acid sequences are presented as a string of one-letter abbreviations, the sequences are presented in the 5' to 3' direction in accordance with common convention, and the phosphates are not indicated.

Definitions

In reference to the present invention, the technical and scientific terms used in the descriptions herein will have the meanings commonly understood by one of ordinary skill in the art, unless specifically defined otherwise. Accordingly, the following terms are intended to have the following meanings.

"EC" number refers to the Enzyme Nomenclature of the Nomenclature Committee of the International Union of Biochemistry and Molecular Biology (NC-IUBMB). The IUBMB biochemical classification is a numerical classification system for enzymes based on the chemical reactions they catalyze.

"ATCC" refers to the American Type Culture Collection whose biorepository collection includes genes and strains.

"NCBI" refers to National Center for Biological Information and the sequence databases provided therein.

"Protein," "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids, as well as polymers comprising D- and L-amino acids, and mixtures of D- and L-amino acids.

"Amino acids" are referred to herein by either their commonly known three-letter symbols or by the one-letter symbols recommended by IUPAC-IUB Biochemical Nomenclature Commission. Nucleotides, likewise, may be referred to by their commonly accepted single letter codes.

As used herein, "polynucleotide" and "nucleic acid" refer to two or more nucleosides that are covalently linked together. The polynucleotide may be wholly comprised of ribonucleotides (i.e., RNA), wholly comprised of 2' deoxyribonucleotides (i.e., DNA), or comprised of mixtures of ribo- and 2' deoxyribonucleotides. While the nucleosides will typically be linked together via standard phosphodiester linkages, the polynucleotides may include one or more non-standard linkages. The polynucleotide may be single-stranded or double-stranded, or may include both single-stranded regions and double-stranded regions. Moreover, while a polynucleotide will typically be composed of the naturally occurring encoding nucleobases (i.e., adenine, guanine, uracil, thymine and cytosine), it may include one or more modified and/or synthetic nucleobases, such as, for example, inosine, xanthine, hypoxanthine, etc. In some embodiments, such modified or synthetic nucleobases are nucleobases encoding amino acid sequences.

"Opine dehydrogenase activity," as used herein, refers to an enzymatic activity in which a carbonyl group of a 2-ketoacid (e.g., pyruvate) and an amino group of a neutral L-amino acid (e.g., L-norvaline) are converted to a secondary amine dicarboxylate compound (e.g., N-[1-(R)-(carboxy)ethyl]-(S)-norvaline).

As used herein, "imine" refers to an organic compound or functional group that contains a nitrogen-carbon double bond, wherein the nitrogen is bonded to hydrogen or an organic group.

"Imine reductase activity," as used herein, refers to an enzymatic activity in which a carbonyl group of a ketone or aldehyde and an amino group a primary or secondary amine (wherein the carbonyl and amino groups can be on separate compounds or the same compound) are converted to a secondary or tertiary amine product compound, in the presence of co-factor NAD(P)H, as illustrated in Scheme 1.

"Imine reductase" or "IRED," as used herein, refers to an enzyme having imine reductase activity. It is to be understood that imine reductases are not limited to engineered polypeptides derived from the wild-type imine reductase from *Pseudonocardia spinosispora*, but may include other enzymes having imine reductase activity, including engineered polypeptides derived from other imine reductase enzymes. Imine reductases as used herein include naturally occurring (wild-type) imine reductase as well as non-naturally occurring engineered polypeptides generated by human manipulation.

As used herein "oxime" refers to an imine with the general formula $R^1R^2C{=}NOR^3$, where $R^1$ is an organic side chain, $R^2$ and $R^3$ may be hydrogen or another organic group.

"Oxime reductase activity," as used herein, refers to an enzymatic activity in which the double bond between the nitrogen and the carbon in the oxime moiety is reduced to a single bond.

"Coding sequence" refers to that portion of a nucleic acid (e.g., a gene) that encodes an amino acid sequence of a protein.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

As used herein, "recombinant," "engineered," and "non-naturally occurring" when used with reference to a cell, nucleic acid, or polypeptide, refer to a material, or a material corresponding to the natural or native form of the material, that has been modified in a manner that would not otherwise exist in nature. In some embodiments, the cell, nucleic acid or polypeptide is identical a naturally occurring cell, nucleic acid or polypeptide, but is produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity" and "percentage homology" are used interchangeably herein to refer to comparisons among polynucleotides or polypeptides, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman (Smith and Waterman, Adv. Appl. Math., 2:482) [1981], by the homology alignment algorithm of Needleman and Wunsch (Needleman and Wunsch, J. Mol. Biol., 48:443 [1970]), by the search for similarity method of Pearson and Lipman (Pearson and Lipman, Proc. Natl. Acad. Sci. USA 85:2444 [1988]), by computerized implementations of these algorithms (e.g., GAP, BESTFIT, FASTA, and TFASTA in the GCG Wisconsin Software Package), or by visual inspection, as known in the art. Examples of algorithms that are suitable for determining percent sequence identity and sequence similarity include, but are not limited to the BLAST and BLAST 2.0 algorithms, which are described by Altschul et al. (See, Altschul et al., J. Mol. Biol., 215: 403-410 [1990]; and Altschul et al., Nucl. Acids Res., 3389-3402 [1977], respectively). Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (See, Henikoff and Henikoff, Proc. Natl. Acad. Sci. USA 89:10915 [1989]). Exemplary determination of sequence alignment and % sequence identity can employ the BESTFIT or GAP programs in the GCG Wisconsin Software package (Accelrys, Madison WI), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides or polypeptides over a "comparison window" to identify and compare local regions of sequence similarity. In some embodiments, a "reference sequence" can be based on a primary amino acid sequence, where the reference sequence is a sequence that can have one or more changes in the primary sequence. For instance, a "reference sequence based on SEQ ID NO:4 having at the residue corresponding to X14 a valine" or X14V refers to a reference sequence in which the corresponding residue at X14 in SEQ ID NO:4, which is a tyrosine, has been changed to valine.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

As used herein, "substantial identity" refers to a polynucleotide or polypeptide sequence that has at least 80 percent sequence identity, at least 85 percent identity, at least between 89 to 95 percent sequence identity, or more usually, at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In some specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). In some embodiments, residue positions that are not identical in sequences being compared differ by conservative amino acid substitutions.

"Corresponding to," "reference to," and "relative to" when used in the context of the numbering of a given amino acid or polynucleotide sequence refer to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered imine reductase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Amino acid difference" or "residue difference" refers to a change in the amino acid residue at a position of a polypeptide sequence relative to the amino acid residue at a corresponding position in a reference sequence. The positions of amino acid differences generally are referred to herein as "Xn," where n refers to the corresponding position in the reference sequence upon which the residue difference is based. For example, a "residue difference at position X25 as compared to SEQ ID NO: 2" refers to a change of the amino acid residue at the polypeptide position corresponding to position 25 of SEQ ID NO:2. Thus, if the reference polypeptide of SEQ ID NO: 2 has a valine at position 25, then a "residue difference at position X25 as compared to SEQ ID NO:2" an amino acid substitution of any residue other than valine at the position of the polypeptide corresponding to position 25 of SEQ ID NO: 2. In most instances herein, the specific amino acid residue difference at a position is indicated as "XnY" where "Xn" specified the corresponding position as described above, and "Y" is the single letter identifier of the amino acid found in the engineered polypeptide (i.e., the different residue than in the reference polypeptide). In some embodiments, more than one amino acid can appear in a specified residue position (i.e., the alternative amino acids can be listed in the form XnY/Z, where Y and Z represent alternate amino acid residues). In some instances (e.g., in Tables 2-2, 3-1, 4-1, and 5-1) the present invention also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. Furthermore, in some instances, a polypeptide of the present invention can include one or more amino acid residue differences relative to a reference sequence, which is indicated by a list of the specified positions where changes are made relative to the reference sequence. In some additional embodiments, the present invention provides engineered polypeptide sequences comprising both conservative and non-conservative amino acid substitutions.

As used herein, "conservative amino acid substitution" refers to a substitution of a residue with a different residue having a similar side chain, and thus typically involves substitution of the amino acid in the polypeptide with amino acids within the same or similar defined class of amino acids. By way of example and not limitation, an amino acid with an aliphatic side chain is substituted with another aliphatic amino acid (e.g., alanine, valine, leucine, and isoleucine); an amino acid with an hydroxyl side chain is substituted with another amino acid with a hydroxyl side chain (e.g., serine and threonine); an amino acid having aromatic side chains is substituted with another amino acid having an aromatic side chain (e.g., phenylalanine, tyrosine, tryptophan, and histidine); an amino acid with a basic side chain is substituted with another amino acid with a basis side chain (e.g., lysine and arginine); an amino acid with an acidic side chain is substituted with another amino acid with an acidic side chain (e.g., aspartic acid or glutamic acid); and/or a hydrophobic or hydrophilic amino acid is replaced with another hydrophobic or hydrophilic amino acid, respectively. Exemplary conservative substitutions are provided in Table 1 below.

TABLE 1

Conservative Amino Acid Substitution Examples

| Residue | Possible Conservative Substitutions |
| --- | --- |
| A, L, V, I | Other aliphatic (A, L, V, I) |
| | Other non-polar (A, L, V, I, G, M) |
| G, M | Other non-polar (A, L, V, I, G, M) |
| D, E | Other acidic (D, E) |
| K, R | Other basic (K, R) |
| N, Q, S, T | Other polar |
| H, Y, W, F | Other aromatic (H, Y, W, F) |
| C, P | None |

"Non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine), (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered imine reductase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. In some embodiments, the improved engineered imine reductase enzymes comprise insertions of one or more amino acids to the naturally occurring polypeptide having imine reductase activity as well as insertions of one or more amino acids to other improved imine reductase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Fragment" as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of the full-length imine reductase polypeptide, for example the polypeptide of SEQ ID NO:2 or engineered imine reductase provided in the even-numbered sequences of SEQ ID NO:4 to 270.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The engineered imine reductase enzymes may be present within a cell, present in the cellular medium, or prepared in various forms, such as lysates or isolated preparations. As such, in some embodiments, the engineered imine reductase enzyme can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure imine reductase composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated engineered imine reductase polypeptide is a substantially pure polypeptide composition.

"Stereoselective" refers to a preference for formation of one stereoisomer over another in a chemical or enzymatic reaction. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereomeric excess.

"Highly stereoselective" refers to a chemical or enzymatic reaction that is capable of converting a substrate or substrates (e.g., substrate compounds (1e) and (2b)), to the corresponding amine product (e.g., compound (3i)), with at least about 85% stereomeric excess.

As used herein, "improved enzyme property" refers to at least one improved property of an enzyme. In some embodiments, the present invention provides engineered imine reductase polypeptides that exhibit an improvement in any enzyme property as compared to a reference imine reductase polypeptide and/or a wild-type imine reductase polypeptide, and/or another engineered imine reductase polypeptide. For the engineered imine reductase polypeptides described herein, the comparison is generally made to the wild-type enzyme from which the imine reductase is derived, although in some embodiments, the reference enzyme can be another improved engineered imine reductase. Thus, the level of "improvement" can be determined and compared between various imine reductase polypeptides, including wild-type, as well as engineered imine reductases. Improved properties include, but are not limited to, such properties as enzymatic activity (which can be expressed in terms of percent conversion of the substrate), thermo stability, solvent stability, pH activity profile, cofactor requirements, refractoriness to inhibitors (e.g., substrate or product inhibition), stereospecificity, and/or stereoselectivity (including enantioselectivity).

"Increased enzymatic activity" refers to an improved property of the engineered imine reductase polypeptides, which can be represented by an increase in specific activity (e.g., product produced/time/weight protein) or an increase in percent conversion of the substrate to the product (e.g., percent conversion of starting amount of substrate to product in a specified time period using a specified amount of imine reductase) as compared to the reference imine reductase enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.2 times the enzymatic activity of the corresponding wild-type enzyme, to as much as 2 times, 5 times, 10 times, 20 times, 25 times, 50 times or more enzymatic activity than the naturally occurring or another engineered imine reductase from which the imine reductase polypeptides were derived Imine reductase activity can be measured by any one of standard assays, such as by monitoring changes in properties of substrates, cofactors, or products. In some embodiments, the amount of products generated can be measured by Liquid Chromatography-Mass Spectrometry (LC-MS). Comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells to minimize variations in amount of enzyme produced by the host cells and present in the lysates.

"Conversion" refers to the enzymatic conversion of the substrate(s) to the corresponding product(s). "Percent conversion" refers to the percent of the substrate that is converted to the product within a period of time under specified conditions. Thus, the "enzymatic activity" or "activity" of a imine reductase polypeptide can be expressed as "percent conversion" of the substrate to the product.

"Thermostable" refers to a imine reductase polypeptide that maintains similar activity (more than 60% to 80% for example) after exposure to elevated temperatures (e.g., 40-80° C.) for a period of time (e.g., 0.5-24 hrs) compared to the wild-type enzyme exposed to the same elevated temperature.

"Solvent stable" refers to an imine reductase polypeptide that maintains similar activity (more than e.g., 60% to 80%) after exposure to varying concentrations (e.g., 5-99%) of solvent (ethanol, isopropyl alcohol, dimethylsulfoxide (DMSO), tetrahydrofuran, 2-methyltetrahydrofuran, acetone, toluene, butyl acetate, methyl tert-butyl ether, etc.) for a period of time (e.g., 0.5-24 hrs) compared to the wild-type enzyme exposed to the same concentration of the same solvent.

"Thermo- and solvent stable" refers to an imine reductase polypeptide that is both thermostable and solvent stable.

The term "stringent hybridization conditions" is used herein to refer to conditions under which nucleic acid hybrids are stable. As known to those of skill in the art, the stability of hybrids is reflected in the melting temperature (T m) of the hybrids. In general, the stability of a hybrid is a function of ion strength, temperature, G/C content, and the presence of chaotropic agents. The $T_m$ values for polynucleotides can be calculated using known methods for predicting melting temperatures (See e.g., Baldino et al., Meth. Enzymol., 168:761-777 [1989]; Bolton et al., Proc. Natl. Acad. Sci. USA 48:1390 [1962]; Bresslauer et al., Proc. Natl. Acad. Sci. USA 83:8893-8897 [1986]; Freier et al., Proc. Natl. Acad. Sci. USA 83:9373-9377 [1986]; Kierzek et al., Biochem., 25:7840-7846 [1986]; Rychlik et al., 1990, Nucl. Acids Res., 18:6409-6412 (erratum, Nucl. Acids Res., 19:698 [1991]); Sambrook et al., supra); Suggs et al., 1981, in *Developmental Biology Using Purified Genes*, Brown et al. [eds.], pp. 683-693, Academic Press, Cambridge, MA [1981]; and Wetmur, Crit. Rev. Biochem. Mol. Biol., 26:227-259) [1991]). In some embodiments, the polynucleotide encodes the polypeptide disclosed herein and hybridizes under defined conditions, such as moderately stringent or highly stringent conditions, to the complement of a sequence encoding an engineered imine reductase enzyme of the present invention.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA, with greater than about 90% identity to target-polynucleotide. Exemplary moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5×Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the imine reductase enzymes may be codon optimized for optimal production from the host organism selected for expression.

As used herein, "preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (See e.g., GCG Codon Preference, Genetics Computer Group Wisconsin Package; CodonW, Peden, University of Nottingham; McInerney, Bioinform., 14:372-73 [1998]; Stenico et al., Nucl. Acids Res., 222437-46 [1994]; Wright, Gene 87:23-29) [1990]). Codon usage tables are available for many different organisms (See e.g., Wada et al., Nucl. Acids Res., 20:2111-2118 [1992]; Nakamura et al., Nucl. Acids Res., 28:292 [2000]; Duret, et al., supra; Henaut and Danchin, in *Escherichia coli* and *Salmonella*, Neidhardt, et al. (eds.), ASM Press, Washington D.C., p. 2047-2066 [1996]). The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (See e.g., Mount, *Bioinformatics: Sequence and Genome Analysis*, Chapter 8, Cold Spring Harbor Laboratory Press, Cold Spring Harbor, N.Y. [2001]; Uberbacher, Meth. Enzymol., 266:259-281 [1996]; and Tiwari et al., Comput. Appl. Biosci., 13:263-270 [1997]).

"Control sequence" is defined herein to include all components, which are necessary or advantageous for the expression of a polynucleotide and/or polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Promoter sequence" refers to a nucleic acid sequence that is recognized by a host cell for expression of a polynucleotide of interest, such as a coding sequence. The promoter sequence contains transcriptional control sequences, which mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"Suitable reaction conditions" refer to those conditions in the biocatalytic reaction solution (e.g., ranges of enzyme loading, substrate loading, cofactor loading, temperature, pH, buffers, co-solvents, etc.) under which an imine reductase polypeptide of the present invention is capable of converting a substrate compound to a product compound (e.g., conversion of compound (2) to compound (1)). Exemplary "suitable reaction conditions" are provided in the present invention and illustrated by the Examples.

"Cofactor regeneration system" or "cofactor recycling system" refers to a set of reactants that participate in a reaction that reduces the oxidized form of the cofactor (e.g., $NADP^+$ to NADPH). Cofactors oxidized by the imine reductase catalyzed reductive amination of the ketone substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst that catalyzes the reduction of the oxidized form of the cofactor by the reductant. Cofactor regeneration systems to regenerate NADH or NADPH from $NAD^+$ or $NADP^+$, respectively, are known in the art and may be used in the methods described herein.

"Formate dehydrogenase" and "FDH" are used interchangeably herein to refer to an NAD or $NADP^+$-dependent enzyme that catalyzes the conversion of formate and NAD or NADP to carbon dioxide and NADH or NADPH, respectively.

"Loading", such as in "compound loading" or "enzyme loading" or "cofactor loading" refers to the concentration or amount of a component in a reaction mixture at the start of the reaction.

"Substrate" in the context of a biocatalyst mediated process refers to the compound or molecule acted on by the biocatalyst. For example, an imine reductase biocatalyst used in the reductive amination processes disclosed herein there is a ketone (or aldehyde) substrate of formula (I), such as cyclohexanone, and an amine substrate of formula (II), such as butylamine.

"Product" in the context of a biocatalyst mediated process refers to the compound or molecule resulting from the action of the biocatalyst. For example, an exemplary product for an imine reductase biocatalyst used in a process disclosed herein is a secondary or tertiary amine compound, such as a compound of formula (III).

"Alkyl" refers to saturated hydrocarbon groups of from 1 to 18 carbon atoms inclusively, either straight chained or branched, more preferably from 1 to 8 carbon atoms inclusively, and most preferably 1 to 6 carbon atoms inclusively. An alkyl with a specified number of carbon atoms is denoted in parenthesis (e.g., $(C_1-C_6)$alkyl refers to an alkyl of 1 to 6 carbon atoms).

"Alkenyl" refers to hydrocarbon groups of from 2 to 12 carbon atoms inclusively, either straight or branched containing at least one double bond but optionally containing more than one double bond.

"Alkynyl" refers to hydrocarbon groups of from 2 to 12 carbon atoms inclusively, either straight or branched containing at least one triple bond but optionally containing more than one triple bond, and additionally optionally containing one or more double bonded moieties.

"Alkylene" refers to a straight or branched chain divalent hydrocarbon radical having from 1 to 18 carbon atoms inclusively, more preferably from 1 to 8 carbon atoms inclusively, and most preferably 1 to 6 carbon atoms inclusively, optionally substituted with one or more suitable substituents. Exemplary "alkylenes" include, but are not limited to, methylene, ethylene, propylene, butylene, and the like.

"Alkenylene" refers to a straight or branched chain divalent hydrocarbon radical having 2 to 12 carbon atoms inclusively and one or more carbon-carbon double bonds, more preferably from 2 to 8 carbon atoms inclusively, and most preferably 2 to 6 carbon atoms inclusively, optionally substituted with one or more suitable substituents.

"Heteroalkyl, "heteroalkenyl," and heteroalkynyl," refer respectively, to alkyl, alkenyl and alkynyl as defined herein in which one or more of the carbon atoms are each independently replaced with the same or different heteroatoms or heteroatomic groups. Heteroatoms and/or heteroatomic groups which can replace the carbon atoms include, but are not limited to, —O—, —S—, —S—O—, —$NR^\gamma$—, —PH—, —S(O)—, —$S(O)_2$—, —$S(O)NR^\gamma$—, —$S(O)_2NR^\gamma$—, and the like, including combinations thereof, where each $R^\gamma$ is independently selected from hydrogen, alkyl, cycloalkyl, heterocycloalkyl, aryl, and heteroaryl.

"Aryl" refers to an unsaturated aromatic carbocyclic group of from 6 to 12 carbon atoms inclusively having a single ring (e.g., phenyl) or multiple condensed rings (e.g., naphthyl or anthryl). Exemplary aryls include phenyl, pyridyl, naphthyl and the like.

"Arylalkyl" refers to an alkyl substituted with an aryl (i.e., aryl-alkyl- groups), preferably having from 1 to 6 carbon atoms inclusively in the alkyl moiety and from 6 to 12 carbon atoms inclusively in the aryl moiety. Such arylalkyl groups are exemplified by benzyl, phenethyl and the like.

"Aryloxy" refers to —$OR^\lambda$ groups, where $R^\lambda$ is an aryl group, which can be optionally substituted.

"Cycloalkyl" refers to cyclic alkyl groups of from 3 to 12 carbon atoms inclusively having a single cyclic ring or multiple condensed rings which can be optionally substituted with from 1 to 3 alkyl groups. Exemplary cycloalkyl groups include, but are not limited to, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures, including bridged ring systems, such as adamantyl, and the like.

"Cycloalkylalkyl" refers to an alkyl substituted with a cycloalkyl (i.e., cycloalkyl-alkyl- groups), preferably having from 1 to 6 carbon atoms inclusively in the alkyl moiety and from 3 to 12 carbon atoms inclusively in the cycloalkyl moiety. Such cycloalkylalkyl groups are exemplified by cyclopropylmethyl, cyclohexylethyl and the like.

"Amino" refers to the group —$NH_2$. Substituted amino refers to the group —$NHR^\eta$, $NR^\eta R^\eta$, and $NR^\eta R^\eta R^\eta$, where each $R^\eta$ is independently selected from substituted or unsubstituted alkyl, cycloalkyl, cycloheteroalkyl, alkoxy, aryl, heteroaryl, heteroarylalkyl, acyl, alkoxycarbonyl, sulfanyl, sulfinyl, sulfonyl, and the like. Typical amino groups include, but are limited to, dimethylamino, diethylamino, trimethylammonium, triethylammonium, methylysulfonylamino, furanyl-oxy-sulfamino, and the like.

"Aminoalkyl" refers to an alkyl group in which one or more of the hydrogen atoms are replaced with one or more amino groups, including substituted amino groups.

"Aminocarbonyl" refers to —C(O)NH$_2$. Substituted aminocarbonyl refers to —C(O)NR$^\eta$R$^\eta$, where the amino group NR$^\eta$R$^\eta$ is as defined herein.

"Oxy" refers to a divalent group —O—, which may have various substituents to form different oxy groups, including ethers and esters.

"Alkoxy" or "alkyloxy" are used interchangeably herein to refer to the group —OR$^\zeta$, wherein R$^\zeta$ is an alkyl group, including optionally substituted alkyl groups.

"Carboxy" refers to —COOH.

"Carbonyl" refers to —C(O)—, which may have a variety of substituents to form different carbonyl groups including acids, acid halides, aldehydes, amides, esters, and ketones.

"Carboxyalkyl" refers to an alkyl in which one or more of the hydrogen atoms are replaced with one or more carboxy groups.

"Aminocarbonylalkyl" refers to an alkyl substituted with an aminocarbonyl group, as defined herein.

"Halogen" or "halo" refers to fluoro, chloro, bromo and iodo.

"Haloalkyl" refers to an alkyl group in which one or more of the hydrogen atoms are replaced with a halogen. Thus, the term "haloalkyl" is meant to include monohaloalkyls, dihaloalkyls, trihaloalkyls, etc. up to perhaloalkyls. For example, the expression "(C$_1$-C$_2$) haloalkyl" includes 1-fluoromethyl, difluoromethyl, trifluoromethyl, 1-fluoroethyl, 1,1-difluoroethyl, 1,2-difluoroethyl, 1,1,1 trifluoroethyl, perfluoroethyl, etc.

"Hydroxy" refers to —OH.

"Hydroxyalkyl" refers to an alkyl group in which in which one or more of the hydrogen atoms are replaced with one or more hydroxy groups.

"Thiol" or "sulfanyl" refers to —SH. Substituted thiol or sulfanyl refers to —S—R$^\eta$, where R$^\eta$ is an alkyl, aryl or other suitable substituent.

"Alkylthio" refers to —SR$^\lambda$, where R$^\lambda$ is an alkyl, which can be optionally substituted. Typical alkylthio group include, but are not limited to, methylthio, ethylthio, n-propylthio, and the like.

"Alkylthioalkyl" refers to an alkyl substituted with an alkylthio group, —SR, where R is an alkyl, which can be optionally substituted.

"Sulfonyl" refers to —SO$_2$—. Substituted sulfonyl refers to -SO$_2$—R$^\eta$, where R$^\eta$ is an alkyl, aryl or other suitable substituent.

"Alkylsulfonyl" refers to —SO$_2$—R$^\eta$, where R$^\eta$ is an alkyl, which can be optionally substituted. Typical alkylsulfonyl groups include, but are not limited to, methylsulfonyl, ethylsulfonyl, n-propylsulfonyl, and the like.

"Alkylsulfonylalkyl" refers to an alkyl substituted with an alkylsulfonyl group, —SO$_2$—R$^\lambda$, where R$^\lambda$ is an alkyl, which can be optionally substituted.

"Heteroaryl" refers to an aromatic heterocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

"Heteroarylalkyl" refers to an alkyl substituted with a heteroaryl (i.e., heteroaryl-alkyl- groups), preferably having from 1 to 6 carbon atoms inclusively in the alkyl moiety and from 5 to 12 ring atoms inclusively in the heteroaryl moiety. Such heteroarylalkyl groups are exemplified by pyridylmethyl and the like.

"Heterocycle", "heterocyclic" and interchangeably "heterocycloalkyl" refer to a saturated or unsaturated group having a single ring or multiple condensed rings, from 2 to 10 carbon ring atoms inclusively and from 1 to 4 hetero ring atoms inclusively selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl). Examples of heterocycles include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

"Heterocycloalkylalkyl" refers to an alkyl substituted with a heterocycloalkyl (i.e., heterocycloalkyl-alkyl-groups), preferably having from 1 to 6 carbon atoms inclusively in the alkyl moiety and from 3 to 12 ring atoms inclusively in the heterocycloalkyl moiety.

"Membered ring" is meant to embrace any cyclic structure. The number preceding the term "membered" denotes the number of skeletal atoms that constitute the ring. Thus, for example, cyclohexyl, pyridine, pyran and thiopyran are 6-membered rings and cyclopentyl, pyrrole, furan, and thiophene are 5-membered rings.

"Fused bicyclic ring" as used herein refers to both unsubstituted and substituted carbocyclic and/or heterocyclic ring moieties having 5 to 8 atoms in each ring, the rings having 2 common atoms.

"Optionally substituted" as used herein with respect to the foregoing chemical groups means that positions of the chemical group occupied by hydrogen can be substituted with another atom (unless otherwise specified) exemplified by, but not limited to carbon, oxygen, nitrogen, or sulfur, or a chemical group, exemplified by, but not limited to, hydroxy, oxo, nitro, methoxy, ethoxy, alkoxy, substituted alkoxy, trifluoromethoxy, haloalkoxy, fluoro, chloro, bromo, iodo, halo, methyl, ethyl, propyl, butyl, alkyl, alkenyl, alkynyl, substituted alkyl, trifluoromethyl, haloalkyl, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, phenyl, aryl, substituted aryl, aryloxy, arylalkyl, arylalkenyl, arylalkynyl, pyridyl, imidazolyl, heteroaryl, substituted heteroaryl, heteroaryloxy, heteroarylalkyl, heteroarylalkenyl, heteroarylalkynyl, cyclopropyl, cyclobutyl, cyclopentyl, cyclohexyl, cycloalkyl, cycloalkenyl, cycloalkylalkyl, substituted cycloalkyl, cycloalkyloxy, pyrrolidinyl, piperidinyl, morpholino, heterocycle, (heterocycle)oxy, and (heterocycle)alkyl; where preferred heteroatoms are oxygen, nitrogen, and sulfur. Additionally, where open valences exist on these substitute chemical groups they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further contemplated that the above substitutions can be made provided that replacing the hydrogen with the substituent does not introduce unacceptable instability to the molecules of the present invention, and is otherwise chemically reasonable. One of ordinary skill in the art would understand that with respect to any chemical group described as optionally substituted, only sterically practical and/or synthetically feasible chemical groups are meant to be included. "Optionally substituted" as used herein refers to all subsequent modifiers in a term or series of chemical groups. For example, in the term "optionally substituted arylalkyl," the "alkyl" portion and the "aryl" portion of the molecule may or may not be substituted, and for the series "optionally substituted alkyl, cycloalkyl, aryl and heteroaryl," the alkyl, cycloalkyl, aryl, and heteroaryl groups, independently of the others, may or may not be substituted.

Oxime Intermediate Formation and Conversion of Imines to Secondary Amines

Formation of an oxime intermediate is an efficient way to produce a starting substrate for an IRED, which can then reduce the compound with high stereoselectivity, generating a product with greater than 95% enantiomeric excess, as shown in Scheme 1. The challenge in this approach is identifying an enzyme that reacts with the desired substrate and identifying mutations that increase the enzyme's efficiency.

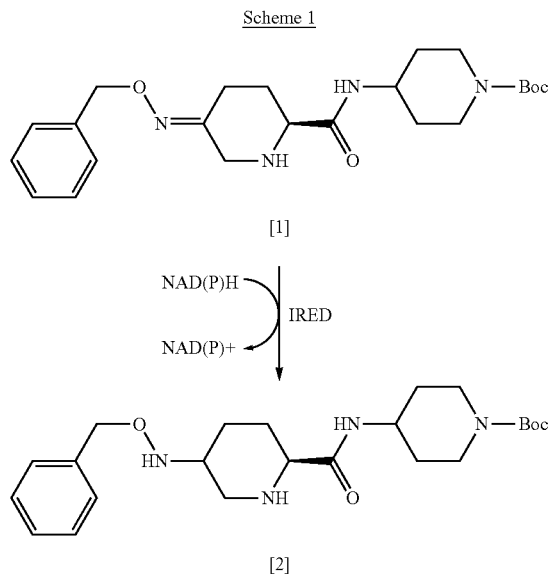

The present invention provides novel biocatalysts and associated methods to use them for the synthesis of chiral secondary amines by direct reduction of imine substrates. The biocatalysts of the disclosure are engineered polypeptide variants of the wild-type gene from *Pseudonocardia spinosispora* which encodes an imine reductase" or "IRED" having the amino acid sequence of SEQ ID NO:2. These engineered polypeptides are capable of catalyzing the conversion of an imine to a secondary amine. The general imine reductase activity of the IREDs is illustrated below in Scheme 2.

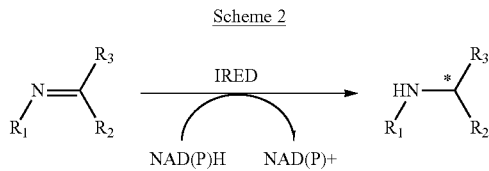

The engineered polypeptides having imine reductase activity of the present invention can accept a wide range of substrates. Accordingly, in the biocatalytic reaction of Scheme 2, the $R_1$ groups of the substrate are selected from a hydrogen atom, or optionally substituted alkyl, alkenyl, alkynyl, alkoxy, arylalkoxy, hydroxyalkyl, carboxy, aminocarbonyl, heteroalkyl, heteroalkenyl, heteroalkynyl, carboxyalkyl, aminoalkyl, alkylamino, haloalkyl, alkylthioalkyl, cycloalkyl, aryl, arylalkyl, heterocycloalkyl, heteroaryl, and heteroarylalkyl; and the $R_2$ and $R_3$ groups of the substrate are independently selected from a hydrogen atom, and optionally substituted alkyl, alkenyl, alkynyl, hydroxyalkyl, carboxy, aminocarbonyl, heteroalkyl, heteroalkenyl, heteroalkynyl, carboxyalkyl, alkylamino, haloalkyl, alkylthioalkyl, cycloalkyl, aryl, arylalkyl, heterocycloalkyl, heteroaryl, and heteroarylalkyl, with the proviso that both $R_2$ and $R_3$ cannot be hydrogen. Optionally, the $R_1$ group and either the $R_2$ and $R_3$ groups of the substrate can be linked to form a 3-membered to 10-membered ring. Similarly, the R2 and R3 groups of the substrate can be linked to form a 3-membered to 10-membered ring As described further herein, the engineered polypeptides having imine reductase activity exhibit stereoselectivity, thus, an imine reductase reaction of Scheme 2 can be used to establish one, two, or more, chiral centers of a product in a single biocatalytic reaction.

In some embodiments, the present invention provides an engineered polypeptide comprising an amino acid sequence having at least 80% sequence identity to an amino acid reference sequence of SEQ ID NO:2 and further comprising one or more amino acid residue differences as compared to the reference amino sequence, wherein the engineered polypeptide has imine reductase activity. In some embodiments of the engineered polypeptide, the imine reductase activity is the activity of Scheme 2.

Engineered Imine Reductase Polypeptides

The present invention provides polypeptides having imine reductase activity, polynucleotides encoding the polypeptides, methods of preparing the polypeptides, and methods for using the polypeptides. Where the description relates to polypeptides, it is to be understood that it can describe the polynucleotides encoding the polypeptides.

Suitable reaction conditions under which the above-described improved properties of the engineered polypeptides carry out the desired reaction can be determined with respect to concentrations or amounts of polypeptide, substrate, co-substrate, buffer, solvent, pH, conditions including temperature and reaction time, and/or conditions with the polypeptide immobilized on a solid support, as further described below and in the Examples.

In some embodiments, exemplary engineered polypeptides having imine reductase activity with improved properties, particularly in the conversion of Compound [1] to Compound[2] comprises an amino acid sequence that has one or more residue differences as compared to SEQ ID NO:2 at the residue positions indicated in Table 2-2.

In some embodiments, exemplary engineered polypeptides having imine reductase activity with improved properties, particularly in the conversion of Compound [1] to Compound [2] comprises an amino acid sequence that has one or more residue differences as compared to SEQ ID NO:270 at the residue positions indicated in Table 3-1.

In some embodiments, exemplary engineered polypeptides having imine reductase activity with improved properties, particularly in the conversion of Compound [1] to Compound [2] comprises an amino acid sequence that has one or more residue differences as compared to SEQ ID NO:230 at the residue positions indicated in Table 4-1.

The structure and function information for exemplary non-naturally occurring (or engineered) polypeptides of the present invention are based on the conversion of Compound [1] to Compound [2], the results of which are shown below in Tables 2-2, 3-1, 4-1, and 5-1, and further described in the Examples. The odd numbered sequence identifiers (i.e., SEQ ID NOs) in these Tables refer to the nucleotide sequence encoding the amino acid sequence provided by the even numbered SEQ ID NOs in these Tables. Exemplary sequences are provided in the electronic sequence listing file accompanying this invention, which is hereby incorporated by reference herein. The amino acid residue differences are based on comparison to the reference sequence of SEQ ID NOS:2, 230, and 270, as indicated.

The naturally occurring amino acid sequence of the *Pseudonocardia spinosispora* imine reductase (SEQ ID NO: 1), was codon-optimized for expression in *Escherichia coli* and synthesized (the polypeptide sequence is provided in SEQ ID NO:2).

The activity of each engineered polypeptide relative to the reference polypeptide of SEQ ID NO:2 230, or 270 was determined as conversion of the substrates described in the Examples herein. In some embodiments, a shake flask powder (SFP) is used as a secondary screen to assess the properties of the engineered imine reductases, the results of which are provided in the Examples. In some embodiments, the SFP forms provide a more purified powder preparation of the engineered polypeptides and can contain the engineered polypeptides that are up to about 30% of total protein.

In some embodiments, the specific enzyme properties are associated with the residues differences as compared to SEQ ID NO:2, 230, and 270 at the residue positions indicated herein. In some embodiments, residue differences affecting polypeptide expression can be used to increase expression of the engineered imine reductase.

In light of the guidance provided herein, it is further contemplated that any of the exemplary engineered polypeptides comprising the even-numbered sequences of SEQ ID NOS: 4-270 find use as the starting amino acid sequence for synthesizing other engineered imine reductase polypeptides, for example by subsequent rounds of evolution that incorporate new combinations of various amino acid differences from other polypeptides in Tables 2-2, 3-1, 4-1, and 5-1, and other residue positions described herein. Further improvements may be generated by including amino acid differences at residue positions that had been maintained as unchanged throughout earlier rounds of evolution.

In some embodiments, the engineered polypeptide having imine reductase activity comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:2 and one or more residue differences as compared to SEQ ID NO:2 at residue positions selected from: 57/211, 87/175, 103/212, 122, 123, 124/178, 124, 132, 134, 169, 171, 173, 175, 176, 178/242, 178, 211, 212, 213, 214, 215, 217, 234, and 235.

In some embodiments, the engineered polypeptide having imine reductase activity comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:2 and one or more residue differences as compared to SEQ ID NO:2, selected from: 57T/211L, 87S/175G, 103H/212C, 122E, 123G, 124A/178I, 124G, 132H/R, 134R, 169N/S, 171W, 173H/I, 175G/H, 176S, 178I//242Y, 178M, 211L/W, 212C/G/V, 213P/R/T/V, 214M, 215L/M, 217I/L, 234L, and 235K.

In some embodiments, the engineered polypeptide having imine reductase activity comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:2 and one or more residue differences as compared to SEQ ID NO:2 at residue positions selected from: A57T/I211L, P87S/M175G, R103H/E212C, L122E, T123G, I124A/V178I, I124G, E132H/R, T134R, A169N/S, Y171W, A173H/I, M175G/H, L176S, V178I/A242Y, V178M, I211L/W, E212C/G/V, A213P/R/T/V, V214M, T215L/M, W217I/L, D234L, and A235K.

In some embodiments, the engineered polypeptide having imine reductase activity comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:270 and one or more residue differences as compared to SEQ ID NO:270, selected from: 123/124/169/171/173/213/235, 123/124/169/212/213/235, 123/169/171/173/212/213/235, 123/169/171/173/213/235, 123/169/173/175/213/235, 123/169/173/212/213, 123/169/175, 123/169/175/212/235, 123/169/212/213, 123/173/175/212/213/235, 123/212/213/235, 123/212/235, 123/169/171/173/175/212/213, 123/169/173, 123/169/212/213/235, 123/213, 124/169, 124/169/173/175/212/213, 124/169/173/212/213, 124/169/173/212/213/235, 124/169/175/212/213/235, 124/169/212/213/235, 124/169/213/235, 124/175/212/213/235, 124/212/213/235, 134/169/176/178/211/214, 134/169/176/178/211, 134/169/176/178/211/217, 134/169/176/211/215/217/234, 134/169/176/211, 134/169/178/211/214/217, 134/169/211/214/217, 134/169/211/217, 134/176/211/214, 134/176/211/215, 134/211/214, 169/171/173/213/235, 169/173/175/213/235, 169/175/212/213/235, 169/176/178/211/214, 169/176/178/211/214/217, 169/176/178/211/217, 169/176/178, 169/176/178/211/214/217, 169/176/211/214, 169/176/211/214/215/234, 169/176/211/214/217, 169/176/211/217, 169/176/214/215/217, 169/178/217, 169/178/234, 169/211/214/215, 169/211/217, 169/212/213, 169/212/213/235, 169/212/213/235, 169/235, 171/173/212/213/235, 173/175/213, 175/213/235, 175/235, 176/178/211/215/217, 176/178/211/217, 176/211/214, 176/214/217, 178/211/214, 178/211/217, 178/215, 211/234, 212/213/235, and 213/235.

In some embodiments, the engineered polypeptide having imine reductase activity comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:270 and one or more residue differences as compared to SEQ ID NO:270, selected from: 123G/124G/169N/171V/173H/213V/235K, 123G/124G/169N/212V/213V/235K, 123G/169N/171V/173H/213V/235K, 123G/169N/171V/173I/212C/213V/235K, 123G/169N/173H/175H/213V/235K, 123G/169N/173I/212G/213T, 123G/169N/175G, 123G/169N/175G/212C/235K, 123G/169N/212G/213V, 123G/173H/175H/212C/213V/235K, 123G/212C/213V/235K, 123G/212G/235K, 123G/169N/171V/173H/175H/212X/213V, 123G/169N/173I, 123G/169N/212G/213V/235K, 123G/213T, 124G/169N, 124A/169N/173I/175H/212G/213V, 124G/169N/173I/212C/213V, 124G/169N/173I/212G/213V, 124G/169N/173I/212V/213V/235K, 124G/169N/175G/212C/213V/235K, 124G/169N/212G/213V/235K, 124G/169N/212V/213V/235K, 124G/175G/212V/

213V/235K, 124G/169N/213V/235K, 124G/212C/213V/ 235K, 124G/212G/213V/235K, 134R/169N/176S/178I// 211L/214M, 134R/169N/176S/178I//211W, 134R/169N/ 176S/178M/211L/217L, 134R/169N/176S/211L/215M/ 217I1234L, 134R/169N/176S/211W, 134R/169N/178M/ 211W/214M/217I, 134R/169N/211W/214M/217L, 134R/ 169N/211W/217L, 134R/176S/211W/214M, 134R/176S/ 211W/215M, 134R/211W/214M, 169N/171V/173I/213V/ 235K, 169N/173I/175H/213V/235K, 169N/175G/212C/ 213V/235K, 169N/M175H/E212G/A213V/A235K 169N/ 176S/178I//211L/214M, 169N/176S/178I//211W/214M/ 217L, 169N/176S/178I//211W/217L 169N/176S/178M, 169N/176S/178M/211W/214M/217I, 169N/176S/211W/ 214M, 169N/176S/211W/214M/215L/234L, 169N/176S/ 211W/217I, 169N/176S/211W/217L, 169N/176S/214M/ 215M/217I, 169N/176S/211L/214M/217I, 169N/178I// 217I, 169N/178M/234L, 169N/211W/214M/215L, 169N/ 211W/217I, 169N/212C/235K, 169N/212C/213V/235K, 169N/212G/213V, 169N/212V/213V/235K, 169N/235K, 171V/173I/212G/213V/235K, 173I/175H/213V, 175H/ 213P/235K, 175H/235K, 176S/178I//211W/215L/217L, 176S/178I//211W/217I, 176S/211L/214M, 176S/214M/ 217L, 178M/211L/214M, 178M/211W/217L, 178I//215M, 211W/234L, 212G/213V/235K, 212V/213V/235K, 213T/ 235K, and 213V/235K.

In some embodiments, the engineered polypeptide having imine reductase activity comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:270 and one or more residue differences as compared to SEQ ID NO:270, selected from: T123G/I124G/A169N/Y171V/ A173H/A213V/A235K, T123G/I124G/A169N/E212V/ A213V/A235K, T123G/A169N/Y171V/A173H/A213V/ A235K, T123G/A169N/Y171V/A173I/E212C/A213V/ A235K, T123G/A169N/A173H/M175H/A213V/A235K, T123G/A169N/A173I/E212G/A213T, T123G/A169N/ M175G, T123G/A169N/M175G/E212C/A235K, T123G/ A169N/E212G/A213V, T123G/A173H/M175H/E212C/ A213V/A235K, T123G/E212C/A213V/A235K, T123G/ E212G/A235K, T123G/A169N/Y171V/A173H/M175H/ E212X/A213V, T123G/A169N/A173I, T123G/A169N/ E212G/A213V/A235K, T123G/A213T, I124G/A169N, I124A/A169N/A17311M175H/E212G/A213V, I124G/ A169N/A173I/E212C/A213V, I124G/A169N/A173I/ E212G/A213V, I124G/A169N/A173I/E212V/A213V/ A235K, I124G/A169N/M175G/E212C/A213V/A235K, I124G/A169N/E212G/A213V/A235K, I124G/A169N/ E212V/A213V/A235K, I124G/M175G/E212V/A213V/ A235K, I124G/A169N/A213V/A235K, I124G/E212C/ A213V/A235K, I124G/E212G/A213V/A235K, T134R/ A169N/L176S/V178I/I211L/V214M, T134R/A169N/ L176S/V178I/I211W, T134R/A169N/L176S/V178M/ I211L/W217L, T134R/A169N/L176S/I211L/T215M/ W217I/D234L, T134R/A169N/L176S/I211W, T134R/ A169N/V178M/I211W/V214M/W217I, T134R/A169N/ I211W/V214M/W217L, T134R/A169N/I211W/W217L, T134R/L176S/I211W/V214M, 134R/L176S/I211W/ T215M, T134R/I211W/V214M, A169N/Y171V/A173I/ A213V/A235K, A169N/A173I/M175H/A213V/A235K, A169N/M175G/E212C/A213V/A235K, A169N/M175H/ E212G/A213V/A235K, A169N/L176S/V178I/I211L/ V214M, A169N/L176S/V178I/I211W/V214M/W217L, A169N/L176S/V178I/I211W/W217L, A169N/L176S/ V178M, A169N/L176S/V178M/I211W/V214M/W217I, A169N/L176S/I211W/V214M, A169N/L176S/I211W/ V214M/T215L/D234L, A169N/L176S/I211W/W217I, A169N/L176S/I211W/W217L, A169N/L176S/V214M/ T215M/W217I, A169N/L176S/I211L/V214M/W217I, A169N/V178I/W217I, A169N/V178M/D234L, A169N/ I211W/V214M/T215L, A169N/I211W/W217I, A169N/ E212C/A235K, A169N/E212C/A213V/A235K, A169N/ E212G/A213V, A169N/E212V/A213V/A235K, A169N/ A235K, Y171V/A173I/E212G/A213V/A235K, A173I/ M175H/A213V, M175H/A213P/A235K, M175H/A235K, L176S/V178I/I211W/T215L/W217L, L176S/V178I/ I211W/W217I, L176S/I211L/V214M, L176S/V214M/ W217L, V178M/I211L/V214M, V178M/I211W/W217L, V178I/T215M, I211W/D234L, E212G/A213V/A235K, E212V/A213V/A235K, A213T/A235K, and A213V/ A235K.

In some embodiments, the engineered polypeptide having imine reductase activity comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:270 and one or more residue differences as compared to SEQ ID NO:230, selected from: 45, 127, 130, 134, 174, 206, 209, 212, 216, 223, 227, and 279.

In some embodiments, the engineered polypeptide having imine reductase activity comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:230 and one or more residue differences as compared to SEQ ID NO:230, selected from: 45I, 127R, 130R, 134L/R, 174M, 206L, 209K/S, 212H/K/R, 216N/R/S, 223N, 227V, and 279V.

In some embodiments, the engineered polypeptide having imine reductase activity comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:230 and one or more residue differences as compared to SEQ ID NO:230, selected from: V45I, G127R, T130R, T134L/R, A174M, M206L, Q209K/S, E212H/K/R, G216N/R/S, D223N, A227V, and D279V.

In some embodiments, the engineered polypeptide having imine reductase activity comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:2 and comprises an even numbered sequences between SEQ ID NOS:4 and 74.

In some embodiments, the engineered polypeptide having activity comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:270 and comprises an even numbered sequences between SEQ ID NOS:76 and 232.

In some embodiments, the engineered polypeptide having activity comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:230 and comprises an even numbered sequences between SEQ ID NOS: 234 and 270.

As will be appreciated by the skilled artisan, in some embodiments, one or a combination of residue differences above that is selected can be kept constant (i.e., maintained) in the engineered imine reductase as a core feature, and additional residue differences at other residue positions incorporated into the sequence to generate additional engineered imine reductase polypeptides with improved properties. Accordingly, it is to be understood for any engineered imine reductase containing one or a subset of the residue differences above, the present invention contemplates other engineered imine reductases that comprise the one or subset of the residue differences, and additionally one or more residue differences at the other residue positions disclosed herein.

As noted above, the engineered polypeptides having imine reductase activity are also capable of converting substrates (e.g., Compound [1]) to products (e.g., Compound [2]). In some embodiments, the engineered imine reductase polypeptide is capable of converting the substrate to the product compound with at least 1.2 fold, 1.5 fold, 2 fold, 3 fold, 4 fold, 5 fold, 10 fold, 20 fold, 30 fold, 40 fold, 50 fold, 60 fold, 70 fold, 80 fold, 90 fold, 100 fold, or more activity relative to the activity of the reference polypeptide of SEQ ID NO:2, 230 or 270.

In some embodiments, the engineered imine reductase polypeptide capable of converting the substrate compounds to the product compounds with at least 2 fold the activity relative to SEQ ID NO:2, 230 and/or 270, comprises an amino acid sequence selected from: the even-numbered sequences in SEQ ID NOS:4 to 270.

In some embodiments, the engineered imine reductase has an amino acid sequence comprising one or more residue differences as compared to SEQ ID NO:2, 230 and/or 270, that increase expression of the engineered imine reductase activity in a bacterial host cell, particularly in E. coli.

In some embodiments, the engineered imine reductase polypeptide with improved properties has an amino acid sequence comprising a sequence selected from the even-numbered sequences in the range: SEQ ID NOS:4 to 270.

In some embodiments, the engineered polypeptide having imine reductase activity, comprises an amino acid sequence having at least 80%, 85%, 86%, 87%, 88%, 89%, 90%, 91%, 92%, 93%, 94%, 95%, 96%, 97%, 98%, or 99% identity to one of the even-numbered sequences in the range: SEQ ID NOS:4-270, and the amino acid residue differences as compared to SEQ ID NO:2, 230 and/or 270, present in any one of the even-numbered sequences in the range: SEQ ID NOS:4-270, as provided in the Examples.

In addition to the residue positions specified above, any of the engineered imine reductase polypeptides disclosed herein can further comprise other residue differences relative to SEQ ID NO:2, 230 and/or 270, at other residue positions (i.e., residue positions other than those included herein). Residue differences at these other residue positions can provide for additional variations in the amino acid sequence without adversely affecting the ability of the polypeptide to carry out the conversion of substrate to product. Accordingly, in some embodiments, in addition to the amino acid residue differences present in any one of the engineered imine reductase polypeptides selected from the even-numbered sequences in the range: SEQ ID NOS:4-270, the sequence can further comprise 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, or 1-50 residue differences at other amino acid residue positions as compared to the SEQ ID NO:2, 229 and/or 270. In some embodiments, the number of amino acid residue differences as compared to the reference sequence can be 1, 2, 3, 4, 5, 6, 7, 8, 9, 10, 11, 12, 13, 14, 15, 16, 17, 18, 19, 20, 21, 22, 23, 24, 25, 30, 30, 35, 40, 45 or 50 residue positions. In some embodiments, the number of amino acid residue differences as compared to the reference sequence can be 1, 2, 3, 4, 5, 6, 7, 8, 9, 10, 11, 12, 13, 14, 15, 16, 18, 20, 21, 22, 23, 24, or 25 residue positions. The residue difference at these other positions can be conservative changes or non-conservative changes. In some embodiments, the residue differences can comprise conservative substitutions and non-conservative substitutions as compared to the naturally occurring imine reductase polypeptide of SEQ ID NOS:2, 229 and/or 270.

In some embodiments, the present invention also provides engineered polypeptides that comprise a fragment of any of the engineered imine reductase polypeptides described herein that retains the functional activity and/or improved property of that engineered imine reductase. Accordingly, in some embodiments, the present invention provides a polypeptide fragment capable of converting substrate to product under suitable reaction conditions, wherein the fragment comprises at least about 80%, 90%, 95%, 96%, 97%, 98%, or 99% of a full-length amino acid sequence of an engineered imine reductase polypeptide of the present invention, such as an exemplary engineered imine reductase polypeptide selected from the even-numbered sequences in the range: SEQ ID NOS:4-270. In some embodiments, the engineered imine reductase polypeptide can have an amino acid sequence comprising a deletion in any one of the engineered imine reductase polypeptide sequences described herein, such as the exemplary engineered polypeptides of the even-numbered sequences in the range: SEQ ID NOS:4-270.

Thus, for each and every embodiment of the engineered imine reductase polypeptides of the invention, the amino acid sequence can comprise deletions of one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 20% of the total number of amino acids, or up to 30% of the total number of amino acids of the imine reductase polypeptides, where the associated functional activity and/or improved properties of the engineered imine reductase described herein are maintained. In some embodiments, the deletions can comprise 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residues. In some embodiments, the number of deletions can be 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residues. In some embodiments, the deletions can comprise deletions of 1, 2, 3, 4, 5, 6, 7, 8, 9, 10, 11, 12, 13, 14, 15, 16, 18, 20, 21, 22, 23, 24, or 25 amino acid residues.

In some embodiments, the engineered imine reductase polypeptide herein can have an amino acid sequence comprising an insertion as compared to any one of the engineered imine reductase polypeptides described herein, such as the exemplary engineered polypeptides of the even-numbered sequences in the range: SEQ ID NOS:4-270. Thus, for each and every embodiment of the imine reductase polypeptides of the invention, the insertions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, 20 or more amino acids, 30 or more amino acids, 40 or more amino acids, or 50 or more amino acids, where the associated functional activity and/or improved properties of the engineered imine reductase described herein is maintained. The insertions can be to amino or carboxy terminus, or internal portions of the imine reductase polypeptide.

In some embodiments, the engineered imine reductase polypeptide herein can have an amino acid sequence comprising a sequence selected from the even-numbered sequences in the range: SEQ ID NOS:4-270, and optionally one or several (e.g., up to 3, 4, 5, or up to 10) amino acid residue deletions, insertions and/or substitutions. In some embodiments, the amino acid sequence has optionally 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residue deletions, insertions and/or substitutions. In some embodiments, the number of amino acid sequence has optionally 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 18, 20, 21, 22, 23, 24, or 25 amino acid residue deletions, insertions and/or substitutions. In some embodiments, the substitutions can be conservative or non-conservative substitutions.

In the above embodiments, the suitable reaction conditions for the engineered polypeptides are provided in Tables 2-2, 3-1, 4-1, and/or 5-1, and as described in the Examples herein.

In some embodiments, the polypeptides of the present invention are fusion polypeptides in which the engineered polypeptides are fused to other polypeptides, such as, by way of example and not limitation, antibody tags (e.g., myc epitope), purification sequences (e.g., His tags for binding to metals), and cell localization signals (e.g., secretion signals). Thus, the engineered polypeptides described herein can be used with or without fusions to other polypeptides.

It is to be understood that the polypeptides described herein are not restricted to the genetically encoded amino acids. In addition to the genetically encoded amino acids, the polypeptides described herein may be comprised, either in whole or in part, of naturally occurring and/or synthetic non-encoded amino acids. Certain commonly encountered non-encoded amino acids of which the polypeptides described herein may be comprised include, but are not limited to: the D-stereomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIte); phenylglycine (Phg); cyclohexylalanine (Cha); norleucine (Nle); naphthylalanine (Nal); 2-chlorophenylalanine (Oct); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Nat); 2-nitrophenylalanine (Onf); 3-nitrophenylalanine (Mnf); 4-nitrophenylalanine (Pnf); 2-cyanophenylalanine (Oct); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Pat); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aGly); propargylglycine (pgGly); homoalanine (hAla); norvaline (nVal); homoleucine (hLeu), homovaline (hVal); homoisoleucine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (See e.g., the various amino acids provided in Fasman, *CRC Practical Handbook of Biochemistry and Molecular Biology*, CRC Press, Boca Raton, FL, pp. 3-70 [1989], and the references cited therein, all of which are incorporated by reference). These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys(methylbenzyl), Cys (nitropyridinesulfenyl), Glu(8-benzylester), Gln(xanthyl), Asn(N-δ-xanthyl), His(bom), His (benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

In some embodiments, the engineered polypeptides can be in various forms, for example, such as an isolated preparation, as a substantially purified enzyme, whole cells transformed with gene(s) encoding the enzyme, and/or as cell extracts and/or lysates of such cells. The enzymes can be lyophilized, spray-dried, precipitated or be in the form of a crude paste, as further discussed below.

In some embodiments, the engineered polypeptides can be provided on a solid support, such as a membrane, resin, solid carrier, or other solid phase material. A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of a solid support can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location.

In some embodiments, the engineered polypeptides having imine reductase activity of the present invention can be immobilized on a solid support such that they retain their improved activity, and/or other improved properties relative to the reference polypeptide of SEQ ID NO: 2, 230 and/or 270. In such embodiments, the immobilized polypeptides can facilitate the biocatalytic conversion of the substrate compounds or other suitable substrates to the product and after the reaction is complete are easily retained (e.g., by retaining beads on which polypeptide is immobilized) and then reused or recycled in subsequent reactions. Such immobilized enzyme processes allow for further efficiency and cost reduction. Accordingly, it is further contemplated that any of the methods of using the imine reductase polypeptides of the present invention can be carried out using the same imine reductase polypeptides bound or immobilized on a solid support.

Methods of enzyme immobilization are well-known in the art. The engineered polypeptides can be bound non-covalently or covalently. Various methods for conjugation and immobilization of enzymes to solid supports (e.g., resins, membranes, beads, glass, etc.) are well known in the art (See e.g., Yi et al., Proc. Biochem., 42(5): 895-898 [2007]; Martin et al., Appl. Microbiol. Biotechnol., 76(4): 843-851 [2007]; Koszelewski et al., J. Mol. Cat. B: Enzymatic, 63: 39-44 [2010]; Truppo et al., Org. Proc. Res. Dev., published online: dx.doi.org/10.1021/op200157c; Hermanson, *Bioconjugate Techniques*, 2$^{nd}$ ed., Academic Press, Cambridge, MA [2008]; Mateo et al., Biotechnol. Prog., 18(3):629-34 [2002]; and "Bioconjugation Protocols: Strategies and Methods," In *Methods in Molecular Biology*, Niemeyer (ed.), Humana Press, New York, NY [2004]; the disclosures of each which are incorporated by reference herein). Solid supports useful for immobilizing the engineered imine reductases of the present invention include but are not limited to beads or resins comprising polymethacrylate with epoxide functional groups, polymethacrylate with amino epoxide functional groups, styrene/DVB copolymer or polymethacrylate with octadecyl functional groups. Exemplary solid supports useful for immobilizing the engineered imine reductase polypeptides of the present invention include, but are not limited to, chitosan beads, Eupergit C, and SEPABEADs (Mitsubishi), including the following different types of SEPABEAD: EC-EP, EC-HFA/S, EXA252, EXE119 and EXE120.

In some embodiments, the polypeptides described herein are provided in the form of kits. The enzymes in the kits may be present individually or as a plurality of enzymes. The kits can further include reagents for carrying out the enzymatic reactions, substrates for assessing the activity of enzymes, as well as reagents for detecting the products. The kits can also include reagent dispensers and instructions for use of the kits.

In some embodiments, the kits of the present invention include arrays comprising a plurality of different imine reductase polypeptides at different addressable position, wherein the different polypeptides are different variants of a reference sequence each having at least one different improved enzyme property. In some embodiments, a plurality of polypeptides immobilized on solid supports are configured on an array at various locations, addressable for robotic delivery of reagents, or by detection methods and/or instruments. The array can be used to test a variety of substrate compounds for conversion by the polypeptides. Such arrays comprising a plurality of engineered polypeptides and methods of their use are known in the art (See e.g., WO2009/008908A2).

Polynucleotides Encoding Engineered Imine Reductases, Expression Vectors and Host Cells In another aspect, the present invention provides polynucleotides encoding the engineered imine reductase polypeptides described herein. The polynucleotides may be operatively linked to one or more heterologous regulatory sequences that control gene expression to create a recombinant polynucleotide capable of expressing the polypeptide. Expression constructs containing a heterologous polynucleotide encoding the engineered imine reductase are introduced into appropriate host cells to express the corresponding imine reductase polypeptide.

As will be apparent to the skilled artisan, availability of a protein sequence and the knowledge of the codons corresponding to the various amino acids provide a description of all the polynucleotides capable of encoding the subject polypeptides. The degeneracy of the genetic code, where the same amino acids are encoded by alternative or synonymous codons, allows an extremely large number of nucleic acids to be made, all of which encode the improved imine reductase enzymes. Thus, having knowledge of a particular amino acid sequence, those skilled in the art could make any number of different nucleic acids by simply modifying the sequence of one or more codons in a way which does not change the amino acid sequence of the protein. In this regard, the present invention specifically contemplates each and every possible variation of polynucleotides that could be made encoding the polypeptides described herein by selecting combinations based on the possible codon choices, and all such variations are to be considered specifically disclosed for any polypeptide described herein, including the amino acid sequences presented in Tables 2-2, 3-1, 4-1, and 5-1. and disclosed in the sequence listing incorporated by reference herein as the even-numbered sequences in the range: SEQ ID NOS:4-270.

In various embodiments, the codons are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. In some embodiments, all codons need not be replaced to optimize the codon usage of the imine reductases since the natural sequence will comprise preferred codons and because use of preferred codons may not be required for all amino acid residues. Consequently, codon optimized polynucleotides encoding the imine reductase enzymes may contain preferred codons at about 40%, 50%, 60%, 70%, 80%, or greater than 90% of codon positions of the full length coding region.

In some embodiments, the polynucleotide comprises a codon optimized nucleotide sequence encoding the naturally occurring imine reductase polypeptide amino acid sequence, as represented by SEQ ID NO:2, 230 and/or 270. In some embodiments, the polynucleotide has a nucleic acid sequence comprising at least 80%, 85%, 90%, 91%, 92%, 93%, 94%, 95%, 96%, 97%, 98%, 99% or more identity to the codon optimized nucleic acid sequences encoding the even-numbered sequences in the range: SEQ ID NOS:4-270. In some embodiments, the polynucleotide has a nucleic acid sequence comprising at least 80%, 85%, 90%, 91%, 92%, 93%, 94%, 95%, 96%, 97%, 98%, 99% or more identity to the codon optimized nucleic acid sequences in the odd-numbered sequences in the range: SEQ ID NOS:3-269. In some embodiments, the codon optimized sequences of the odd-numbered sequences in the range: SEQ ID NOS:3-269, enhance expression of the encoded, wild-type imine reductase, providing preparations of enzyme capable of converting substrate to product.

In some embodiments, the polynucleotides are capable of hybridizing under highly stringent conditions to a reference sequence selected from the odd-numbered sequences in SEQ ID NOS:3-269, or a complement thereof, and encodes a polypeptide having imine reductase activity.

In some embodiments, as described above, the polynucleotide encodes an engineered polypeptide having imine reductase activity with improved properties as compared to SEQ ID NO:2, 230 and/or 270, wherein the polypeptide comprises an amino acid sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NO:2, 230 and/or 270, and one or more residue differences as compared to SEQ ID NO:2, 230 and/or 270, wherein the sequence is selected from the even-numbered sequences in the range: SEQ ID NOS:4-270. In some embodiments, the reference amino acid sequence is selected from the even-numbered sequences in the range: SEQ ID NOS:4-270. In some embodiments, the reference amino acid sequence is SEQ ID NO:2, while in some other embodiments, the reference sequence is SEQ ID NO:230, and in still some other embodiments, the reference sequence is SEQ ID NO:270.

In some embodiments, the polynucleotide encodes a imine reductase polypeptide capable of converting substrate to product with improved properties as compared to SEQ ID NO:2, 230, and/or 270, wherein the polypeptide comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:2, 230, and/or 270.

In some embodiments, the polynucleotide encoding the engineered imine reductase comprises an polynucleotide sequence selected from the odd-numbered sequences in the range: SEQ ID NOS:3-269.

In some embodiments, the polynucleotides are capable of hybridizing under highly stringent conditions to a reference polynucleotide sequence selected from the odd-numbered sequences in the range: SEQ ID NOS:3-269, or a complement thereof, and encodes a polypeptide having imine reductase activity with one or more of the improved properties described herein. In some embodiments, the polynucleotide capable of hybridizing under highly stringent conditions encodes a imine reductase polypeptide comprising an amino acid sequence having at least 80%, 85%, 86%, 87%, 88%, 89%, 90%, 91%, 92%, 93%, 94%, 95%, 96%, 97%, 98%, 99% or more identity to SEQ ID NO:2, that has an amino acid sequence comprising one or more residue differences as compared to SEQ ID NO:2, at residue positions selected from: 57/211, 87/175, 103/212, 122, 123, 124/178, 124, 132, 134, 169, 171, 173, 175, 176, 178/242, 178, 211, 212, 213, 214, 215, 217, 234, and 235.

In some embodiments, the polynucleotides are capable of hybridizing under highly stringent conditions to a reference polynucleotide sequence selected from the odd-numbered sequences in the range: SEQ ID NOS:3-269, or a complement thereof, and encodes a polypeptide having imine reductase activity with one or more of the improved properties described herein. In some embodiments, the polynucleotide capable of hybridizing under highly stringent conditions encodes a imine reductase polypeptide comprising an amino acid sequence having at least 80%, 85%, 86%, 87%, 88%, 89%, 90%, 91%, 92%, 93%, 94%, 95%, 96%, 97%, 98%, 99% or more identity to SEQ ID NO:270, that has an amino acid sequence comprising one or more residue differences as compared to SEQ ID NO:270, at residue positions selected from: 123/124/169/171/173/213/235, 123/124/169/212/213/235, 123/169/171/173/212/213/235, 123/169/171/173/213/235, 123/169/173/175/213/235, 123/169/173/212/213, 123/169/175,123/169/175/212/235, 123/169/212/213, 123/173/175/212/213/235, 123/212/213/235, 123/212/235, 123/169/171/173/175/212/213, 123/169/173, 123/169/212/213/235, 123/213, 124/169, 124/169/173/175/212/213, 124/169/173/212/213, 124/169/173/212/213/235, 124/169/175/212/213/235, 124/169/212/213/235, 124/169/213/235, 124/175/212/213/235, 124/212/213/235, 134/169/176/178/211/214, 134/169/176/178/211, 134/169/176/178/211/217, 134/169/176/211/215/217/234, 134/169/176/211, 134/169/178/211/214/217, 134/169/211/214/217, 134/169/211/217, 134/176/211/214, 134/176/211/215, 134/211/214, 169/171/173/213/235, 169/173/175/213/235, 169/175/212/213/235, 169/176/178/211/214, 169/176/178/211/214/217, 169/176/178/211/217, 169/176/178, 169/176/178/211/214/217, 169/176/211/214, 169/176/211/214/215/234, 169/176/211/214/217, 169/176/211/217, 169/176/214/215/217, 169/178/217, 169/178/234, 169/211/214/215, 169/211/217, 169/212/213, 169/212/235, 169/212/213/235, 169/235, 171/173/212/213/235, 173/175/213, 175/213/235, 175/235, 176/178/211/215/217, 176/178/211/217, 176/211/214, 176/214/217, 178/211/214, 178/211/217, 178/215, 211/234, 212/213/235, and 213/235.

In some embodiments, the polynucleotide capable of hybridizing under highly stringent conditions encodes an engineered polypeptide having imine reductase activity with improved properties comprising an amino acid sequence having at least 80%, 85%, 86%, 87%, 88%, 89%, 90%, 91%, 92%, 93%, 94%, 95%, 96%, 97%, 98%, 99% or more identity to SEQ ID NO:229, and one or more residue differences as compared to SEQ ID NO:229 at residue positions selected from: 45, 127, 130, 134, 174, 206, 209, 212, 216, 223, 227, and 279.

In some embodiments, the polynucleotide capable of hybridizing under highly stringent conditions encodes an engineered polypeptide having imine reductase activity with improved properties comprising an amino acid sequence having at least 80%, 85%, 86%, 87%, 88%, 89%, 90%, 91%, 92%, 93%, 94%, 95%, 96%, 97%, 98%, 99% or more identity to SEQ ID NO:2, 230 and/or 270. In some embodiments, the polynucleotides encode the polypeptides described herein but have at least about 80%, 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered imine reductase. In some embodiments, the reference polynucleotide sequence is selected from SEQ ID NOS:3-269.

In some embodiments, the polynucleotide capable of hybridizing under highly stringent conditions encodes an engineered polypeptide having imine reductase activity with improved properties comprising an amino acid sequence having at least 80%, 85%, 86%, 87%, 88%, 89%, 90%, 91%, 92%, 93%, 94%, 95%, 96%, 97%, 98%, 99% or more identity to SEQ ID NO:2. In some embodiments, the polynucleotides encode the polypeptides described herein but have at least about 80%, 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered imine reductase. In some embodiments, the reference polynucleotide sequence is selected from SEQ ID NOS:3-73.

In some embodiments, the polynucleotide capable of hybridizing under highly stringent conditions encodes an engineered polypeptide having imine reductase activity with improved properties comprising an amino acid sequence having at least 80%, 85%, 86%, 87%, 88%, 89%, 90%, 91%, 92%, 93%, 94%, 95%, 96%, 97%, 98%, 99% or more identity to SEQ ID NO:270. In some embodiments, the polynucleotides encode the polypeptides described herein but have at least about 80%, 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered imine reductase. In some embodiments, the reference polynucleotide sequence is selected from SEQ ID NOS:75-231.

In some embodiments, the polynucleotide capable of hybridizing under highly stringent conditions encodes an engineered polypeptide having imine reductase activity with improved properties comprising an amino acid sequence having at least 80%, 85%, 86%, 87%, 88%, 89%, 90%, 91%, 92%, 93%, 94%, 95%, 96%, 97%, 98%, 99% or more identity to SEQ ID NO: 229. In some embodiments, the polynucleotides encode the polypeptides described herein but have at least about 80%, 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered imine reductase. In some embodiments, the reference polynucleotide sequence is selected from SEQ ID NOS:233-268.

The present invention also provides engineered polynucleotides encoding engineered imine reductase polypeptides, wherein the engineered polynucleotides comprise substitution(s) at positions 12/15/18/21/27, 169/631/633, 259/523/524/525, 308/634/635/636, 364/365/366, 367/368/369, 370/371, 370/371/372/532, 394/396, 394/395/396, 401/402, 505/506/507, 512/513, 517/518/519, 523/524/525, 526/527/528, 532/534, 532/724/725, 631/633, 631/632/633, 634/635/636, 635/636, 637/638, 637/639, 637/639, 638/639, 640, 643/644/645, 644/645, 649/650/651, 700/701/702, and 703/704/705, and wherein the positions are numbered with reference to SEQ ID NO:1.

In some embodiments, the engineered polynucleotides encoding engineered imine reductase polypeptides comprise at least one of the following substitution(s)/substitution sets selected from 12A/15T/18G/21C/27A, 169A/631C/633T, 259T/523G/524G/525T, 308A/634T/635G/636T, 364G/365A/366A, 367G/368G/369T, 370G/371G, 370G/371C/372A/532A, 394C/396T, 394A/395G/396G, 401G/402G, 505A/506A/507T, 505A/506G/507T, 512G/513G, 517A/518T/519T, 517C/518A/519T, 523C/524A/525T, 523G/524G/525T, 526A/527G/528T, 532A/534G, 532A/724T/725A, 631C/633T, 631T/632G/633G, 634T/635G/636T, 635G/636T, 635T/636T, 637A/638G, 637A/639A, 637C/639A, 638T/639T, 640A, 643T/644T/645G, 644T/645G, 649A/650T/651T, 649C/650T/651T, 700T/701T/702G, and 703A/704A/705A, and wherein the positions are numbered with reference to SEQ ID NO:1.

In some embodiments, the engineered polynucleotides encoding engineered imine reductase polypeptides comprise at least one of the following substitution(s)/substitution sets selected from C12A/C15T/A18G/T21C/T27A, G169A/A631C/C633T, C259T/A523G/T524G/G525T, G308A/G634T/A635G/A636T, C364G/T365A/G366A, A367G/C368G/C369T, A370G/T371G, A370G/T371C/T372A/G532A, G394C/A396T, G394A/A395G/A396G, C401G/C402G, G505A/C506A/A507T, G505A/C506G/A507T, A512G/T513G, G517A/C518A/A519T, G517C/C518A/A519T, A523C/T524A/G525T, A523G/T524G/G525T, C526A/T527G/G528T, G532A/C534G, G532A/G724T/C725A, A631C/C633T, A631T/T632G/C633G, G634T/A635G/A636T, A635G/A636T, A635G/A636T, A635T/A636T, G637A/C638G, G637A/G639A, G637C/G639A, C638T/G639T, G640A, A643T/C644T/C645G, C644T/C645G, T649A/G650T/G651T, T649C/G650T/G651T, G700T/A701T/C702G, and G703A/C704A/C705A, and wherein the positions are numbered with reference to SEQ ID NO:1.

The present invention also provides engineered polynucleotides encoding engineered imine reductase polypeptides, wherein the engineered polynucleotides comprise substitution(s) at positions 367/368/369/505/506/507/513/519/523/524/525/634/635/636/639/703/704/705, 369/370/371/372/505/506/507/513/519/638/703/704/705, 369/370/371/372/507/513/519/523/524/525/635/638/703/704/705, 369/505/506/507/511/512/517/518/519/638/703/704/705, 369/505/506/507/513/517/518/519/523/524/525/638/703/704/705, 369/505/506/507/513/519/523/524/525/634/635/636/638/703/704/705, 369/505/506/507/513/519/635/638/703/704/705, 401/402/505/506/507/526/527/532/534/631/632/633/645/702, 401/402/505/506/507/526/527/532/534/631/633/640/645/702, 401/402/505/506/507/526/527/532/534/631/633/645/649/650/651/702, 401/402/505/506/507/526/527/534/631/632/633/645/702, 401/402/505/506/507/526/527/534/631/633/644/645/649/650/651/700/701, 401/402/505/506/507/526/532/534/631/632/633/640/645/649/650/651/702, 401/402/505/506/507/526/534/631/632/633/640/645/649/650/651/702, 401/402/505/506/507/526/534/631/632/633/645/649/650/651/702, 401/402/507/526/527/534/631/632/633/640/645/702, 401/402/507/526/527/534/631/632/633/644/645/702, 401/402/526/534/631/632/633/640/645/702, 402/505/506/507/526/527/532/534/631/632/633/640/645/649/650/651/702, 402/505/506/507/526/527/532/534/702, 402/505/506/507/526/527/532/534/631/633/640/645/702, 402/505/506/507/526/527/532/534/631/632/633/640/645/649/650/651/702, 402/505/506/507/526/527/534/631/633/640/645/649/650/651/702, 402/505/506/507/526/527/534/631/632/633/640/643/644/645/700/701, 402/505/506/507/526/527/534/631/632/633/640/645/702, 402/505/506/507/526/527/534/631/632/633/645/649/650/651/702, 402/505/506/507/526/527/534/631/632/633/645/649/650/651/702, 402/505/506/507/526/527/534/633/640/644/645/649/650/651/702, 402/505/506/507/526/532/534/633/645/700/701, 402/505/506/507/526/532/534/631/632/633/645/649/650/651, 402/505/506/507/526/534/631/632/633/645/649/650/651/702, 402/507/526/527/532/534/631/632/633/643/644/645/649/650/651/702, 402/507/526/527/532/534/631/632/633/645/649/650/651/702, 402/507/526/532/534/631/633/640/645, 402/507/526/532/534/631/632/633/645/649/650/651/702, 402/526/527/534/631/633/640/645/702, 505/506/507/526/527/532/534/631/632/633/640/645/649/650/651/702, 505/506/507/526/527/532/534/631/632/633/645/649/650/651/702, 505/506/507/526/534/631/632/633/640/643/644/645, 507/526/527/534/633/640/645/649/650/651/702, 507/526/532/534/644/645/702, and 631/632/633/645/700/701, and wherein the positions are numbered with reference to SEQ ID NO:269.

In some embodiments, the engineered polynucleotides encoding engineered imine reductase polypeptides comprise at least one of the following substitution(s)/substitution sets selected from 367G/368G/369T/505A/506A/507T/513C/519C/523G/524G/525C/634T/635G/636C/639T/703A/704A/705G, 369G/370G/371G/372C/505A/506A/507T/513C/519C/638T/703A/704A/705G, 369G/370G/371G/372C/507C/513C/519C/523G/524G/525C/635T/638T/703A/704A/705G, 369G/505A/506A/507T/511G/512T/517A/518T/519T/638T/703A/704A/705G, 369G/505A/506A/507T/513C/517A/518T/519T/523C/524A/525C/638T/703A/704A/705G, 369G/505A/506A/507T/513C/

519C/523G/524G/525C/634T/635G/636C/638T/703A/ 704A/705G, 369G/505A/506A/507T/513C/519C/635T/ 638T/703A/704A/705G, 401G/402G/505A/506A/507C/ 526T/527C/532A/534G/631C/633A/645T/649C/650T/ 651A/702T, 401G/402G/505A/506A/507C/526T/527C/ 532A/534T/631C/633A/640A/645T/702T, 401G/402G/ 505A/506A/507C/526T/527C/532A/534T/631T/632G/ 633G/645T/702T, 401G/402G/505A/506A/507C/526T/ 527C/534G/631C/633A/644T/645G/649A/650T/651A/ 700C/701T, 401G/402G/505A/506A/507C/526T/527C/ 534T/631T/632G/633G/645T/702T, 401G/402G/505A/ 506A/507C/526T/532A/534G/631T/632G/633G/640A/ 645T/649A/650T/651A/702T, 401G/402G/505A/506A/ 507C/526T/534G/631T/632G/633G/640A/645T/649C/ 650T/651A/702T, 401G/402G/505A/506A/507C/526T/ 534T/631T/632G/633G/645T/649C/650T/651A/702T, 401G/402G/507C/526T/527C/534T/631T/632G/633G/ 640A/645T/702T, 401G/402G/507C/526T/527C/534T/ 631T/632G/633G/644T/645G/702T, 401G/402G/526T/ 534G/631T/632G/633G/640A/645T/702T, 402G/505A/ 506A/507C/526T/527C/532A/534T/631T/632G/633G/ 640A/645T/649C/650T/651A/702T, 402G/505A/506A/ 507C/526T/527C/532A/534G/702T, 402G/505A/506A/ 507C/526T/527C/532A/534T/631C/633A/640A/645T/ 702T, 402G/505A/506A/507C/526T/527C/532A/534T/ 631T/632G/633G/640A/645T/649C/650T/651A/702T, 402G/505A/506A/507C/526T/527C/534G/631C/633A/ 640A/645T/649A/650T/651A/702T, 402G/505A/506A/ 507C/526T/527C/534G/631T/632G/633G/640A/643T/ 644T/645G/700C/701T, 402G/505A/506A/507C/526T/ 527C/534G/631T/632G/633G/640A/645T/702T, 402G/ 505A/506A/507C/526T/527C/534G/631T/632G/633G/ 645T/649C/650T/651A/702T, 402G/505A/506A/507C/ 526T/527C/534T/631T/632G/633G/645T/649A/650T/ 651A/702T, 402G/505A/506A/507C/526T/527C/534T/ 633A/640A/644T/645G/649A/650T/651A/702T, 402G/ 505A/506A/507C/526T/532A/534G/633A/645T/700C/ 701T, 402G/505A/506A/507C/526T/532A/534T/645T/ 649A/650T/651A, 402G/505A/506A/507C/526T/534G/ 631T/632G/633G/645T/649A/650T/651A/702T, 402G/ 507C/526T/527C/532A/534T/631T/632G/633G/643T/ 644T/645G/649C/650T/651A/702T, 402G/507C/526T/ 527C/532A/534T/631T/632G/633G/645T/649A/650T/ 651A/702T, 402G/507C/526T/532A/534A/631C/633A/ 640A/645T, 402G/507C/526T/532A/534G/631T/632G/ 633G/645T/649C/650T/651A/702T, 402G/526T/527C/ 534T/631C/633A/640A/645T/702T, 505A/506A/507C/ 526T/527C/532A/534G/631T/632G/633G/640A/645T/ 649A/650T/651A/702T, 505A/506A/507C/526T/527C/ 532A/534T/631T/632G/633G/645T/649C/650T/651A/ 702T, 505A/506A/507C/526T/534G/631T/632G/633G/ 640A/643T/644T/645G, 507C/526T/527C/534G/633A/ 640A/645T/649C/650T/651A/702T, 507C/526T/527C/ 534G/633A/640A/645T/649C/650T/651A/702T, 507C/ 526T/532A/534T/644T/645G/702T, and 631T/632G/633G/ 645T/700C/701T, and wherein the positions are numbered with reference to SEQ ID NO:269.

In some embodiments, the engineered polynucleotides encoding engineered imine reductase polypeptides comprise at least one of the following substitution(s)/substitution sets selected from A367G/C368G/C369T/G505A/C506A/ A507T/C513C/A519C/A523G/T524G/G525C/G634T/ A635G/A636G/G639T/G703A/C704A/C705G, C369G/ A370G/A371G/T372G/G505A/C506A/A507T/T513C/ A519C/C638T/G703A/C704A/C705G, C369G/A370G/ T371G/T372C/A507C/T513C/519C/A523G/T524G/ G525C/A635G/C638T/G703A/C704A/C705G, C369G/ G505A/C506A/A507T/T511G/A512T/G517A/C518T/ A519T/C638T/G703A/C704A/C705G, C369G/G505A/ C506A/A507T/T513C/G517A/C518T/A519T/A523C/ T524A/G525C/C638T/G703A/C704A/C705G, C369G/ G505A/C506A/A507T/T513C/A519C/A523G/T524G/ G525C/G634T/A635G/A636C/C638T/G703A/C704A/ C705G, C369G/G505A/C506A/A507T/T513C/A519C/ A635T/C638T/G703A/C704A/C705G, C401G/C402G/ G505A/C506A/A507C/C526T/T527C/G532A/C534G/ A631C/C633A/C645T/T649C/G65 OT/G651A/C702T, C401G/C402G/G505A/C506A/A507C/C526T/T527C/ G532A/C534T/A631C/C633A/G640A/C645T/C702T, C401G/C402G/G505A/C506A/A507C/C526T/T527C/ G532A/C534T/A631T/T632G/C633G/C645T/C702T, C401G/C402G/G505A/C506A/A507C/C526T/T527C/ C534G/A631C/C633A/C644T/C645G/T649A/G65 OT/G651A/G700C/A701T, C401G/C402G/G505A/C506A/ A507C/C526T/T527C/C534T/A631T/T632G/C633G/ C645T/C702T, C401G/C402G/G505A/C506A/A507C/ C526T/G532A/C534G/A631T/T632G/C633G/G640A/ C645T/T649A/G650T/G651A/C702T, C401G/C402G/ G505A/C506A/A507C/C526T/C534G/A631T/T632G/ C633G/G640A/C645T/T649C/G65 OT/G651A/C702T, C401G/C402G/G505A/C506A/A507C/C526T/C534T/ A631T/T632G/C633G/C645T/T649C/G650T/G651A/ C702T, C401G/C402G/A507C/C526T/T527C/C534G/ A631T/T632G/C633G/G640A/C645T/C702T, C401G/ C402G/A507C/C526T/T527C/C534G/A631T/T632G/ C633G/C644T/C645G/C702T, C401G/C402G/C526T/ C534G/A631T/T632G/C633G/G640A/C645 T/C702T, C402G/G505A/C506A/A507C/C526T/T527C/G532A/ C534T/A631T/T632G/C633G/G640A/C645T/T649C/ G650T/G651A/C702T, C402G/G505A/C506A/A507C/ C526T/T527C/G532A/C534G/C702T, C402G/G505A/ C506A/A507C/C526T/T527C/G532A/C534T/A631C/ C633A/G640A/C645T/C702T, C402G/G505A/C506A/ A507C/C526T/T527C/G532A/C534T/A631T/T632G/ C633G/G640A/C645T/T649C/G650T/G651A/C702T, C402G/G505A/C506A/A507C/C526T/T527C/C534G/ A631C/C633A/G640A/C645T/T649A/G650T/G651A/ C702T, C402G/G505A/C506A/A507C/C526T/T527C/ C534G/A631T/T632G/C633G/G640A/A643T/C644T/ C645G/G700C/A701T, C402G/G505A/C506A/A507C/ C526T/T527C/C534G/A631T/T632G/C633G/G640A/ C645T/C702T, C402G/G505A/C506A/A507C/C526T/ T527C/C534G/A631T/T632G/C633G/C645T/T649C/ G650T/G651A/C702T, C402G/G505A/C506A/A507C/ C526T/T527C/C534T/A631T/T632G/C633G/C645T/ T649A/G650T/G651A/C702T, C402G/G505A/C506A/ A507C/C526T/T527C/C534T/C633A/G640A/C644T/ C645G/T649A/G650T/G651A/C702T, C402G/G505A/ C506A/A507C/C526T/G532A/C534G/C633A/C645T/ G700C/A701T, C402G/G505A/C506A/A507C/C526T/ G532A/C534T/C645T/T649A/G650T/G651A, C402G/ G505A/C506A/A507C/C526T/C534G/A631T/T632G/ C633G/C645T/T649A/G650T/G651A/C702T, C402G/ A507C/C526T/T527C/G532A/C534T/A631T/T632G/ C633G/A643T/C644T/C645G/T649C/G65 OT/G651A/ C702T, C402G/A507C/C526T/T527C/G532A/C534T/ A631T/T632G/C633G/C645T/T649A/G650T/G651A/ C702T, C402G/A507C/C526T/G532A/C534G/A631C/ C633A/G640A/C645T, C402G/A507C/C526T/G532A/ C534G/A631T/T632G/C633G/C645T/T649C/G650T/ G651A/C702T, C402G/C526T/T527 C/C534T/A631C/ C633A/G640A/C645 T/C702T, G505A/C506A/A507 C/C526T/T527 C/G532A/C534G/A631T/T632G/C633G/ G640A/C645T/T649A/G65 OT/G651A/C702T, G505A/

C506A/A507 C/C526T/T527 C/G532A/C534T/A631 T/T632G/C633G/C645 T/T649C/G650T/G651A/C702T, G505A/C506A/A507 C/C526T/C534G/A631 T/T632G/ C633G/G640A/A643 T/C644T/C645G, A507 C/C526T/ T527 C/C534G/C633A/G640A/C645 T/T649C/G650T/ G651A/C702T, A507 C/C526T/G532A/C534T/C644T/ C645G/C702T, and A631T/T632G/C633G/C645T/G700C/ A701T, and wherein the positions are numbered with reference to SEQ ID NO:269.

The present invention also provides engineered polynucleotides encoding engineered imine reductase polypeptides, wherein the engineered polynucleotides comprise substitution(s) at positions 133, 379/381, 388/389/390, 400/401/402, 401/402, 520/521/522, 616/618, 625, 625/626/627, 634, 634/635/636, 634/636, 646, 646/647, 646, 667, 680/681, and 836/837, and wherein the positions are numbered with reference to SEQ ID NO:229.

In some embodiments, the engineered polynucleotides encoding engineered imine reductase 133A, 379A/381G, 388C/389G/390T, 400C/401T/402T, 401G/402G, 520A/521T/522G, 616C/618T, 625A, 625A/626G/627T, 634A, 634A/635G/636G, 634C/636T, 646A, 646A/647A, 646C, 667A, 680T/681T, and 836T/837T, and wherein the positions are numbered with reference to SEQ ID NO:229.

In some embodiments, the engineered polynucleotides encoding engineered imine reductase polypeptides comprise at least one of the following substitution(s)/substitution sets selected from G133A, G379A/C381G, A388C/C389G/C390T, A400C/C401T/C402T, C401G/C402G, G520A/C521T/A522G, A616C/G618T, C625A, C625A/A626G/A627T, G634A, G634A/A635G/A636G, G634C/A636T, G646A, G646A/G647A, G646C, G667A, C680T/C681T, and A836T/C837T, and wherein the positions are numbered with reference to SEQ ID NO:229.

In some embodiments, an isolated polynucleotide encoding any of the engineered imine reductase polypeptides provided herein is manipulated in a variety of ways to provide for expression of the polypeptide. In some embodiments, the polynucleotides encoding the polypeptides are provided as expression vectors where one or more control sequences is present to regulate the expression of the polynucleotides and/or polypeptides. Manipulation of the isolated polynucleotide prior to its insertion into a vector may be desirable or necessary depending on the expression vector. The techniques for modifying polynucleotides and nucleic acid sequences utilizing recombinant DNA methods are well known in the art.

In some embodiments, the control sequences include among other sequences, promoters, leader sequences, polyadenylation sequences, propeptide sequences, signal peptide sequences, and transcription terminators. As known in the art, suitable promoters can be selected based on the host cells used. For bacterial host cells, suitable promoters for directing transcription of the nucleic acid constructs of the present application, include, but are not limited to the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (See e.g., Villa-Kamaroff et al., Proc. Natl Acad. Sci. USA 75: 3727-3731 [1978]), as well as the tac promoter (See e.g., DeBoer et al., Proc. Natl Acad. Sci. USA 80: 21-25 [1983]). Exemplary promoters for filamentous fungal host cells, include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (See e.g., WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof. Exemplary yeast cell promoters can be from the genes can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are known in the art (See e.g., Romanos et al., Yeast 8:423-488 [1992]).

In some embodiments, the control sequence is a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice finds use in the present invention. For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are known in the art (See e.g., Romanos et al., supra).

In some embodiments, the control sequence is a suitable leader sequence, a non-translated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells include, but are not limited to those obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP). The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells include, but are not limited to those from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are also known in the art (See e.g., Guo and Sherman, Mol. Cell. Bio., 15:5983-5990 [1995]).

In some embodiments, the control sequence is a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. Any signal peptide coding region that directs the expressed polypeptide into the secretory pathway of a host cell of choice finds use for expression of the engineered imine reductase polypeptides provided herein. Effective signal peptide coding regions for bacterial host cells include, but are not limited to the signal peptide coding regions obtained from the genes for *Bacillus* NClB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are known in the art (See e.g., Simonen and Palva, Microbiol. Rev., 57:109-137) [1993]). Effective signal peptide coding regions for filamentous fungal host cells include, but are not limited to the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase. Useful signal peptides for yeast host cells include, but are not limited to those from the genes for *Saccharomyces cerevisiae* alpha-factor and *Saccharomyces cerevisiae* invertase.

In some embodiments, the control sequence is a propeptide coding region that codes for an amino acid sequence positioned at the amino terminus of a polypeptide. The resultant polypeptide is referred to as a "proenzyme," "propolypeptide," or "zymogen," in some cases). A propolypeptide can be converted to a mature active polypeptide by catalytic or autocatalytic cleavage of the propeptide from the propolypeptide. The propeptide coding region includes, but is not limited to the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thennophila* lactase (See e.g., WO 95/33836). Where both signal peptide and propeptide regions are present at the amino terminus of a polypeptide, the propeptide region is positioned next to the amino terminus of a polypeptide and the signal peptide region is positioned next to the amino terminus of the propeptide region.

In some embodiments, regulatory sequences are also utilized. These sequences facilitate the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include, but are not limited to the lac, tac, and trp operator systems. In yeast host cells, suitable regulatory systems include, but are not limited to the ADH2 system or GAL1 system. In filamentous fungi, suitable regulatory sequences include, but are not limited to the TAKA alpha-amylase promoter, *Aspergillus niger* glucoamylase promoter, and *Aspergillus oryzae* glucoamylase promoter.

The present invention also provides recombinant expression vectors comprising a polynucleotide encoding an engineered imine reductase polypeptide, and one or more expression regulating regions such as a promoter and a terminator, a replication origin, etc., depending on the type of hosts into which they are to be introduced. In some embodiments, the various nucleic acid and control sequences described above are combined together to produce a recombinant expression vector which includes one or more convenient restriction sites to allow for insertion or substitution of the nucleic acid sequence encoding the variant imine reductase polypeptide at such sites. Alternatively, the polynucleotide sequence(s) of the present invention are expressed by inserting the polynucleotide sequence or a nucleic acid construct comprising the polynucleotide sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), that can be conveniently subjected to recombinant DNA procedures and can result in the expression of the variant imine reductase polynucleotide sequence. The choice of the vector will typically depend on the compatibility of the vector with the host cell into which the vector is to be introduced. The vectors may be linear or closed circular plasmids.

In some embodiments, the expression vector is an autonomously replicating vector (i.e., a vector that exists as an extra-chromosomal entity, the replication of which is independent of chromosomal replication, such as a plasmid, an extra-chromosomal element, a minichromosome, or an artificial chromosome). The vector may contain any means for assuring self-replication. In some alternative embodiments, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

In some embodiments, the expression vector preferably contains one or more selectable markers, which permit easy selection of transformed cells. A "selectable marker" is a gene the product of which provides for biocide or viral resistance, resistance to heavy metals, prototrophy to auxotrophy, and the like. Examples of bacterial selectable markers include, but are not limited to the dal genes from *Bacillus subtilis* or *Bacillus licheniformis*, or markers, which confer antibiotic resistance such as ampicillin, kanamycin, chloramphenicol or tetracycline resistance. Suitable markers for yeast host cells include, but are not limited to ADE2, HIS3, LEU2, LYS2, MET3, TRP1, and URA3. Selectable markers for use in a filamentous fungal host cell include, but are not limited to, amdS (acetamidase), argB (ornithine carbamoyltransferases), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. In another aspect, the present invention provides a host cell comprising a polynucleotide encoding at least one engineered imine reductase polypeptide of the present invention, the polynucleotide being operatively linked to one or more control sequences for expression of the engineered imine reductase enzyme(s) in the host cell. Host cells for use in expressing the polypeptides encoded by the expression vectors of the present invention are well known in the art and include but are not limited to, bacterial cells, such as *E. coli, Vibrio fluvialis, Streptomyces* and *Salmonella typhimurium* cells; fungal cells, such as yeast cells (e.g., *Saccharomyces cerevisiae* and *Pichia pastoris* [ATCC Accession No. 201178]); insect cells such as *Drosophila* S2 and *Spodoptera* Sf9 cells; animal cells such as CHO, COS, BHK, 293, and Bowes melanoma cells; and plant cells. Exemplary host cells are *Escherichia coli* strains (e.g., W3110 (AthuA) and BL21).

Accordingly, in another aspect, the present invention provides methods for producing the engineered imine reductase polypeptides, where the methods comprise culturing a host cell capable of expressing a polynucleotide encoding the engineered imine reductase polypeptide under conditions suitable for expression of the polypeptide. In some embodiments, the methods further comprise the steps of isolating and/or purifying the imine reductase polypeptides, as described herein.

Appropriate culture media and growth conditions for the above-described host cells are well known in the art. Polynucleotides for expression of the imine reductase polypeptides may be introduced into cells by various methods known in the art. Techniques include, among others, electroporation, biolistic particle bombardment, liposome mediated transfection, calcium chloride transfection, and protoplast fusion.

The engineered imine reductases with the properties disclosed herein can be obtained by subjecting the polynucleotide encoding the naturally occurring or engineered imine reductase polypeptide to mutagenesis and/or directed evolution methods known in the art, and as described herein. An exemplary directed evolution technique is mutagenesis and/or DNA shuffling (See e.g., Stemmer, Proc. Natl. Acad. Sci. USA 91:10747-10751 [1994]; WO 95/22625; WO 97/0078; WO 97/35966; WO 98/27230; WO 00/42651; WO 01/75767 and U.S. Pat. No. 6,537,746). Other directed evolution procedures that can be used include, among others, staggered extension process (StEP), in vitro recombination (See e.g., Zhao et al., Nat. Biotechnol., 16:258-261 [1998]), mutagenic PCR (See e.g., Caldwell et al., PCR Methods Appl., 3:S136-S140 [1994]), and cassette mutagenesis (See e.g., Black et al., Proc. Natl. Acad. Sci. USA 93:3525-3529 [1996]).

For example, mutagenesis and directed evolution methods can be readily applied to polynucleotides to generate variant libraries that can be expressed, screened, and assayed. Mutagenesis and directed evolution methods are well known in the art (See e.g., U.S. Pat. Nos. 5,605,793, 5,830,721, 6,132,970, 6,420,175, 6,277,638, 6,365,408, 6,602,986, 7,288,375, 6,287,861, 6,297,053, 6,576,467, 6,444,468, 5,811238, 6,117,679, 6,165,793, 6,180,406, 6,291,242, 6,995,017, 6,395,547, 6,506,602, 6,519,065, 6,506,603, 6,413,774, 6,573,098, 6,323,030, 6,344,356, 6,372,497, 7,868,138, 5,834,252, 5,928,905, 6,489,146, 6,096,548, 6,387,702, 6,391,552, 6,358,742, 6,482,647, 6,335,160, 6,653,072, 6,355,484, 6,303,344, 6,319,713, 6,613,514, 6,455,253, 6,579,678, 6,586,182, 6,406,855, 6,946,296, 7,534,564, 7,776,598, 5,837,458, 6,391,640, 6,309,883, 7,105,297, 7,795,030, 6,326,204, 6,251,674, 6,716,631, 6,528,311, 6,287,862, 6,335,198, 6,352,859, 6,379,964, 7,148,054, 7,629,170, 7,620,500, 6,365,377, 6,358,740, 6,406,910, 6,413,745, 6,436,675, 6,961,664, 6,537,746, 7,430,477, 7,873,499, 7,702,464, 7,783,428, 7,747,391, 7,747,393, 7,751,986, 6,376,246, 6,426,224, 6,423,542, 6,479,652, 6,319,714, 6,521,453, 6,368,861, 7,421,347, 7,058,515, 7,024,312, 7,620,502, 7,853,410, 7,957,912, 7,904,249, 8,383,346, 8,504,498, 8,768,871, 8,762,066, 8,849,575, and all related non-US counterparts; Ling et al., Anal. Biochem., 254:157-78 [1997]; Dale et al., Meth. Mol. Biol., 57:369-74 [1996]; Smith, Ann. Rev. Genet., 19:423-462 [1985]; Botstein et al., Science, 229:1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; WO 2009/152336, WO 2009/102901, WO 2009/102899, WO 2011/035105, WO 2013/138339, WO 2013/003290, WO 2014/120819, WO 2014/120821, WO 2015/0134315, and WO 2015/048573, all of which are incorporated herein by reference).

In some embodiments, the enzyme clones obtained following mutagenesis treatment are screened by subjecting the enzymes to a defined temperature (or other assay conditions, such as testing the enzyme's activity over a broad range of substrates) and measuring the amount of enzyme activity remaining after heat treatments or other assay conditions. Clones containing a polynucleotide encoding a imine reductase polypeptide are then sequenced to identify the nucleotide sequence changes (if any), and used to express the enzyme in a host cell. Measuring enzyme activity from the expression libraries can be performed using any suitable method known in the art (e.g., standard biochemistry techniques, such as HPLC analysis).

In some embodiments, the clones obtained following mutagenesis treatment can be screened for engineered imine reductases having one or more desired improved enzyme properties (e.g., improved regioselectivity). Measuring enzyme activity from the expression libraries can be performed using the standard biochemistry techniques, such as HPLC analysis and/or derivatization of products (pre or post separation), for example, using dansyl chloride or OPA (See e.g., Yaegaki et al., J Chromatogr. 356(1):163-70 [1986]).

When the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical ligation methods, or polymerase mediated methods) to form any desired continuous sequence. For example, polynucleotides and oligonucleotides encoding portions of the imine reductase can be prepared by chemical synthesis as known in the art (e.g., the classical phosphoramidite method of Beaucage et al., Tet. Lett. 22:1859-69 [1981], or the method described by Matthes et al., EMBO J. 3:801-05 [1984]) as typically practiced in automated synthetic methods. According to the phosphoramidite method, oligonucleotides are synthesized (e.g., in an automatic DNA synthesizer), purified, annealed, ligated and cloned in appropriate vectors. In addition, essentially any nucleic acid can be obtained from any of a variety of commercial sources. In some embodiments, additional variations can be created by synthesizing oligonucleotides containing deletions, insertions, and/or substitutions, and combining the oligonucleotides in various permutations to create engineered imine reductases with improved properties.

Accordingly, in some embodiments, a method for preparing the engineered imine reductases polypeptide comprises: (a) synthesizing a polynucleotide encoding a polypeptide comprising an amino acid sequence having at least about 80%, 85%, 86%, 87%, 88%, 89%, 90%, 91%, 92%, 93%, 94%, 95%, 96%, 97%, 98%, or 99% or more sequence identity to an amino acid sequence selected from the even-numbered sequences of SEQ ID NOS:4-74, and having one or more residue differences as compared to SEQ ID NO:2 at residue positions selected from: 57/211, 87/175, 103/212, 122, 123, 124/178, 124, 132, 134, 169, 171, 173, 175, 176, 178/242, 178, 211, 212, 213, 214, 215, 217, 234, and 235; and (b) expressing the imine reductase polypeptide encoded by the polynucleotide.

Accordingly, in some embodiments, a method for preparing the engineered imine reductases polypeptide comprises: (a) synthesizing a polynucleotide encoding a polypeptide comprising an amino acid sequence having at least about 80%, 85%, 86%, 87%, 88%, 89%, 90%, 91%, 92%, 93%, 94%, 95%, 96%, 97%, 98%, or 99% or more sequence identity to an amino acid sequence selected from the even-numbered sequences of SEQ ID NOS:4-74, and having one or more residue differences as compared to SEQ ID NO:2, selected from: 57T/211L, 87S/175G, 103H/212C, 122E, 123G, 124A/178I, 124G, 132H/R, 134R, 169N/S, 171W, 173H/I, 175G/H, 176S, 178I//242Y, 178M, 211L/W, 212C/G/V, 213P/R/T/V, 214M, 215L/M, 217I/L, 234L, and 235K.

Accordingly, in some embodiments, a method for preparing the engineered imine reductases polypeptide comprises: (a) synthesizing a polynucleotide encoding a polypeptide comprising an amino acid sequence having at least about 80%, 85%, 86%, 87%, 88%, 89%, 90%, 91%, 92%, 93%, 94%, 95%, 96%, 97%, 98%, or 99% or more sequence identity to an amino acid sequence selected from the even-numbered sequences of SEQ ID NOS:4-74, and having one or more residue differences as compared to SEQ ID NO:2, selected from: A57T/I211L, P87S/M175G, R103H/E212C, L122E, T123G, I124A/V178I, I124G, E132H/R, T134R, A169N/S, Y171W, A173H/I, M175G/H, L176S, V178I/A242Y, V178M, I211L/W, E212C/G/V, A213P/R/T/V, V214M, T215L/M, W217I/L, D234L, and A235K.

Accordingly, in some embodiments, a method for preparing the engineered imine reductases polypeptide comprises: (a) synthesizing a polynucleotide encoding a polypeptide comprising an amino acid sequence having at least about 80%, 85%, 86%, 87%, 88%, 89%, 90%, 91%, 92%, 93%, 94%, 95%, 96%, 97%, 98%, or 99% or more sequence identity to an amino acid sequence selected from the even-numbered sequences of SEQ ID NOS:76-232, and having one or more residue differences as compared to SEQ ID NO:270 at residue positions selected from: 123/124/169/171/173/213/235, 123/124/169/212/213/235, 123/169/171/173/212/213/235, 123/169/171/173/213/235, 123/169/173/175/213/235, 123/169/173/212/213, 123/169/175, 123/169/175/212/235, 123/169/212/213, 123/173/175/212/213/235, 123/212/213/235, 123/212/235, 123/169/171/173/175/212/213, 123/169/173, 123/169/212/213/235, 123/213, 124/169, 124/169/173/175/212/213, 124/169/173/212/213, 124/169/173/212/213/235, 124/169/175/212/213/235, 124/169/212/213/235, 124/169/213/235, 124/175/212/213/235, 124/212/213/235, 134/169/176/178/211/214, 134/169/176/178/211, 134/169/176/178/211/217, 134/169/176/211/215/217/234, 134/169/176/211, 134/169/178/211/214/217, 134/169/211/214/217, 134/169/211/217, 134/176/211/214, 134/176/211/215, 134/211/214, 169/171/173/213/235, 169/173/175/213/235, 169/175/212/213/235, 169/176/178/211/214, 169/176/178/211/214/217, 169/176/178/211/217, 169/176/178, 169/176/178/211/214/217, 169/176/211/214, 169/176/211/214/215/234, 169/176/211/214/217, 169/176/211/217, 169/176/214/215/217, 169/178/217, 169/178/234, 169/211/214/215, 169/211/217, 169/212/213, 169/212/235, 169/212/213/235, 169/235, 171/173/212/213/235, 173/175/213, 175/213/235, 175/235, 176/178/211/215/217, 176/178/211/217, 176/211/214, 176/214/217, 178/211/214, 178/211/217, 178/215, 211/234, 212/213/235, and 213/235.

Accordingly, in some embodiments, a method for preparing the engineered imine reductases polypeptide comprises: (a) synthesizing a polynucleotide encoding a polypeptide comprising an amino acid sequence having at least about 80%, 85%, 86%, 87%, 88%, 89%, 90%, 91%, 92%, 93%, 94%, 95%, 96%, 97%, 98%, or 99% or more sequence identity to an amino acid sequence selected from the even-numbered sequences of SEQ ID NOS:76-232, and having one or more residue differences as compared to SEQ ID NO:270, selected from: 123G/124G/169N/171V/173H/213V/235K, 123G/124G/169N/212V/213V/235K, 123G/169N/171V/173H/213V/235K, 123G/169N/171V/173I/212C/213V/235K, 123G/169N/173H/175H/213V/235K, 123G/169N/173I/212G/213T, 123G/169N/175G, 123G/169N/175G/212C/235K, 123G/169N/212G/213V, 123G/173H/175H/212C/213V/235K, 123G/212C/213V/235K, 123G/212G/235K, 123G/169N/171V/173H/175H/212X/213V, 123G/169N/173I, 123G/169N/212G/213V/235K, 123G/213T, 124G/169N, 124A/169N/173I/175H/212G/213V, 124G/169N/173I/212C/213V, 124G/169N/173I/212G/213V, 124G/169N/173I/212V/213V/235K, 124G/169N/175G/212C/213V/235K, 124G/169N/212G/213V/235K, 124G/169N/212V/213V/235K, 124G/175G/212V/213V/235K, 124G/169N/213V/235K, 124G/212C/213V/235K, 124G/212G/213V/235K, 134R/169N/176S/178I/211L/214M, 134R/169N/176S/178I//211W, 134R/169N/176S/178M/211L/217L, 134R/169N/176S/211L/215M/217L/234L, 134R/169N/176S/211W, 134R/169N/178M/211W/214M/217I, 134R/169N/211W/214M/217L, 134R/169N/211W/217L, 134R/176S/211W/214M, 134R/176S/211W/215M, 134R/211W/214M, 169N/171V/173I/213V/235K, 169N/173I/175H/213V/235K, 169N/175G/212C/213V/235K, 169N/M175H/E212G/A213V/A235K, 169N/176S/178I/211L/214M, 169N/176S/178I/211W/214M/217L, 169N/176S/178/I211W/217L, 169N/176S/178M, 169N/176S/178M/211W/214M/217I, 169N/176S/211W/214M, 169N/176S/211W/214M/215L/234L, 169N/176S/211W/217I, 169N/176S/211W/217L, 169N/176S/214M/215M/217I, 169N/176S/211L/214M/217I, 169N/178I//217I, 169N/178M/234L, 169N/211W/214M/215L, 169N/211W/217I, 169N/212C/235K, 169N/212C/213V/235K, 169N/212G/213V, 169N/212V/213V/235K, 169N/235K, 171V/173I/212G/213V/235K, 173I/175H/213V, 175H/213P/235K, 175H/235K, 176S/178I//211W/215L/217L, 176S/178I//211W/217I, 176S/211L/214M, 176S/214M/217L, 178M/211L/214M, 178M/211W/217L, 178I//215M, 211W/234L, 212G/213V/235K, 212V/213V/235K, 213T/235K, and 213V/235K; and (b) expressing the imine reductase polypeptide encoded by the polynucleotide.

Accordingly, in some embodiments, a method for preparing the engineered imine reductases polypeptide comprises: (a) synthesizing a polynucleotide encoding a polypeptide comprising an amino acid sequence having at least about 80%, 85%, 86%, 87%, 88%, 89%, 90%, 91%, 92%, 93%, 94%, 95%, 96%, 97%, 98%, or 99% or more sequence identity to an amino acid sequence selected from the even-numbered sequences of SEQ ID NOS:76-232, and having one or more residue differences as compared to SEQ ID NO:270, selected from: T123G/I124G/A169N/Y171V/ A173H/A213V/A235K, T123G/I124G/A169N/E212V/ A213V/A235K, T123G/A169N/Y171V/A173H/A213V/ A235K, T123G/A169N/Y171V/A173I/E212C/A213V/ A235K, T123G/A169N/A173H/M175H/A213V/A235K, T123G/A169N/A173I/E212G/A213T, T123G/A169N/ M175G, T123G/A169N/M175G/E212C/A235K, T123G/ A169N/E212G/A213V, T123G/A173H/M175H/E212C/ A213V/A235K, T123G/E212C/A213V/A235K, T123G/ E212G/A235K, T123G/A169N/Y171V/A173H/M175H/ E212X/A213V, T123G/A169N/A173I, T123G/A169N/ E212G/A213V/A235K, T123G/A213T, I124G/A169N, I124A/A169N/A17311M175H/E212G/A213V, I124G/ A169N/A173I/E212C/A213V, I124G/A169N/A173I/ E212G/A213V, I124G/A169N/A173I/E212V/A213V/ A235K, I124G/A169N/M175G/E212C/A213V/A235K, I124G/A169N/E212G/A213V/A235K, I124G/A169N/ E212V/A213V/A235K, I124G/M175G/E212V/A213V/ A235K, I124G/A169N/A213V/A235K, I124G/E212C/ A213V/A235K, I124G/E212G/A213V/A235K, T134R/ A169N/L176S/V178I/I211L/V214M, T134R/A169N/ L176S/V178I/I211W, T134R/A169N/L176S/V178M/ I211L/W217L, T134R/A169N/L176S/I211L/T215M/ W217I/D234L, T134R/A169N/L176S/I211W, T134R/ A169N/V178M/I211W/V214M/W217I, T134R/A169N/ I211W/V214M/W217L, T134R/A169N/I211W/W217L, T134R/L176S/I211W/V214M, 134R/L176S/I211W/ T215M, T134R/I211W/V214M, A169N/Y171V/A173/ A213V/A235K, A169N/A17311M175H/A213V/A235K, A169N/M175G/E212C/A213V/A235K, A169N/M175H/ E212G/A213V/A235K, A169N/L176S/V178I/I211L/ V214M, A169N/L176S/V178I/I211W/V214M/W217L, A169N/L176S/V178I/I211W/W217L, A169N/L176S/ V178M, A169N/L176S/V178M/I211W/V214M/W217I, A169N/L176S/I211W/V214M, A169N/L176S/I211W/ V214M/T215L/D234L, A169N/L176S/I211W/W217I, A169N/L176S/I211W/W217L, A169N/L176S/V214M/ T215M/W217I, A169N/L176S/I211L/V214M/W217I, A169N/V178I/W217I, A169N/V178M/D234L, A169N/ I211W/V214M/T215L, A169N/I211W/W217I, A169N/ E212C/A235K, A169N/E212C/A213V/A235K, A169N/ E212G/A213V, A169N/E212V/A213V/A235K, A169N/ A235K, Y171V/A173I/E212G/A213V/A235K, A173I/ M175H/A213V, M175H/A213P/A235K, M175H/A235K, L176S/V178I/I211W/T215L/W217L, L176S/V178I/ I211W/W217I, L176S/I211L/V214M, L176S/V214M/ W217L, V178M/I211L/V214M, V178M/I211W/W217L, V178I/T215M, I211W/D234L, E212G/A213V/A235K, E212V/A213V/A235K, A213T/A235K, and A213V/ A235K.

Accordingly, in some embodiments, a method for preparing the engineered imine reductases polypeptide comprises: (a) synthesizing a polynucleotide encoding a polypeptide comprising an amino acid sequence having at least about 80%, 85%, 86%, 87%, 88%, 89%, 90%, 91%, 92%, 93%, 94%, 95%, 96%, 97%, 98%, or 99% or more sequence identity to an amino acid sequence selected from the even-numbered sequences of SEQ ID NOS:234-268, and having one or more residue differences as compared to SEQ ID NO:230 at residue positions selected from: 45, 127, 130, 134, 174, 206, 209, 212, 216, 223, 227, and 279.

Accordingly, in some embodiments, a method for preparing the engineered imine reductases polypeptide comprises: (a) synthesizing a polynucleotide encoding a polypeptide comprising an amino acid sequence having at least about 80%, 85%, 86%, 87%, 88%, 89%, 90%, 91%, 92%, 93%, 94%, 95%, 96%, 97%, 98%, or 99% or more sequence identity to an amino acid sequence selected from the even-numbered sequences of SEQ ID NOS:234-268, and having one or more residue differences as compared to SEQ ID NO:230, selected from: 45I, 127R, 130R, 134L/R, 174M, 206L, 209K/S, 212H/K/R, 216N/R/S, 223N, 227V, and 279V; and (b) expressing the imine reductase polypeptide encoded by the polynucleotide.

Accordingly, in some embodiments, a method for preparing the engineered imine reductases polypeptide comprises: (a) synthesizing a polynucleotide encoding a polypeptide comprising an amino acid sequence having at least about 80%, 85%, 86%, 87%, 88%, 89%, 90%, 91%, 92%, 93%, 94%, 95%, 96%, 97%, 98%, or 99% or more sequence identity to an amino acid sequence selected from the even-numbered sequences of SEQ ID NOS:234-268, and having one or more residue differences as compared to SEQ ID NO:230, selected from: V45I, G127R, T130R, T134L/R, A174M, M206L, Q209K/S, E212H/K/R, G216N/R/S, D223N, A227V, and D279V.

In some embodiments of the method, the polynucleotide encodes an engineered imine reductase that has optionally one or several (e.g., up to 3, 4, 5, or up to 10) amino acid residue deletions, insertions and/or substitutions. In some embodiments, the amino acid sequence has optionally 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 18, 20, 21, 22, 23, 24, or 25 amino acid residue deletions, insertions and/or substitutions. In some embodiments, the substitutions can be conservative or non-conservative substitutions.

In some embodiments, any of the engineered imine reductase enzymes expressed in a host cell can be recovered from the cells and/or the culture medium using any one or more of the well-known techniques for protein purification, including, among others, lysozyme treatment, sonication, filtration, salting-out, ultra-centrifugation, and chromatography. Suitable solutions for lysing and the high efficiency extraction of proteins from bacteria, such as E. coli, are commercially available (e.g., CelLytic B™, Sigma-Aldrich, St. Louis MO).

Chromatographic techniques for isolation of the imine reductase polypeptide include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques may be used to isolate the improved imine reductase enzymes. For affinity chromatography purification, any antibody which specifically binds the imine reductase polypeptide may be used. For the production of antibodies, various host animals, including but not limited to rabbits, mice, rats, etc., may be immunized by injection with a imine reductase polypeptide, or a fragment thereof. The imine reductase polypeptide or fragment may be attached to a suitable carrier, such as BSA, by means of a side chain functional group or linkers attached to a side chain functional group. In some embodiments, the affinity purification can use a specific ligand bound by the imine reductase or dye affinity column (See e.g., EP0641862; Stellwagen, "Dye Affinity Chromatography," *In Current Protocols in Protein Science*, Unit 9.2-9.2.16 [2001]).

Methods of Using the Engineered Imine Reductase Enzymes

In some embodiments, the imine reductases described herein find use in processes for converting a suitable substrate to its product.

In the embodiments provided herein and illustrated in the Examples, various ranges of suitable reaction conditions that can be used in the processes, include but are not limited to, substrate loading, co-substrate loading, pH, temperature, buffer, solvent system, polypeptide loading, and reaction time. Further suitable reaction conditions for carrying out the process for biocatalytic conversion of substrate compounds to product compounds using an engineered imine reductases described herein can be readily optimized in view of the guidance provided herein by routine experimentation that includes, but is not limited to, contacting the engineered imine reductase polypeptide and substrate compound under experimental reaction conditions of concentration, pH, temperature, and solvent conditions, and detecting the product compound.

The substrate compound(s) in the reaction mixtures can be varied, taking into consideration, for example, the desired amount of product compound, the effect of substrate concentration on enzyme activity, stability of enzyme under reaction conditions, and the percent conversion of substrate to product. In some embodiments, the suitable reaction conditions comprise a substrate compound loading of at least about 0.5 to about 25 g/L, 1 to about 25 g/L, 5 to about 25 g/L, about 10 to about 25 g/L, or 20 to about 25 g/L. In some embodiments, the suitable reaction conditions comprise a substrate compound loading of at least about 0.5 g/L, at least about 1 g/L, at least about 5 g/L, at least about 10 g/L, at least about 15 g/L, at least about 20 g/L, or at least about 30 g/L, or even greater.

In carrying out the imine reductase mediated processes described herein, the engineered polypeptide may be added to the reaction mixture in the form of a purified enzyme, partially purified enzyme, whole cells transformed with gene(s) encoding the enzyme, as cell extracts and/or lysates of such cells, and/or as an enzyme immobilized on a solid support. Whole cells transformed with gene(s) encoding the engineered imine reductase enzyme or cell extracts, lysates thereof, and isolated enzymes may be employed in a variety of different forms, including solid (e.g., lyophilized, spray-dried, and the like) or semisolid (e.g., a crude paste). The cell extracts or cell lysates may be partially purified by precipitation (ammonium sulfate, polyethyleneimine, heat treatment or the like, followed by a desalting procedure prior to lyophilization (e.g., ultrafiltration, dialysis, etc.). Any of the enzyme preparations (including whole cell preparations) may be stabilized by crosslinking using known crosslinking agents, such as, for example, glutaraldehyde or immobilization to a solid phase (e.g., Eupergit C, and the like).

The gene(s) encoding the engineered imine reductase polypeptides can be transformed into host cell separately or together into the same host cell. For example, in some embodiments one set of host cells can be transformed with gene(s) encoding one engineered imine reductase polypeptide and another set can be transformed with gene(s) encoding another engineered imine reductase polypeptide. Both sets of transformed cells can be utilized together in the reaction mixture in the form of whole cells, or in the form of lysates or extracts derived therefrom. In other embodiments, a host cell can be transformed with gene(s) encoding multiple engineered imine reductase polypeptide. In some embodiments the engineered polypeptides can be expressed in the form of secreted polypeptides and the culture medium containing the secreted polypeptides can be used for the imine reductase reaction.

In some embodiments, the improved activity and/or regioselectivity and/or stereoselectivity of the engineered imine reductase polypeptides disclosed herein provides for processes wherein higher percentage conversion can be achieved with lower concentrations of the engineered polypeptide. In some embodiments of the process, the suitable reaction conditions comprise an engineered polypeptide amount of about 1% (w/w), 2% (w/w), 5% (w/w), 10% (w/w), 20% (w/w), 30% (w/w), 40% (w/w), 50% (w/w), 75% (w/w), 100% (w/w) or more of substrate compound loading.

In some embodiments, the engineered polypeptide is present at about 0.01 g/L to about 50 g/L; about 0.05 g/L to about 50 g/L; about 0.1 g/L to about 40 g/L; about 1 g/L to about 40 g/L; about 2 g/L to about 40 g/L; about 5 g/L to about 40 g/L; about 5 g/L to about 30 g/L; about 0.1 g/L to about 10 g/L; about 0.5 g/L to about 10 g/L; about 1 g/L to about 10 g/L; about 0.1 g/L to about 5 g/L; about 0.5 g/L to about 5 g/L; or about 0.1 g/L to about 2 g/L. In some embodiments, the imine reductase polypeptide is present at about 0.01 g/L, 0.05 g/L, 0.1 g/L, 0.2 g/L, 0.5 g/L, 1, 2 g/L, 5 g/L, 10 g/L, 15 g/L, 20 g/L, 25 g/L, 30 g/L, 35 g/L, 40 g/L, or 50 g/L.

During the course of the reaction, the pH of the reaction mixture may change. The pH of the reaction mixture may be maintained at a desired pH or within a desired pH range. This may be done by the addition of an acid or a base, before and/or during the course of the reaction. Alternatively, the pH may be controlled by using a buffer. Accordingly, in some embodiments, the reaction condition comprises a buffer. Suitable buffers to maintain desired pH ranges are known in the art and include, by way of example and not limitation, borate, phosphate, 2-(N-morpholino)ethanesulfonic acid (MES), 3-(N-morpholino)propanesulfonic acid (MOPS), acetate, triethanolamine, and 2-amino-2-hydroxymethyl-propane-1,3-diol (Tris), and the like. In some embodiments, the reaction conditions comprise water as a suitable solvent with no buffer present.

In the embodiments of the process, the reaction conditions comprise a suitable pH. The desired pH or desired pH range can be maintained by use of an acid or base, an appropriate buffer, or a combination of buffering and acid or base addition. The pH of the reaction mixture can be controlled before and/or during the course of the reaction. In some embodiments, the suitable reaction conditions comprise a solution pH from about 4 to about 10, pH from about 5 to about 10, pH from about 5 to about 9, pH from about 6 to about 9, pH from about 6 to about 8. In some embodiments, the reaction conditions comprise a solution pH of about 4, 4.5, 5, 5.5, 6, 6.5, 7, 7.5, 8, 8.5, 9, 9.5, or 10.

In the embodiments of the processes herein, a suitable temperature is used for the reaction conditions, for example, taking into consideration the increase in reaction rate at higher temperatures, and the activity of the enzyme during the reaction time period. Accordingly, in some embodiments, the suitable reaction conditions comprise a temperature of about 10° C. to about 60° C., about 10° C. to about 55° C., about 15° C. to about 60° C., about 20° C. to about 60° C., about 20° C. to about 55° C., about 25° C. to about 55° C., or about 30° C. to about 50° C. In some embodiments, the suitable reaction conditions comprise a temperature of about 10° C., 15° C., 20° C., 25° C., 30° C., 35° C., 40° C., 45° C., 50° C., 55° C., or 60° C. In some embodiments, the temperature during the enzymatic reaction can be maintained at a specific temperature throughout the course of the reaction. In some embodiments, the temperature during the enzymatic reaction can be adjusted over a temperature profile during the course of the reaction.

In some embodiments, the processes of the invention are carried out in a solvent. Suitable solvents include water, aqueous buffer solutions, organic solvents, polymeric solvents, and/or co-solvent systems, which generally comprise aqueous solvents, organic solvents and/or polymeric solvents. The aqueous solvent (water or aqueous co-solvent system) may be pH-buffered or unbuffered. In some embodiments, the processes using the engineered imine reductase polypeptides can be carried out in an aqueous co-solvent system comprising an organic solvent (e.g., ethanol, isopropanol (IPA), dimethyl sulfoxide (DMSO), dimethylformamide (DMF) ethyl acetate, butyl acetate, 1-octanol, heptane, octane, methyl t butyl ether (MTBE), toluene, and the like), ionic or polar solvents (e.g., 1-ethyl 4 methylimidazolium tetrafluoroborate, 1-butyl-3-methylimidazolium tetrafluoroborate, 1-butyl 3 methylimidazolium hexafluorophosphate, glycerol, polyethylene glycol, and the like). In some embodiments, the co-solvent can be a polar solvent, such as a polyol, dimethylsulfoxide (DMSO), or lower alcohol. The non-aqueous co- solvent component of an aqueous co-solvent system may be miscible with the aqueous component, providing a single liquid phase, or may be partly miscible or immiscible with the aqueous component, providing two liquid phases. Exemplary aqueous co-solvent systems can comprise water and one or more co-solvents selected from an organic solvent, polar solvent, and polyol solvent. In general, the co-solvent component of an aqueous co-solvent system is chosen such that it does not adversely inactivate the imine reductase enzyme under the reaction conditions. Appropriate co-solvent systems can be readily identified by measuring the enzymatic activity of the specified engineered imine reductase enzyme with a defined substrate of interest in the candidate solvent system, utilizing an enzyme activity assay, such as those described herein.

In some embodiments of the process, the suitable reaction conditions comprise an aqueous co-solvent, where the co-solvent comprises ethanol at about 1% to about 50% (v/v), about 1 to about 40% (v/v), about 2% to about 40% (v/v), about 5% to about 30% (v/v), about 10% to about 30% (v/v), or about 10% to about 20% (v/v). In some embodiments of the process, the suitable reaction conditions can comprise an aqueous co-solvent comprising ethanol at about 1% (v/v), about 5% (v/v), about 10% (v/v), about 15% (v/v), about 20% (v/v), about 25% (v/v), about 30% (v/v), about 35% (v/v), about 40% (v/v), about 45% (v/v), or about 50% (v/v).

In some embodiments, the reaction conditions comprise a surfactant for stabilizing or enhancing the reaction. Surfactants can comprise non-ionic, cationic, anionic and/or amphiphilic surfactants. Exemplary surfactants, include by way of example and not limitation, nonyl phenoxypolyethoxylethanol (NP40), TRITON™ X-100 polyethylene glycol tert-octylphenyl ether, polyoxyethylene-stearylamine, cetyltrimethylammonium bromide, sodium oleylamidosulfate, polyoxyethylene-sorbitanmonostearate, hexadecyldimethylamine, etc. Any surfactant that may stabilize or enhance the reaction may be employed. The concentration of the surfactant to be employed in the reaction may be generally from 0.1 to 50 mg/ml, particularly from 1 to 20 mg/ml.

In some embodiments, the reaction conditions include an antifoam agent, which aids in reducing or preventing formation of foam in the reaction solution, such as when the reaction solutions are mixed or sparged. Anti-foam agents include non-polar oils (e.g., minerals, silicones, etc.), polar oils (e.g., fatty acids, alkyl amines, alkyl amides, alkyl sulfates, etc.), and hydrophobic (e.g., treated silica, polypropylene, etc.), some of which also function as surfactants. Exemplary anti-foam agents include, Y-30® (Dow Corning), poly-glycol copolymers, oxy/ethoxylated alcohols, and polydimethylsiloxanes. In some embodiments, the anti-foam can be present at about 0.001% (v/v) to about 5% (v/v), about 0.01% (v/v) to about 5% (v/v), about 0.1% (v/v) to about 5% (v/v), or about 0.1% (v/v) to about 2% (v/v). In some embodiments, the anti-foam agent can be present at about 0.001% (v/v), about 0.01% (v/v), about 0.1% (v/v), about 0.5% (v/v), about 1% (v/v), about 2% (v/v), about 3% (v/v), about 4% (v/v), or about 5% (v/v) or more as desirable to promote the reaction.

The quantities of reactants used in the imine reductase reaction will generally vary depending on the quantities of product desired, and concomitantly the amount of imine reductase substrate employed. Those having ordinary skill in the art will readily understand how to vary these quantities to tailor them to the desired level of productivity and scale of production.

In some embodiments, the order of addition of reactants is not critical. The reactants may be added together at the same time to a solvent (e.g., monophasic solvent, biphasic aqueous co-solvent system, and the like), or alternatively, some of the reactants may be added separately, and some together at different time points. For example, the cofactor, co-substrate and substrate may be added first to the solvent.

The solid reactants (e.g., enzyme, salts, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a pre-chilled lyophilization chamber, followed by the application of a vacuum.

For improved mixing efficiency when an aqueous co-solvent system is used, the imine reductase, and co-substrate may be added and mixed into the aqueous phase first. The imine reductase substrate may be added and mixed in, followed by the organic phase or the substrate may be dissolved in the organic phase and mixed in. Alternatively, the imine reductase substrate may be premixed in the organic phase, prior to addition to the aqueous phase.

The processes of the present invention are generally allowed to proceed until further conversion of substrate to product does not change significantly with reaction time (e.g., less than 10% of substrate being converted, or less than 5% of substrate being converted). In some embodiments, the reaction is allowed to proceed until there is complete or near complete conversion of substrate to product. Transformation of substrate to product can be monitored using known methods by detecting substrate and/or product, with or without derivatization. Suitable analytical methods include gas chromatography, HPLC, MS, and the like.

In some embodiments of the process, the suitable reaction conditions comprise a substrate loading of at least about 5 g/L, 10 g/L, 20 g/L, or more, and wherein the method results in at least about 50%, 60%, 70%, 80%, 90%, 95% or greater conversion of substrate compound to product compound in about in about 24 h or less, in about 12 h or less, in about 6 h or less, or in about 4 h or less.

The engineered imine reductase polypeptides of the present invention when used in the process under suitable reaction conditions result in an excess of the desired product in at least 90%, 95%, 96%, 97%, 98%, 99%, or greater diastereomeric excess over undesired product(s).

In some further embodiments of the processes for converting substrate compound to product compound using the engineered imine reductase polypeptides, the suitable reaction conditions can comprise an initial substrate loading to the reaction solution which is then contacted by the polypeptide. This reaction solution is then further supplemented with additional substrate compound as a continuous or batchwise addition over time at a rate of at least about 1 g/L/h, at least about 2 g/L/h, at least about 4 g/L/h, at least about 6 g/L/h, or higher. Thus, according to these suitable reaction conditions, polypeptide is added to a solution having an initial substrate loading of at least about 1 g/L, 5 g/L, or 10 g/L. This addition of polypeptide is then followed by continuous addition of further substrate to the solution at a rate of about 2 g/L/h, 4 g/L/h, or 6 g/L/h until a much higher final substrate loading of at least about 30 g/L or more, is reached. Accordingly, in some embodiments of the process, the suitable reaction conditions comprise addition of the polypeptide to a solution having an initial substrate loading of at least about 1 g/L, 5 g/L, or 10 g/L followed by addition of further substrate to the solution at a rate of about 2 g/L/h, 4 g/L/h, or 6 g/L/h until a final substrate loading of at least about 30 g/L, or more, is reached. This substrate supplementation reaction condition allows for higher substrate loadings to be achieved while maintaining high rates of conversion of substrate to product of at least about 5%, 25%, 50%, 75%, 90% or greater conversion of substrate.

In some embodiments, additional reaction components or additional techniques carried out to supplement the reaction conditions. These can include taking measures to stabilize or prevent inactivation of the enzyme, reduce product inhibition, shift reaction equilibrium to formation of the desired product.

In further embodiments, any of the above described process for the conversion of substrate compound to product compound can further comprise one or more steps selected from: extraction; isolation; purification; and crystallization of product compound. Methods, techniques, and protocols for extracting, isolating, purifying, and/or crystallizing the product from biocatalytic reaction mixtures produced by the above disclosed processes are known to the ordinary artisan and/or accessed through routine experimentation. Additionally, illustrative methods are provided in the Examples below.

Various features and embodiments of the invention are illustrated in the following representative examples, which are intended to be illustrative, and not limiting.

EXPERIMENTAL

The following Examples, including experiments and results achieved, are provided for illustrative purposes only and are not to be construed as limiting the present invention.

In the Examples below, the following abbreviations apply: ppm (parts per million); M (molar); mM (millimolar), uM and µM (micromolar); nM (nanomolar); mol (moles); gm and g (gram); mg (milligrams); ug and µg (micrograms); L and l (liter); ml and mL (milliliter); cm (centimeters); mm (millimeters); um and µm (micrometers); sec. (seconds); min(s) (minute(s)); h(s) and hr(s) (hour(s)); U (units); MW (molecular weight); rpm (rotations per minute); psi and PSI (pounds per square inch); ° C. (degrees Centigrade); RT and rt (room temperature); CAM and cam (chloramphenicol); DMSO (dimethylsulfoxide); PMBS (polymyxin B sulfate); IPTG (isopropyl β-D-1-thiogalactopyranoside); LB (Luria-Bertani broth); TB (Terrific Broth; 12 g/L bacto-tryptone, 24 g/L yeast extract, 4 mL/L glycerol, 65 mM potassium phosphate, pH 7.0, 1 mM MgSO$_4$); HEPES (HEPES zwitterionic buffer; 4-(2-hydroxyethyl)-piperazineethanesulfonic acid); SFP (shake flask powder); CDS (coding sequence); DNA (deoxyribonucleic acid); RNA (ribonucleic acid); *E. coli* W3110 (commonly used laboratory *E. coli* strain, available from the *Coli* Genetic Stock Center [CGSC], New Haven, CT); HTP (high throughput); HPLC (high pressure liquid chromatography); FIOPC (fold improvements over positive control); Microfluidics (Microfluidics, Corp., Westwood, MA); Sigma-Aldrich (Sigma-Aldrich, St. Louis, MO; Difco (Difco Laboratories, BD Diagnostic Systems, Detroit, MI); Agilent (Agilent Technologies, Inc., Santa Clara, CA); Corning (Corning, Inc., Palo Alto, CA); Dow Corning (Dow Corning, Corp., Midland, MI); and Gene Oracle (Gene Oracle, Inc., Mountain View, CA).

Example 1

Production of Engineered Polypeptides Having Imine Reductase Activity

Gene Synthesis and Optimization:

The polynucleotide sequence encoding wild-type imine reductase from *Pseudonocardia spinosispora* (SEQ ID NO: 1), was codon-optimized for expression in *Escherichia coli* and synthesized (SEQ ID NO:2). The synthetic gene of SEQ ID NO: 2 was cloned into a pCK110900 vector system (See e.g., US Pat. Appln. Publn. No. 2006/0195947, hereby incorporated by reference in its entirety) and subsequently expressed in *E. coli* W3110f/mA under the control of the lac promoter.

High-Throughput (HTP) Growth, Expression, and Lysate Preparation:

In a 96-well format, single colonies were picked and grown in 180 µL LB containing 1% glucose and 30 µg/mL CAM, at 30° C., 200 rpm, 85% humidity. Following overnight growth, 20 µL of the grown cultures were transferred into a deep well plate containing 380 µL of TB with 30 µg/mL chloramphenicol (CAM). Each variant was grown in duplicate to produce enough of the target enzyme for activity determination. The cultures were grown at 30° C., 250 rpm, with 85% humidity. When the optical density (OD600) of the cultures reached 0.6-0.8, expression of the imine reductase gene was induced by addition of IPTG to a final concentration of 1 mM. Following induction, growth was continued for 18-20 hours. After growth, the duplicate cultures were pooled, and cells were harvested by centrifugation at 4000 rpm at 4° C. for 10 minutes and the media discarded. The cell pellets were stored at −80° C. until ready for use. Prior to carrying out the reaction, cell pellets were resuspended in 250 µL of lysis buffer containing 100 mM HEPES, pH 8, with 1 g/L lysozyme and 0.5 g/L PMBS. The plates were agitated with medium-speed shaking for 2 hours on a microtiter plate shaker at room temperature. The plates were then centrifuged at 4000 rpm for 20 minutes at 4° C., and the clarified supernatants were used in the HTP assay reaction described below.

Production of Shake Flask Powders (SFP)

Shake-flask procedures can be used to generate engineered imine reductase polypeptide shake-flask powders (SFP), which are useful for secondary screening assays and/or use in the biocatalytic processes described herein. Shake flask powder (SFP) preparation of enzymes provides a more purified preparation (e.g., up to 30% of total protein) of the engineered enzyme, as compared to the cell lysate used in HTP assays and also allows for the use of more concentrated enzyme solutions. To start the cultures, a single colony of *E. coli*, containing a plasmid encoding an engineered polypeptide of interest, was inoculated into 50 mL LB with 30 μg/mL CAM and 1% glucose. The culture was grown overnight (at least 16 hours) in an incubator at 30° C., with shaking at 250 rpm. Following the overnight growth, the $OD_{600}$ of the culture was measured. The grown culture was diluted into 250 mL of TB with 30 Kg/mL CAM, in a 1 L shakeflask, to a final $OD_{600}$ of 0.2. The 250 mL culture was grown at 30° C. at 250 rpm, until $OD_{600}$ reached 0.6-0.8. Expression of the imine reductase gene was induced by addition of IPTG to a final concentration of 1 mM, and growth was continued for an additional 18-20 hours. Cells were harvested by transferring the culture into a pre-weighed centrifuge bottle, then centrifuged at 4000 rpm for 20 minutes, at 4° C. The cell pellet was resuspended and washed with 30 mL of cold 50 mM potassium phosphate, pH 8 buffer, and re-centrifuged at 4000 rpm for 20 minutes at 4° C. The supernatant was discarded and the remaining cell pellet was weighed. The cells were kept frozen at −80° C. for at least 2 hours prior to lysis. In some embodiments, the cells are stored at −80° C. until ready to use. For lysis, the cell pellet was resuspended in 6 mL of cold 50 mM potassium phosphate, pH 8.0 per 1 g cell pellet. The resuspended cells were lysed using a MICROFLUIDIZER®-M110L high pressure homogenizer (Microfluidics). Cell debris was removed by centrifugation at 10,000 rpm for 60 minutes at 4° C. The clarified lysate was collected, frozen at −80° C., and then lyophilized, using standard methods known in the art. Lyophilization of frozen clarified lysate provides a dry shake-flask powder comprising crude engineered polypeptide.

Example 2

Evolution and Screening of Engineered Polypeptides Derived from SEQ ID NO:2 for Improved Stability and Imine Reductase Activity in Preparing Compound [2]

The engineered polynucleotide encoding the polypeptide having imine reductase activity of SEQ ID NO:2 was used to generate the further engineered polypeptide variants of Table 2-2. Libraries of engineered genes were produced using well established techniques known in the art (e.g., saturation mutagenesis, recombination of previously identified beneficial mutations). Polypeptides encoded by the genes were produced in HTP and soluble lysate was generated, as described in Example 1. Each variant was tested for activity towards Compound [2] production.

The enzyme assay was carried out in a 96-well format, in 100 μL, total volume/well, which included 85% HTP lysate, 16 mM oxime, 100 mM HEPES, pH 8, 10% DMSO, 1 g/L GDH-105, 3 g/L $NADP^+$, and 100 mM glucose. The reactions were performed by adding the following into each well: (i) 10 μL of GDH cofactor recycling pre-mix (pre-mix contains 1M glucose, 30 g/L $NADP^+$, 10 g/L GDH-105 in 100 mM HEPES, pH 8); (ii) 85 μL, of the HTP clarified lysate (prepared as described in Example 1); and (iii) 10 μL of the 160 mM oxime stock solution in DMSO. The reaction plate was heat-sealed and shaken at 400 rpm, at 30° C. for 24 hours. The reaction was quenched by adding 100 μL $CH_3CN$ with 0.1% formic acid. The sample was then shaken in a microtiter plate shaker at room temperature, and then centrifuged at 4000 rpm at 4° C. for 10 mM. The quenched sample was further diluted 5× with $CH_3CN$ with 0.1% formic acid prior to LC/MS analysis. The LC/MS 4000 QTRAP run parameters are described in Table 2-1 below.

LC-MS Analysis for Resolution of Compound [2].

The HTP assay mixtures prepared as described in Example 2, were analyzed for formation of Compound [2] by LC-MS in MRM mode using the MRM transition: 433.3/377. Additional relevant LC-MS instrumental parameters and conditions were as shown below.

TABLE 2-1

| LC-MS Run Parameters | |
|---|---|
| Instrument | Agilent HPLC 1200 series, AB Sciex API 4000 |
| Column | Agilent Eclipse Plus C18, 1.8 um, 4.6 × 50 mm, with Agilent Eclipse Plus C18 guard |
| Mobile Phase | Gradient (A: 75% water, 25% methanol with 0.1% formic acid; B: 75% acetonitrile, 25% methanol with 0.1% formic acid) |
| | Time(min)　　　　　% B |
| | 0.00　　　　　23 |
| | 4.50　　　　　23 |
| | 5.00　　　　　95 |
| | 5.50　　　　　95 |
| | 5.55　　　　　23 |
| | 7.00　　　　　23 |
| Flow Rate | 0.5 mL/min |
| Run time | 7.0 min |
| Peak Retention Times | Compound [2] at 3.6 min; Oxime at 4.6 and 5.8 min |
| Column Temperature | 60° C. |
| Injection Volume | 10 μL |
| MS Detection | Sciex 4000 QTRAP; Product MRM 433.3/377.2; Oxime MRM 431.1/375.3 |
| MS Conditions | MODE: MRM; POLARITY: positive; CUR: 15; IS: 5500; CAD High; TEM: 550° C.; GS1: 80; GS2: 80; DP: 41; EP: 7.5; CE: 21 for product, 17 for oxime; CXP: 6; DT: 100 |

Activity relative to SEQ ID NO: 2 was calculated as peak area of Compound [2] generated by the variant over the peak area of Compound [2] produced by SEQ ID NO:2. The IRED variants listed in Table 2-2 have improved imine reductase activity compared to the starting polypeptide (i.e., SEQ ID NO:2). Beneficial mutations were determined, and one of the most improved variant was chosen as the backbone for the next round of evolution.

TABLE 2-2

| Enzyme Activity of IRED Variants Compared to SEQ ID NO: 1/2 | | | | |
|---|---|---|---|---|
| DNA SEQ ID NO: | Peptide SEQ ID NO: | Nucleotide Mutations (Relative to SEQ ID NO: 1) | Peptide Mutations (Relative to SEQ ID NO: 2) | Relative Improvement to SEQ ID NO: 1/2 |
| 3 | 4 | A367G/C368G/C369T | T123G | + |
| 5 | 6 | G394C/A396T | E132H | + |
| 7 | 8 | A370G/T371C/T372A/G532A | I124A/V178I | ++ |

TABLE 2-2-continued

Enzyme Activity of IRED Variants Compared to SEQ ID NO: 1/2

| DNA SEQ ID NO: | Peptide SEQ ID NO: | Nucleotide Mutations (Relative to SEQ ID NO: 1) | Peptide Mutations (Relative to SEQ ID NO: 2) | Relative Improvement to SEQ ID NO: 1/2 |
|---|---|---|---|---|
| 9 | 10 | A370G/T371G | I124G | + |
| 11 | 12 | G517C/C518A/A519T | A173H | ++ |
| 13 | 14 | G505A/C506A/A507T | A169N | +++ |
| 15 | 16 | G700T/A701T/C702G | D234L | + |
| 17 | 18 | A512G/T513G | Y171W | ++ |
| 19 | 20 | G532G/G724T/C725A | V178I/A242Y | + |
| 21 | 22 | G637A/G639A | A213T | + |
| 23 | 24 | T649C/G650T/G651T | W217L | + |
| 25 | 26 | G637A/C638G | A213R | + |
| 27 | 28 | G394A/A395G/A396G | E132R | + |
| 29 | 30 | C259T/A523G/T524G/G525T | P87S/M175G | ++ |
| 31 | 32 | C526A/T527G/G528T | L176S | +++ |
| 33 | 34 | A523G/T524G/G525T | M175G | ++ |
| 35 | 36 | C638T/G639T | A213V | ++ |
| 37 | 38 | G517A/C518T/A519T | A173I | + |
| 39 | 40 | C364G/T365A/G366A | L122E | + |
| 41 | 42 | G637C/G639A | A213P | ++ |
| 43 | 44 | T649A/G650T/G651T | W217I | +++ |
| 45 | 46 | G505A/C506A/A507T | A169S | + |
| 47 | 48 | A523C/T524A/G525T | M175H | + |
| 49 | 50 | G703C/A704C/A705A | A235K | ++ |
| 51 | 52 | G308A/G634T/A635G/A636T | R103H/E212C | +++ |
| 53 | 54 | A643T/C644T/C645G | T215L | ++ |
| 55 | 56 | G532A/C534G | V178M | +++ |
| 57 | 58 | G634T/A635G/A636T | E212C | ++ |
| 59 | 60 | C401G/C402G | T134R | +++ |
| 61 | 62 | A635T/A636T | E212V | ++ |
| 63 | 64 | C644T/C645G | T215M | ++ |
| 65 | 66 | A631T/T632G/C633G | I211W | +++ |
| 67 | 68 | G169A/A631C/C633T | A57T/I211L | +++ |
| 69 | 70 | A631C/C633T | I211L | +++ |
| 71 | 72 | A635G/A636T | E212G | ++ |
| 73 | 74 | G640A | V214M | ++ |

| Key for Table 2-2 | |
|---|---|
| + | 1.5 < FIOPC < 2.0 |
| ++ | 2.0 < FIOPC < 3.0 |
| +++ | FIOPC > 3.0 |

Example 3

Evolution and Screening of Engineered Polynucleotides Derived from SEQ ID NO:2 for Improved Expression and Imine Reductase Activity in Production of Compound [2]

The engineered polynucleotide encoding the polypeptide having imine reductase activity of SEQ ID NO:2 was used to generate the further engineered polynucleotide on Table 3-1. Libraries of engineered genes were produced using well established techniques known in the art (e.g., saturation mutagenesis, recombination of previously identified beneficial mutations). Polypeptides encoded by the genes were produced in HTP and soluble lysate was generated, as described in Example 1. Each variant was tested for activity towards Compound [2] production.

The enzyme assay was carried out in a 96-well format, in 100 µL, total volume/well, which included 85% HTP lysate, 16 mM oxime, 100 mM HEPES, pH 8, 10% DMSO, 1 g/L GDH-105, 3 g/L NADP$^+$, and 100 mM glucose. The reactions were performed by adding the following into each well: (i) 10 µL of GDH cofactor recycling pre-mix (pre-mix contains 1M glucose, 30 g/L NADP$^+$, 10 g/L GDH-105 in 100 mM HEPES, pH 8); (ii) 85 µL, of the HTP clarified lysate (prepared as described in Example 1); and (iii) 10 µL of the 160 mM oxime stock solution in DMSO. The reaction plate was heat-sealed and shaken at 400 rpm, at 30° C. for 24 hours. The reaction was quenched by adding 100 µL CH$_3$CN with 0.1% formic acid. The sample was then shaken in a microtiter plate shaker at room temperature, and then centrifuged at 4000 rpm at 4° C. for 10 mM. The quenched sample was further diluted 5× with CH$_3$CN with 0.1% formic acid prior to LC/MS analysis. The LC/MS 4000 QTRAP run parameters are described in Table 2-1.

TABLE 3-1

Enzyme Activity of IRED Variant Compared to SEQ ID NO: 1/2

| DNA SEQ ID NO: | Peptide SEQ ID NO: | Nucleotide Mutations (Relative to SEQ ID NO: 1) | Peptide Mutations (Relative to SEQ ID NO: 2) | Relative Improvement to SEQ ID NO: 1/2 |
|---|---|---|---|---|
| 269 | 270 | C12A/C15T/A18G/T21C/T27A | | ++ |

| Key for Table 3-1 | |
|---|---|
| + | 1.5 < FIOPC < 2.0 |
| ++ | 2.0 < FIOPC < 3.0 |

Example 4

Improvement Over SEQ ID NO: 269 for the Production of Compound [2]

The polynucleotide sequence SEQ ID NO: 269 was selected as a parent enzyme after screening variants as described in Examples 2 and 3. Libraries of engineered genes were produced using well established techniques known in the art (e.g., saturation mutagenesis, recombination of previously identified beneficial mutations). The polypeptides encoded by each gene were produced in HTP and the soluble lysate was generated as described in Example 1.

The enzyme assay was carried out in a 96-well format, in 100 tiL total volume/well, which included 85% HTP lysate, 16 mM oxime, 100 mM HEPES, pH 8, 10% DMSO, 1 g/L GDH-105, 3 g/L NADP$^+$, and 100 mM glucose. The reactions were performed by adding the following into each well: (i) 10 µL of GDH cofactor recycling pre-mix (pre-mix contains 1 M glucose, 30 g/L NADP$^+$, 10 g/L GDH-105 in 100 mM HEPES, pH 8)/(ii) 85 µL of the HTP clarified lysate (prepared as described above)/and (iii) 10 µL of the 160 mM oxime stock solution in DMSO. The reaction plate was heat-sealed and shaken at 400 rpm, at 30° C. for 24 hours. The reaction was quenched by adding 100 µL CH$_3$CN with 0.1% formic acid. The sample was then shaken in a microtiter plate shaker at room temperature, and then centrifuged at 4000 rpm at 4° C. for 10 mM. The quenched sample was further diluted 5× with CH$_3$CN with 0.1% formic acid prior to LC/MS analysis. The LC/MS 4000 QTRAP run parameters are described in Table 2-1.

Activity relative to the enzyme encoded by SEQ ID NO: 269 (i.e., SEQ ID NO:270) was calculated as the peak area of Compound [2] produced by the variant over the Compound [2] peak area of the SEQ ID NO:270. The polypeptides listed in Table 4-1 have improved imine reductase activity compared to the starting polypeptide. Beneficial mutations were identified and one of the most improved variant was chosen as the parent for the next round of evolution.

TABLE 4-1

Enzyme Activity of IRED Variants Compared to SEQ ID NO: 269/270

| DNA SEQ ID NO: | Peptide SEQ ID NO: | Nucleotide Mutations (Relative to SEQ ID NO: 269) | Peptide Mutations (Relative to SEQ ID NO: 270) | Relative Improvement to SEQ ID NO: 269/270 |
|---|---|---|---|---|
| 75 | 76 | A367G/C368G/C369T/G505A/C506A/A507T/T513C/A519C/A523G/T524G/G525C/G634T/A635G/A636C/G639T/G703A/C704A/C705G | T123G/I124G/A169N/Y171V/A173H/A213V/A235K | ++++++ |
| 77 | 78 | C369G/G505A/C506A/A507T/T513C/A519C/A635T/C638T/G703A/C704A/C705G | I124G/A169N/A173I/E212G/A213V | ++++++ |
| 79 | 80 | C369G/G505A/C506A/A507T/T513C/A519C/A523G/T524G/G525C/G634T/A635G/A636C/C638T/G703A/C704A/C705G | I124G/A169N/M175G/E212C/A213V/A235K | ++++++ |
| 81 | 82 | C369G/G505A/C506A/A507T/T511G/A512T/G517A/C518T/A519T/C638T/G703A/C704A/C705G | Y171V/A173I/E212G/A213V/A235K | ++++++ |
| 83 | 84 | C369G/A370G/T371G/T372C/G505A/C506A/A507T/T513C/A519C/C638T/G703A/C704A/C705G | A169N/A235K | ++++++ |
| 85 | 86 | C369G/A370G/T371G/T372C/A507C/T513C/A519C/A523G/T524G/G525C/A635T/C638T/G703A/C704A/C705G | T123G/A169N/A173H/M175H/A213V/A235K | +++++ |
| 87 | 88 | C369G/G505A/C506A/A507T/T513C/G517A/C518T/A519T/A523C/T524A/G525C/C638T/G703A/C704A/C705G | T123G/A169N/A173I/E212G/A213T | +++++ |
| 89 | 90 | C402G/G505A/C506A/A507C/C526T/T527C/C534G/A631T/T632G/C633G/C645T/T649C/G650T/G651A/C702T | I124G/E212G/A213V/A235K | +++++ |
| 91 | 92 | C401G/C402G/G505A/C506A/A507C/C526T/C534G/A631T/T632G/C633G/G640A/C645T/T649C/G650T/G651A/C702T | T123G/A173H/M175H/E212C/A213V/A235K | +++++ |
| 93 | 94 | C401G/C402G/G505A/C506A/A507C/C526T/G532A/C534G/A631T/T632G/C633G/G640A/C645T/T649A/G650T/G651A/C702T | A169N/E212G/A213V | +++++ |
| 95 | 96 | C402G/A507C/C526T/G532A/C534G/A631T/T632G/C633G/C645T/T649C/G650T/G651A/C702T | M175H/A235K | +++++ |
| 97 | 98 | C401G/C402G/A507C/C526T/T527C/C534G/A631T/T632G/C633G/C644T/C645G/C702T | I124G/A169N | +++++ |
| 99 | 100 | C402G/G505A/C506A/A507C/C526T/T527C/C534G/A631T/T632G/C633G/G640A/C645T/C702T | A169N/E212C/A235K | +++++ |
| 101 | 102 | C401G/C402G/G505A/C506A/A507C/C526T/T527C/C534T/A631T/T632G/C633G/C645T/C702T | T123G/E212G/A235K | +++++ |
| 103 | 104 | C402G/G505A/C506A/A507C/C526T/T527C/C534T/C633A/G640A/C644T/C645G/T649A/G650T/G651A/C702T | A173I/M175H/A213V | +++++ |
| 105 | 106 | C402G/G505A/C506A/A507C/C526T/C534G/A631T/T632G/C633G/C645T/T649A/G650T/G651A/C702T | A213T/A235K | +++++ |
| 107 | 108 | C401G/C402G/C526T/C534G/A631T/T632G/C633G/G640A/C645T/C702T | M175H/A213P/A235K | +++++ |
| 109 | 110 | C401G/C402G/A507C/C526T/T527C/C534G/A631T/T632G/C633G/G640A/C645T/C702T | I124G/A169N/E212G/A213V/A235K | +++++ |
| 111 | 112 | C402G/G505A/C506A/A507C/C526T/T527C/C534G/A631C/C633A/G640A/C645T/T649A/G650T/G651A/C702T | I124G/A169N/E212V/A213V/A235K | +++++ |

TABLE 4-1-continued

Enzyme Activity of IRED Variants Compared to SEQ ID NO: 269/270

| DNA SEQ ID NO: | Peptide SEQ ID NO: | Nucleotide Mutations (Relative to SEQ ID NO: 269) | Peptide Mutations (Relative to SEQ ID NO: 270) | Relative Improvement to SEQ ID NO: 269/270 |
|---|---|---|---|---|
| 113 | 114 | C402G/G505A/C506A/A507C/C526T/G532A/C534G/C633A/C645T/G700C/A701T | T123G/A169N/E212G/A213V | +++++ |
| 115 | 116 | G505A/C506A/A507C/C526T/T527C/G532A/C534T/A631T/T632G/C633G/C645T/T649C/G650T/G651A/C702T | E212V/A213V/A235K | ++++ |
| 117 | 118 | C402G/G505A/C506A/A507C/C526T/T527C/G532A/C534T/A631T/T632G/C633G/G640T/C645T/T649C/G650T/G651A/C702T | T123G/E212C/A213V/A235K | ++++ |
| 119 | 120 | A631T/T632G/C633G/C645T/G700C/A701T | T123G/A169N/Y171V/A173H/A213V/A235K | ++++ |
| 121 | 122 | A507C/C526T/T527C/C534G/C633A/G640A/C645T/T649C/G650T/G651A/C702T | I124G/E212C/A213V/A235K | ++++ |
| 123 | 124 | C402G/A507C/C526T/T527C/G532A/C534T/A631T/T632G/C633G/A643T/C644T/C645T/T649C/G650T/G651A/C702T | I124G/A169N/A173I/E212V/A213V/A235K | ++++ |
| 125 | 126 | C402G/A507C/C526T/T527C/G532A/C534T/A631T/T632G/C633G/C645T/T649A/G650T/G651A/C702T | T123G/A169N/A173I | ++++ |
| 127 | 128 | C402G/G505A/C506A/A507C/C526T/T527C/G532A/C534G/C702T | A169N/E212C/A213V/A235K | ++++ |
| 129 | 130 | C402G/G505A/C506A/A507C/C526T/G532A/C534T/C645T/T649A/G650T/G651A | T123G/A169N/Y171V/A173H/M175H/E212X/A213V | ++++ |
| 131 | 132 | C401G/C402G/G505A/C506A/A507C/C526T/T527C/G532A/C534T/A631T/T632G/C633G/C645T/C702T | T123G/A213T | ++++ |
| 133 | 134 | G505A/C506A/A507C/C526T/C534G/A631T/T632G/C633G/G640A/A643T/C644T/C645G | T123G/A169N/E212G/A213V/A235K | ++++ |
| 135 | 136 | A507C/C526T/G532A/C534T/C644T/C645G/C702T | T123G/I124G/A169N/E212V/A213V/A235K | ++++ |
| 137 | 138 | C401G/C402G/G505A/C506A/A507C/C526T/T527C/C534G/A631C/C633A/C644T/C645G/T649A/G650T/G651A/G700C/A701T | A213V/A235K | ++++ |
| 139 | 140 | C402G/G505A/C506A/A507C/C526T/T527C/C534G/A631T/T632G/C633G/G640A/A643T/C644T/C645G/G700C/A701T | E212G/A213V/A235K | ++++ |
| 141 | 142 | C402G/A507C/C526T/G532A/C534G/A631C/C633A/G640A/C645T | I124G/A169N/A173I/E212C/A213V | ++++ |
| 143 | 144 | C402G/C526T/T527C/C534T/A631C/C633A/G640A/C645T/C702T | T123G/A169N/Y171V/A173I/E212C/A213V/A235K | ++++ |
| 145 | 146 | C401G/C402G/G505A/C506A/A507C/C526T/T527C/G532A/C534G/A631C/C633A/C645T/G650T/G651A/C702T | I124A/A169N/A173I/M175H/E212G/A213V | ++++ |
| 147 | 148 | C401G/C402G/G505A/C506A/A507C/C526T/C534T/A631T/T632G/C633G/C645T/T649C/G650T/G651A/C702T | A169N/M175H/E212G/A213V/A235K | ++++ |
| 149 | 150 | C402G/G505A/C506A/A507C/C526T/T527C/C534T/A631T/T632G/C633G/C645T/T649A/G650T/G651A/C702T | T123G/A169N/M175G | ++++ |
| 151 | 152 | C402G/G505A/C506A/A507C/C526T/T527C/G532A/C534T/A631C/C633A/G640A/C645T/C702T | T123G/A169N/M175G/E212C/A235K | ++++ |
| 153 | 154 | G505A/C506A/A507C/C526T/T527C/G532A/C534T/A631T/T632G/C633G/G640A/C645T/T649A/G650T/G651A/C702T | A169N/E212V/A213V/A235K | ++++ |
| 155 | 156 | C401G/C402G/G505A/C506A/A507C/C526T/T527C/G532A/C534T/A631C/C633A/G640A/C645T/C702T | A169N/M175G/E212C/A213V/A235K | ++++ |

TABLE 4-1-continued

Enzyme Activity of IRED Variants Compared to SEQ ID NO: 269/270

| DNA SEQ ID NO: | Peptide SEQ ID NO: | Nucleotide Mutations (Relative to SEQ ID NO: 269) | Peptide Mutations (Relative to SEQ ID NO: 270) | Relative Improvement to SEQ ID NO: 269/270 |
|---|---|---|---|---|
| 157 | 158 | A367G/C368G/C369T/G505A/C506A/A507T/T513C/A519C/A523G/T524G/G525C/G634T/A635G/A636C/G639T/G703A/C704A/C705G | A169N/Y171V/A173I/A213V/A235K | ++++ |
| 159 | 160 | C369G/G505A/C506A/A507T/T513C/A519C/A635T/C638T/G703A/C704A/C705G | I124G/A169N/A213V/A235K | ++++ |
| 161 | 162 | C369G/G505A/C506A/A507T/T513C/A519C/A523G/T524G/G525C/G634T/A635G/A636C/C638T/G703A/C704A/C705G | I124G/M175G/E212V/A213V/A235K | ++++ |
| 163 | 164 | C369G/G505A/C506A/A507T/T511G/A512T/G517A/C518T/A519T/C638T/G703A/C704A/C705G | A169N/A173I/M175H/A213V/A235K | ++++ |
| 165 | 166 | C369G/A370G/T371G/T372C/G505A/C506A/A507T/T513C/A519C/C638T/G703A/C704A/C705G | A169N/L176S/I211W/W217L | ++++ |
| 167 | 168 | C369G/A370G/T371G/T372C/A507C/T513C/A519C/A523G/T524G/G525C/A635T/C638T/G703A/C704A/C705G | T134R/A169N/I211W/V214M/W217L | ++++ |
| 169 | 170 | C369G/G505A/C506A/A507T/T513C/G517A/C518T/A519T/A523C/T524A/G525C/C638T/G703A/C704A/C705G | T134R/A169N/V178M/I211W/V214M/W217I | ++++ |
| 171 | 172 | C402G/G505A/C506A/A507C/C526T/T527C/C534G/A631T/T632G/C633G/C645T/T649C/G650T/G651A/C702T | V178M/I211W/W217L | ++++ |
| 173 | 174 | C401G/C402G/G505A/C506A/A507C/C526T/C534G/A631T/T632G/C633G/G640A/C645T/T649C/G650T/G651A/C702T | T134R/L176S/I211W/T215M | ++++ |
| 175 | 176 | C401G/C402G/G505A/C506A/A507C/C526T/G532A/C534G/A631T/T632G/C633G/G640A/C645T/T649A/G650T/G651A/C702T | A169N/L176S/I211W/V214M | ++++ |
| 177 | 178 | C402G/A507C/C526T/G532A/C534G/A631T/T632G/C633G/C645T/T649C/G650T/G651A/C702T | T134R/A169N/L176S/I211W | ++++ |
| 179 | 180 | C401G/C402G/A507C/C526T/T527C/C534G/A631T/T632G/C633G/C644T/C645T/C702T | A169N/L176S/V214M/T215M/W217I | ++++ |
| 181 | 182 | C402G/G505A/C506A/A507C/C526T/T527C/C534G/A631T/T632G/C633G/G640A/C645T/C702T | A169N/I211W/W217I | ++++ |
| 183 | 184 | C401G/C402G/G505A/C506A/A507C/C526T/T527C/C534T/A631T/T632G/C633G/C645T/C702T | T134R/I211W/V214M | ++++ |
| 185 | 186 | C402G/G505A/C506A/A507C/C526T/T527C/C534T/C633A/G640A/C644T/C645G/T649A/G650T/G651A/C702T | T134R/L176S/I211W/V214M | ++++ |
| 187 | 188 | C402G/G505A/C506A/A507C/C526T/C534G/A631T/T632G/C633G/C645T/T649A/G650T/G651A/C702T | A169N/L176S/I211L/V214M/W217I | ++++ |
| 189 | 190 | C401G/C402G/C526T/C534G/A631T/T632G/C633G/G640A/C645T/C702T | A169N/V178M/D234L | ++++ |
| 191 | 192 | C401G/C402G/A507C/C526T/T527C/C534G/A631T/T632G/C633G/G640A/C645T/C702T | A169N/L176S/V178I/I211W/W217L | ++++ |
| 193 | 194 | C402G/G505A/C506A/A507C/C526T/T527C/C534G/A631T/C633A/G640A/C645T/T649A/G650T/G651A/C702T | A169N/L176S/V178I/I211W/V214M/W217L | ++++ |
| 195 | 196 | C402G/G505A/C506A/A507C/C526T/G532A/C534G/C633A/C645T/G700C/A701T | I211W/D234L | +++ |
| 197 | 198 | G505A/C506A/A507C/C526T/T527C/G532A/C534T/A631T/T632G/C633G/C645T/T649C/G650T/G651A/C702T | L176S/V214M/W217L | +++ |

TABLE 4-1-continued

Enzyme Activity of IRED Variants Compared to SEQ ID NO: 269/270

| DNA SEQ ID NO: | Peptide SEQ ID NO: | Nucleotide Mutations (Relative to SEQ ID NO: 269) | Peptide Mutations (Relative to SEQ ID NO: 270) | Relative Improvement to SEQ ID NO: 269/270 |
|---|---|---|---|---|
| 199 | 200 | C402G/G505A/C506A/A507C/C526T/T527C/G532A/C534T/A631T/T632G/C633G/G640A/C645T/T649C/G650T/G651A/C702T | L176S/V178I/I211W/T215L/W217L | +++ |
| 201 | 202 | A631T/T632G/C633G/C645T/G700C/A701T | L176S/V178I/I211W/W217I | +++ |
| 203 | 204 | A507C/C526T/T527C/C534G/C633A/G640A/C645T/T649C/G650T/G651A/C702T | A169N/L176S/V178M | +++ |
| 205 | 206 | C402G/A507C/C526T/T527C/G532A/C534T/A631T/T632G/C633G/A643T/C644T/C645G/T649C/G650T/G651A/C702T | A169N/V178I/W217I | +++ |
| 207 | 208 | C402G/A507C/C526T/T527C/G532A/C534T/A631T/T632G/C633G/C645T/T649A/G650T/G651A/C702T | T134R/A169N/L176S/V178I/I211W | +++ |
| 209 | 210 | C402G/G505A/C506A/A507C/C526T/T527C/G532A/C534G/C702T | A169N/I211W/V214M/T215L | +++ |
| 211 | 212 | C402G/G505A/C506A/A507C/C526T/G532A/C534T/C645T/T649A/G650T/G651A | V178I/T215M | +++ |
| 213 | 214 | C401G/C402G/G505A/C506A/A507C/C526T/T527C/G532A/C534T/A631T/T632G/C633G/C645T/C702T | T134R/A169N/L176S/I211L/T215M/W217I/D234L | +++ |
| 215 | 216 | G505A/C506A/A507C/C526T/C534G/A631T/T632G/C633G/G640A/A643T/C644T/C645G | A169N/L176S/I211W/V214M/T215L/D234L | +++ |
| 217 | 218 | A507C/C526T/G532A/C534T/C644T/C645G/C702T | V178M/I211L/V214M | +++ |
| 219 | 220 | C401G/C402G/G505A/C506A/A507C/C526T/T527C/C534G/A631C/C633A/C644T/C645G/T649A/G650T/G651A/G700C/A701T | L176S/I211L/V214M | +++ |
| 221 | 222 | C402G/G505A/C506A/A507C/C526T/T527C/C534G/A631T/T632G/C633G/G640A/A643T/C644T/C645G/G700C/A701T | T134R/A169N/L176S/V178M/I211L/W217L | +++ |
| 223 | 224 | C402G/A507C/C526T/G532A/C534G/A631C/C633A/G640A/C645T | T134R/A169N/I211W/W217L | +++ |
| 225 | 226 | C402G/C526T/T527C/C534T/A631C/C633A/G640A/C645T/C702T | A169N/L176S/I211W/W217I | +++ |
| 227 | 228 | C401G/C402G/G505A/C506A/A507C/C526T/T527C/G532A/C534G/A631C/C633A/C645T/T649C/G650T/G651A/C702T | A169N/L176S/V178I/I211L/V214M | +++ |
| 229 | 230 | C401G/C402G/G505A/C506A/A507C/C526T/C534T/A631T/T632G/C633G/C645T/T649C/G650T/G651A/C702T | A169N/L176S/V178M/I211W/V214M/W217I | ++ |
| 231 | 232 | C402G/G505A/C506A/A507C/C526T/T527C/C534T/A631T/T632G/C633G/C645T/T649A/G650T/G651A/C702T | T134R/A169N/L176S/V178I/I211L/V214M | ++ |

| Key for Table 4-1 | |
|---|---|
| ++ | 2 < FIOPC < 3 |
| +++ | 3 < FIOPC < 10 |
| ++++ | 10 < FIOPC < 50 |
| +++++ | 50 < FIOPC < 100 |
| ++++++ | FIOPC > 100 |

Example 5

Improvement Over the Polypeptide Encoded by SEQ ID NO: 229 in the Production of Compound [2]

The polynucleotide sequence SEQ ID NO: 229 was selected as a parent sequence, after screening variants as described in Example 3. Libraries of engineered genes were produced using well established techniques, as known in the art (e.g., saturation mutagenesis, recombination of previously identified beneficial mutations). The polypeptides encoded by each gene were produced in HTP, using a similar method described in Example 1. Because the polypeptide encoded by SEQ ID NO: 229 produced significantly higher product compared to previous parent enzymes, only a single 400 μL culture of each variant was grown. Lysis was carried out using the same method described in Example 1.

The enzyme assay was carried out in a 96-well format, in 100 μL total volume/well, which included 20% HTP lysate, 16 mM oxime, 100 mM HEPES, pH 8, 10% DMSO, 1 g/L GDH-105, 3 g/L NADP$^+$, and 100 mM glucose. The reactions were performed by adding the following into each well: (i) 70 μL of GDH cofactor recycling pre-mix (pre-mix contains 0.143 M glucose, 4.28 g/L NADP$^+$, 1.43 g/L GDH-105 in 100 mM HEPES, pH 8)/(ii) 20 μL of the HTP clarified lysate (prepared as described above)/and (iii) 10 μL of the 160 mM oxime stock solution in DMSO. The reaction plate was heat-sealed and shaken at 400 rpm, at 30° C. for 24 hours. The reaction was quenched by adding 100 μL CH$_3$CN with 0.1% formic acid. The sample was then shaken in a microtiter plate shaker at room temperature, and then centrifuged at 4000 rpm at 4° C. for 10 mM. The quenched sample was further diluted 10× with CH$_3$CN with 0.1% formic acid prior to LC/MS analysis. The LC/MS 4000 QTRAP run parameters are described in Example 2.

Activity relative to the polypeptide encoded by SEQ ID NO: 229 was calculated as the product peak area produced by the variant over the product peak area of the polypeptide encoded by SEQ ID NO:229. The IRED variants in Table 5-1 have improved imine reductase activity compared to the starting polypeptide.

TABLE 5-1

Enzyme Activity of IRED Variants Compared to SEQ ID NO: 229/230

| DNA SEQ ID NO: | Peptide SEQ ID NO: | Nucleotide Mutations (Relative to SEQ ID NO: 229) | Peptide Mutations (Relative to SEQ ID NO: 230) | Relative Improvement to SEQ ID NO: 229/230 |
|---|---|---|---|---|
| 233 | 234 | G667A | D223N | + |
| 235 | 236 | A836T/C837T | D279V | + |
| 237 | 238 | C680T/C681T | A227V | + |
| 239 | 240 | G379A/C381G | G127R | + |
| 241 | 242 | G646A | G216S | + |
| 243 | 244 | G520A/C521T/A522G | A174M | + |
| 245 | 246 | G634C/A636T | E212H | + |
| 247 | 248 | G634A/A635G/A636G | E212R | + |
| 249 | 250 | G634A | E212K | + |
| 251 | 252 | C625A/A626G/A627T | Q209S | + |
| 253 | 254 | G646C | G216R | +++ |
| 255 | 256 | A616C/G618T | M206L | ++ |
| 257 | 258 | A400C/C401T/C402T | T134L | +++ |
| 259 | 260 | A388C/C389G/C390T | T130R | + |
| 261 | 262 | G646A/G647A | G216N | + |
| 263 | 264 | G133A | V45I | + |
| 265 | 266 | C625A | Q209K | ++ |
| 267 | 268 | C401G/C402G | T134R | + |

| Key for Table 5-1 | |
|---|---|
| + | 1.5 < FIOPC < 2.0 |
| ++ | 2.0 < FIOPC < 3.0 |
| +++ | FIOPC > 3.0 |

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An engineered polynucleotide encoding an engineered imine or oxime reductase polypeptide comprising an amino acid sequence with at least 80% sequence identity to a reference sequence of SEQ ID NO: 14, and wherein said engineered polypeptide has imine reductase activity.

2. The engineered polynucleotide encoding an engineered imine or oxime reductase polypeptide of claim 1, wherein said polypeptide comprises an arginine or serine at position 169, wherein said position is numbered with reference to SEQ ID NO:2.

3. An engineered polynucleotide comprising SEQ ID NO: 13.

4. The engineered polynucleotide encoding an engineered imine or oxime reductase polypeptide of claim 1, wherein the engineered polynucleotides comprise substitution(s) at positions 505/506/507, wherein the positions are numbered with reference to SEQ ID NO:1.

5. The engineered polynucleotide encoding the engineered imine or oxime reductase polypeptide of claim 4, wherein said engineered polynucleotide comprises at least one of the following substitution(s)/substitution sets selected from 505A/506A/507T and wherein the positions are numbered with reference to SEQ ID NO:1.

6. The engineered polynucleotide encoding the engineered imine or oxime reductase polypeptide of claim 4, wherein said engineered polynucleotide comprises at least one of the following substitution(s)/substitution sets selected from G505A/C506A/A507T and G505A/C506G/A507T, and wherein the positions are numbered with reference to SEQ ID NO:1.

7. The engineered polynucleotide encoding an engineered imine or oxime reductase polypeptide of claim 1, wherein the engineered polynucleotides comprise substitution(s) at positions 367/368/369/505/506/507/513/519/523/524/525/ 634/635/636/639/703/704/705, 369/370/371/372/505/506/ 507/513/519/638/703/704/705, 369/505/506/507/511/512/ 517/518/519/638/703/704/705, 369/505/506/507/513/517/ 518/519/523/524/525/638/703/704/705, 369/505/506/507/ 513/519/523/524/525/634/635/636/638/703/704/705, 369/ 505/506/507/513/519/635/638/703/704/705, 401/402/505/ 506/507/526/527/532/534/631/632/633/645/702, 401/402/ 505/506/507/526/527/532/534/631/633/640/645/702, 401/ 402/505/506/507/526/527/532/534/631/633/645/649/650/ 651/702, 401/402/505/506/507/526/527/534/631/632/633/ 645/702, 401/402/505/506/507/526/527/534/631/633/644/ 645/649/650/651/700/701, 401/402/505/506/507/526/532/ 534/631/632/633/640/645/649/650/651/702, 401/402/505/ 506/507/526/534/631/632/633/640/645/649/650/651/702, 401/402/505/506/507/526/534/631/632/633/645/649/650/ 651/702, 402/505/506/507/526/527/532/534/631/632/633/ 640/645/649/650/651/702, 402/505/506/507/526/527/532/ 534/702, 402/505/506/507/526/527/532/534/631/633/640/ 645/702, 402/505/506/507/526/527/532/534/631/632/633/ 640/645/649/650/651/702, 402/505/506/507/526/527/534/ 631/633/640/645/649/650/651/702, 402/505/506/507/526/ 527/534/631/632/633/640/643/644/645/700/701, 402/505/ 506/507/526/527/534/631/632/633/640/645/702, 402/505/ 506/507/526/527/534/631/632/633/645/649/650/651/702, 402/505/506/507/526/527/534/631/632/633/645/649/650/ 651/702, 402/505/506/507/526/527/534/633/640/644/645/ 649/650/651/702, 402/505/506/507/526/532/534/633/645/ 700/701, 402/505/506/507/526/532/534/645/649/650/651, 402/505/506/507/526/534/631/632/633/645/649/650/651/ 702, 505/506/507/526/527/532/534/631/632/633/640/645/ 649/650/651/702, 505/506/507/526/527/532/534/631/632/ 633/645/649/650/651/702, and 505/506/507/526/534/631/ 632/633/640/643/644/645, wherein the positions are numbered with reference to SEQ ID NO:269.

8. The engineered polynucleotide encoding the engineered imine or oxime reductase polypeptide of claim 7, wherein said engineered polynucleotide comprises at least one of the following substitution(s)/substitution sets selected from 367G/368G/369T/505A/506A/507T/513C/519C/ 523G/524G/525C/634T/635G/636C/639T/703A/704A/ 705G, 369G/370G/371G/372C/505A/506A/507T/513C/ 519C/638T/703A/704A/705G, 369G/505A/506A/507T/ 511G/512T/517A/518T/519T/638T/703A/704A/705G, 369G/505A/506A/507T/513C/517A/518T/519T/523C/ 524A/525C/638T/703A/704A/705G, 369G/505A/506A/ 507T/513C/519C/523G/524G/525C/634T/635G/636C/ 638T/703A/704A/705G, 369G/505A/506A/507T/513C/ 519C/635T/638T/703A/704A/705G, 401G/402G/505A/ 506A/507C/526T/527C/532A/534G/631C/633A/645T/ 649C/650T/651A/702T, 401G/402G/505A/506A/507C/ 526T/527C/532A/534T/631C/633A/640A/645T/702T, 401G/402G/505A/506A/507C/526T/527C/532A/534T/ 631/632G/633G/645T/702T, 401G/402G/505A/506A/ 507C/526T/527C/534G/631C/633A/644T/645G/649A/ 650T/651A/700C/701T, 401G/402G/505A/506A/507C/ 526T/527C/534/631T/632G/633G/645T/702T, 401G/ 402G/505A/506A/507C/526T/532A/534G/631T/632G/ 633G/640A/645T/649A/650T/651A/702T, 401G/402G/ 505A/506A/507C/526T/534G/631T/632G/633G/640A/ 645T/649C/650T/651A/702T, 401G/402G/505A/506A/ 507C/526T/534T/631T/632G/633G/645T/649C/650T/ 651A/702T, 402G/505A/506A/507C/526T/527C/532A/ 534T/631T/632G/633G/640A/645T/649C/650T/651A/ 702T, 402G/505A/506A/507C/526T/527C/532A/534G/ 702T, 402G/505A/506A/507C/526T/527C/532A/534T/ 631C/633A/640A/645T/702T, 402G/505A/506A/507C/ 526T/527C/532A/534T/631T/632G/633G/640A/645T/ 649C/650T/651A/702T, 402G/505A/506A/507C/526T/ 527C/534G/631C/633A/640A/645T/649A/650T/651A/ 702T, 402G/505A/506A/507C/526T/527C/534G/631T/ 632G/633G/640A/643T/644T/645G/700C/701T, 402G/ 505A/506A/507C/526T/527C/534G/631T/632G/633G/ 640A/645T/702T, 402G/505A/506A/507C/526T/527C/ 534G/631T/632G/633G/645T/649C/650T/651A/702T, 402G/505A/506A/507C/526T/527C/534T/631T/632G/ 633G/645T/649A/650T/651A/702T, 402G/505A/506A/ 507C/526T/527C/534T/633A/640A/644T/645G/649A/ 650T/651A/702T, 402G/505A/506A/507C/526T/532A/ 534G/633A/645T/700C/701T, 402G/505A/506A/507C/

526T/532A/534T/645T/649A/650T/651A, 402G/505A/ 506A/507C/526T/534G/631T/632G/633G/645T/649A/ 650T/651A/702T, 505A/506A/507C/526T/527C/532A/ 534G/631T/632G/633G/640A/645T/649A/650T/651A/ 702T, 505A/506A/507C/526T/527C/532A/534T/631T/ 632G/633G/645T/649C/650T/651A/702T, and 505A/506A/ 507C/526T/534G/631T/632G/633G/640A/643T/644T/ 645G, wherein the positions are numbered with reference to SEQ ID NO:269.

9. The engineered polynucleotide encoding the engineered imine or oxime reductase polypeptide of claim 7, wherein said engineered polynucleotide comprises at least one of the following substitution(s)/substitution sets selected from A367G/C368G/C369T/G505A/C506A/A507T/ T513C/A519C/A523G/T524G/G525C/G634T/A635G/A6 36C/G639T/G703A/C704A/C705G, C369G/A370G/ T371G/T372C/G505A/C506A/A507T/T513C/A519C/ C638T/G703A/C704A/C705G, C369G/G505A/C506A/ A507T/T511G/A512T/G517A/C518T/A519T/C638T/ G703A/C704A/C705G, C369G/G505A/C506A/A507T/ T513C/G517A/C518T/A519T/A523C/T524A/G525C/ C638T/G703A/C704A/C705G, C369G/G505A/C506A/ A507T/T513C/A519C/A523G/T524G/G525C/G634T/ A635G/A636C/C638T/G703A/C704A/C705G, C369G/ G505A/C506A/A507T/T513C/A519C/A635T/C638T/ G703A/C704A/C705G, C401G/C402G/G505A/C506A/ A507C/C526T/T527C/G532A/C534G/A631C/C633A/ C645T/T649C/G650T/G651A/C702T, C401G/C402G/ G505A/C506A/A507C/C526T/T527C/G532A/C534T/ A631C/C633A/G640A/C645T/C702T, C401G/C402G/ G505A/C506A/A507C/C526T/T527C/G532A/C534T/ A631T/T632G/C633G/C645T/C702T, C401G/C402G/ G505A/C506A/A507C/C526T/T527C/C534G/A631C/ C633A/C644T/C645G/T649A/G650T/G651A/G700C/ A701T, C401G/C402G/G505A/C506A/A507C/C526T/ T527C/C534T/A631T/T632G/C633G/C645T/C702T, C401G/C402G/G505A/C506A/A507C/C526T/G532A/ C534G/A631T/T632G/C633G/G640A/C645T/T649A/ G650T/G651A/C702T, C401G/C402G/G505A/C506A/ A507C/C526T/C534G/A631T/T632G/C633G/G640A/ C645T/T649C/G650T/G651A/C702T, C401G/C402G/ G505A/C506A/A507C/C526T/C534T/A631T/T632G/ C633G/C645T/T649C/G650T/G651A/C702T, C402G/ G505A/C506A/A507C/C526T/T527C/G532A/C534T/ A631T/T632G/C633G/G640A/C645T/T649C/G650T/ G651A/C702T, C402G/G505A/C506A/A507C/C526T/ T527C/G532A/C534G/C702T, C402G/G505A/C506A/ A507C/C526T/T527C/G532A/C534T/A631C/C633A/ G640A/C645T/C702T, C402G/G505A/C506A/A507C/ C526T/T527C/G532A/C534T/A631T/T632G/C633G/ G640A/C645T/T649C/G650T/G651A/C702T, C402G/ G505A/C506A/A507C/C526T/T527C/C534G/A631C/ C633A/G640A/C645T/T649A/G650T/G651A/C702T, C402G/C505A/C506A/A507C/C526T/T527C/C534G/ A631T/T632G/C633G/G640A/A643T/C644T/C645G/ G700C/A701T, C402G/G505A/C506A/A507C/C526T/ T527C/C534G/A631T/T632G/C633G/G640A/C645T/ C702T, C402G/G505A/C506A/A507C/C526T/T527C/ C534G/A631T/T632G/C633G/C645T/T649C/G650T/ G651A/C702T, C402G/G505A/C506A/A507C/C526T/ T527C/C534T/A631T/T632G/C633G/C645T/T649A/ G650T/G651A/C702T, C402G/G505A/C506A/A507C/ C526T/T527C/C534T/C633A/G640A/C644T/C645G/ T649A/G650T/G651A/C702T, C402G/G505A/C506A/ A507C/C526T/G532A/C534G/C633A/C645T/G700C/ A701T, C402G/G505A/C506A/A507C/C526T/G532A/ C534T/C645T/T649A/G650T/G651A, C402G/G505A/ C506A/A507C/C526T/C534G/A631T/T632G/C633G/ C645T/T649A/G650T/G651A/C702T, G505A/C506A/ A507C/C526T/T527C/G532A/C534G/A631T/T632G/ C633G/G640A/C645T/T649A/G650T/G651A/C702T, G505A/C506A/A507C/C526T/T527C/G532A/C534T/ A631T/T632G/C633G/C645T/T649C/G650T/G651A/ C702T, and G505A/C506A/A507C/C526T/C534G/A631T/ T632G/C633G/G640A/A643T/C644T/C645G, wherein the positions are numbered with reference to SEQ ID NO:269.

10. The engineered polynucleotide encoding an engineered imine or oxime reductase polypeptide of claim 4, wherein the engineered polynucleotide further comprises substitution(s) at positions 133, 379/381, 388/389/390, 400/ 401/402, 401/402, 520/521/522, 616/618, 625, 625/626/627, 634, 634/635/636, 634/636, 646, 646/647, 646, 667, 680/ 681, and 836/837, wherein the positions are numbered with reference to SEQ ID NO:229.

11. The engineered polynucleotide encoding the engineered imine or oxime reductase polypeptide of claim 10, wherein said engineered polynucleotide further comprises at least one of the following substitution(s)/substitution sets selected from 133A, 379A/381G, 388C/389G/390T, 400C/ 401T/402T, 401G/402G, 520A/521T/522G, 616C/618T, 625A, 625A/626G/627T, 634A, 634A/635G/636G, 634C/ 636T, 646A, 646A/647A, 646C, 667A, 680T/681T, and 836T/837T, wherein the positions are numbered with reference to SEQ ID NO:229.

12. The engineered polynucleotide encoding the engineered imine or oxime reductase polypeptide of claim 10, wherein said engineered polynucleotide further comprises at least one of the following substitution(s)/substitution sets selected from G133A, G379A/C381G, A388C/C389G/ C390T, A400C/C401T/C402T, C401G/C402G, G520A/ C521T/A522G, A616C/G618T, C625A, C625A/A626G/ A627T, G634A, G634A/A635G/A636G, G634C/A636T, G646A, G646A/G647A, G646C, G667A, C680T/C681T, and A836T/C837T, wherein the positions are numbered with reference to SEQ ID NO:229.

13. A vector comprising the engineered polynucleotide of claim 1.

14. The vector of claim 13, further comprising at least one control sequence.

15. A host cell comprising the vector of claim 13.

16. The host cell of claim 15, wherein said host cell produces at least one engineered polypeptide of claim 1.

* * * * *